(12) United States Patent
Dantanarayana et al.

(10) Patent No.: US 10,773,044 B2
(45) Date of Patent: Sep. 15, 2020

(54) VENT ADAPTOR FOR A RESPIRATORY THERAPY SYSTEM

(71) Applicant: ResMed Pty Ltd, Bella Vista, New South Wales (AU)

(72) Inventors: Muditha Pradeep Dantanarayana, Sydney (AU); Justin John Formica, Sydney (AU); Richard Llewelyn Jones, Sydney (AU); Joseph Samuel Ormrod, Sydney (AU); Chia Ik Tan, Sydney (AU); Jamie Graeme Wehbeh, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 256 days.

(21) Appl. No.: 15/760,403

(22) PCT Filed: Sep. 23, 2016

(86) PCT No.: PCT/AU2016/050893
§ 371 (c)(1),
(2) Date: Mar. 15, 2018

(87) PCT Pub. No.: WO2017/049358
PCT Pub. Date: Mar. 30, 2017

(65) Prior Publication Data
US 2018/0264222 A1 Sep. 20, 2018

Related U.S. Application Data

(60) Provisional application No. 62/222,604, filed on Sep. 23, 2015.

(51) Int. Cl.
*A61M 16/08* (2006.01)
*A61M 16/10* (2006.01)
(Continued)

(52) U.S. Cl.
CPC .... *A61M 16/0816* (2013.01); *A61M 16/0616* (2014.02); *A61M 16/0875* (2013.01);
(Continued)

(58) Field of Classification Search
CPC .. A61M 16/00; A61M 16/0066; A61M 16/06; A61M 16/08; A61M 16/0816;
(Continued)

(56) References Cited

U.S. PATENT DOCUMENTS 2,944,547 A 7/1960 Ziherl et al.
3,419,029 A * 12/1968 Staub .................. A61M 16/208
128/205.24
(Continued)

FOREIGN PATENT DOCUMENTS

CN 104203324 A 12/2014
EP 1938856 A1 7/2008
(Continued)

OTHER PUBLICATIONS

Extended European Search Report dated Jun. 3, 2019 issued in European Application No. 16847656.2 (9 pages).
(Continued)

*Primary Examiner* — Joseph D. Boecker
(74) *Attorney, Agent, or Firm* — Nixon & Vanderhye P.C.

(57) ABSTRACT

A fluid connector between patient interface and a respiratory therapy device and a vent adaptor for a respiratory pressure therapy system. The fluid connector comprising two parts, the first of which includes a seal and a latching portion and the second a complementary latching portion configured to engage the former to provide a fluid flow patch between the two parts. The vent adaptor comprising a vent assembly comprising a vent housing and an annular plate including an
(Continued)

array of holes to discharge the pressurised gas to atmosphere and an deformable membrane which presses against the annular plate.

23 Claims, 124 Drawing Sheets

(51) Int. Cl.
*A61M 16/20* (2006.01)
*A61M 16/16* (2006.01)
*A61M 16/06* (2006.01)
*A61M 16/00* (2006.01)

(52) U.S. Cl.
CPC ...... *A61M 16/1045* (2013.01); *A61M 16/161* (2014.02); *A61M 16/208* (2013.01); *A61M 16/0683* (2013.01); *A61M 16/16* (2013.01); *A61M 2016/0021* (2013.01); *A61M 2016/0033* (2013.01); *A61M 2202/0225* (2013.01); *A61M 2205/3584* (2013.01); *A61M 2205/3592* (2013.01); *A61M 2205/42* (2013.01); *A61M 2205/50* (2013.01)

(58) Field of Classification Search
CPC .......... A61M 16/0825; A61M 16/0833; A61M 16/085; A61M 16/0866; A61M 16/0875; A61M 16/1045; A61M 16/208; A62B 18/00; A62B 18/02
See application file for complete search history.

(56) References Cited

U.S. PATENT DOCUMENTS

| | | | |
|---|---|---|---|
| 4,458,679 A | 7/1984 | Ward | |
| 4,782,832 A | 11/1988 | Trimble et al. | |
| 4,944,310 A | 7/1990 | Sullivan | |
| 4,997,217 A | 3/1991 | Kunze | |
| 5,271,601 A | 12/1993 | Bonzer et al. | |
| 5,685,296 A | 11/1997 | Zdrojkowski et al. | |
| 5,762,382 A | 6/1998 | Pernetti et al. | |
| 5,896,857 A | 4/1999 | Hely et al. | |
| 5,937,851 A | 8/1999 | Serowski et al. | |
| 6,532,959 B1 | 3/2003 | Berthon-Jones | |
| 6,581,594 B1 | 6/2003 | Drew et al. | |
| 6,584,977 B1* | 7/2003 | Serowski | A61M 16/06 128/206.24 |
| 6,662,803 B2 | 12/2003 | Gradon et al. | |
| 7,096,864 B1 | 8/2006 | Mayer et al. | |
| 7,302,950 B2 | 12/2007 | Berthon-Jones et al. | |
| 7,866,944 B2 | 1/2011 | Kenyon et al. | |
| 7,987,847 B2 | 8/2011 | Wickham | |
| 8,439,035 B2 | 5/2013 | Dantanarayana et al. | |
| 8,544,465 B2 | 10/2013 | Smith et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2004/0094157 A1* | 5/2004 | Dantanarayana | A61B 5/0876 128/206.21 |
| 2005/0199240 A1* | 9/2005 | Hall | A61M 16/06 128/206.26 |
| 2009/0044808 A1 | 2/2009 | Guney | |
| 2009/0050156 A1 | 2/2009 | Ng et al. | |
| 2009/0120434 A1 | 5/2009 | Smith et al. | |
| 2009/0133694 A1 | 5/2009 | Solci et al. | |
| 2009/0260628 A1* | 10/2009 | Flynn, Sr. | A61M 16/0078 128/203.28 |
| 2010/0000534 A1 | 1/2010 | Kooij et al. | |
| 2010/0083969 A1 | 4/2010 | Crumblin et al. | |
| 2010/0282262 A1 | 11/2010 | Boussignac | |
| 2011/0067709 A1 | 3/2011 | Doshi et al. | |
| 2012/0012111 A1* | 1/2012 | Howe, Jr. | A61M 16/1055 128/205.12 |
| 2012/0325205 A1 | 12/2012 | Allum et al. | |
| 2012/0325218 A1 | 12/2012 | Brambilla et al. | |
| 2013/0184602 A1 | 7/2013 | Brambilla | |
| 2016/0008558 A1* | 1/2016 | Huddart | A61M 16/06 128/205.25 |
| 2016/0220781 A1* | 8/2016 | Arrowsmith | A61M 16/208 |
| 2016/0250438 A1* | 9/2016 | Harwood | A61M 16/0875 128/201.13 |
| 2017/0065786 A1* | 3/2017 | Stephenson | A61M 16/06 |
| 2019/0209804 A1* | 7/2019 | Dantanarayana | A61M 16/208 |
| 2019/0351173 A1* | 11/2019 | Dantanarayana | A61M 16/0816 |

FOREIGN PATENT DOCUMENTS

| | | |
|---|---|---|
| GB | 2500061 A1 | 9/2013 |
| WO | WO 98/004310 A1 | 2/1998 |
| WO | WO 98/034665 A1 | 8/1998 |
| WO | WO 2000/078381 A1 | 12/2000 |
| WO | WO 02/051486 A1 | 7/2002 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | 2009/127049 A1 | 10/2009 |
| WO | 2010/067237 A2 | 6/2010 |
| WO | WO 2010/135785 A1 | 12/2010 |
| WO | WO 2011/080604 A1 | 7/2011 |
| WO | WO 2012/171072 A1 | 12/2012 |
| WO | WO 2013/020167 A1 | 2/2013 |
| WO | WO 2014/097068 A1 | 6/2014 |
| WO | 2014/129913 A1 | 8/2014 |
| WO | WO 2014/205513 A1 | 12/2014 |
| WO | WO 2015/013761 A1 | 2/2015 |
| WO | 2015/041545 A1 | 3/2015 |
| WO | WO 2016/041019 A1 | 3/2016 |
| WO | WO 2016/141430 A1 | 9/2016 |

OTHER PUBLICATIONS

"*Respiratory Physiology*", by John B. West, Lippincott Williams & Wilkins, 9$^{th}$ edition published 2012 (8 pages).
Notification of Transmittal of International Preliminary Report on Patentability issued in Application No. PCT/AU2016/050893, dated Sep. 21, 2014, 44 pages.
International Search Report issued in Application No. PCT/AU2016/050893, dated Jan. 13, 2017, 6 pages.
Written Opinion issued in Application No. PCT/AU2016/050893, dated Jan. 13, 2017, 7 pages.
Office Action dated Feb. 3, 2020 issued in Chinese Application No. 201680058868.4 with English translation (8 pages).

* cited by examiner

Nose - Anterolateral view

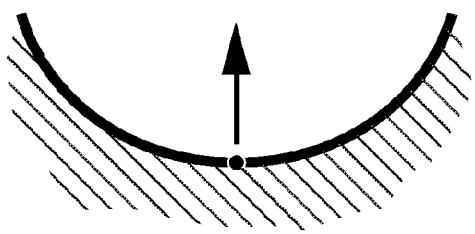
FIG. 3B — Relatively Large Positive Curvature
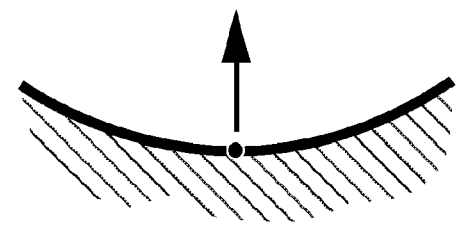
FIG. 3C — Relatively Small Positive Curvature
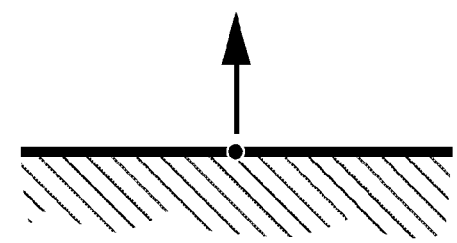
FIG. 3D — Zero Curvature
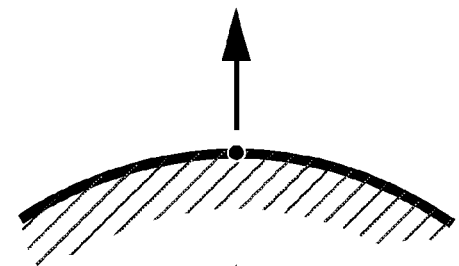
FIG. 3E — Relatively Small Negative Curvature
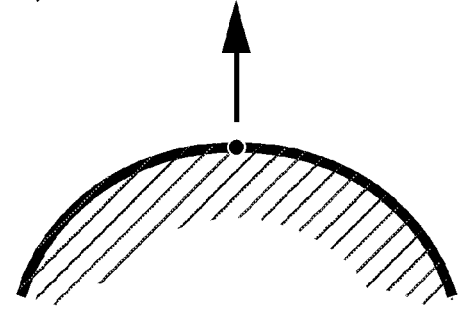
FIG. 3F — Relatively Large Negative Curvature

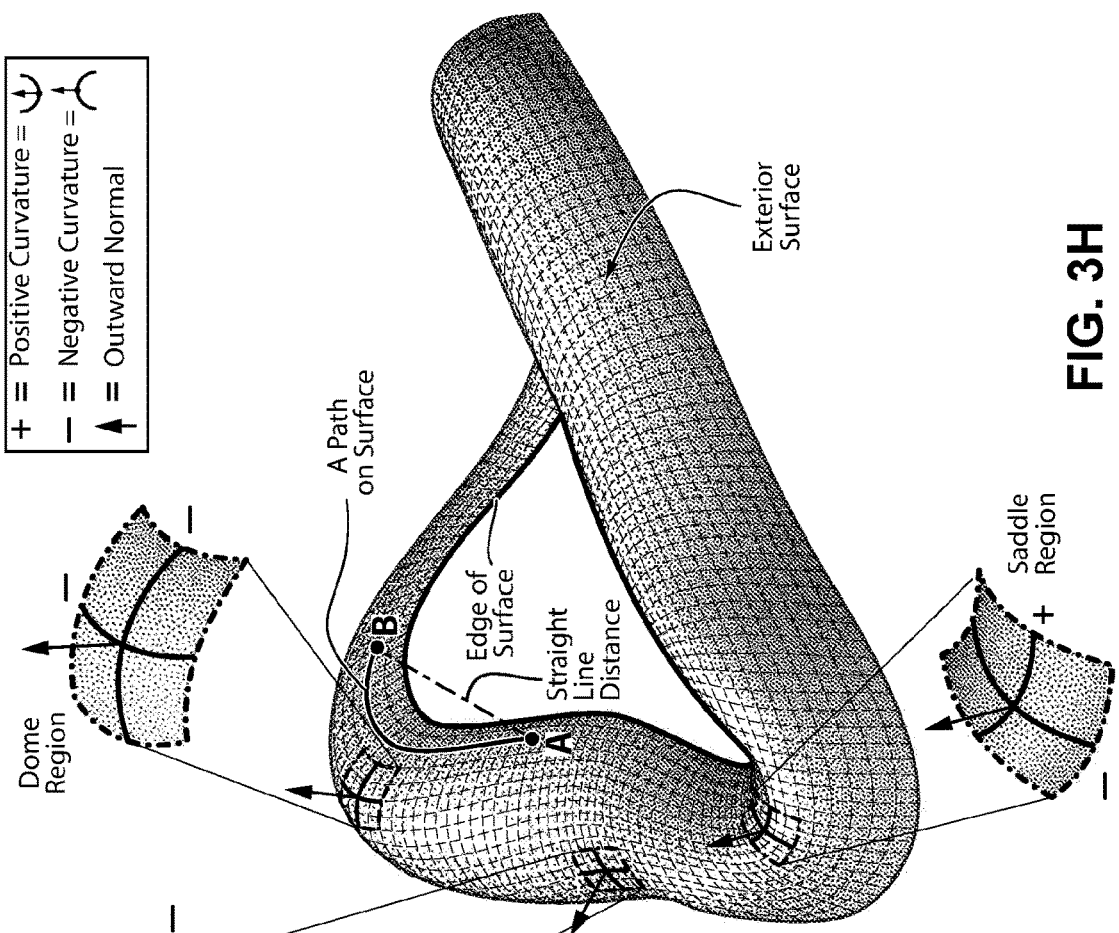
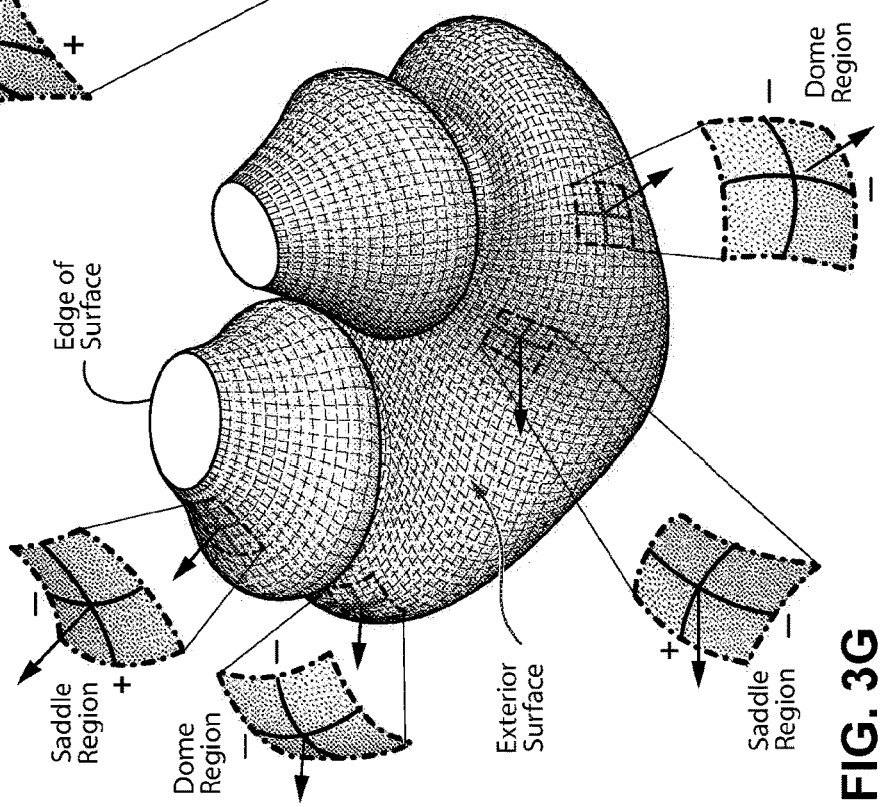
FIG. 3H
FIG. 3G

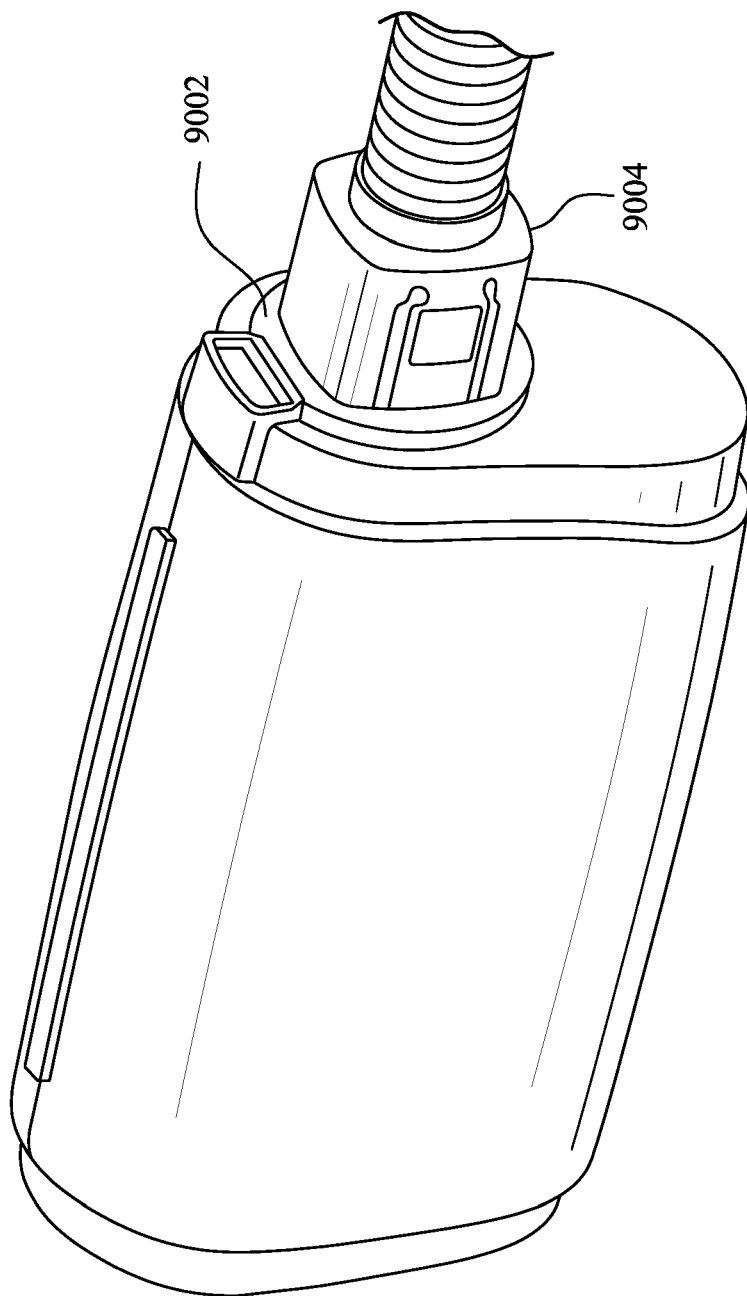

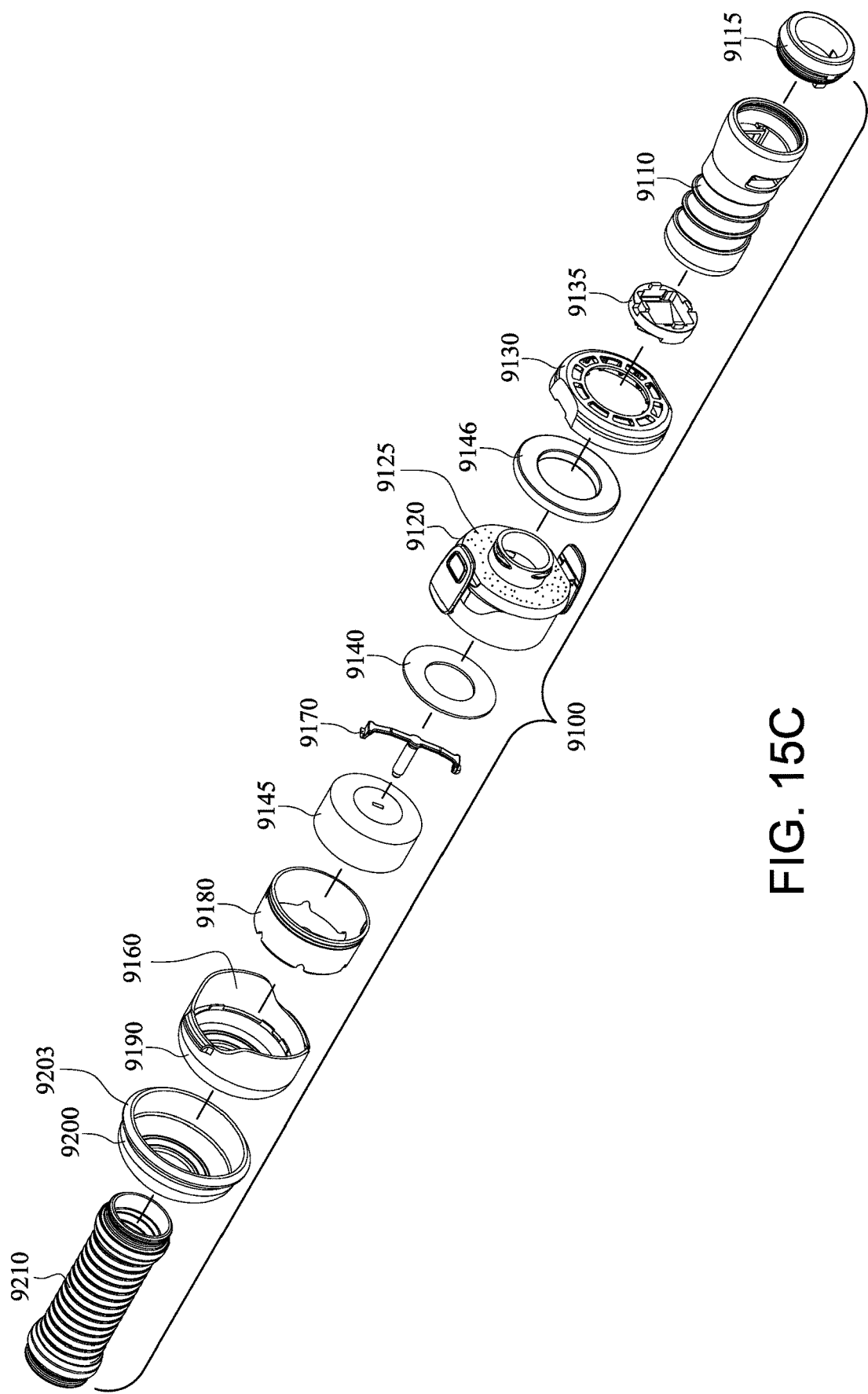

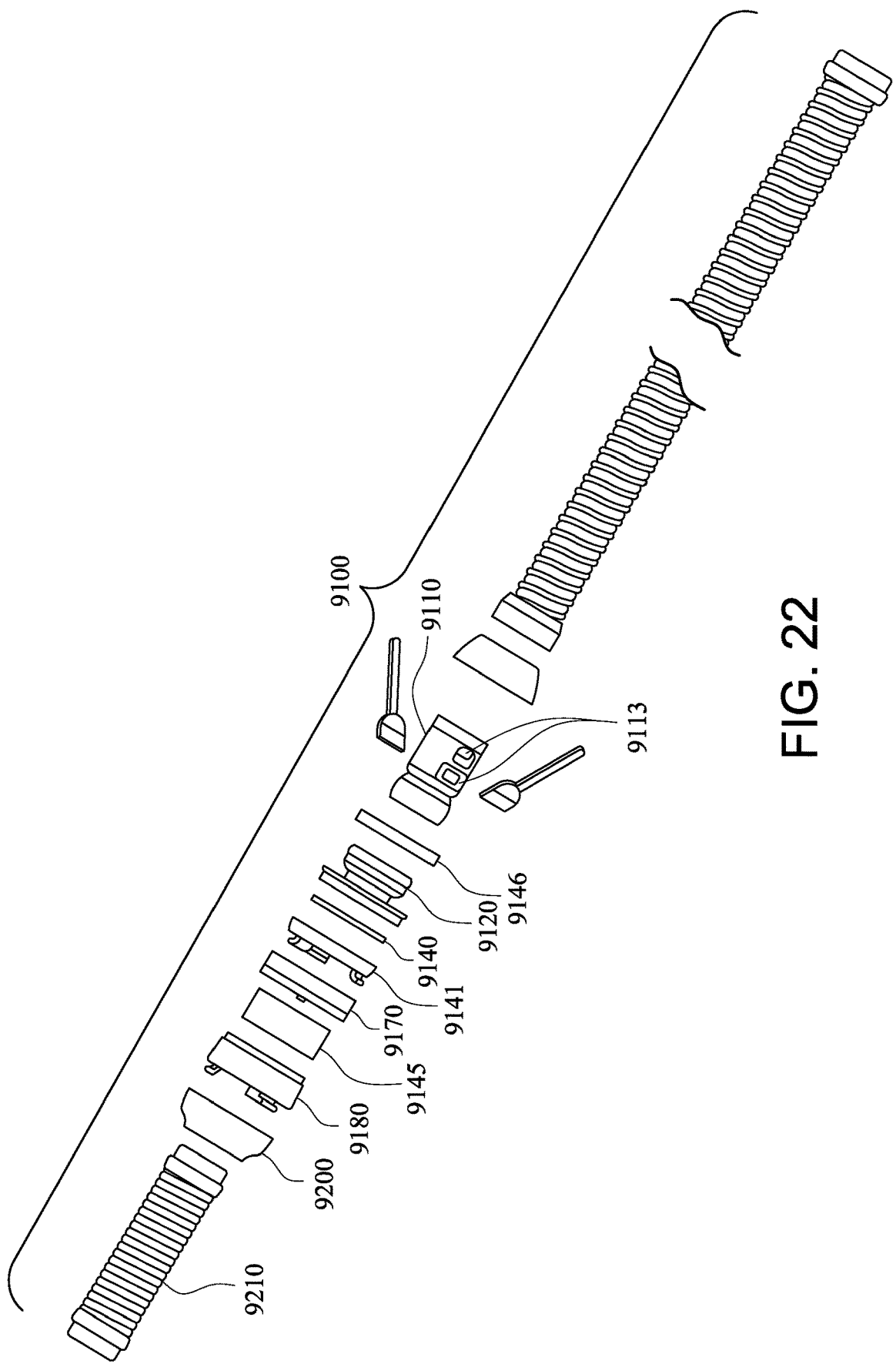

VENT ADAPTOR FOR A RESPIRATORY THERAPY SYSTEM

1 CROSS-REFERENCE TO RELATED APPLICATIONS

This application is the U.S. national phase of International Application No. PCT/AU2016/050893 filed Sep. 23, 2016, which designated the U.S. and claims the benefit of U.S. Provisional Application No. 62/222,604, filed on Sep. 23, 2015, the entire contents of each of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory Insufficiency is an umbrella term for respiratory disorders in which patients are unable to ventilate enough to balance the $CO_2$ in their blood if their metabolic activity rises much above rest. Respiratory insufficiency may encompass some or all of the following disorders.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory insufficiency, in forms such as OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Vent Technologies

Some forms of patient interface systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2: 2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage™ (*) | nasal | 29.5 | 21.5 | 1998 |
| ResMed UltraMirage™ | nasal | 36 (3) | 28 (3) | 2000 |
| ResMed Mirage Activa™ | nasal | 32 (3) | 24 (3) | 2002 |
| ResMed Mirage Micro™ | nasal | 30 (3) | 22 (3) | 2008 |
| ResMed Mirage™ SoftGel | nasal | 29 (3) | 22 (3) | 2008 |
| ResMed Mirage™ FX | nasal | 26 (3) | 18 (3) | 2010 |
| ResMed Mirage Swift™ (*) | nasal pillows | 37 | 29 | 2004 |
| ResMed Mirage Swift™ II | nasal pillows | 28 (3) | 20 (3) | 2005 |
| ResMed Mirage Swift™ LT | nasal pillows | 25 (3) | 17 (3) | 2008 |
| ResMed AirFit P10 | nasal pillows | 21 (3) | 13 (3) | 2014 |

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

(*) one specimen only, measured using test method specified in ISO 3744 in CPAP mode at 10 cmH$_2$O)Sound pressure values of a variety of objects are listed below

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound power level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.4 Diagnosis and Monitoring Systems

Clinical experts may be able to diagnose or monitor patients adequately based on person observation. However, there are circumstances where a clinical expert may not be available, or a clinical expert may not be affordable. In some circumstances different clinical experts may disagree on a patient's condition. A given clinical expert may apply a different standard at different times. With a busy clinical practice, a clinician may have difficulty keeping up with evolving patient management guidelines.

Polysomnography (PSG) is a conventional system for diagnosis and prognosis of cardio-pulmonary disorders, and typically involves expert clinical staff to both apply and/or interpret. PSG typically involves the placement of 15 to 20 contact sensors on a person in order to record various bodily signals such as electroencephalography (EEG), electrocardiography (ECG), electrooculograpy (EOG), electromyography (EMG), etc. However, while they may be suitable for their usual application in a clinical setting, such systems are complicated and potentially expensive, and/or may be uncomfortable or impractical for a patient at home trying to sleep.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

A first form of the present technology includes a connector set with a compliant face seal between a first end and a second end of the connector set and with a retention mechanism that couples the first end and the second end together.

A second form of the present technology comprises a fluid connector for delivery of breathing gas to a patient from a respiratory pressure therapy device, the fluid connector comprising a first end with a first opening for a fluid flow, a seal portion extending around a periphery of the first opening, and a latching portion, a second end with a second opening for the fluid flow, a sealing surface extending around a periphery of the second opening and configured to engage the seal portion to form a face seal, and a complementary latching portion configured to engage with the latching portion, wherein the face seal allows the breathing gas to travel between the first opening and the second opening, and the engagement between the latching portion and the complementary latching portion secures the first end with the second end.

A third form of the present technology comprises a system for providing respiratory therapy to a patient, the system comprising a respiratory pressure therapy device; an air circuit; a patient interface connected to the air circuit and a means for preventing the respiratory pressure therapy device from being connected to the air circuit with an industry standard connection.

A fourth form of the present technology comprises a method of providing a fluid connection to deliver breathing gas to a patient from a respiratory pressure therapy device, the method comprising engaging a latch between a first end and a second end of the fluid connection; and engaging a face seal around a first opening in the first end and around a second opening in the second end, wherein one of the first end and the second end corresponds to the respiratory pressure therapy device.

A fifth form of the present technology comprises a first half of a fluid connector system for delivery of breathing gas to a patient from a respiratory pressure therapy device, the first half comprising connector portion with a first opening for a fluid flow, a seal portion extending around a periphery of the first opening, and a latching portion, wherein the seal portion is configured to seal against a sealing surface extending around a periphery of a second opening to form a face seal with a second half of the fluid connector system, and the latching portion is configured to latch with another latching portion of the second half of the fluid connector system.

A sixth form of the present technology comprises a first half of a fluid connector system for delivery of breathing gas to a patient from a respiratory pressure therapy device, the first half comprising a connector portion with a first opening for a fluid flow, a sealing surface around a periphery of the first opening, and a latching portion, wherein the sealing surface is configured to receive a seal portion extending around a periphery of a second opening to form a face seal with a second half of the fluid connector system, and the latching portion is configured to latch with another latching portion of the second half of the fluid connector system.

A seventh form of the present technology comprises a fluid connector for delivery of breathing gas to a patient from a respiratory pressure therapy device, the fluid connector comprising a first end with a first interior portion for a fluid flow and a first retaining portion, and a second end with a second interior portion for the fluid flow and a complementary retaining portion configured to engage with the retaining portion, wherein the first interior portion and the second interior portion have a first shape perpendicular to a flow direction, the retaining portion and the complementary retaining portion have a second shape perpendicular to the flow direction, and the first shape and the second shape are different.

An eighth form of the present technology comprises a system for providing respiratory therapy to a patient, the system comprising a respiratory pressure therapy device; an air circuit; a patient interface connected to the air circuit, the patient interface being specially adapted to operate with the respiratory pressure therapy device; and a means for ensuring that the patient interface that is specially adapted to operate with the respiratory pressure therapy device is connected to the respiratory pressure therapy device.

In examples of at least one of the first through eighth forms of the present technology, (a) the first end is connected to a respiratory pressure therapy device including a blower and the second end is connected to a fluid conduit; (b) the respiratory pressure therapy device is configured to provide treatment pressure for the sleep related breathing disorder; (c) the sealing surface is flat; (d) the sealing surface is substantially perpendicular to a direction of the fluid flow from the first end to the second end; (e) the sealing surface is beveled; (d) the sealing surface extends circumferentially around the second opening; (e) the sealing surface is formed on a flange that extends radially from a tube defining the second opening; (f) the flange extends substantially perpendicularly from the tube; (g) the tube extends beyond the flange in a direction towards the seal portion; (h) the tube extends at least partially though the seal portion when the complementary latching portion is engaged with the latching portion; (i) the seal portion is compliant in a direction of engagement between the first end and the second end; (j) the seal portion includes a frustoconical portion; (k) the frustoconical portion contacts the sealing surface to form the face seal; (l) the seal portion includes a partial spherical surface; (m) the partial spherical surface contacts the sealing surface to form the face seal; (n) the seal portion includes a bellows-shaped or partial bellows-shaped portion; (o) the bellows-shaped or partial bellows-shaped portion contacts the sealing surface to form the face seal; (p) when the first end and the second end are connected the seal portion is configured to engage the sealing surface before the latching portion and the complementary latching portion engage; (q) the seal portion is compliant in a direction radial to an axis defined by a direction of engagement between the first end and the second end; (r) the seal portion is configured to expand and engage the sealing surface due to internal pressurization of the first end when a gap exists between the seal portion and the sealing surface in an unpressurized state; (s) contact between the seal portion and the sealing surface causes the seal portion to compress against the sealing and against an airflow direction that is from the first opening to the second opening; (t) compression of the seal portion does not cause significant compressive forces; (u) a force required to compress the seal portion is less than a force required to engage the latching portion with the complementary latching portion; (v) the force required to compress the seal portion is less than half of the force required to engage the latching portion with the complementary latching portion; (w) the force required to compress the seal portion is less than one tenth of the force required to engage the latching portion with the complementary latching portion; (x) at least one of the seal portion and the sealing surface includes sufficient contact area between the seal portion and the sealing surface to form a seal when respective centers of the seal portion and the sealing surface are not aligned with one another; (y) the second end comprises an inner portion and an outer portion and the inner portion is rotatably coupled to the outer portion; (z) the inner portion comprises the sealing surface; (aa) the inner portion is rigidly connected to a fluid conduit; (bb) the outer portion comprises the complementary latching portion; (cc) the complementary latching portion comprises a cantilevered portion with a protrusion that is configured to engage the latching portion; (dd) the cantilevered portion is configured to be depressed to engage or disengage the complementary latching portion from the latching portion and allow engagement or disengagement between the first end and the second end; (ee) the first end comprises a travel limit to constrain the second end from moving in a direction of engagement between the first end and the second end; (ff) the travel limit is a flange around the first opening and the second end comprises a stop surface configured to contact the flange; (gg) the latching portion constrains the second end from moving in a direction opposite to the direction of engagement, and the travel limit and latching portion together define a movement distance of the second end when the first end and the second end are engaged; (hh) the seal portion is configured to seal against the sealing surface throughout the movement distance, the movement distance being a non-zero distance; (ii) the seal portion is configured to form a seal with the sealing surface with a worst case manufacturing tolerance and after a predetermined amount of wear and/or creep in the fluid connector; (jj) the fluid connector is configured to provide negligible pressure drop when air is flowing through the fluid connector throughout a patient's breathing cycle and at pressures between 4 cm $H_2O$ to 40 cm $H_2O$; (kk) the first end is a female connection and the second end is a male connection; (ll) the female connection and the male connection have profiles that are non-circular; (mm) the first end includes a port in fluid communication with an interior of the seal portion and separated from the first opening and the second opening; (nn) the first opening and the second opening are interior portions of tubes; (oo) the first end is connected to a respiratory pressure therapy device including a blower and the second end is connected to an adapter for a fluid conduit connector; (pp) the fluid connector further comprises an industry standard fluid connection, wherein the industry standard fluid connection is in fluid communication with the first opening and on an end opposite the seal portion; (qq) the fluid connector further comprises an industry standard fluid connection, wherein the industry standard fluid connection is in fluid communication with the first opening and on an end opposite the sealing surface; (rr) the first shape is a circle and the second shape includes properties of a circle and a square; and/or (ss) one of the first interior portion and the second interior portion includes a first male portion and the other of the first interior portion and the second interior portion includes a first female portion, the first male portion and the first female portion including the first shape, and one of the retaining portion and the complementary retaining portion includes a second male portion and the other of the retaining portion and the complementary retaining portion includes a second female portion, the second male portion and the second female portion including the second shape.

An aspect of one form of the present technology is a portable RPT device, including a fluid connector, that may be carried by a person, e.g., around the home of the person.

Another aspect of the present technology is directed to a vent assembly for a respiratory pressure therapy (RPT) system. The vent assembly comprising: a vent housing defining a central orifice for the flow of pressurized gas to pass through the vent assembly from the delivery conduit to the patient interface, the vent housing having an annular surface around the central orifice, and the annular surface having a plurality of holes to discharge pressurized gas to atmosphere; and a membrane positioned adjacent to the annular surface, wherein the membrane is movable such that the membrane is urged against the annular surface of the vent housing as the pressure of the pressurized gas within the vent assembly increases.

Another aspect of the present technology is directed to an RPT system, comprising: the vent assembly described in the preceding paragraph; an RPT device configured to generate a flow of pressurized gas in the range of 4-20 cm H2O; a patient interface configured to deliver the flow of pressurized gas to the patient's airways, the patient interface being non-vented; and a delivery conduit configured to deliver the flow of pressurized gas from the RPT device to the patient interface.

In examples of the vent assembly and the RPT system described in the two preceding paragraphs, (a) the plurality of holes may comprise a first group of holes and a second group of holes, the first group of holes being proximal to the central orifice relative to the second group of holes, (b) the membrane may be shaped and dimensioned such that the membrane does not cover the first group of holes, (c) the membrane may be structured to cover more of the second group of holes as the pressure of the pressurized gas within the vent assembly increases, (d) the first group of holes may be positioned upstream of the second group of holes relative to the flow of pressurized gas, (e) the vent assembly may further comprise a retaining structure to retain the membrane in a position adjacent to the annular surface of the vent housing, (f) the membrane may further comprise an elastic material, (g) the membrane may be ring-shaped, (h) the membrane may not be joined to the vent housing, (i) the membrane may be shaped and dimensioned such that an outer edge of the membrane is adjacent to an inner periphery of the vent housing, and/or (j) each of the plurality of holes may have a shape that converges from an internal surface of the vent housing to an external surface of the vent housing.

Another aspect of the present technology is directed to a vent adaptor for a for a respiratory pressure therapy (RPT) system. The vent adaptor comprises: a vent assembly comprising: a vent housing defining a central orifice for the flow of pressurized gas to pass through the vent assembly from the delivery conduit to the patient interface, the vent housing having an annular surface around the central orifice, and the annular surface having a plurality of holes to discharge pressurized gas to atmosphere; and a membrane positioned adjacent to the annular surface; and a diffusing member.

Another aspect of the present technology is directed to an RPT system. The RPT system comprising: the vent adaptor described in the preceding paragraph; an RPT device configured to generate a flow of pressurized gas in the range of 4-20 cm H2O; a patient interface configured to deliver the flow of pressurized gas to the patient's airways, the patient interface being non-vented; and a delivery conduit configured to deliver the flow of pressurized gas from the RPT device to the patient interface.

In examples of the vent adaptor and the RPT system described in the two preceding paragraphs, (a) the membrane may be movable such that the membrane is urged against the annular surface of the vent housing as the pressure of the pressurized gas within the vent assembly increases, (b) the plurality of holes may comprise a first group of holes and a second group of holes, the first group of holes being proximal to the central orifice relative to the second group of holes, (c) the membrane may be shaped and dimensioned such that the membrane does not cover the first group of holes, (d) the membrane may be structured to cover more of the second group of holes as the pressure of the pressurized gas within the vent assembly increases, (e) the first group of holes may be positioned upstream of the second group of holes relative to the flow of pressurized gas, (f) the vent adaptor may further comprise a retaining structure to retain the membrane in a position adjacent to the annular surface of the vent housing, (g) the membrane may further comprise an elastic material, (h) the membrane may be ring-shaped, (i) the membrane may not be joined to the vent housing, (j) the membrane may be shaped and dimensioned such that an outer edge of the membrane is adjacent to an inner periphery of the vent housing, (k) each of the plurality of holes may have a shape that converges from an internal surface of the vent housing to an external surface of the vent housing, (l) the vent adaptor may comprise a heat and moisture exchanger (HME) that may be positioned downstream of the plurality of holes relative to the flow of pressurized gas, (m) the diffusing member may be positioned on the exterior of the vent housing to at least partly cover the plurality of holes, (n) the vent adaptor may further comprise a blocking member having an air-impermeable material, the blocking member preventing gas exiting from the plurality of holes from flowing through the diffusing member to atmosphere in a linear path, (o) the diffusing member and the blocking member may be configured to direct the gas exiting from the plurality of holes outward from the diffusing member in an orientation different than the plurality of holes, (p) the diffusing member may provide a flow path parallel to a surface of the blocking member that is in contact with the diffusing member, (q) the diffusing member may be a porous material, (r) the diffusing member may be an open cell foam, and/or (s) the diffusing member may be a fibrous material.

An aspect of the present technology is directed to a vent system for use with a patient interface during respiratory therapy of a patient with a therapy flow of gas pressurized above ambient pressure, the vent system providing a vent flow of gas to discharge gas exhaled by the patient from a pressurized volume, the vent flow being continuous during the respiratory therapy. The vent system comprises a vent housing comprising a base having an inlet for the therapy flow of gas extending through the base and at least one first orifice extending through the base to allow gas to be discharged to atmosphere from the pressurized volume; at least one second orifice to allow gas to be discharged to atmosphere from the pressurized volume; and a membrane positioned adjacent to the base.

An aspect of the present technology is directed to a vent system for use with a patient interface during respiratory therapy of a patient with a therapy flow of gas pressurized above ambient pressure, the vent system providing a vent flow of gas to discharge gas exhaled by the patient from a pressurized volume, the vent flow being continuous during the respiratory therapy. The vent system comprises a vent housing comprising a base having at least one first orifice extending through the base to allow gas to be discharged to atmosphere from the pressurized volume; at least one second orifice to allow gas to be discharged to atmosphere from the pressurized volume; and a membrane positioned adjacent to the base, wherein the pressurized volume is in fluid communication with atmosphere through the at least one first orifice and the at least one second orifice throughout a therapeutic pressure range, and wherein the membrane is elastically deformable due to pressure within the pressurized volume to apportion the vent flow between the at least one first orifice and the at least one second orifice throughout the therapeutic pressure.

In examples, (a) the vent housing may comprise an outer wall and an inner wall, the inner wall defining an inlet for the therapy flow of gas, and the base may be positioned between the outer wall and the inner wall, (b) the base the base may comprise an inner base and an outer base, (c) the outer base may be adjacent to the outer wall, the inner base may be adjacent to the outer base, and the inner base may be adjacent to the inner wall, (d) the at least one first orifice may comprise a plurality of inner orifices and the at least one second orifice may comprise a plurality of outer orifices, (e) the plurality of outer orifices may pass through the outer base and the plurality of inner orifices may pass between the outer base and the inner base, (f) the vent system may comprise a plurality of base connectors to join the inner base and the outer base and to divide the plurality of inner orifices, (g) the vent system may comprise a plurality of membrane spacers extending from the inner base, (h) the membrane may be supported over the plurality of inner orifices on the outer base and the membrane spacers, (i) the vent housing may comprise a base divider between the inner base and the outer base and the membrane may be supported over the plurality of inner orifices on the base divider and the membrane spacers, (j) the plurality of membrane spacers may define a plurality of membrane spacer gaps between adjacent ones of the plurality of membrane spacers, (k) the membrane may include an atmosphere-side surface adjacent to the inner base and the outer base of the vent housing and an inner surface defining a membrane opening and an inner base membrane passage for the washout flow may be defined between the atmosphere-side surface of the membrane and the inner base of the vent housing, (l) an inner wall membrane passage for the washout flow may be defined between the inner surface of the membrane and the inner wall of the vent housing, (m) the inner base may comprise a plurality of inner base slots between adjacent ones of the plurality of membrane spacers, (n) the outer base may comprise a plurality of lateral membrane supports that are configured to prevent the membrane from covering the plurality of outer orifices, (o) the vent housing may comprise a plurality of recesses opposite the outer base and at least one of the plurality of outer orifices may open into a corresponding one of the plurality of recesses, (p) the inner wall may extend above the inner base and the outer base, (q) the inner wall may extend below the inner base and the outer base, (r) the membrane may comprises an elastically deformable material, (s) the elastically deformable material may comprise silicone, (t) the vent housing may be formed from a single, homogeneous piece of a relatively rigid material, (u) the relatively rigid material may be polycarbonate, (v) the outer wall, the inner wall, the inner base, the outer base, and the membrane may be circular, (w) the outer wall, the inner wall, the inner base, the outer base, and the membrane may be concentric, and/or (x) the membrane may not be attached to the vent housing such that the membrane is freely movable towards and away from the base.

Another aspect of the present technology is directed to a patient interface comprising: a seal-forming structure; a plenum chamber joined to the seal-forming structure; a positioning and stabilising structure to secure the patient interface on the patient in use; and the vent system according to any of the aspects and/or examples disclosed in the two immediately preceding paragraphs. The patient interface may comprise a vent connector tube or a decoupling structure to fluidly connect the vent system to the plenum chamber.

Another aspect of the present technology is directed to a vent system for use with a patient interface during respiratory therapy of a patient with a therapy flow of gas pressurized above ambient pressure, the vent system providing a vent flow of gas to discharge gas exhaled by the patient from a pressurized volume, the vent flow being continuous during the respiratory therapy. The vent system comprises a vent housing a base having at least one first orifice extending through the base to allow gas to be discharged to atmosphere from the pressurized volume; at least one second orifice to allow gas to be discharged to atmosphere from the pressurized volume; and a membrane positioned adjacent to the base, wherein the pressurized volume is in fluid communication with atmosphere through the at least one first orifice and the at least one second orifice throughout a therapeutic pressure range, wherein the membrane is configured such that an increase in pressure within the pressurized volume causes the membrane to restrict a first vent flow through the at least one first orifice throughout the therapeutic pressure range, and wherein restriction of the first vent flow through the at least one first orifice causes an increase in a second vent flow through the at least one second orifice such that the vent flow through the at least one first orifice and the at least one second orifice is approximately constant throughout the therapeutic pressure range.

In examples, (a) the vent housing may comprise an outer wall and an inner wall, the inner wall defining an inlet for the therapy flow of gas, and the base may be positioned between the outer wall and the inner wall, (b) the washout flow may be greater than or equal to the sum of the first vent flow and the second vent flow, (c) the membrane may be elastically deformable toward the base in use such that the first vent flow is restricted as the membrane is deflected towards the base, (d) the membrane may be configured to deflect closer to the base as the therapy pressure increases above a threshold therapy pressure value, (e) the membrane may be configured to decrease the first vent flow such that the second vent flow increases as the membrane is deflected closer to the base due to increasing the therapy pressure above the threshold therapy pressure value, (f) the at least one first orifice may comprise a plurality of inner orifices and the at least one second orifice may comprise a plurality of outer orifices, (g) the base may comprise an inner base and an outer base, (h) the vent system may comprise a plurality of membrane spacers extending from the inner base, (i) the membrane may be supported over the plurality of inner orifices on the outer base and the membrane spacers such that increasing the therapy pressure above a threshold therapy pressure value causes the membrane to deflect towards the inner base, (j) the membrane may be configured such that a membrane-inner base gap defined between the membrane and the inner base decreases as the therapy pressure is increased above the threshold therapy pressure value, (k) the membrane may be configured such that as the membrane-inner base gap decreases the first vent flow decreases and the second vent flow increases, (l) the membrane may comprise an elastically deformable material, (m) the elastically deformable material may comprise silicone, (n) the vent housing may be formed from a single, homogeneous piece of a relatively rigid material, (o) the relatively rigid material may be polycarbonate, (p) the outer wall, the inner wall, the inner base, the outer base, and the membrane may be circular, (q) the outer wall, the inner wall, the inner base, the outer base, and the membrane may be concentric, and/or (r) the membrane may not be attached to the vent housing such that the membrane is freely movable towards and away from the base.

Another aspect of the present technology is directed to a patient interface comprising: a seal-forming structure; a plenum chamber joined to the seal-forming structure; a positioning and stabilising structure to secure the patient interface on the patient in use; and the vent system according to any of the aspects and/or examples disclosed in the two immediately preceding paragraphs. The patient interface may comprise a vent connector tube or a decoupling structure to fluidly connect the vent system to the plenum chamber.

Another aspect of the present technology is directed to a patient interface that may comprise: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of the patient's face surrounding an entrance to the patient's airways such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure to provide an elastic force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use, and a portion of the tie being dimensioned and structured to engage in use a portion of the patient's head in a region of a parietal bone, wherein the positioning and stabilising structure has a non-rigid decoupling portion; and a vent system for use with a patient interface during respiratory therapy of a patient with a therapy flow of gas pressurized above ambient pressure, the vent system providing a vent flow of gas to discharge gas exhaled by the patient from a pressurized volume, the vent flow being continuous during the respiratory therapy, the vent system comprising: a vent housing a base having at least one first orifice extending through the base to allow gas to be discharged to atmosphere from the pressurized volume; at least one second orifice to allow gas to be discharged to atmosphere from the pressurized volume; and a membrane positioned adjacent to the base, wherein the pressurized volume is in fluid communication with atmosphere through the at least one first orifice and the at least one second orifice throughout a therapeutic pressure range, wherein the membrane is configured such that an increase in pressure within the pressurized volume causes the membrane to restrict a first vent flow through the at least one first orifice throughout the therapeutic pressure range, and wherein restriction of the first vent flow through the at least one first orifice causes an increase in a second vent flow through the at least one second orifice such that the vent flow through the at least one first orifice and the at least one second orifice is approximately constant throughout the therapeutic pressure range, and wherein the patient interface is configured to allow the patient to breath from ambient through their mouth in the absence of a flow of pressurised air through the plenum chamber inlet port, or the patient interface is configured to leave the patient's mouth uncovered.

In examples, (a) the vent housing may comprise an outer wall and an inner wall, the inner wall defining an inlet for the therapy flow of gas, and the base may be positioned between the outer wall and the inner wall, (b) the washout flow may be greater than or equal to the sum of the first vent flow and the second vent flow, (c) the membrane may be elastically deformable toward the base in use such that the first vent flow is restricted as the membrane is deflected towards the base, (d) the membrane may be configured to deflect closer to the base as the therapeutic pressure increases above a threshold therapeutic pressure value, (e) the membrane may be configured to decrease the first vent flow such that the second vent flow increases as the membrane is deflected closer to the base due to increasing the therapeutic pressure above the threshold therapeutic pressure value, (f) the base may comprise an inner base and an outer base, (g) the at least one first orifice may comprise a plurality of inner orifices and the at least one second orifice may comprise a plurality of outer orifices, (h) the vent system may comprise a plurality of membrane spacers extending from the inner base, (i) the membrane may be supported over the plurality of inner orifices on the outer base and the membrane spacers, (j) the vent housing may comprise a base divider between the inner base and the outer base and the membrane may be supported over the plurality of inner orifices on the base divider and the membrane spacers, (k) the outer base may comprise a plurality of lateral membrane supports that are configured to prevent the membrane from covering the plurality of outer orifices, (l) the membrane may comprise an elastically deformable material, (m) the elastically deformable material may comprise silicone, (n) the vent housing may be formed from a single, homogeneous piece of a relatively rigid material, (o) the relatively rigid material may be polycarbonate, (p) the outer wall, the inner wall, the inner base, the outer base, and the membrane may be circular, (q) the outer wall, the inner wall, the inner base, the outer base, and the membrane may be concentric, (r) the membrane may not be attached to the vent housing such that the membrane is freely movable towards and away from the base, and/or (s) the patient interface may comprise a vent connector tube or a decoupling structure to fluidly connect the vent system to the plenum chamber.

Another aspect of the present technology is directed to a patient interface that may comprise: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of the patient's face surrounding an entrance to the patient's airways such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure to provide an elastic force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use, and a portion of the tie being dimensioned and structured to engage in use a portion of the patient's head in a region of a parietal bone, wherein the positioning and stabilising structure has a non-rigid decoupling portion; and a vent system to provide a vent flow of gas to discharge gas exhaled by the patient from a pressurized volume, the vent flow being continuous during the respiratory therapy, the vent flow comprising a first vent flow and a second vent flow, the vent system comprising: a vent housing comprising a base having at least one first orifice extending through the base for the first vent flow; at least one second orifice for the second vent flow; and a membrane positioned adjacent to the base, wherein the pressurized volume is in fluid communication with atmosphere through the at least one first orifice and the at least one second orifice throughout a therapeutic pressure range, wherein the membrane is configured to be elastically deformed by pressure within the pressurized volume such that increased deformation due to increased pressure decreases the first vent flow through the at least one first orifice and increases the second vent flow through the at least one second orifice to maintain a substantially constant vent flow throughout the therapeutic pressure range, and wherein the patient interface is configured to allow the patient to breath from ambient through their mouth in the absence of a flow of pressurised air through the plenum chamber inlet port, or the patient interface is configured to leave the patient's mouth uncovered.

In examples, (a) the vent housing may comprise an outer wall and an inner wall, the inner wall defining an inlet for the therapy flow of gas, and the base may be positioned between the outer wall and the inner wall, (b) the washout flow may be greater than or equal to the sum of the first vent flow and the second vent flow, (c) the membrane may be elastically deformable toward the base in use such that the first vent flow is restricted as the membrane is deflected towards the base, (d) the membrane may be configured to deflect closer to the base as the therapeutic pressure increases above a threshold therapeutic pressure value, (e) the membrane may be configured to decrease the first vent flow such that the second vent flow increases as the membrane is deflected closer to the base due to increasing the therapeutic pressure above the threshold therapeutic pressure value, (f) the base may comprise an inner base and an outer base, (g) the at least one first orifice may comprise a plurality of inner orifices and the at least one second orifice may comprise a plurality of outer orifices, (h) the vent system may comprise a plurality of membrane spacers extending from the inner base, (i) the membrane may be supported over the plurality of inner orifices on the outer base and the membrane spacers, (j) the vent housing may comprise a base divider between the inner base and the outer base and the membrane may be supported over the plurality of inner orifices on the base divider and the membrane spacers, (k) the outer base may comprise a plurality of lateral membrane supports that are configured to prevent the membrane from covering the plurality of outer orifices, (l) the membrane may comprise an elastically deformable material, (m) the elastically deformable material may comprise silicone, (n) the vent housing may be formed from a single, homogeneous piece of a relatively rigid material, (o) the relatively rigid material may be polycarbonate, (p) the outer wall, the inner wall, the inner base, the outer base, and the membrane may be circular, (q) the outer wall, the inner wall, the inner base, the outer base, and the membrane may be concentric, (r) the membrane may not be attached to the vent housing such that the membrane is freely movable towards and away from the base, and/or (s) the patient interface may comprise a vent connector tube or a decoupling structure to fluidly connect the vent system to the plenum chamber.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 1A:
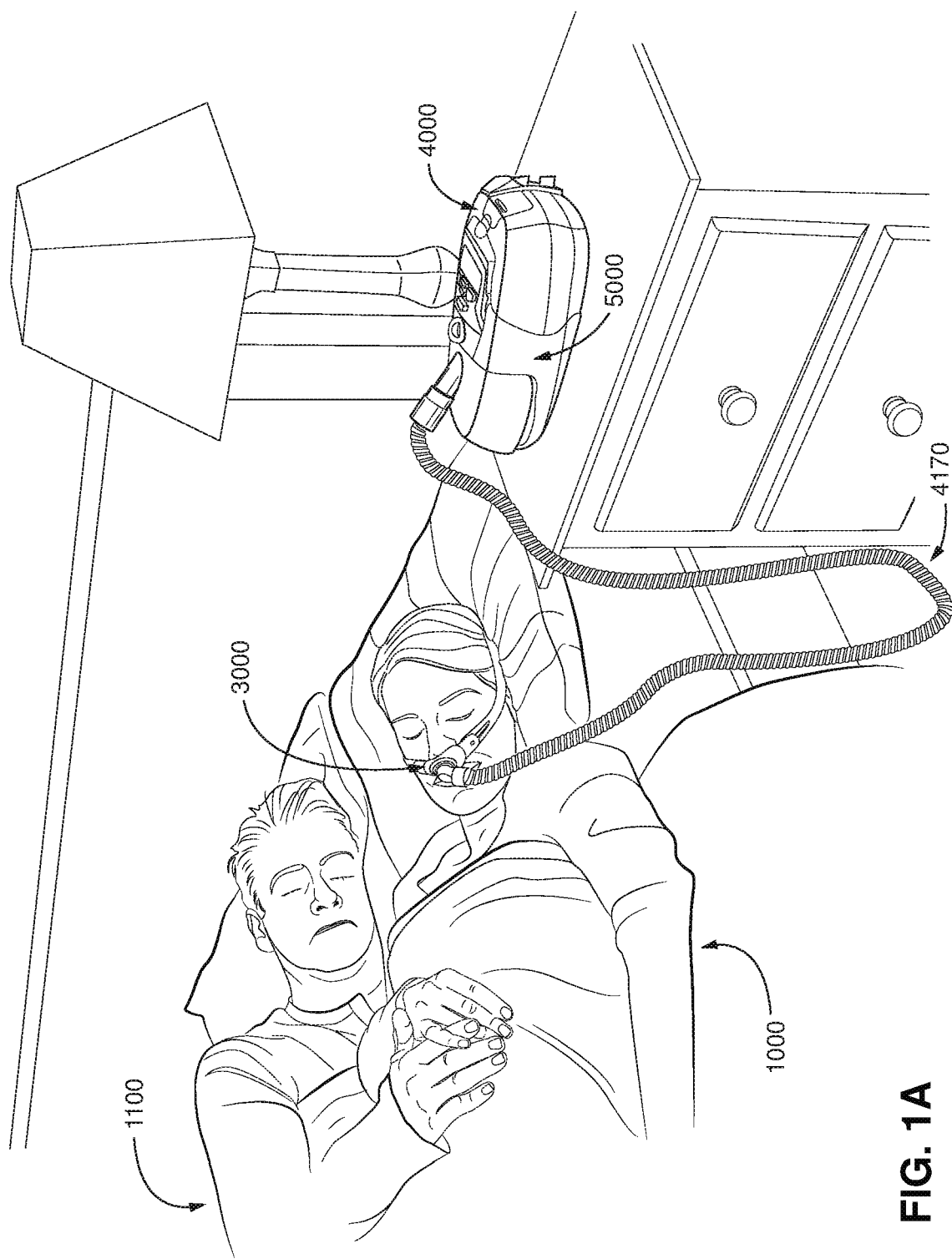
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
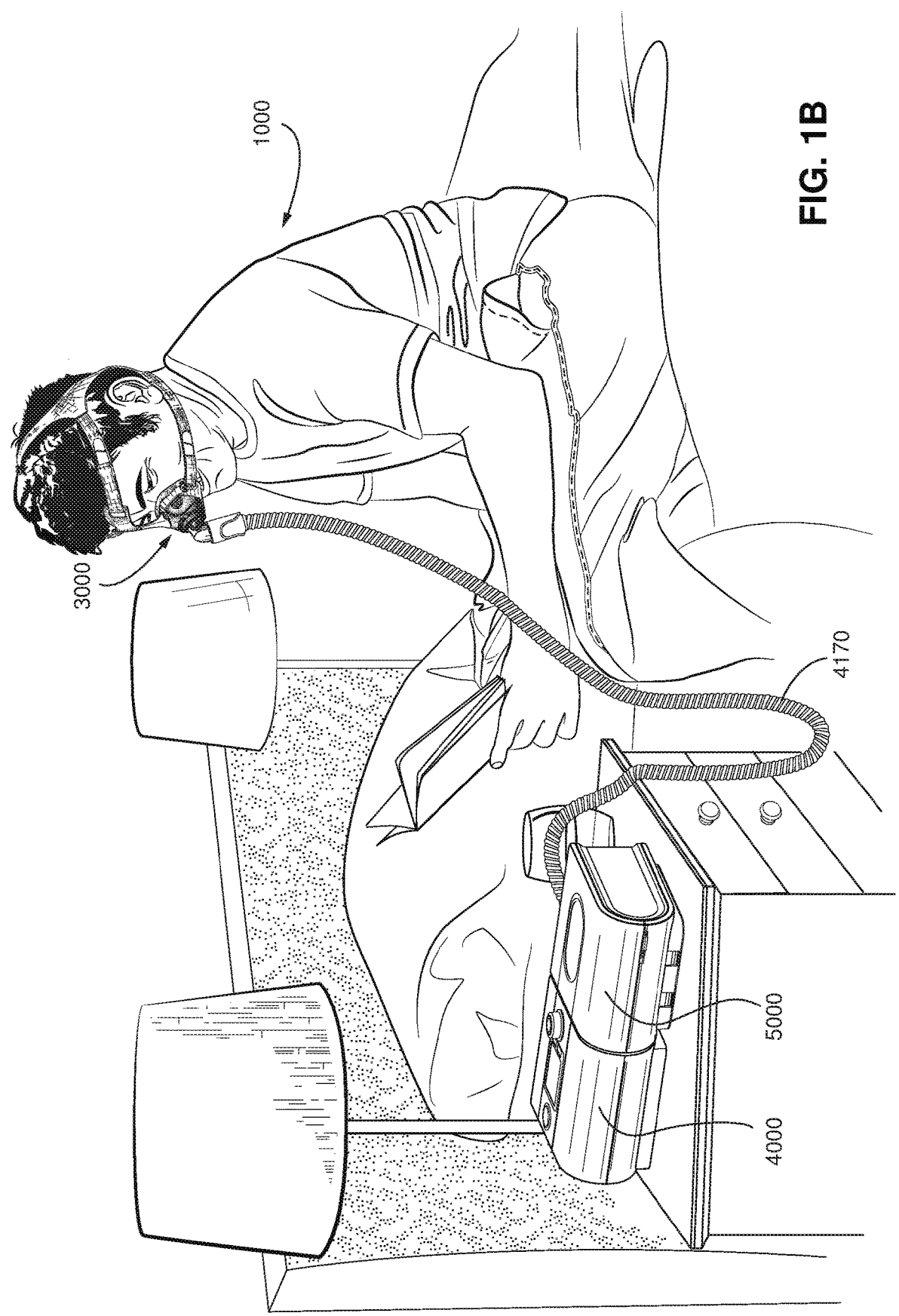
Figure 1C:
Figure 2A:
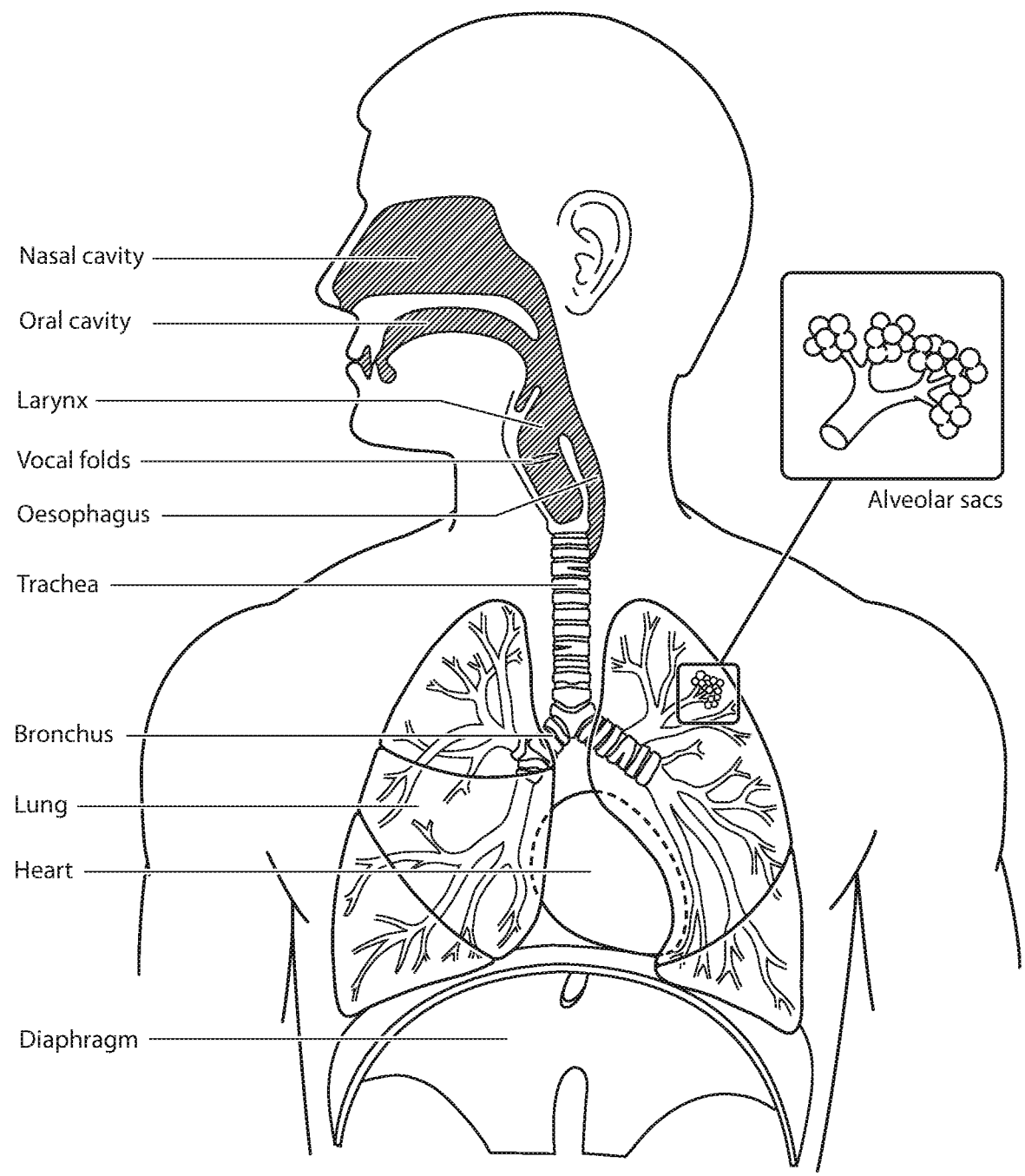

FIG. 2A shows an overview of a human respiratory system including the nasal and oral cavities, the larynx, vocal folds, oesophagus, trachea, bronchus, lung, alveolar sacs, heart and diaphragm.

Figure 2B:
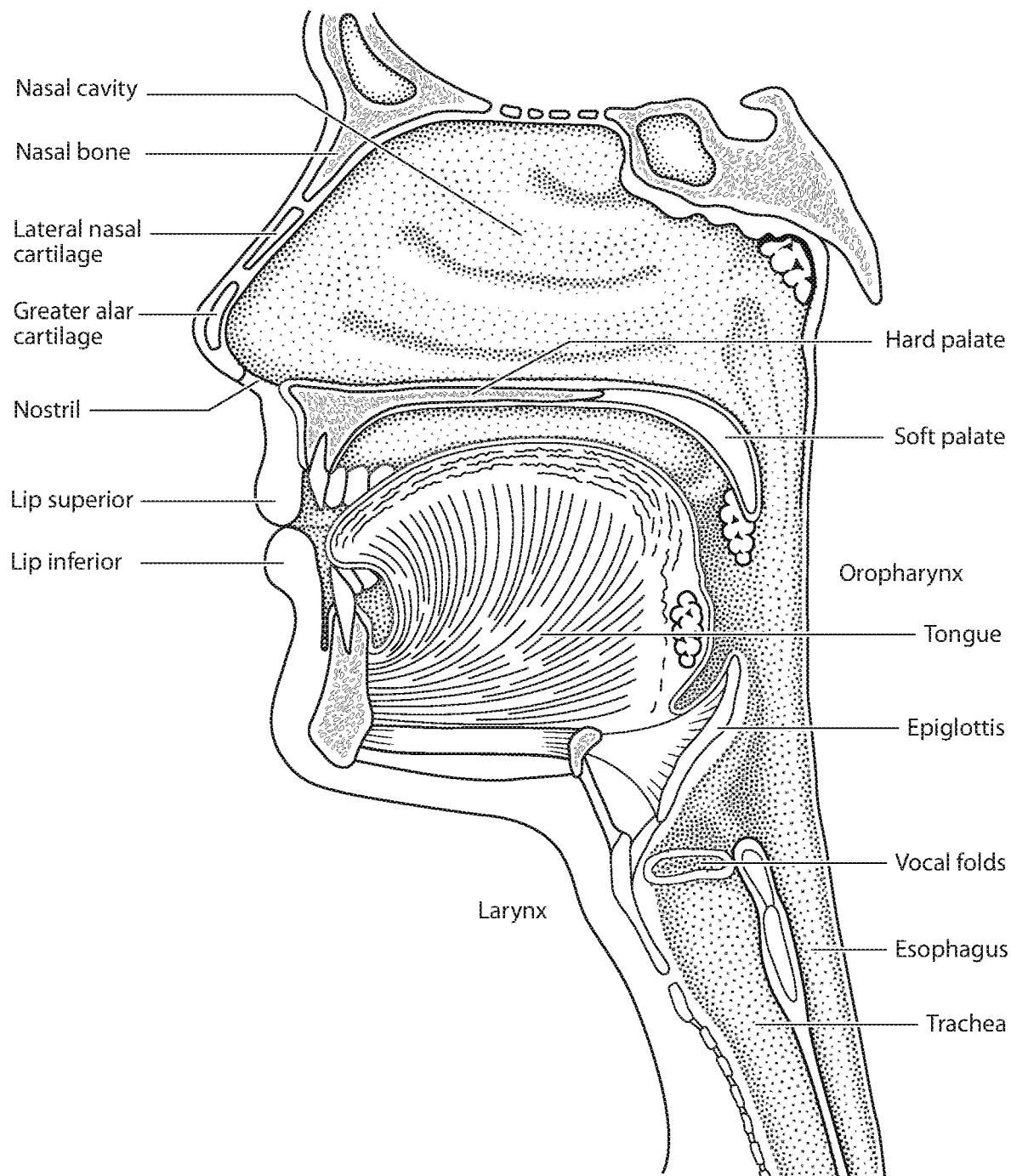

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
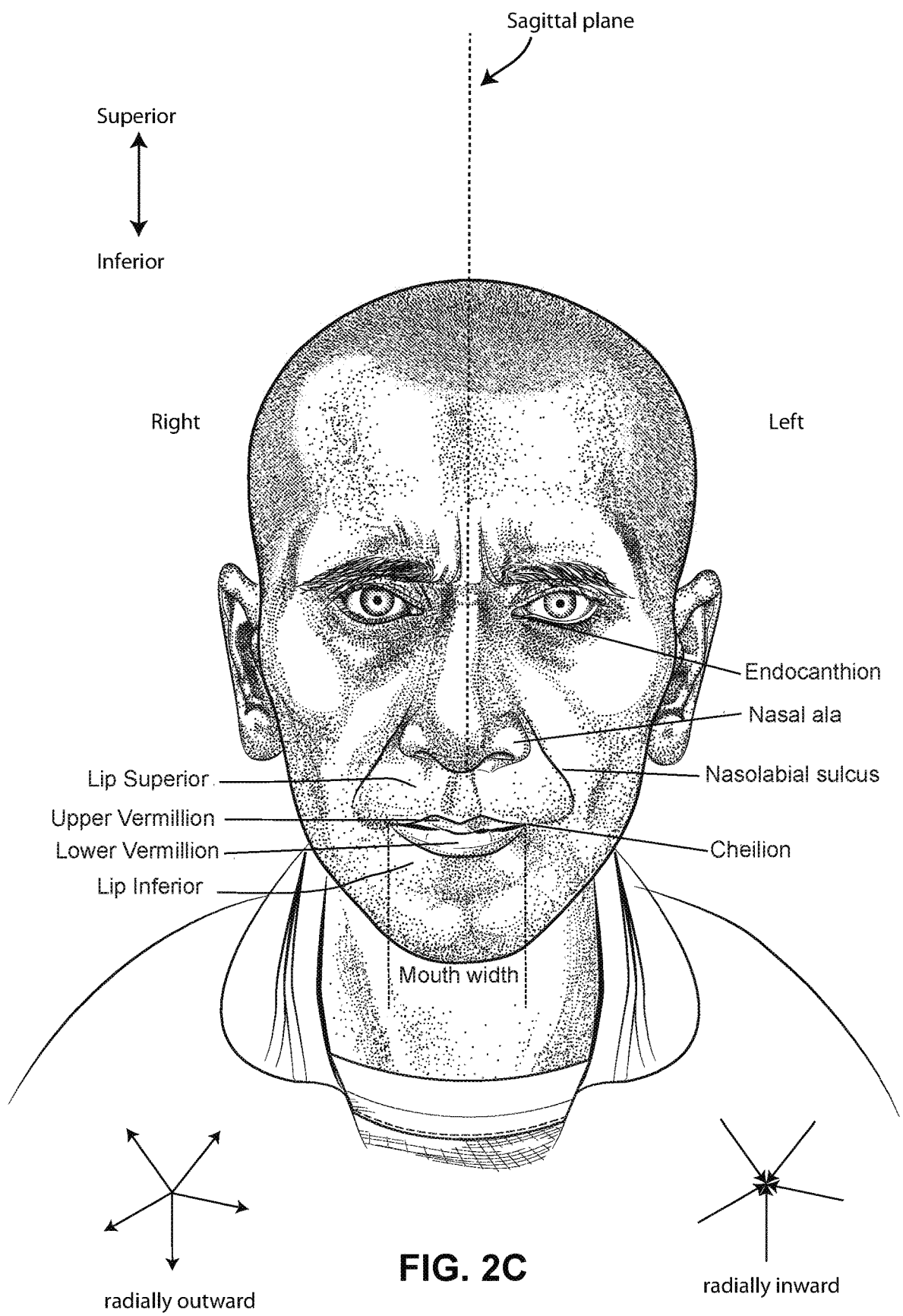

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
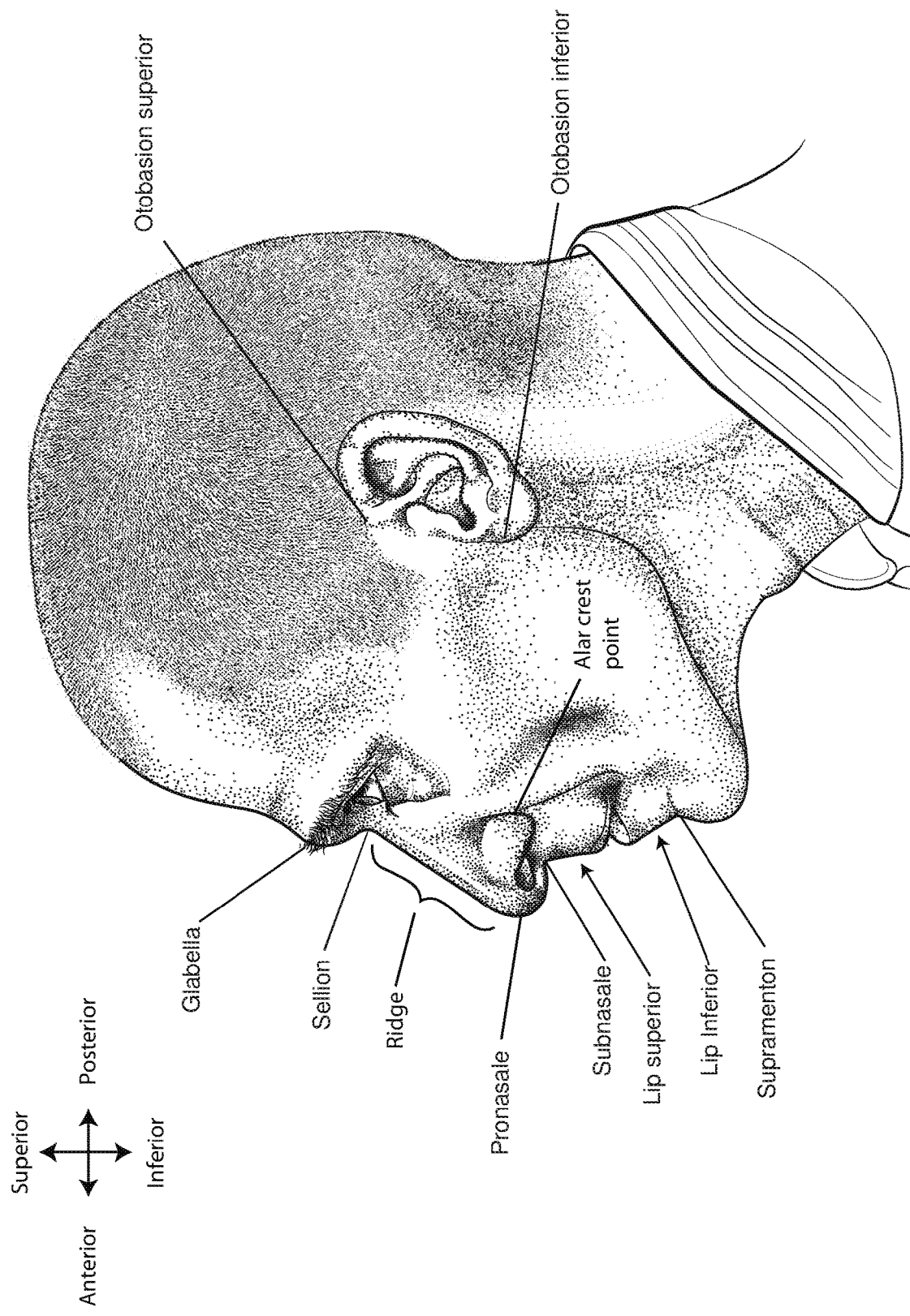

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
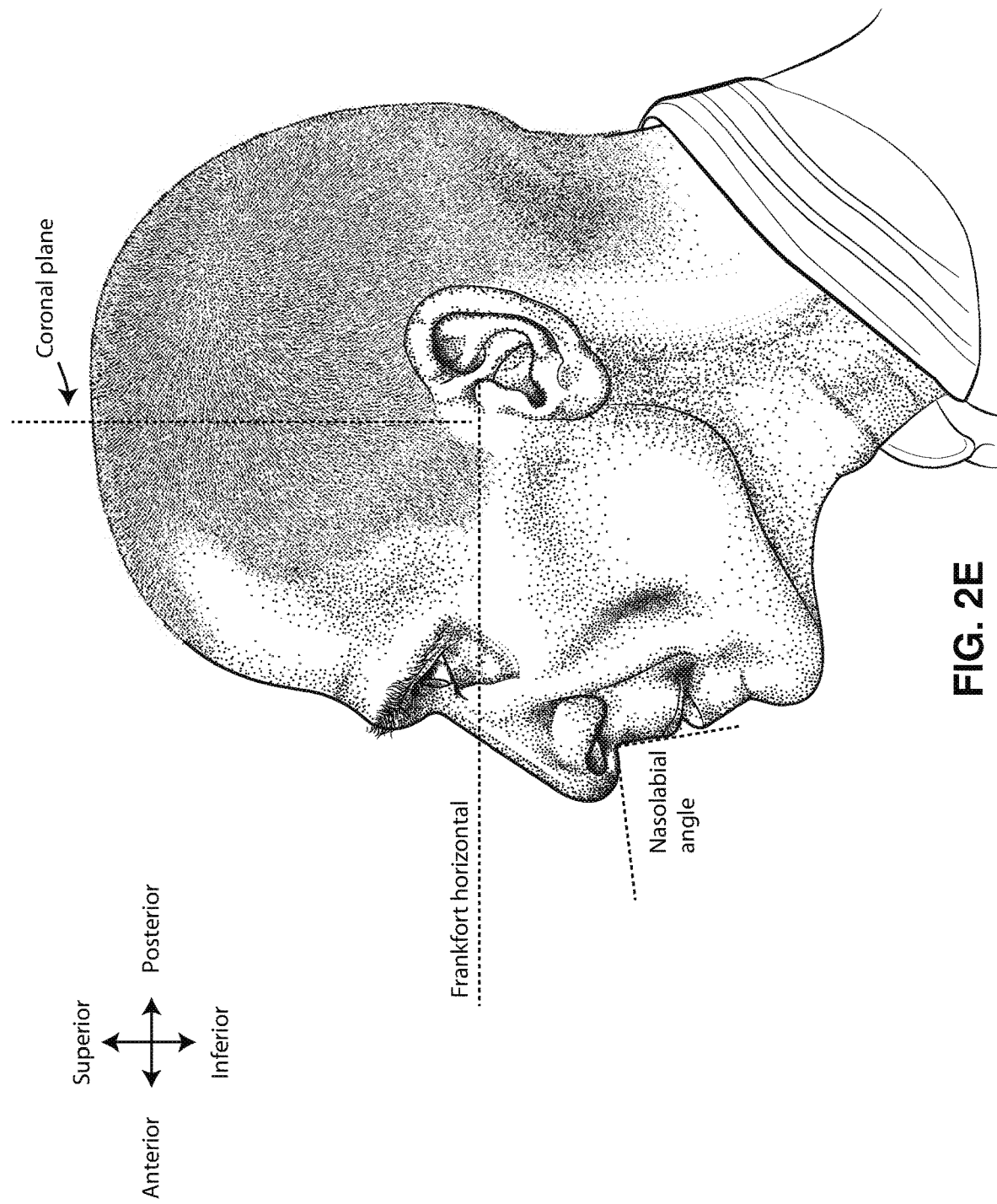

FIG. 2E is a further side view of a head. The approximate locations of the Frankfort horizontal and nasolabial angle are indicated. The coronal plane is also indicated.

Figure 2F:
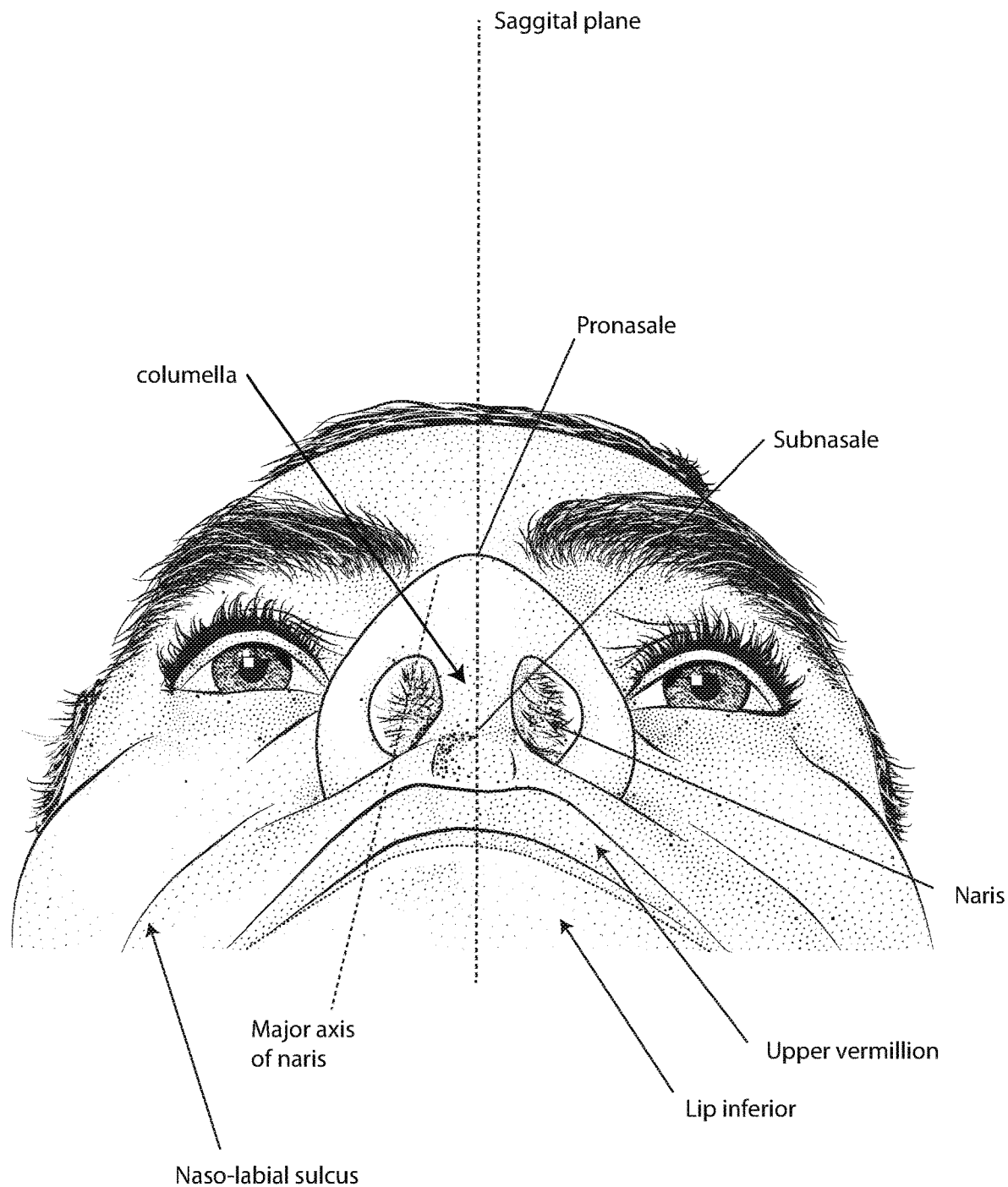

FIG. 2F shows a base view of a nose with several features identified including naso-labial sulcus, lip inferior, upper Vermilion, naris, subnasale, columella, pronasale, the major axis of a naris and the sagittal plane.

Figure 2I:
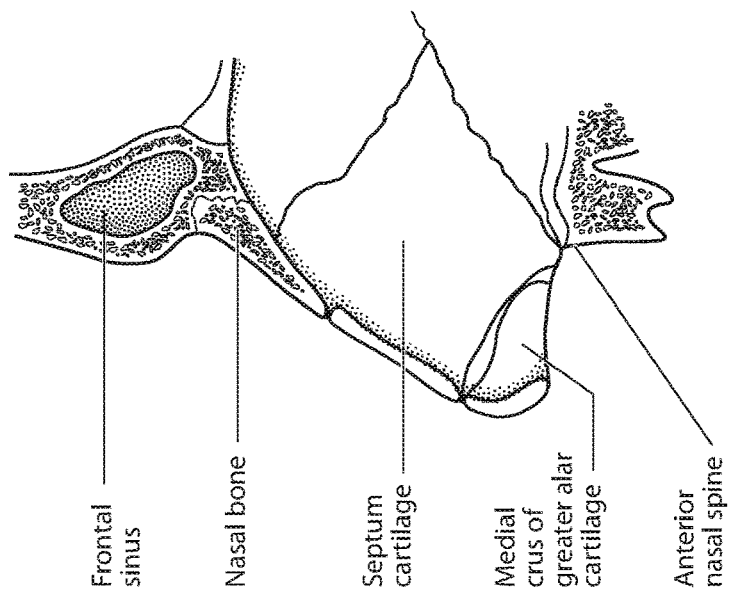
Figure 2H:
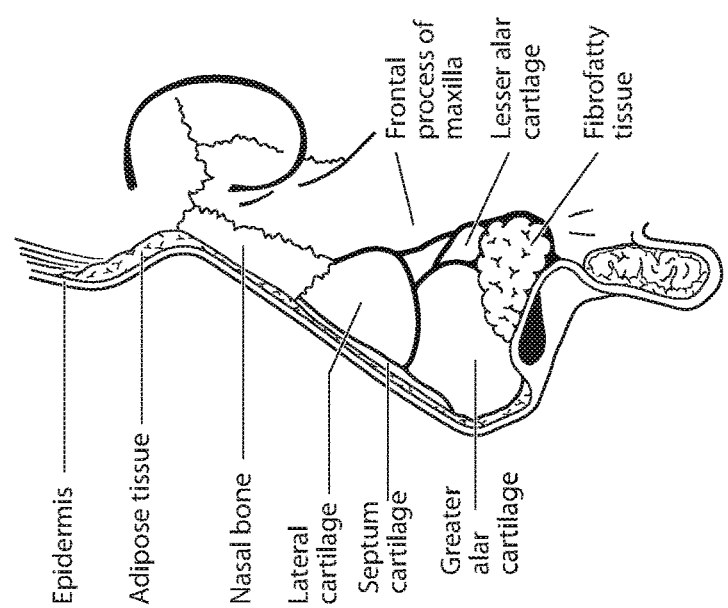
Figure 2G:

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
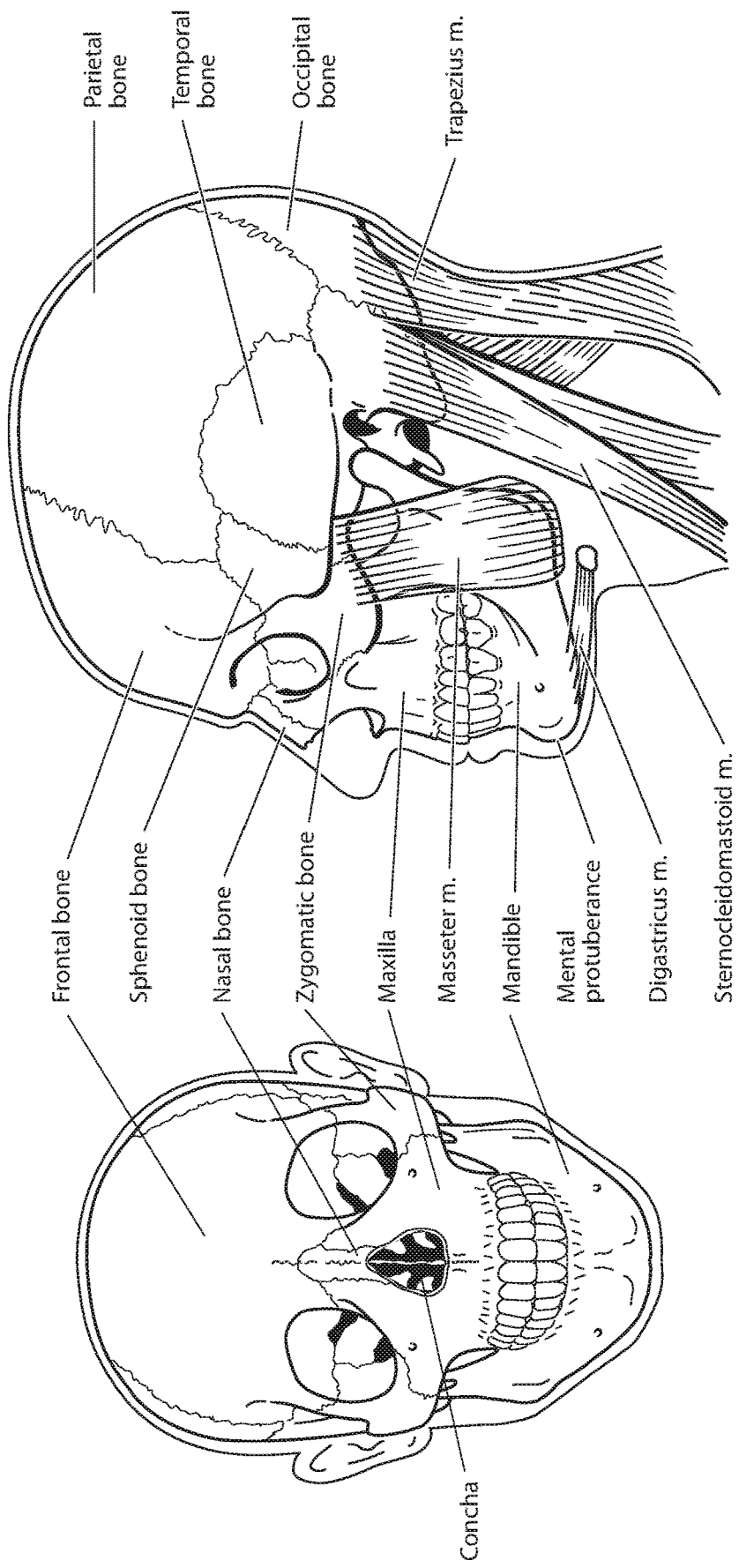

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
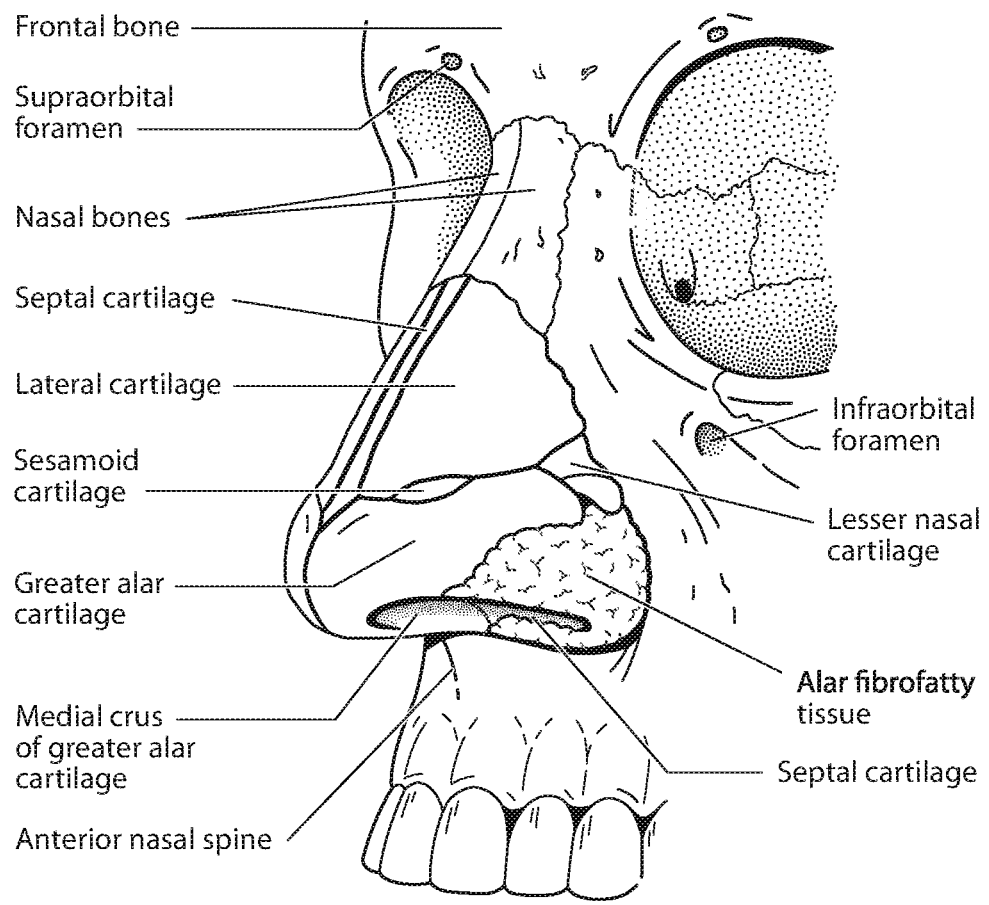

FIG. 2L shows an anterolateral view of a nose.

4.3 Patient Interface

Figure 3A:
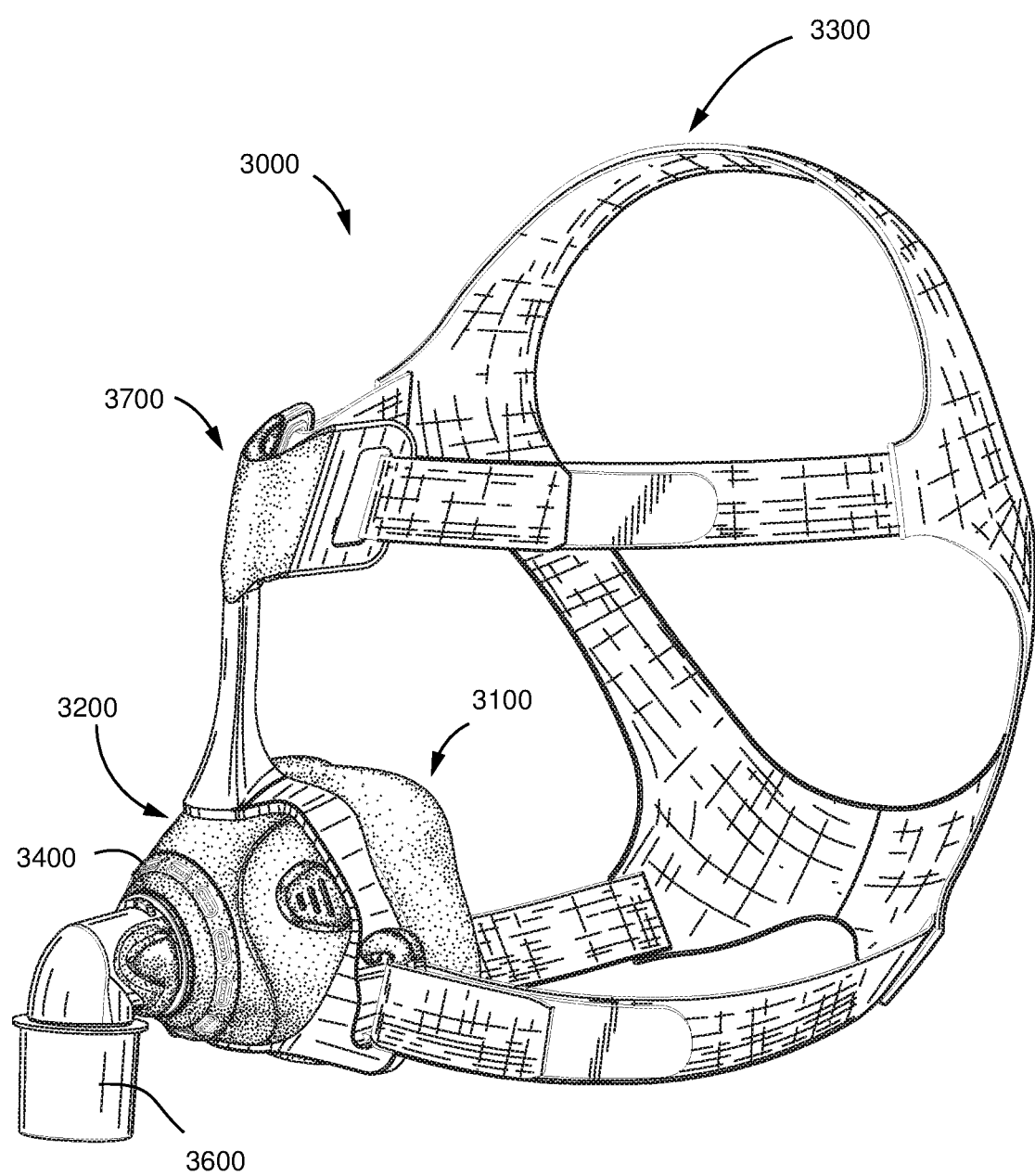

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

4.4 RPT Device

Figure 4A:
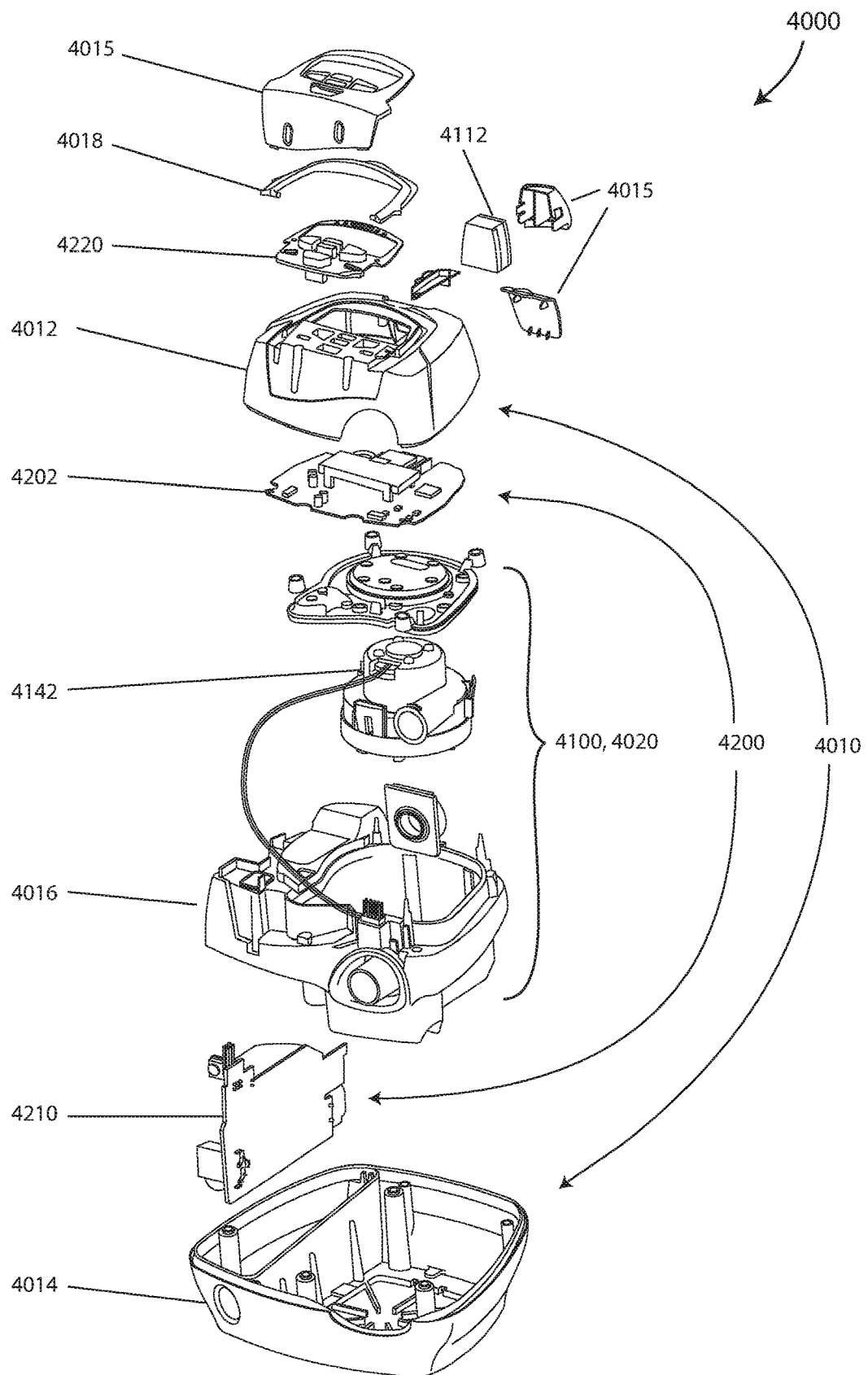

FIG. 4A shows an RPT device in accordance with one form of the present technology.

Figure 4B:
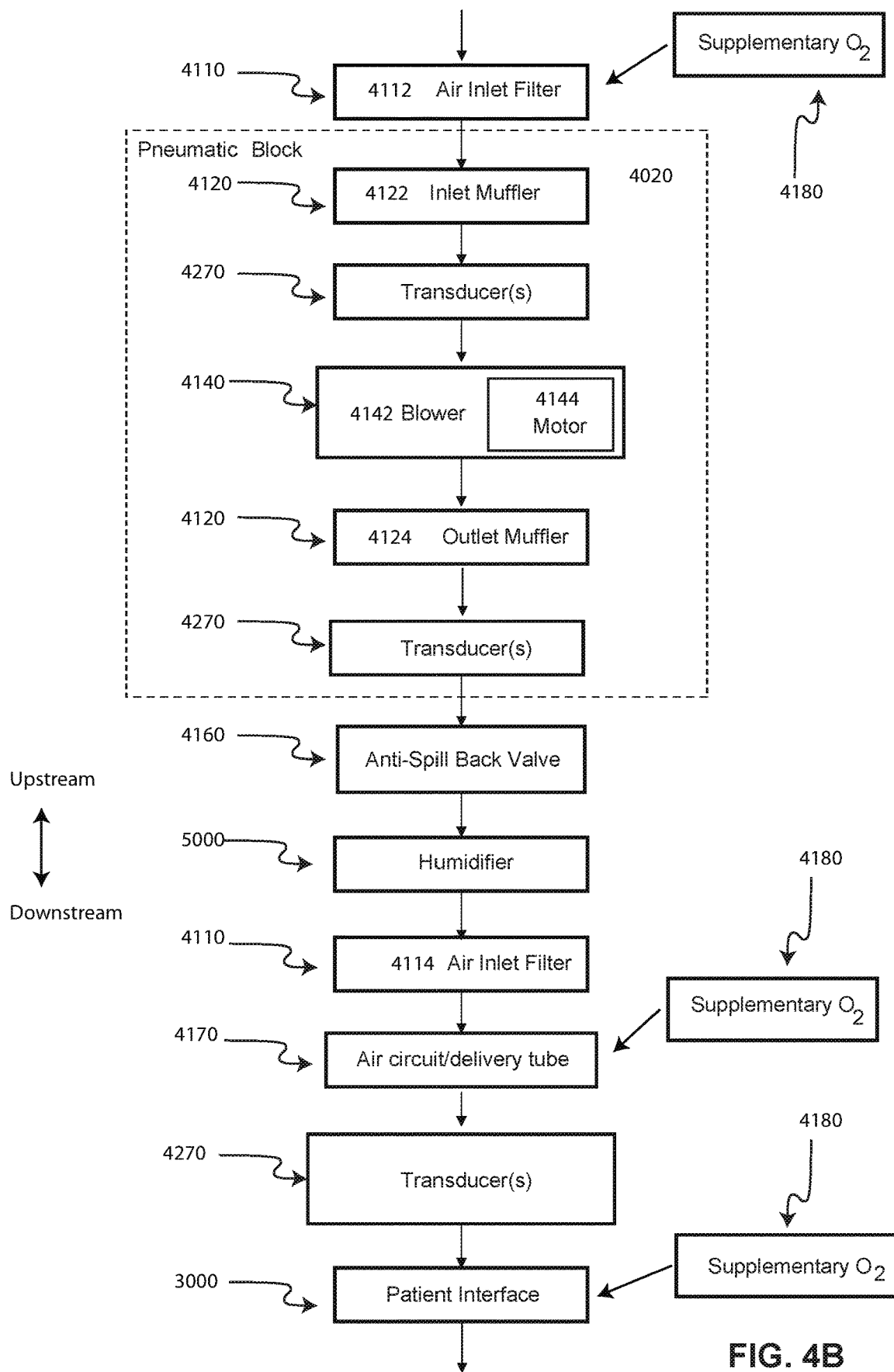

FIG. 4B is a schematic diagram of the pneumatic path of an RPT device in accordance with one form of the present technology. The directions of upstream and downstream are indicated.

Figure 4C:
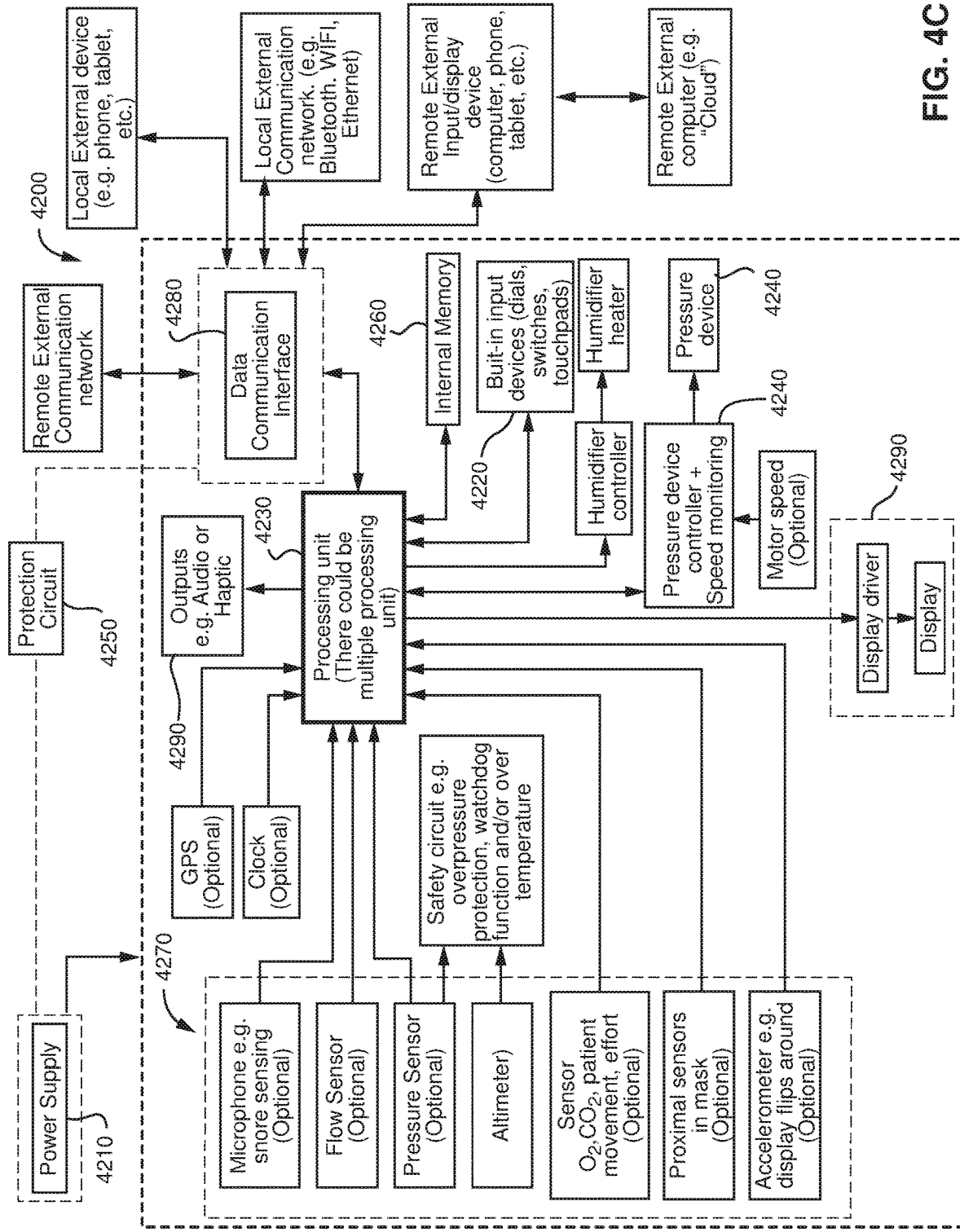

FIG. 4C is a schematic diagram of the electrical components of an RPT device in accordance with one form of the present technology.

Figure 4D:
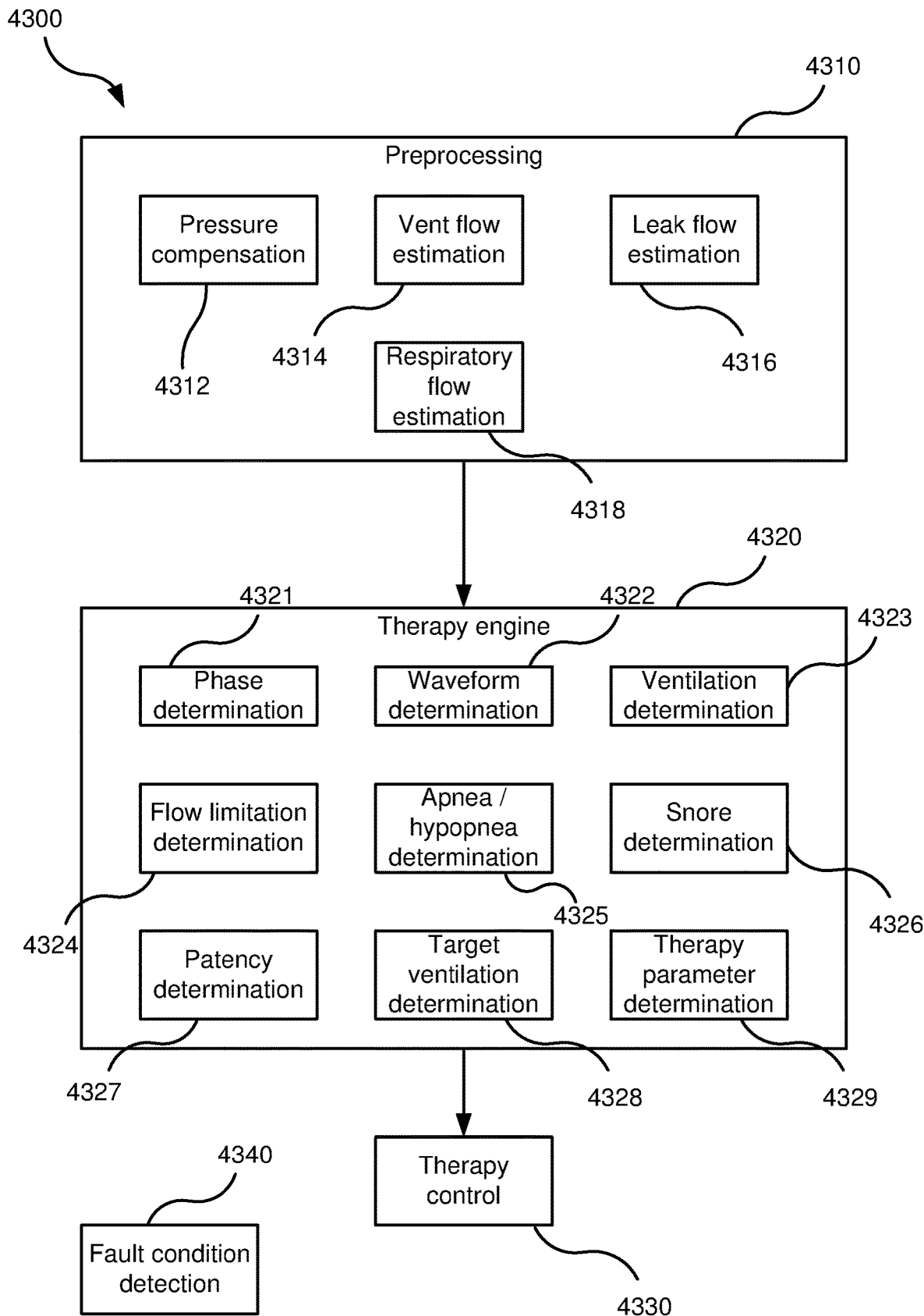

FIG. 4D is a schematic diagram of the algorithms implemented in an RPT device in accordance with one form of the present technology.

Figure 4E:
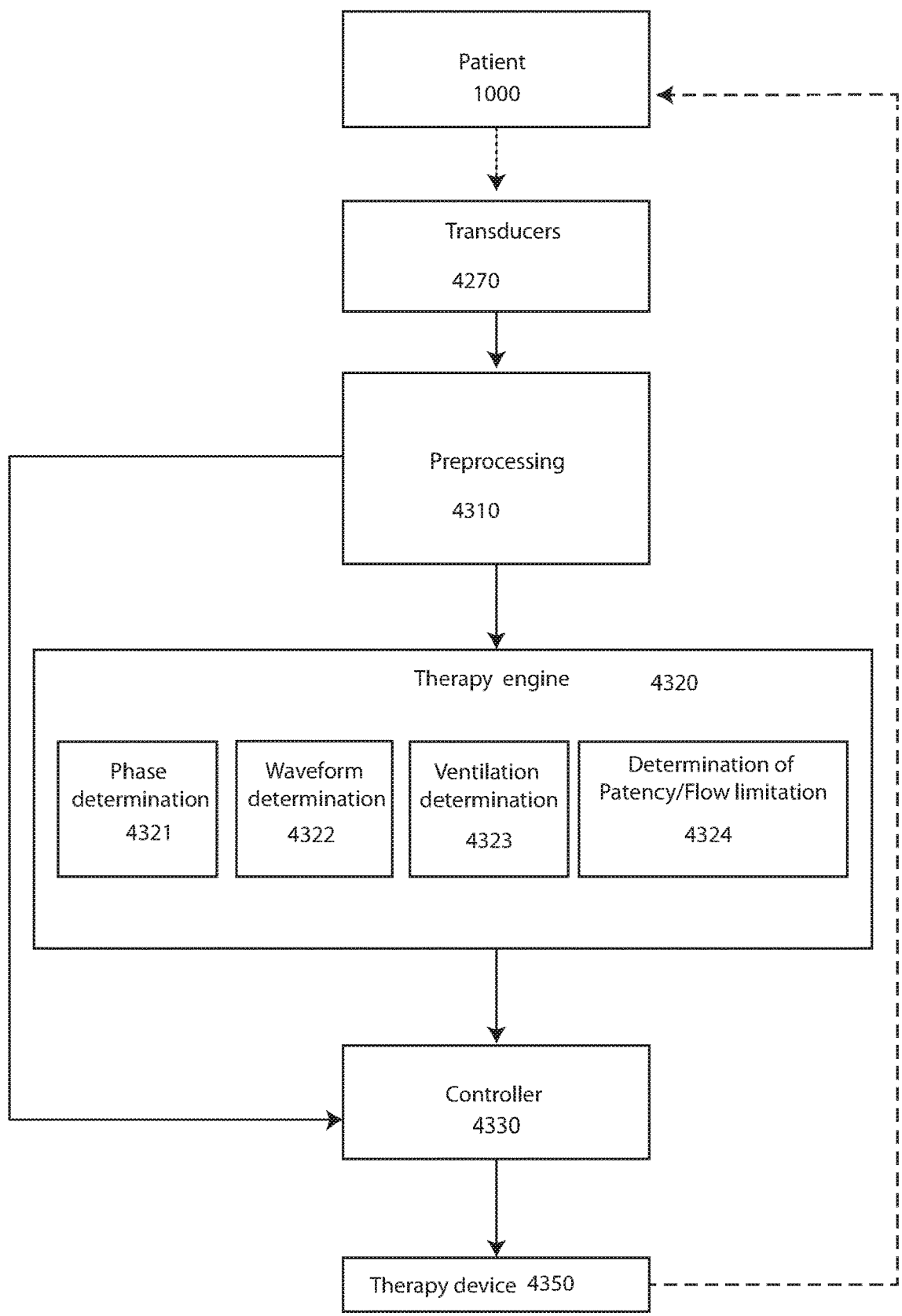

FIG. 4E is a flow chart illustrating a method carried out by the therapy engine module of FIG. 4D in accordance with one form of the present technology.

4.5 Humidifier

Figure 5A:
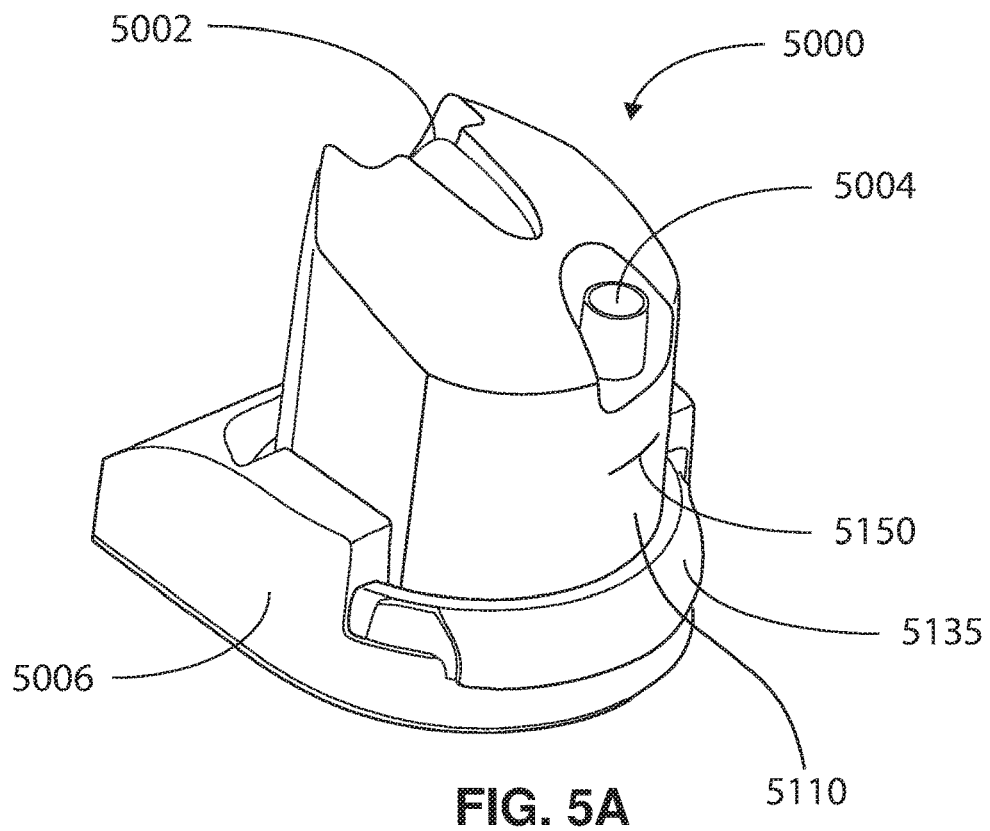

FIG. 5A shows an isometric view of a humidifier in accordance with one form of the present technology.

Figure 5B:
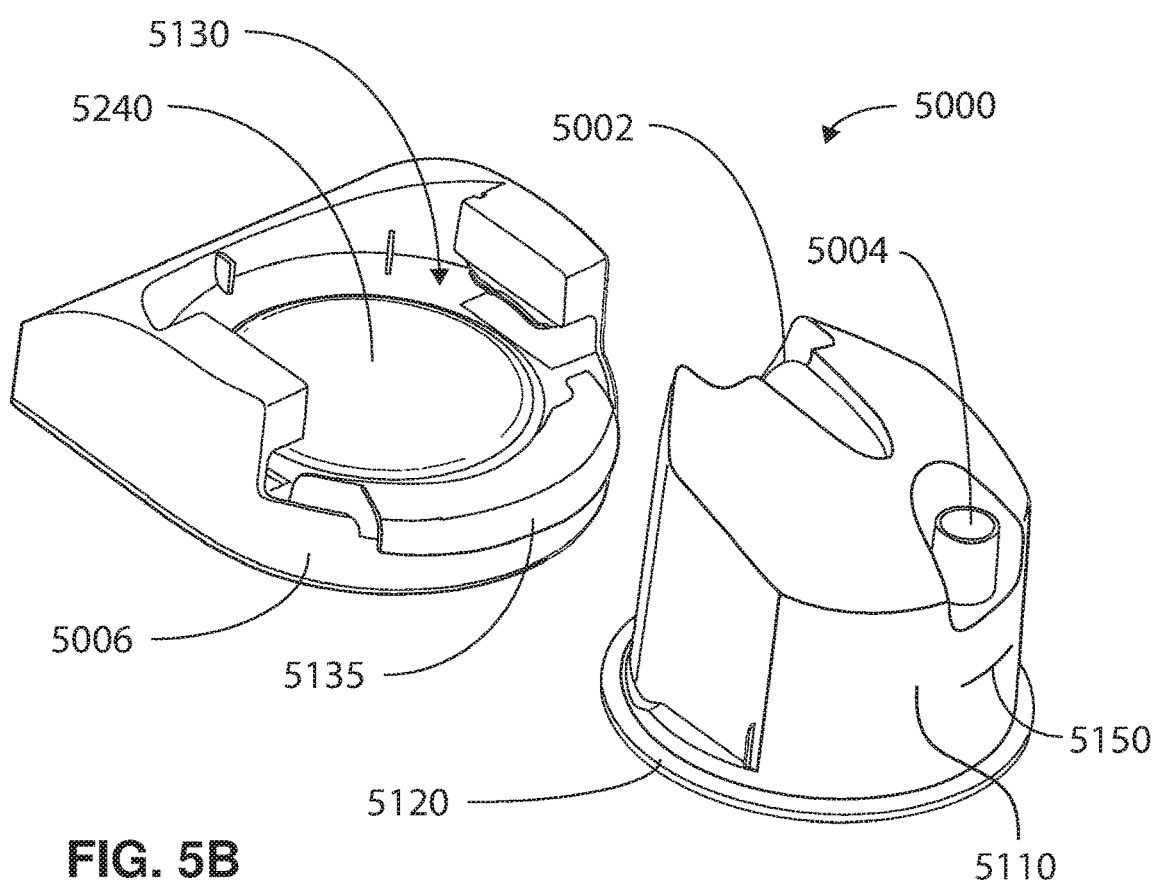

FIG. 5B shows an isometric view of a humidifier in accordance with one form of the present technology, showing a humidifier reservoir 5110 removed from the humidifier reservoir dock 5130.

Figure 5C:
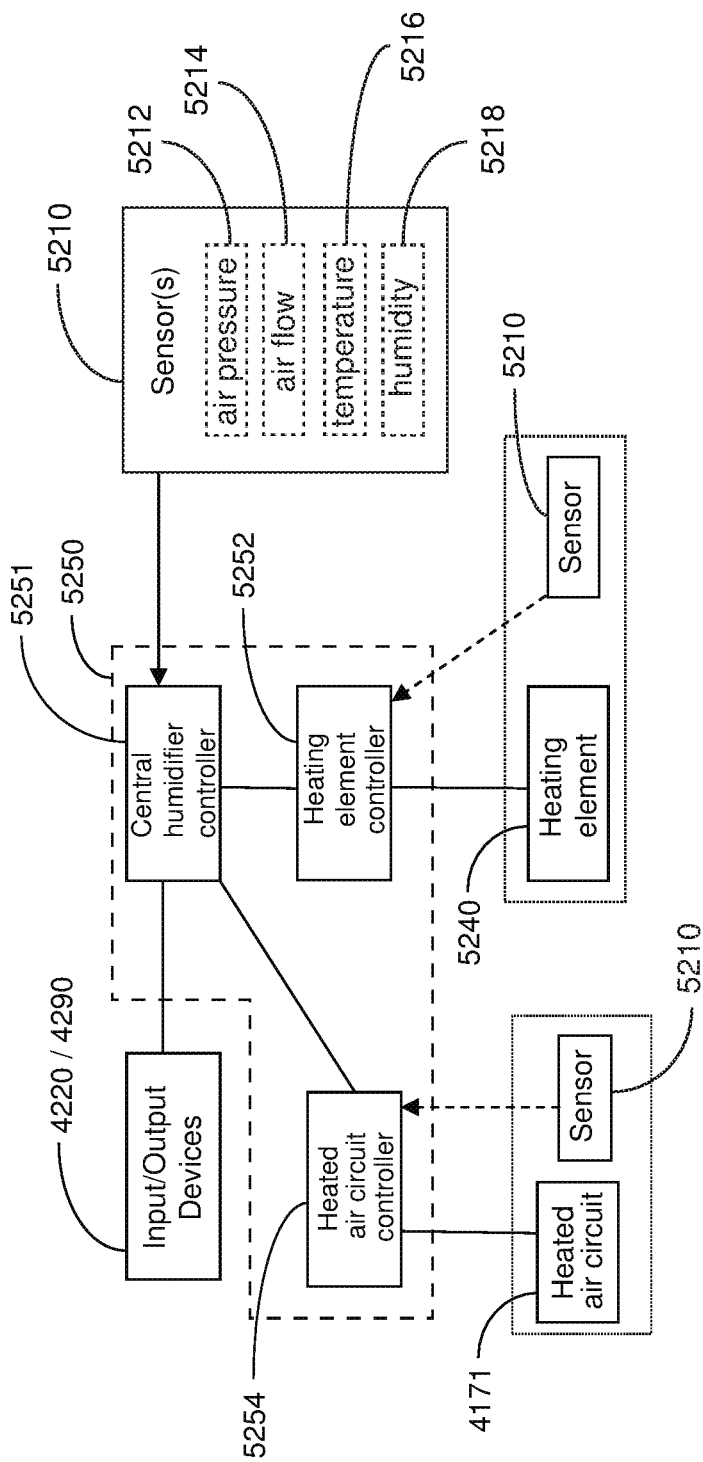

FIG. 5C shows a schematic of a humidifier in accordance with one form of the present technology.

4.6 Vent Adaptor

Figure 6A:
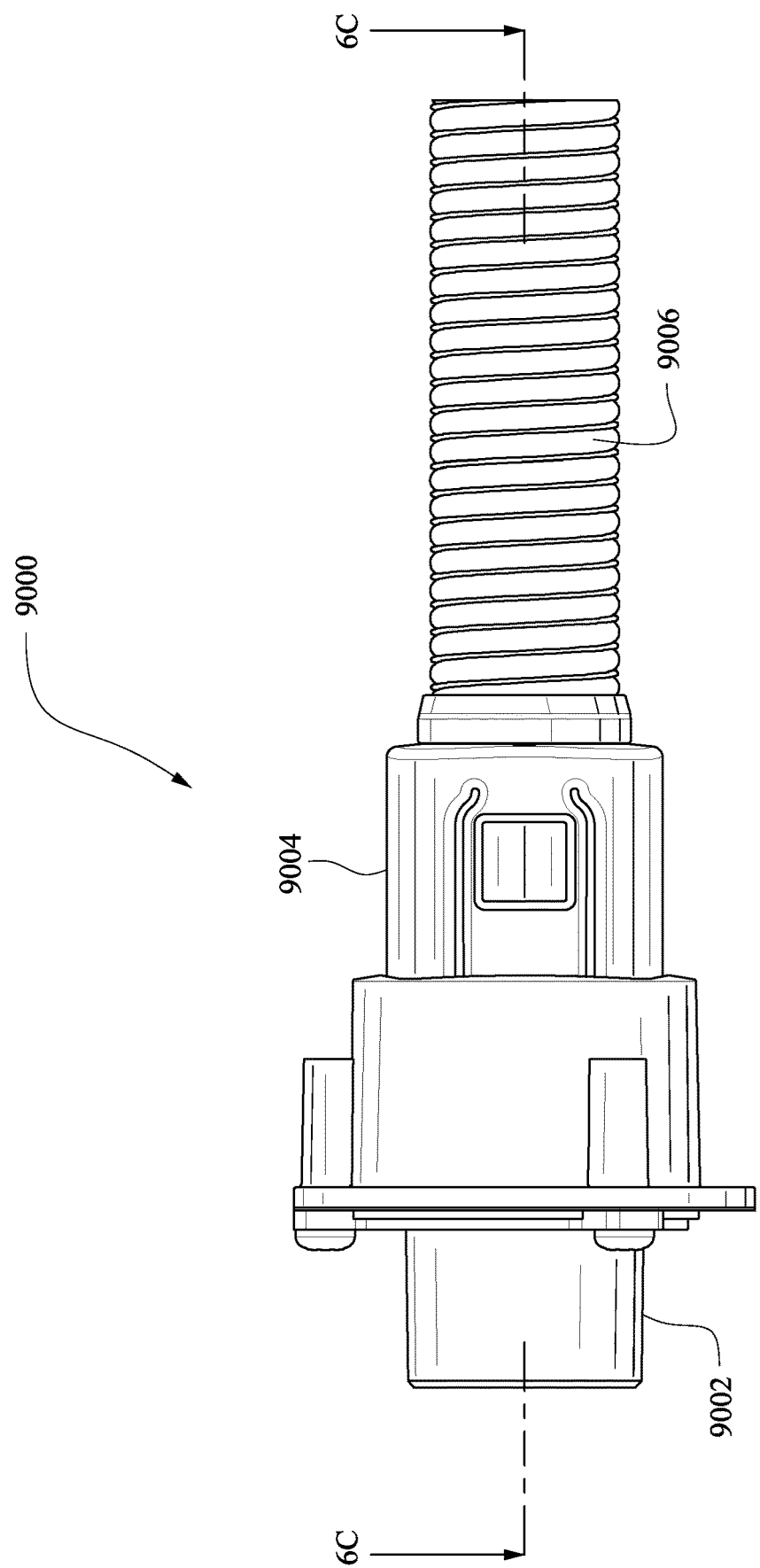

FIG. 6A shows a side view of a fluid connector with a first end and a second end mated with one another.

Figure 6B:
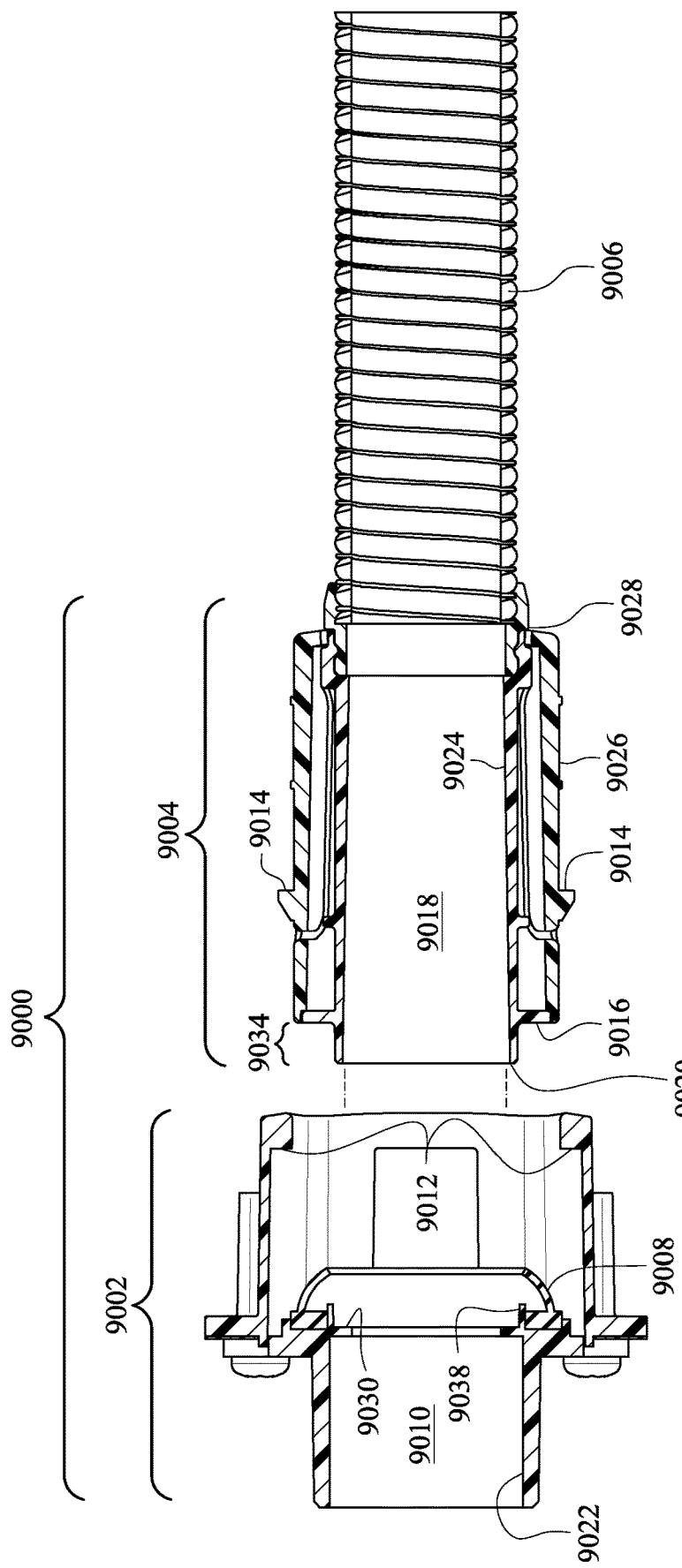

FIG. 6B shows a side, cross-sectional view of a fluid connector with a first end and a second end disengaged from one another.

Figure 6C:
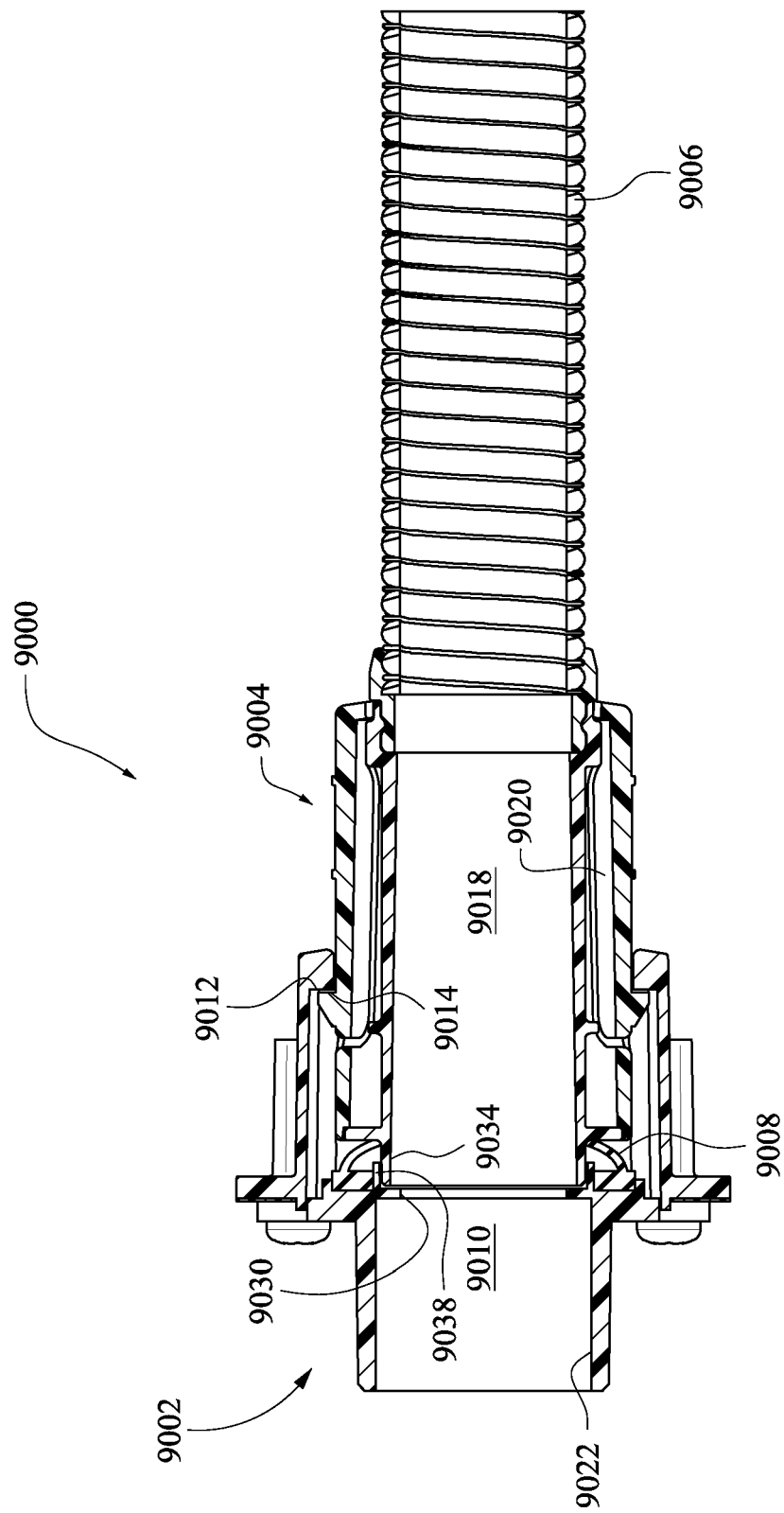

FIG. 6C shows a side, cross-sectional view of a fluid connector with a first end and a second end mated with one another.

Figure 6D:
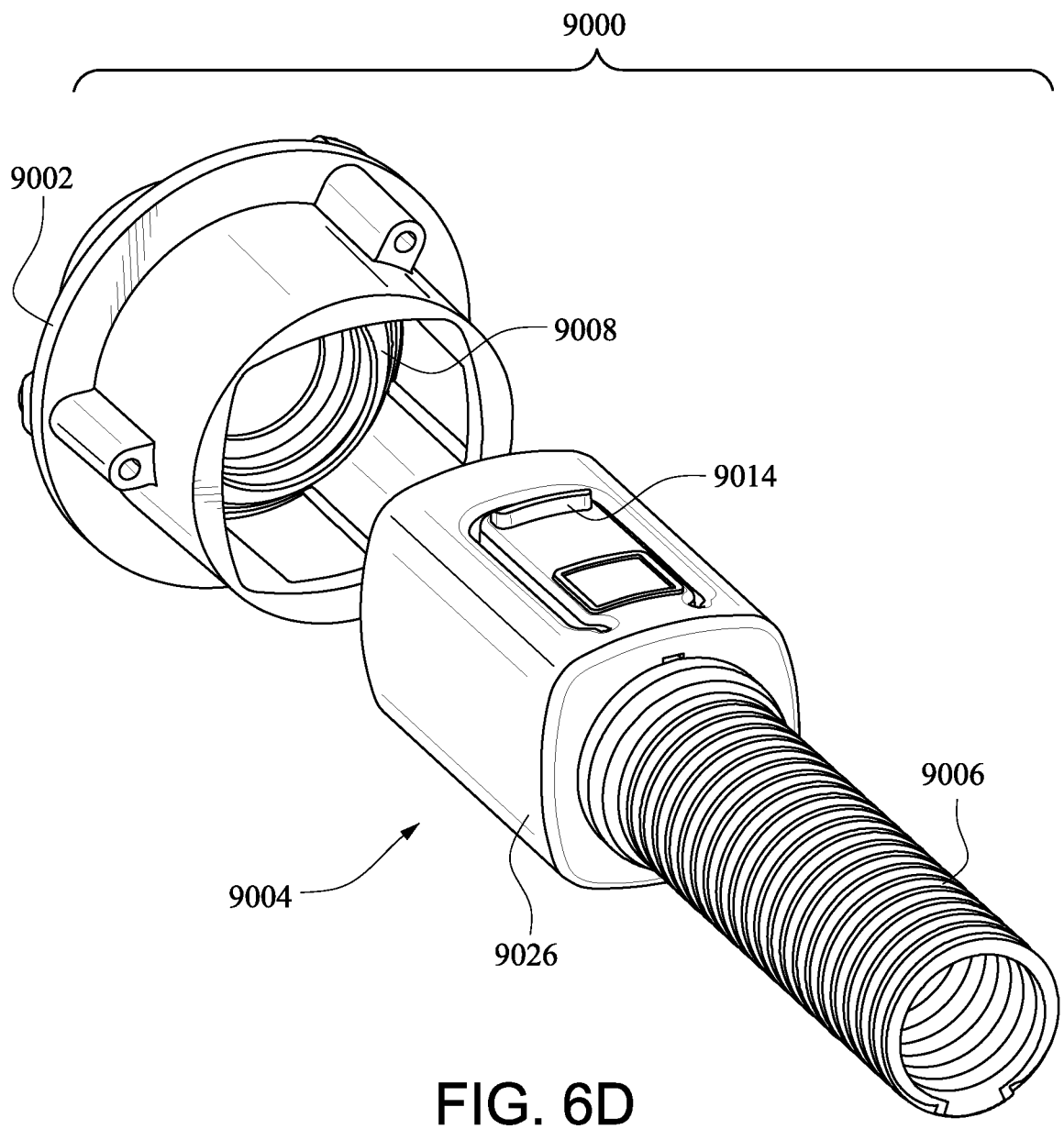

FIG. 6D shows a perspective view of a fluid connector with a first end and a second end separated from one another with an interior of the first end being visible.

Figure 6E:
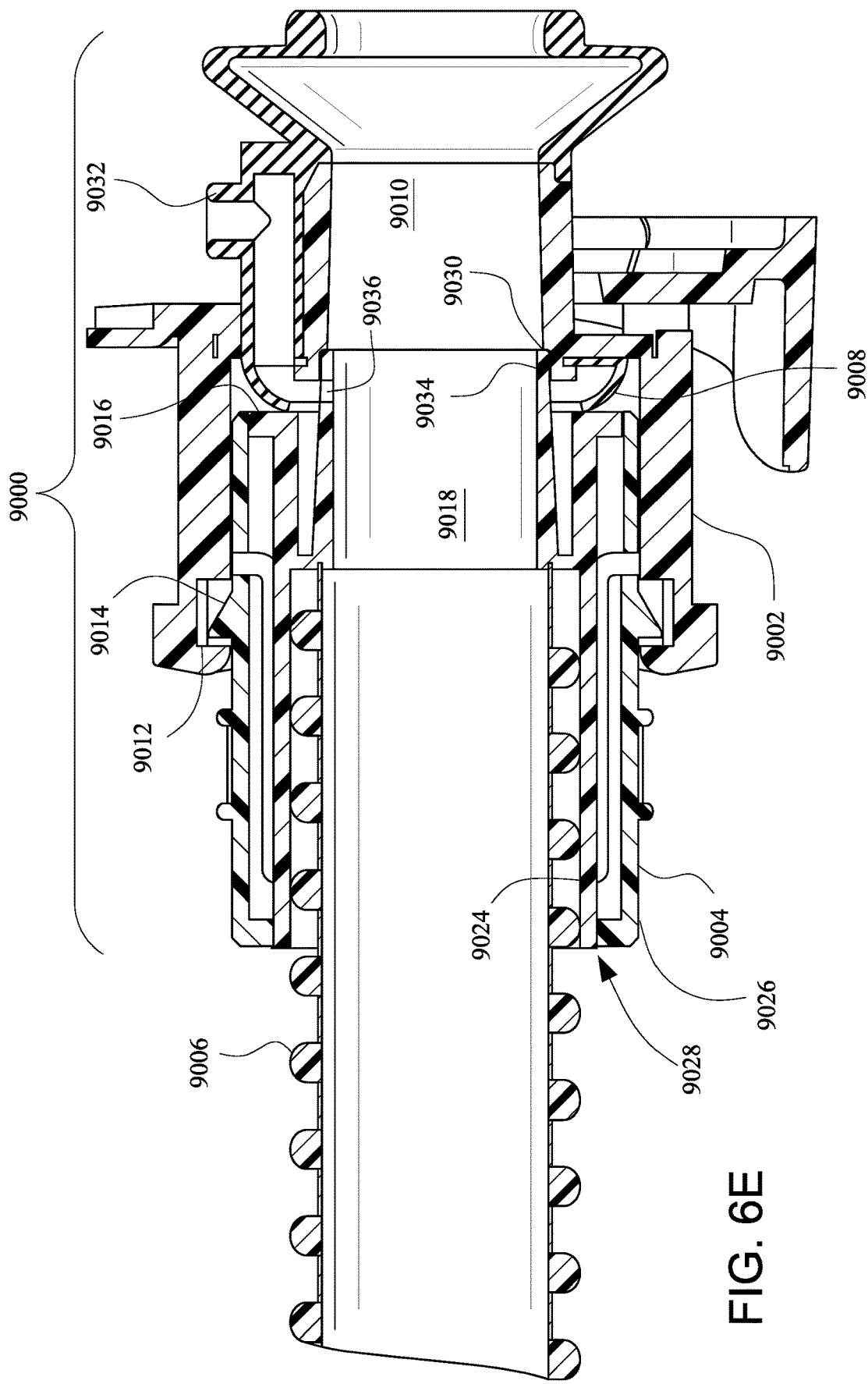

FIG. 6E shows a cross-sectional view of a fluid connector with an additional fluid port.

FIG. 6F shows a fluid connector with a first end and a second end connected together and the first end integrated into an RTP device.

Figure 6G:
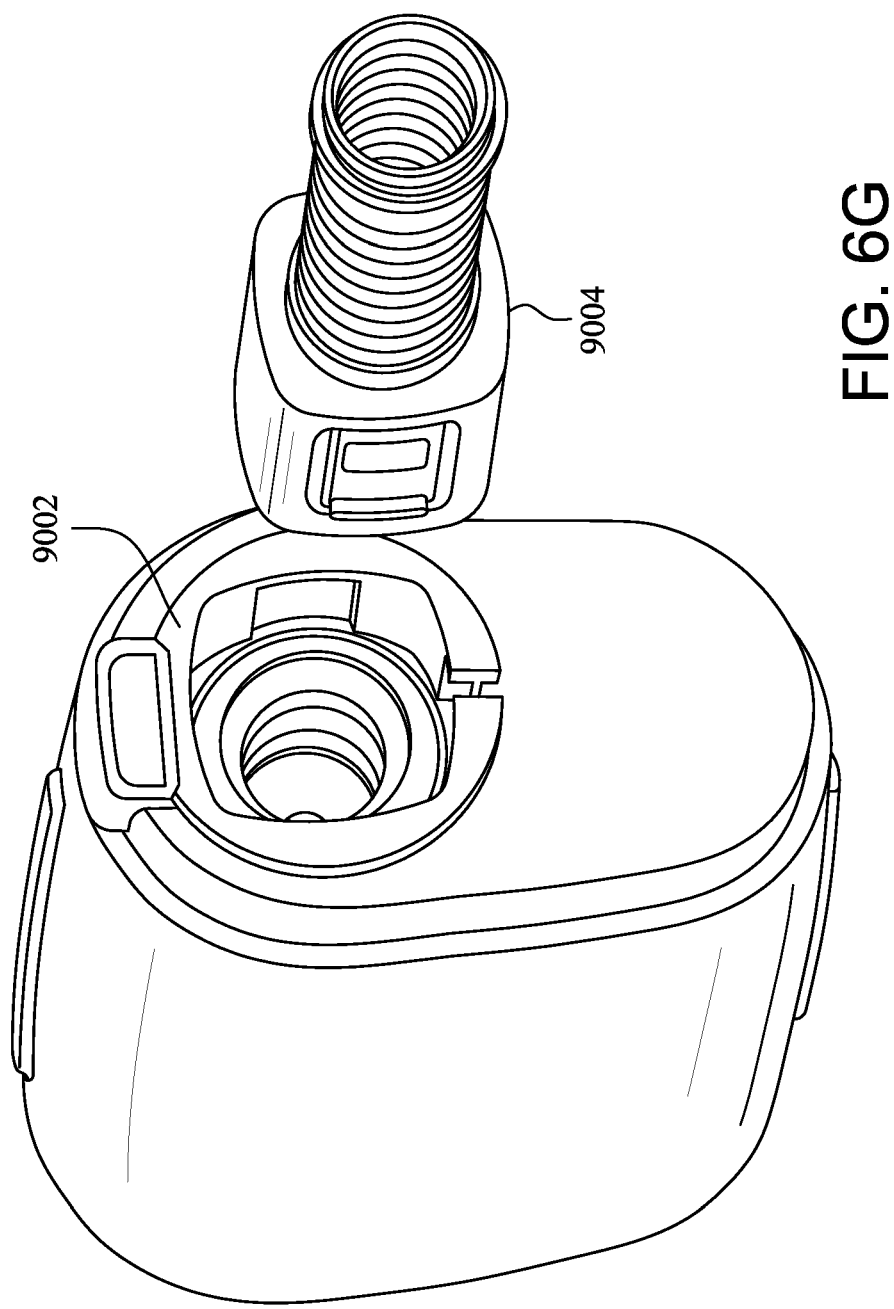
Figure 6H:
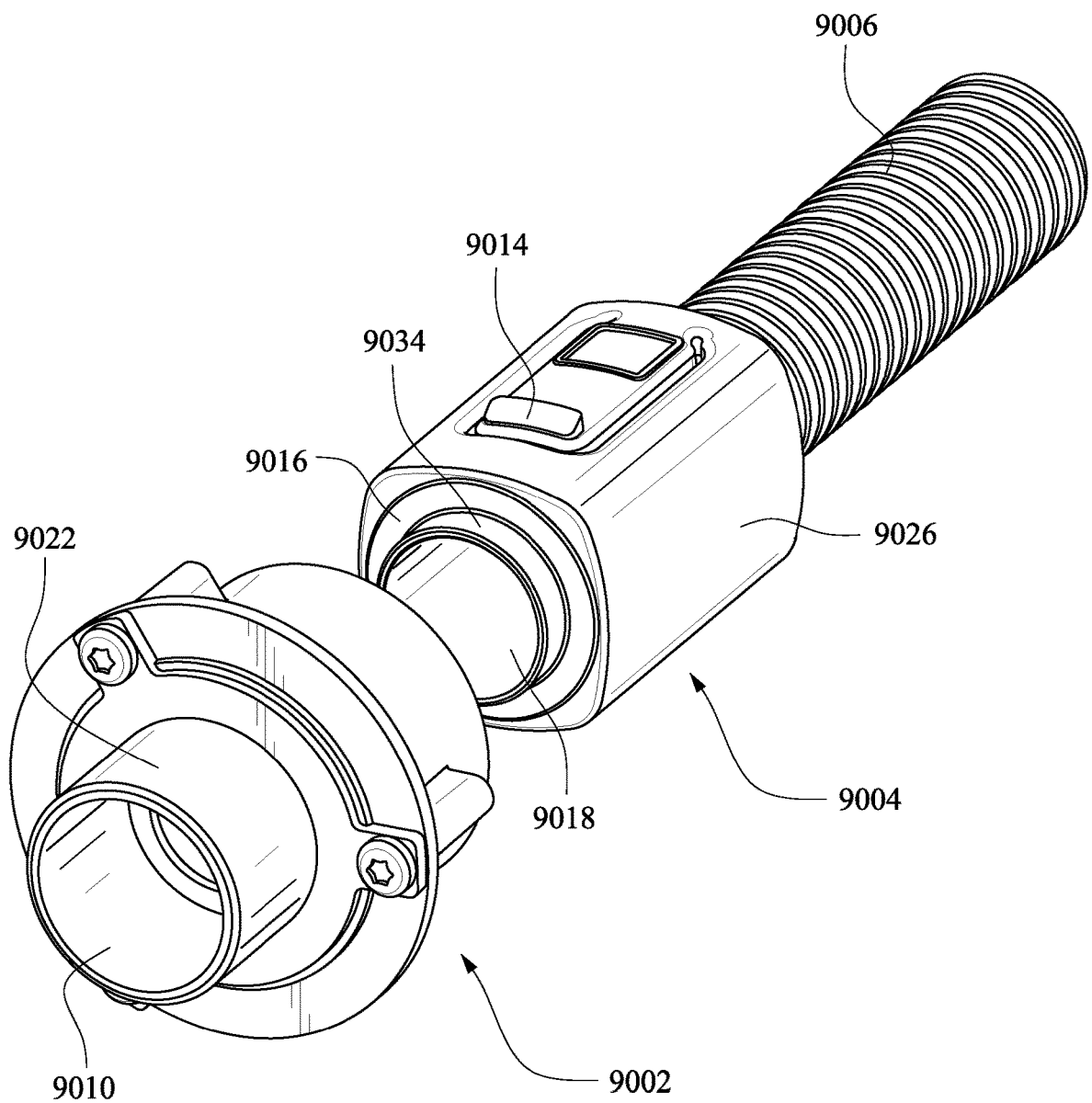

FIG. 6G shows a fluid connector with a first end and a second end disconnected and the first end integrated into an RTP device FIG. 6H shows a perspective view of a fluid connector with a first end and a second end separated from one another with the sealing surface of the second end being visible.

Figure 7A:
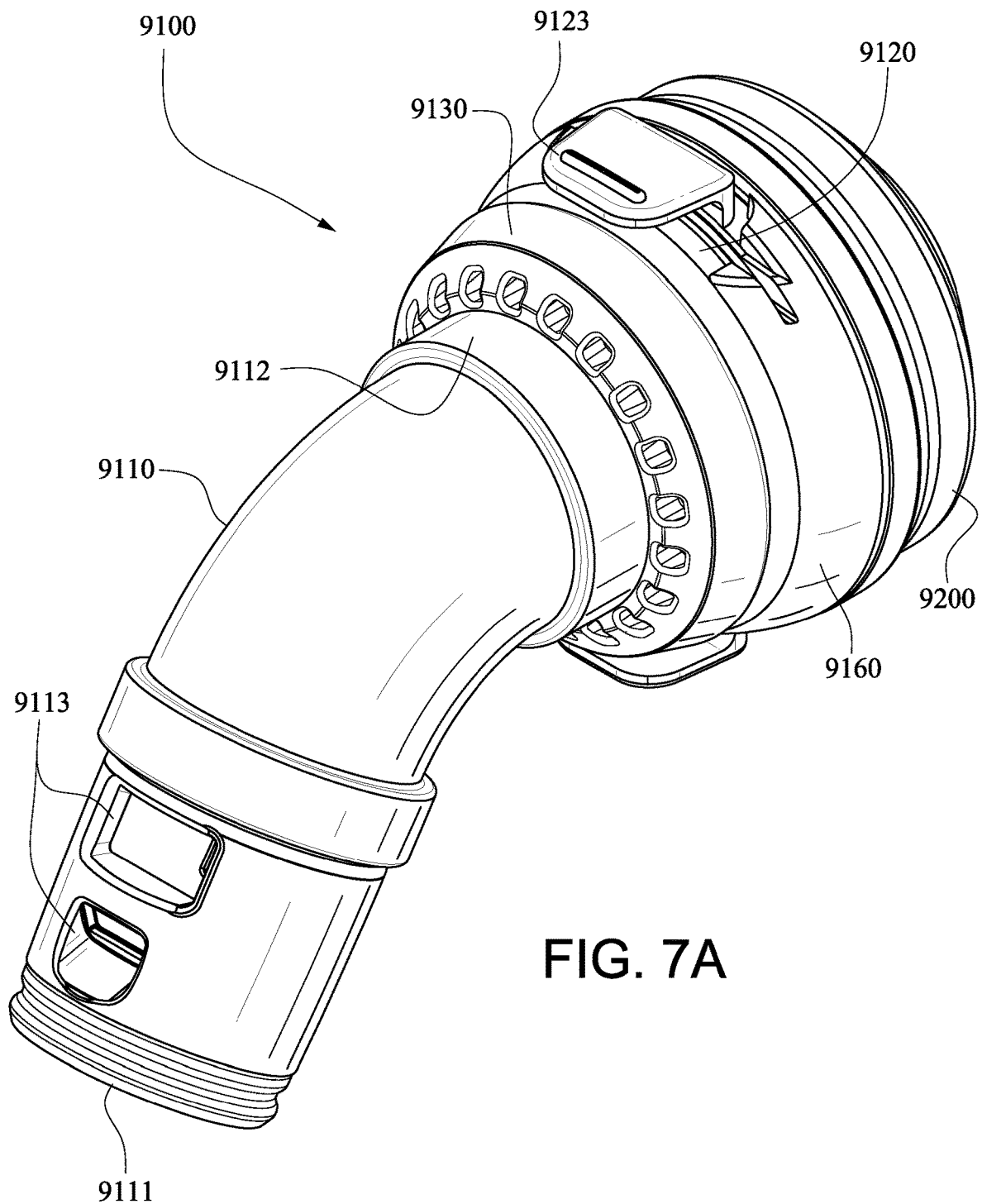

FIG. 7A shows a perspective view of a vent adaptor according to an example of the present technology.

Figure 7B:
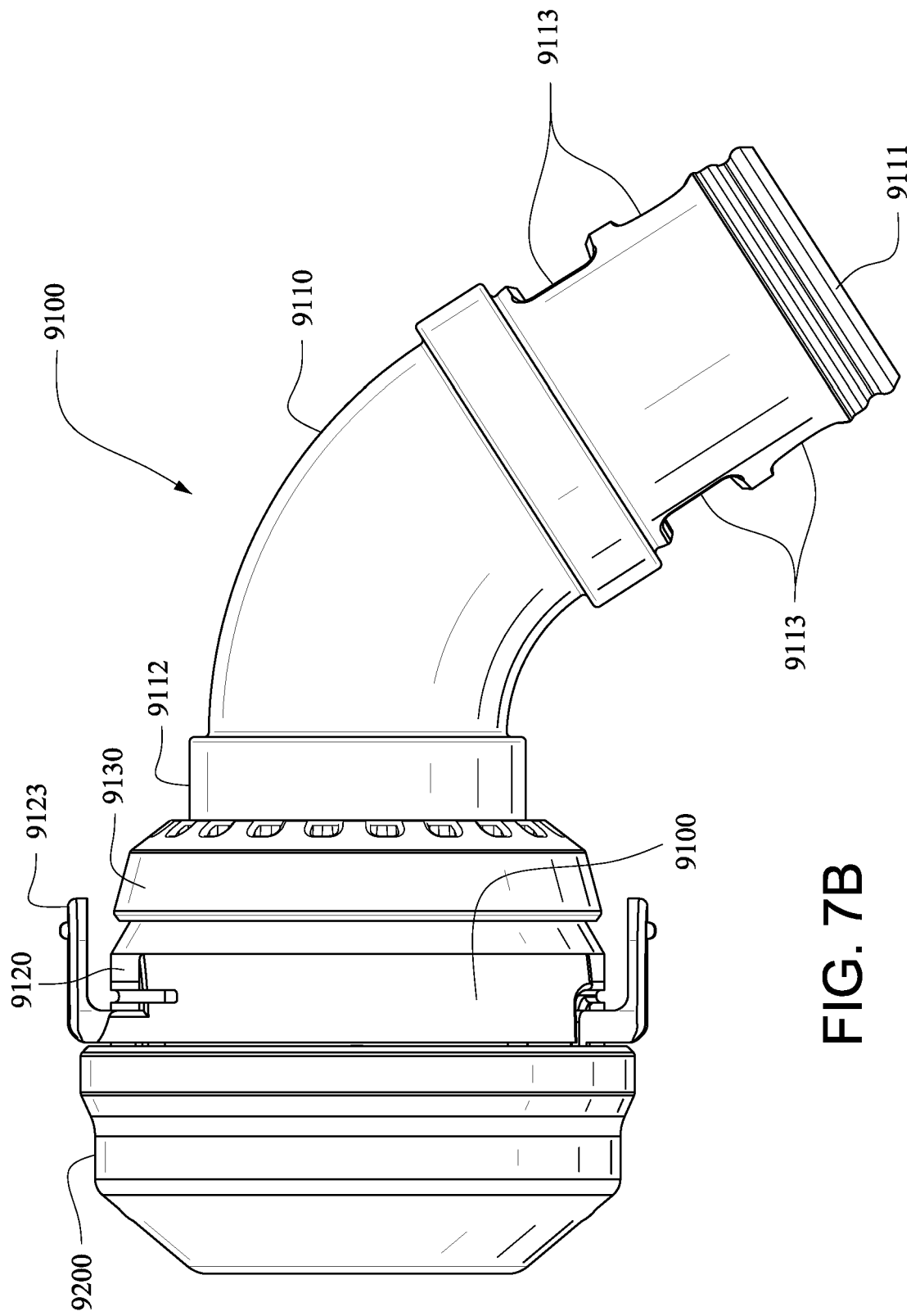

FIG. 7B shows a side view of a vent adaptor according to an example of the present technology.

Figure 7C:
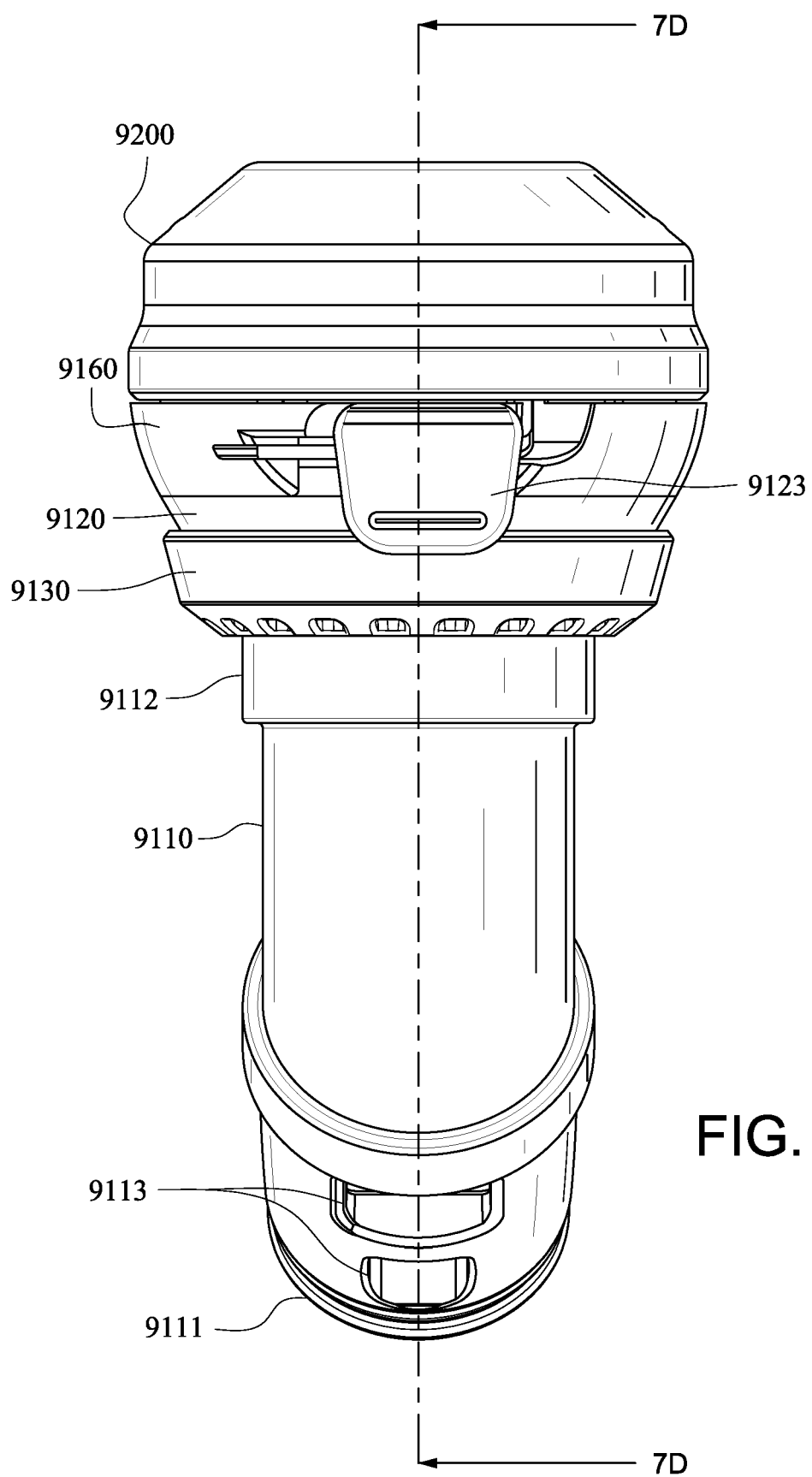

FIG. 7C shows a top view of a vent adaptor according to an example of the present technology.

Figure 7D:
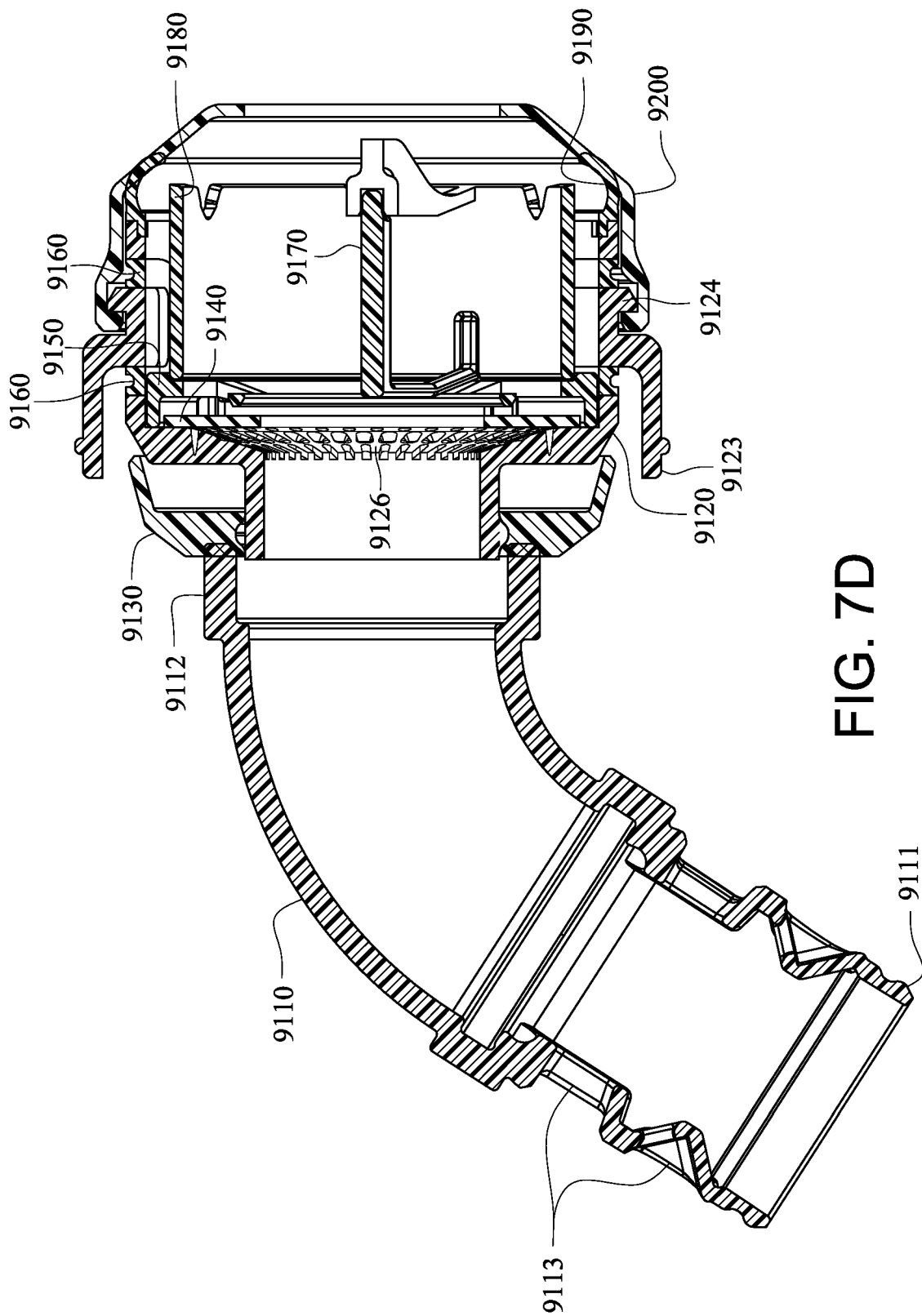

FIG. 7D shows a cross-section view of a vent adaptor according to an example of the present technology taken through line 7D-7D of FIG. 7C.

Figure 7E:
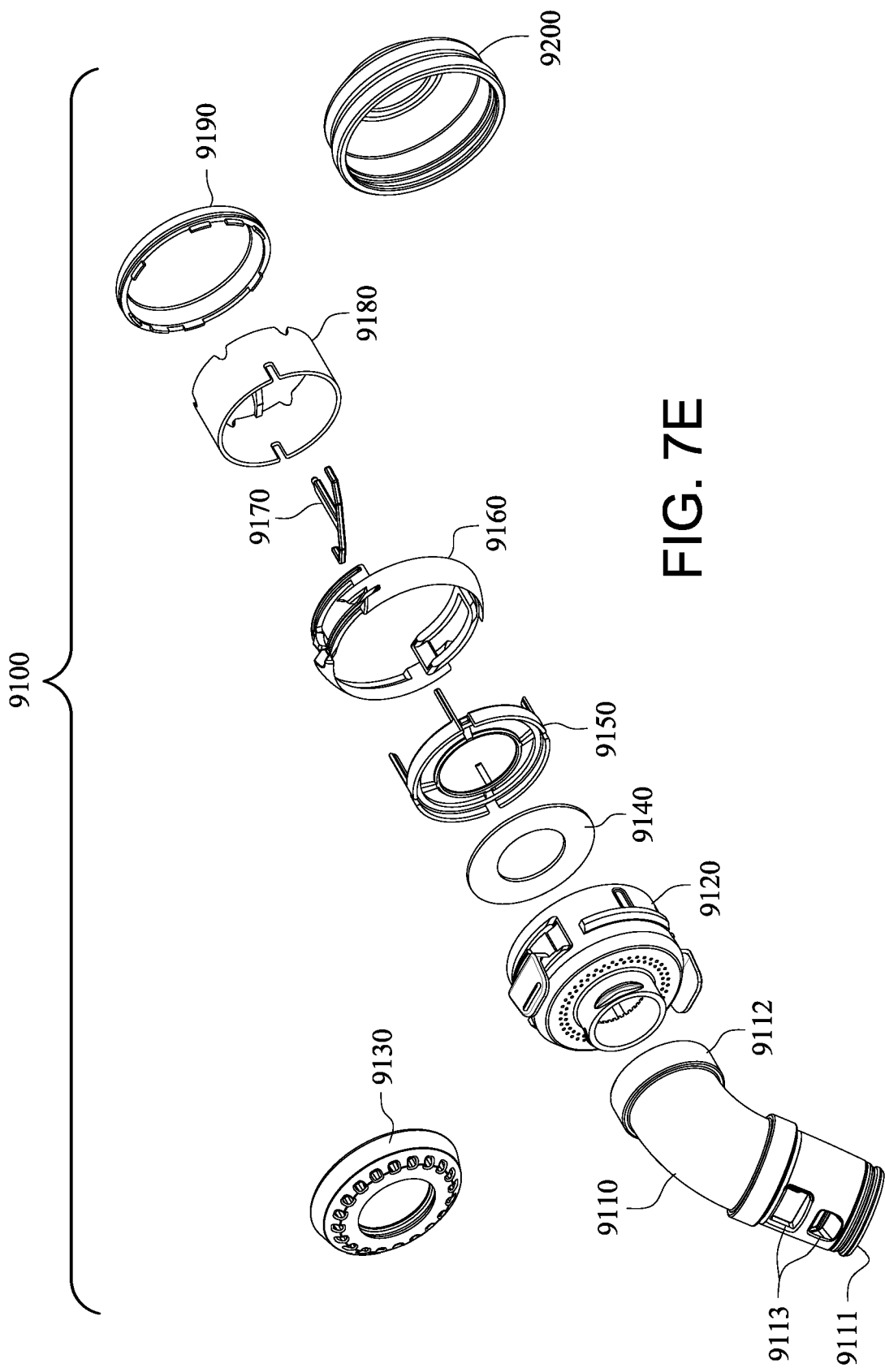

FIG. 7E shows an exploded view of a vent adaptor according to an example of the present technology.

Figure 7F:
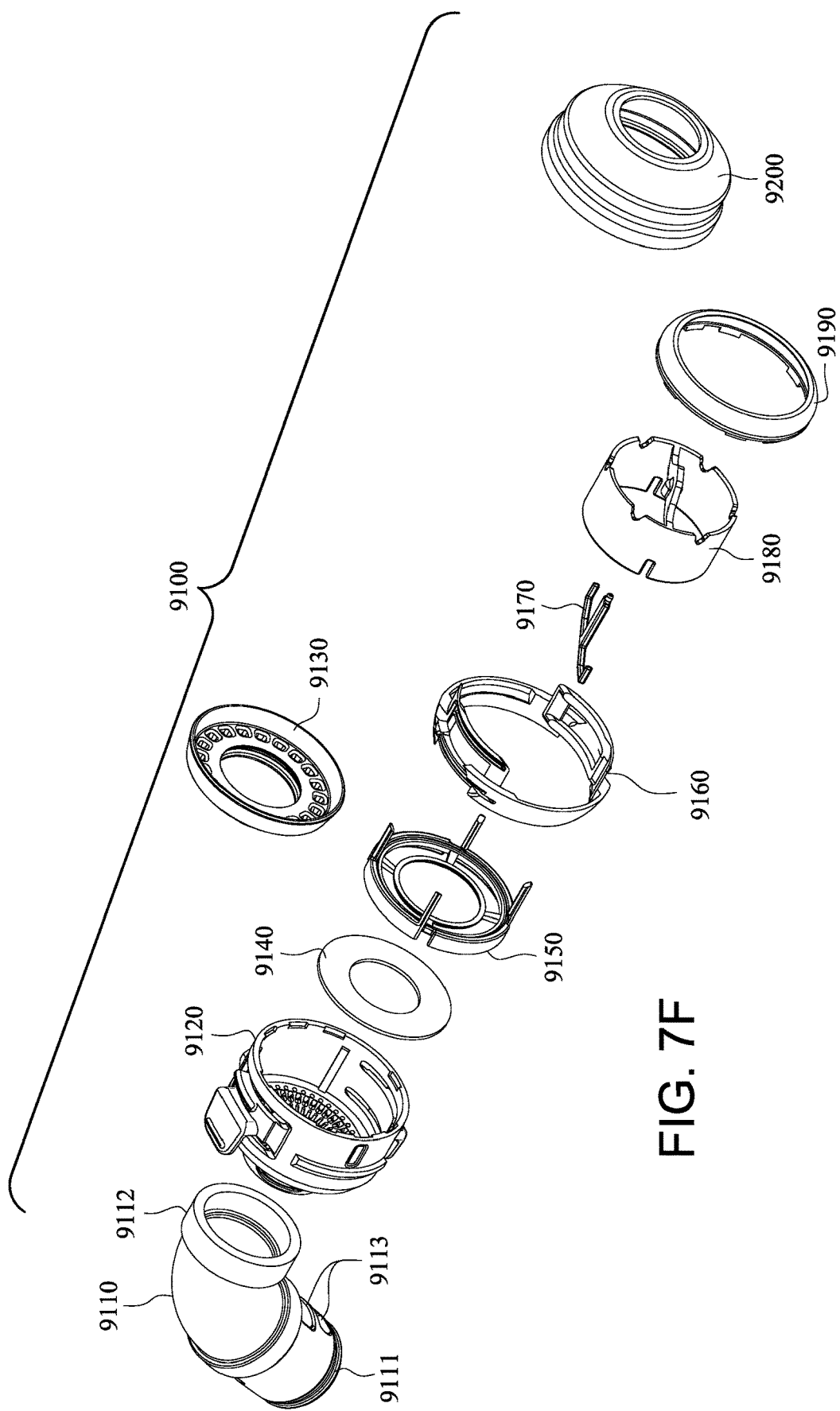

FIG. 7F shows another exploded view of a vent adaptor according to an example of the present technology.

Figure 8A:
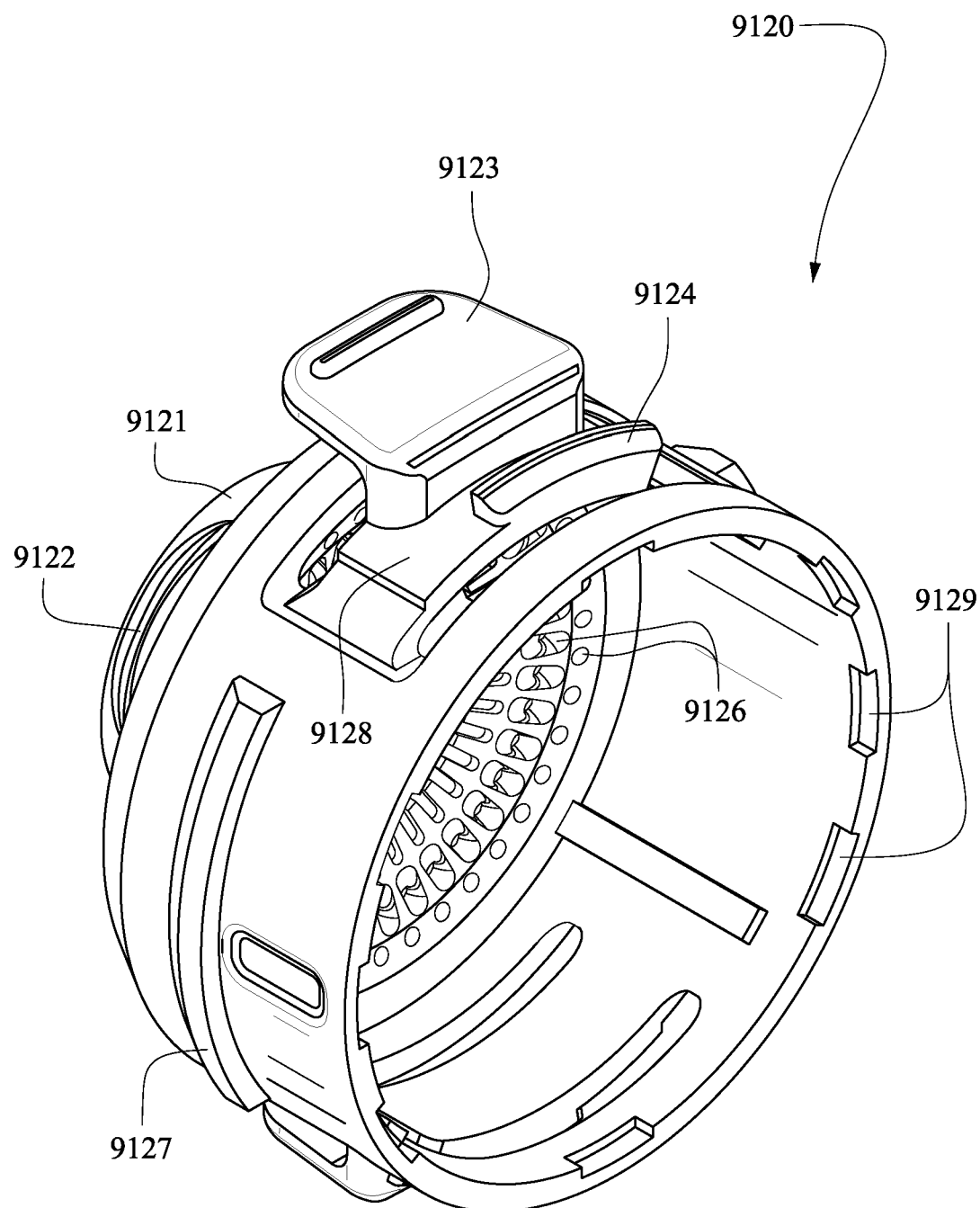

FIG. 8A shows a perspective view of a vent housing according to an example of the present technology.

Figure 8B:
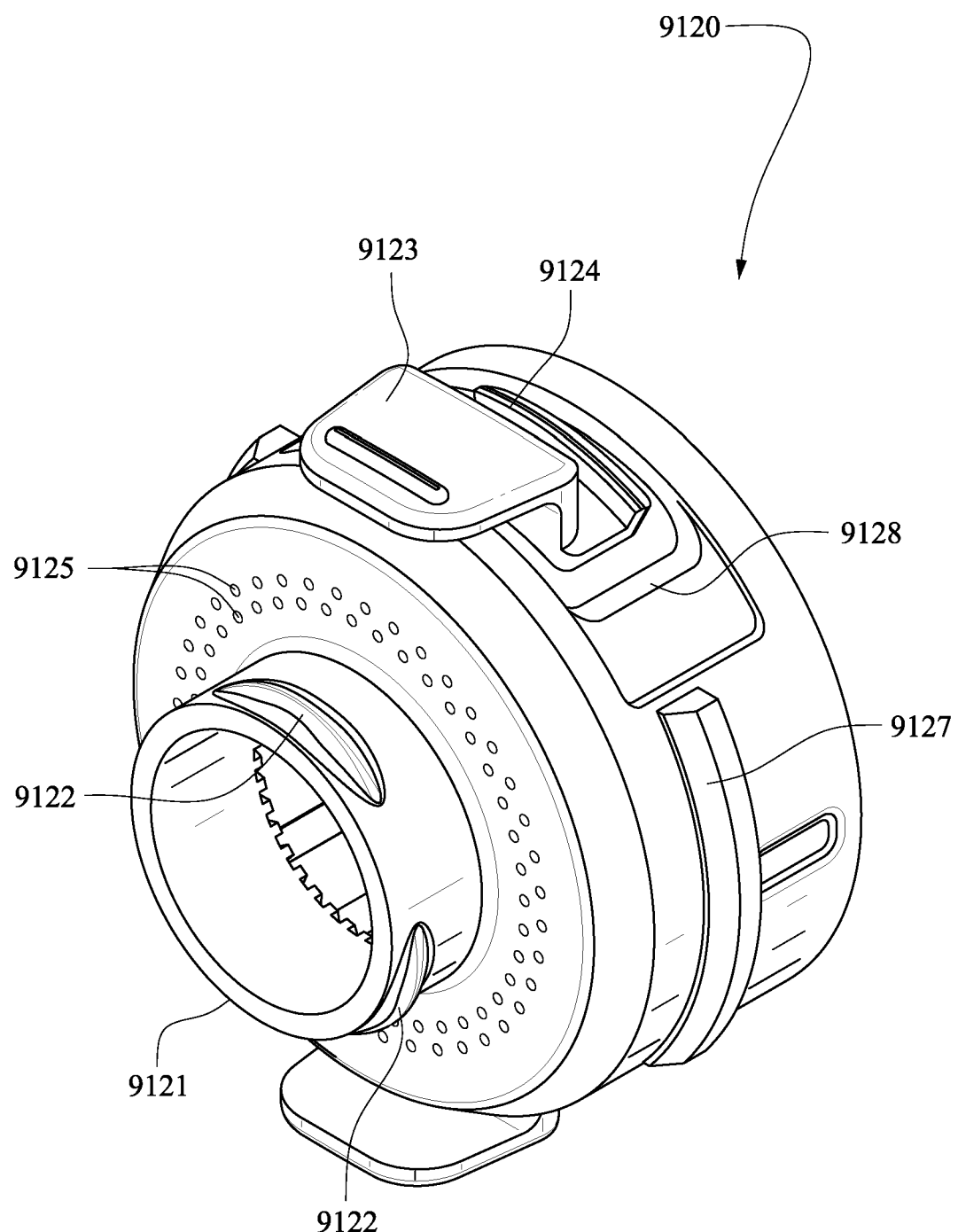

FIG. 8B shows another perspective view of a vent housing according to an example of the present technology.

Figure 8C:
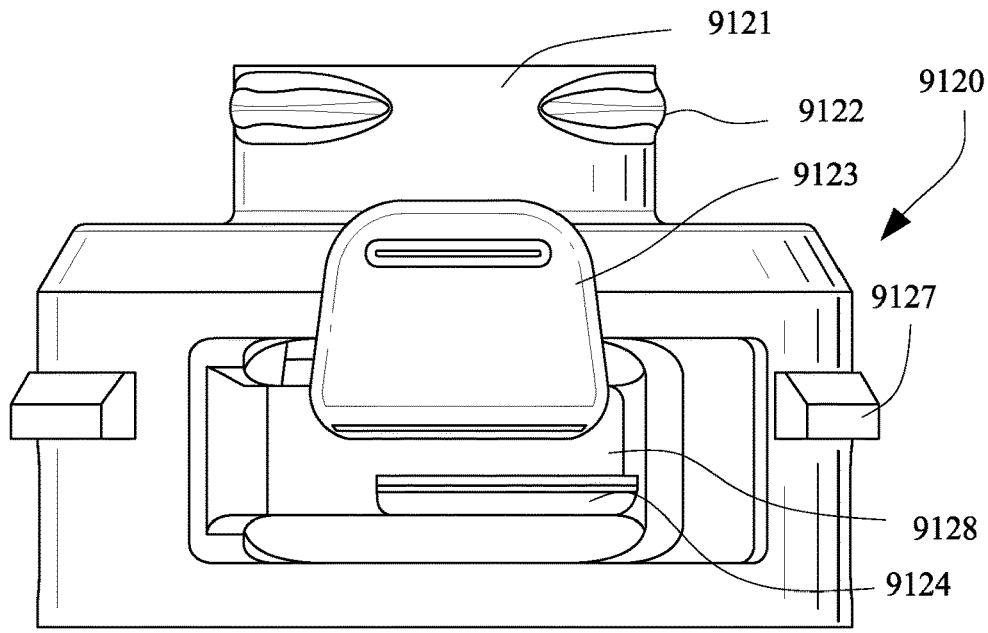

FIG. 8C shows a side view of a vent housing according to an example of the present technology.

Figure 8D:
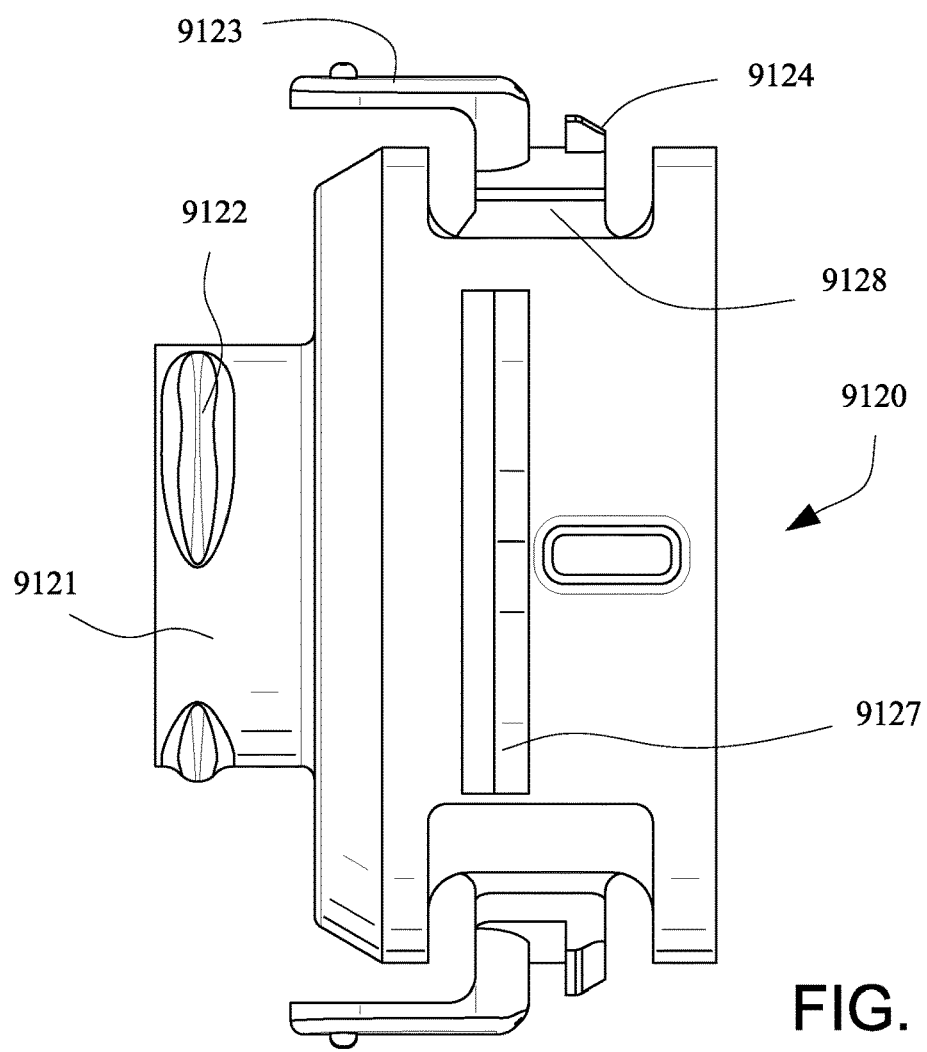

FIG. 8D shows another side view of a vent housing according to an example of the present technology.

Figure 8E:
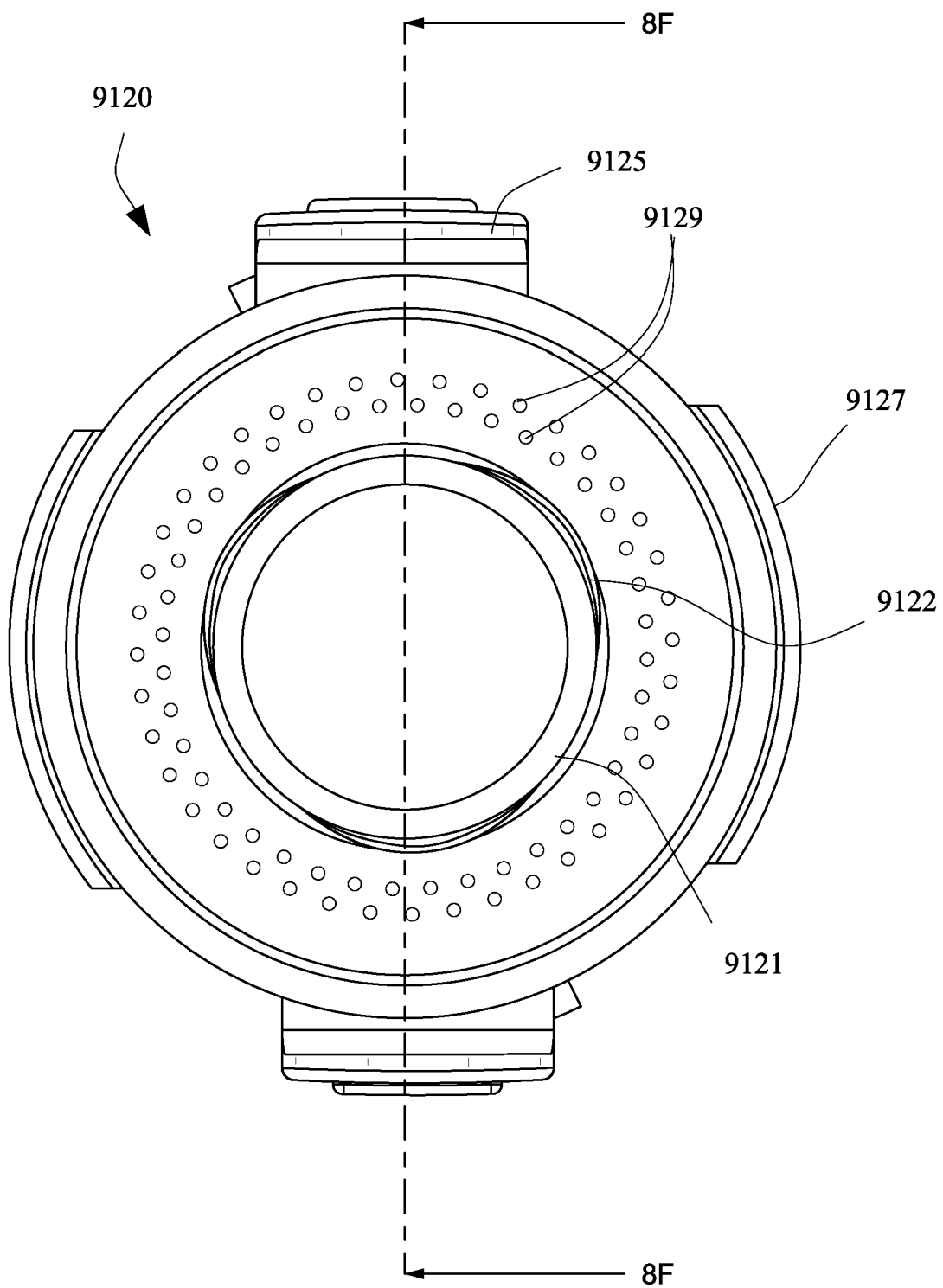

FIG. 8E shows a top view of a vent housing according to an example of the present technology.

Figure 8F:
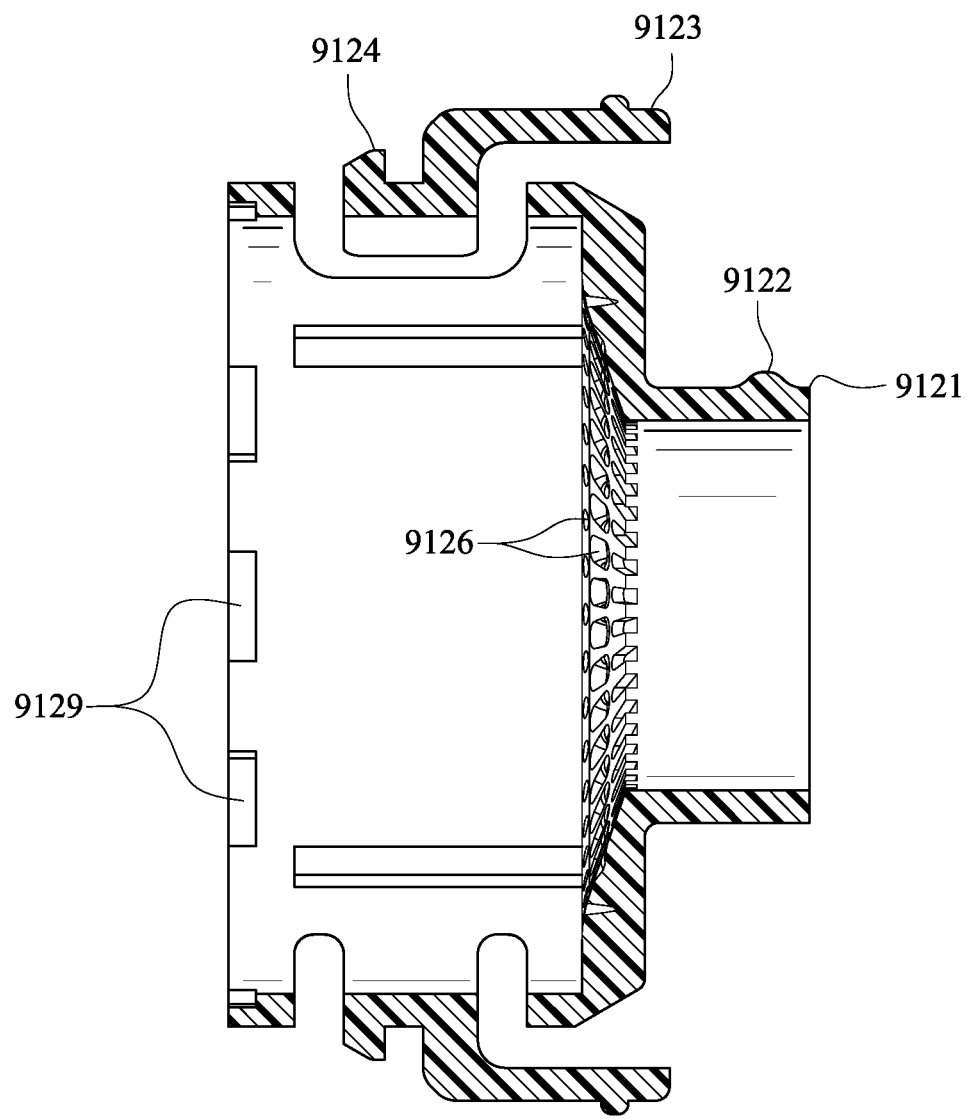

FIG. 8F shows a cross-section view of a vent housing according to an example of the present technology taken through line 8F-8F of FIG. 8E.

Figure 9A:
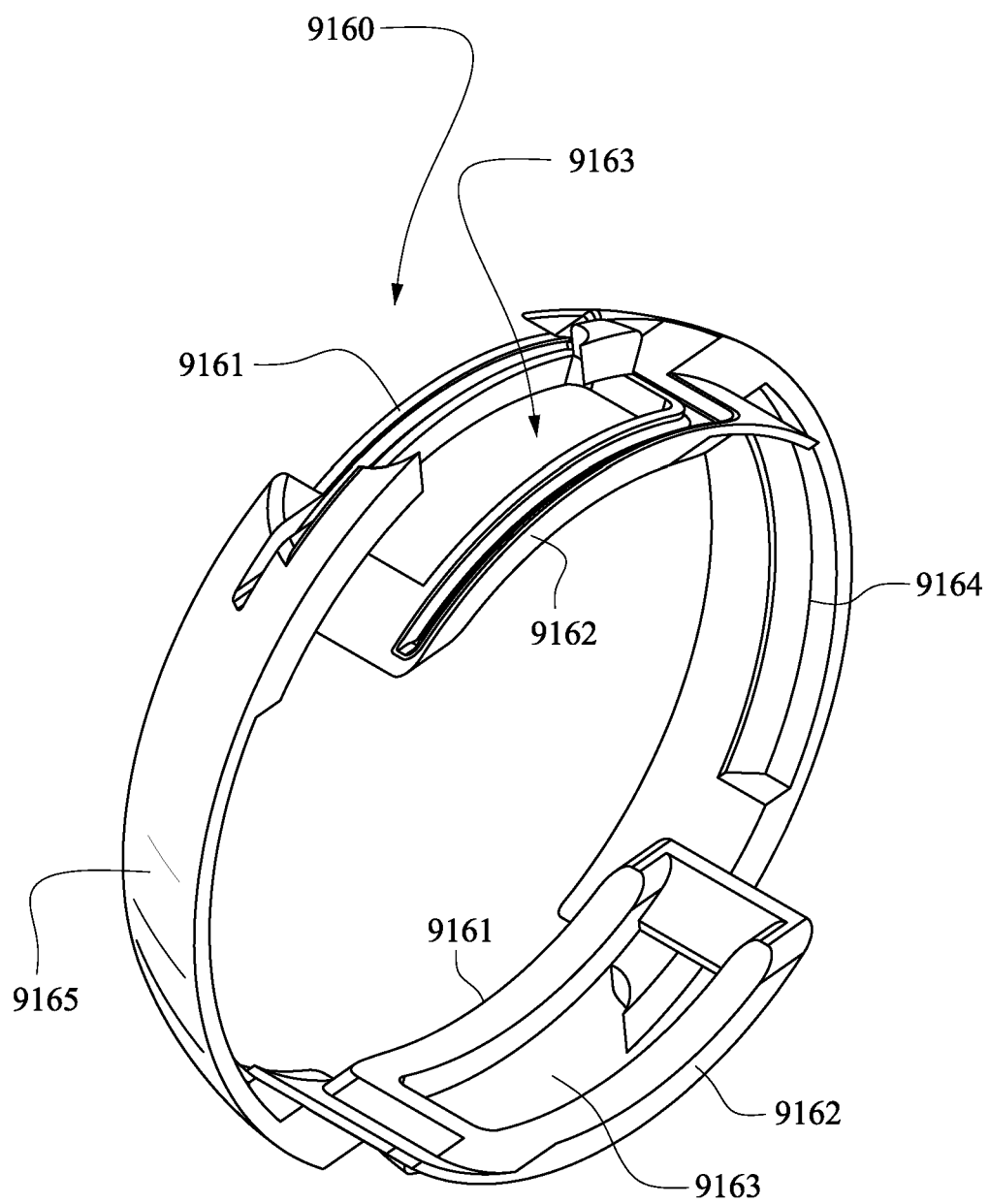

FIG. 9A shows a perspective view of a vent housing connector according to an example of the present technology.

Figure 9B:
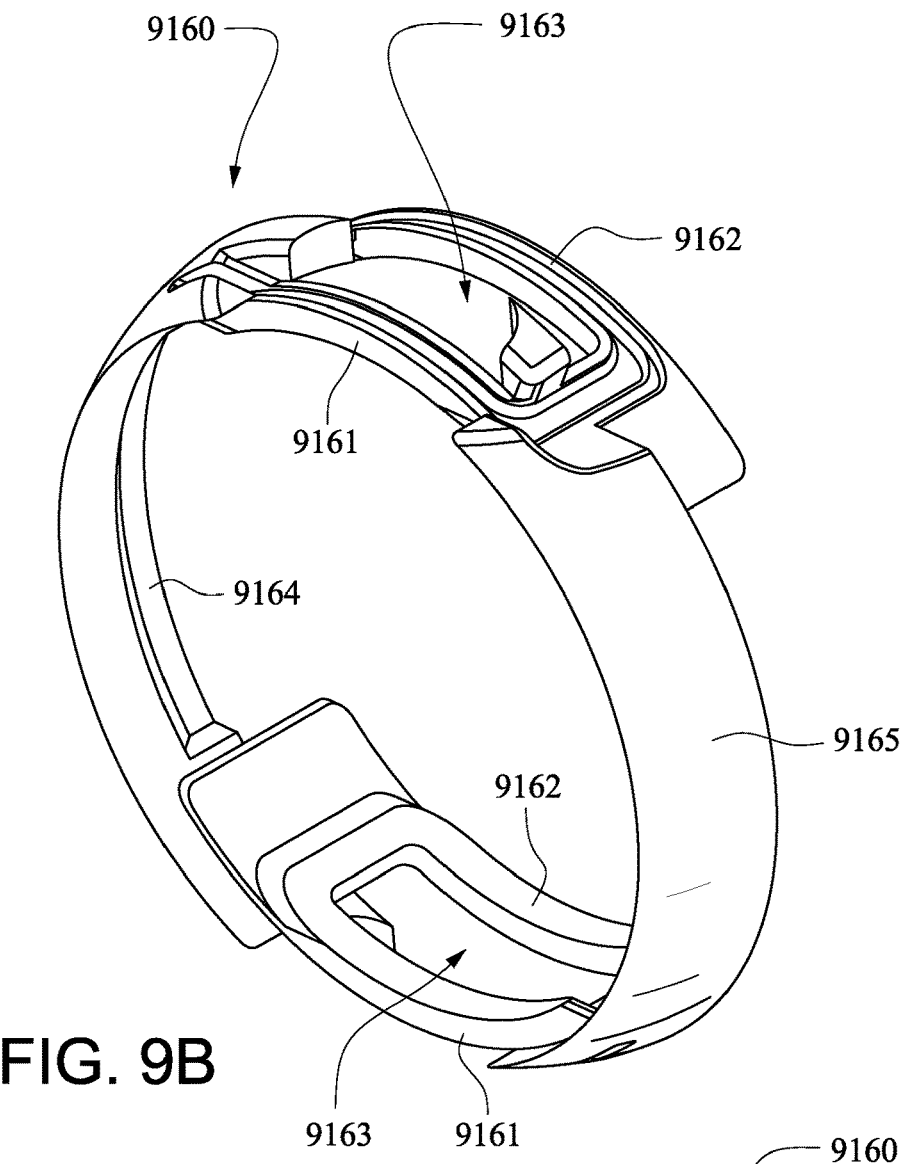

FIG. 9B shows another perspective view of a vent housing connector according to an example of the present technology.

Figure 9C:
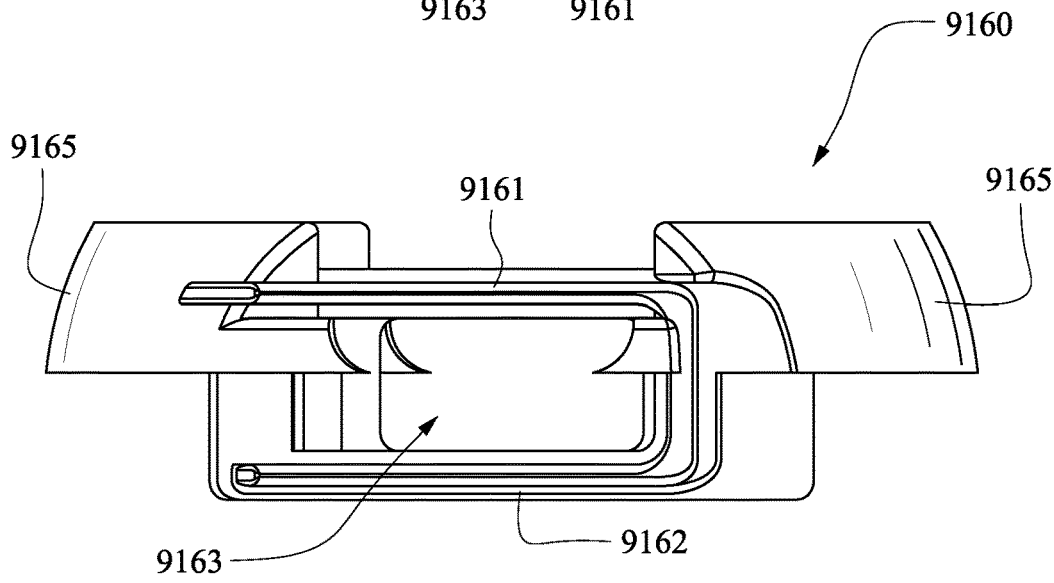

FIG. 9C shows a side view of a vent housing connector according to an example of the present technology.

Figure 9D:
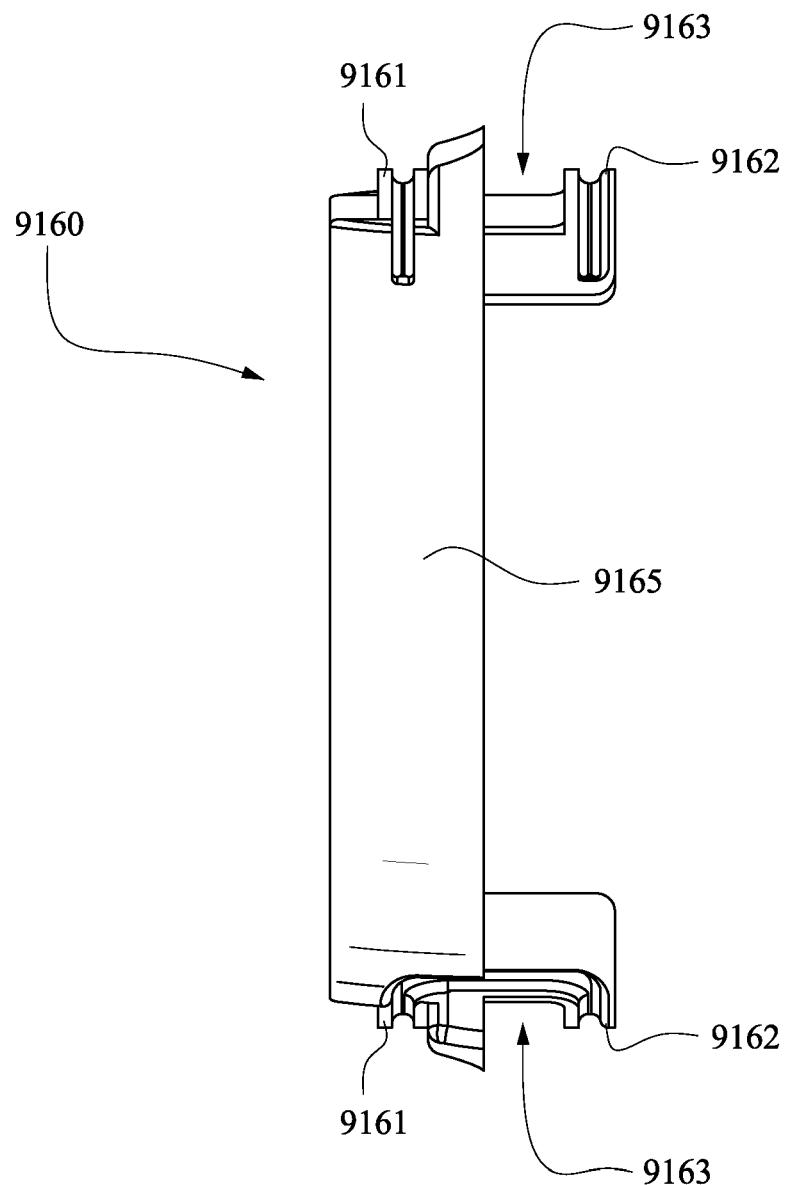

FIG. 9D shows another side view of a vent housing connector according to an example of the present technology.

Figure 9E:
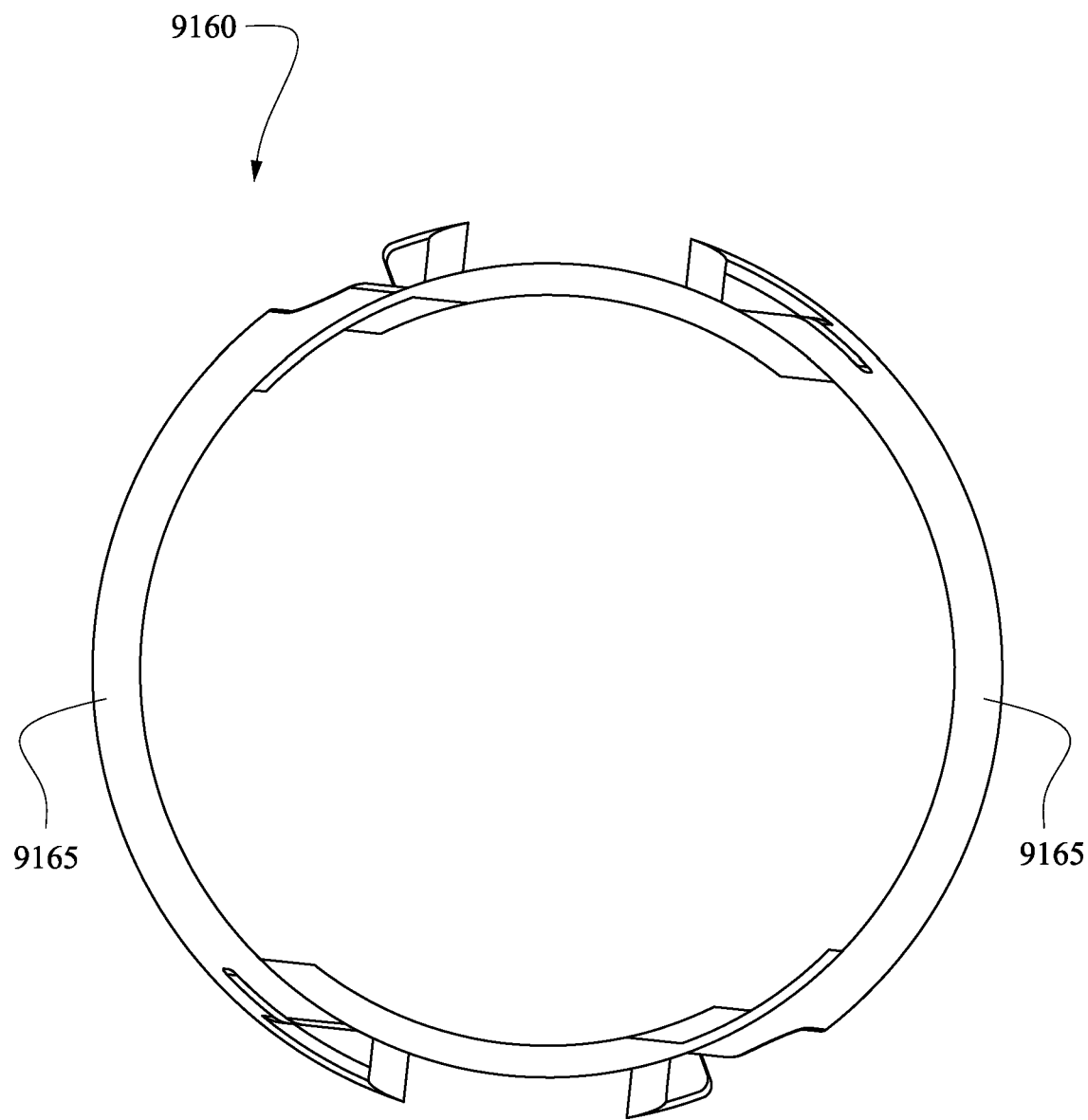

FIG. 9E shows a top view of a vent housing connector according to an example of the present technology.

Figure 10A:
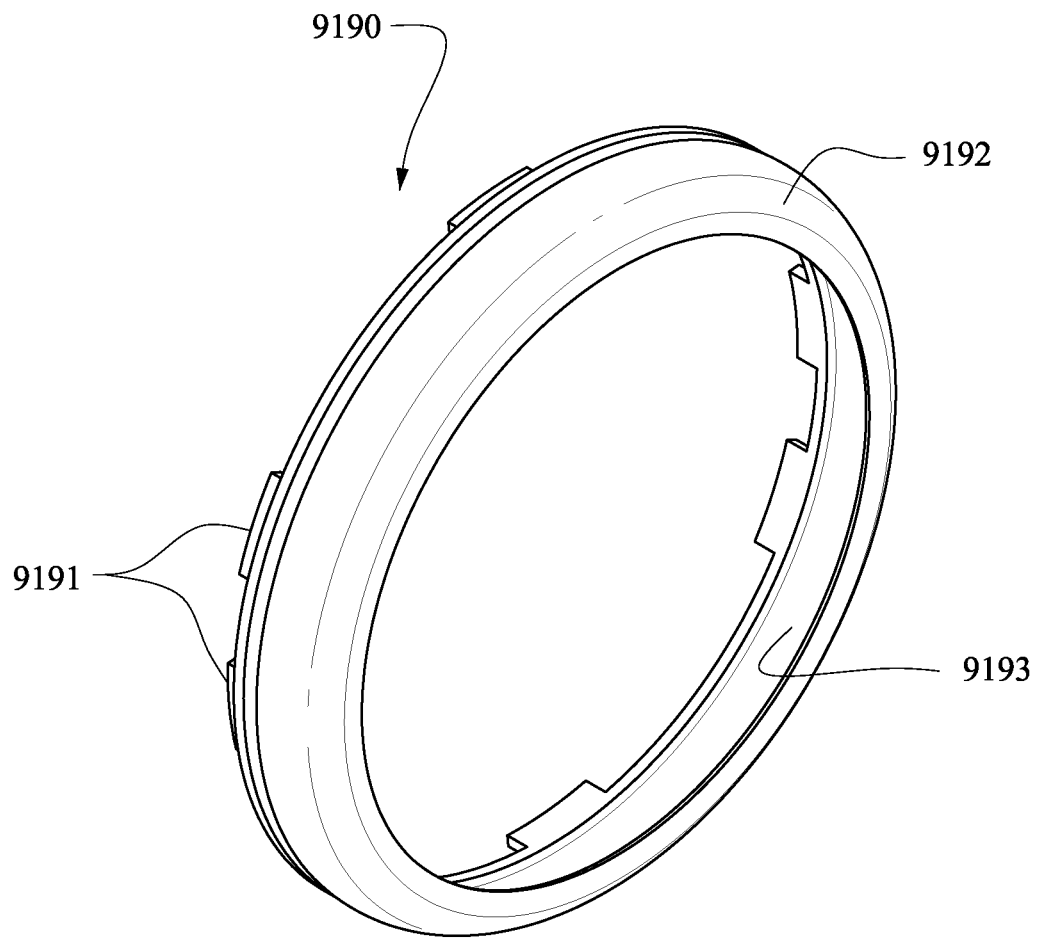

FIG. 10A shows a perspective view of a bellows seal according to an example of the present technology.

Figure 10B:
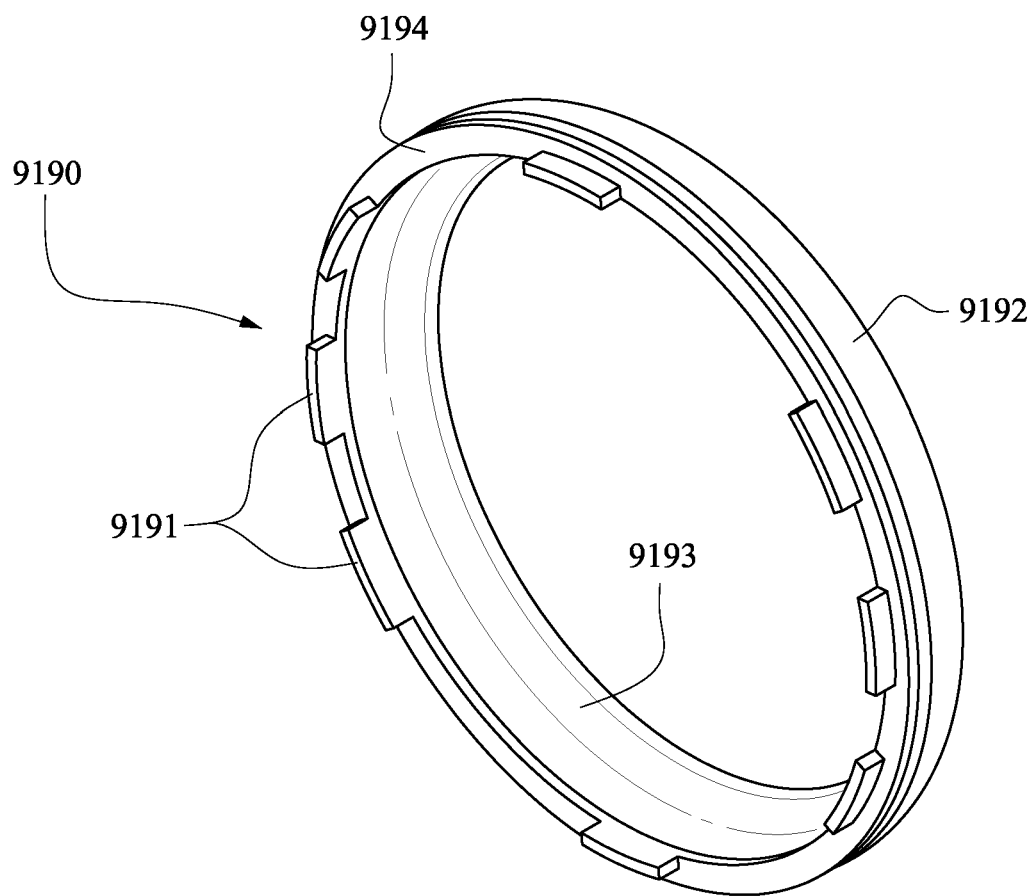

FIG. 10B shows another perspective view of a bellows seal according to an example of the present technology.

Figure 10C:
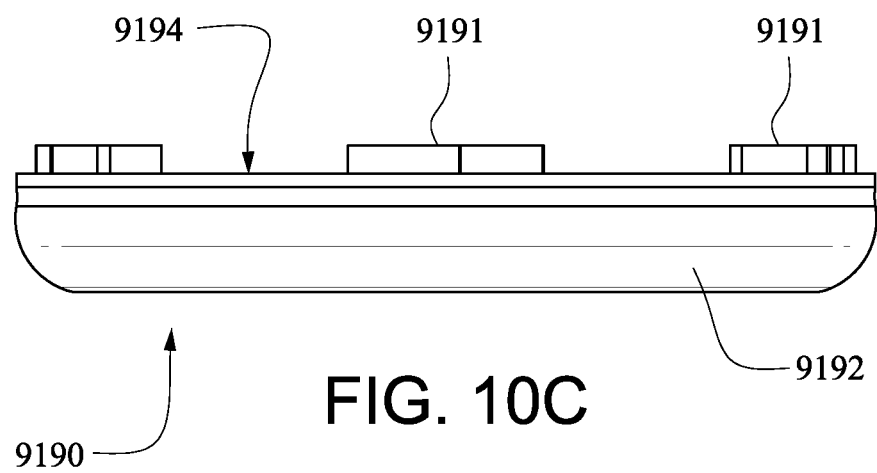

FIG. 10C shows a side view of a bellows seal according to an example of the present technology.

Figure 10D:
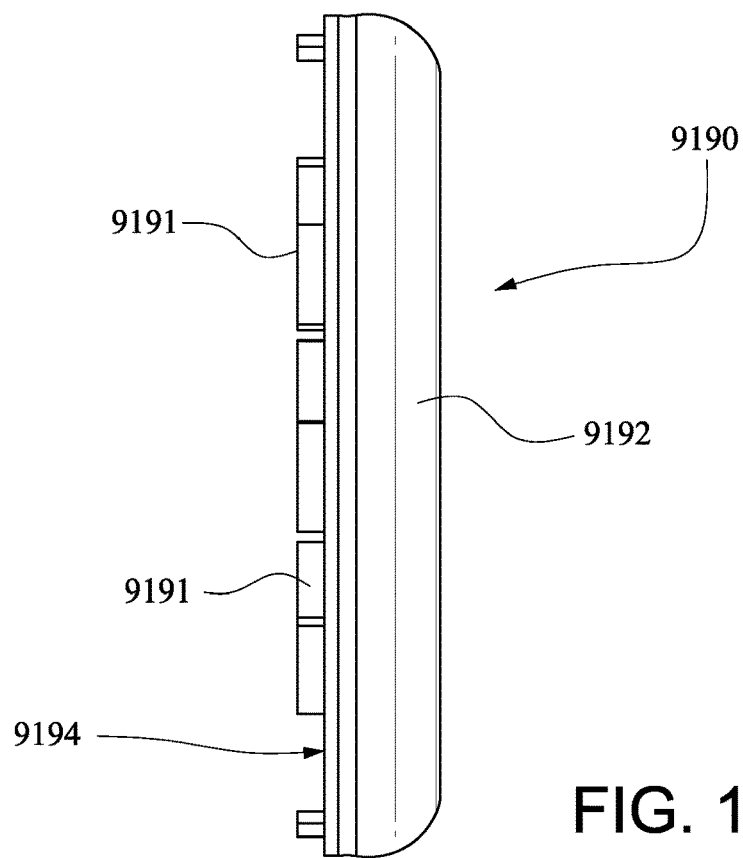

FIG. 10D shows another side view of a bellows seal according to an example of the present technology.

Figure 10E:
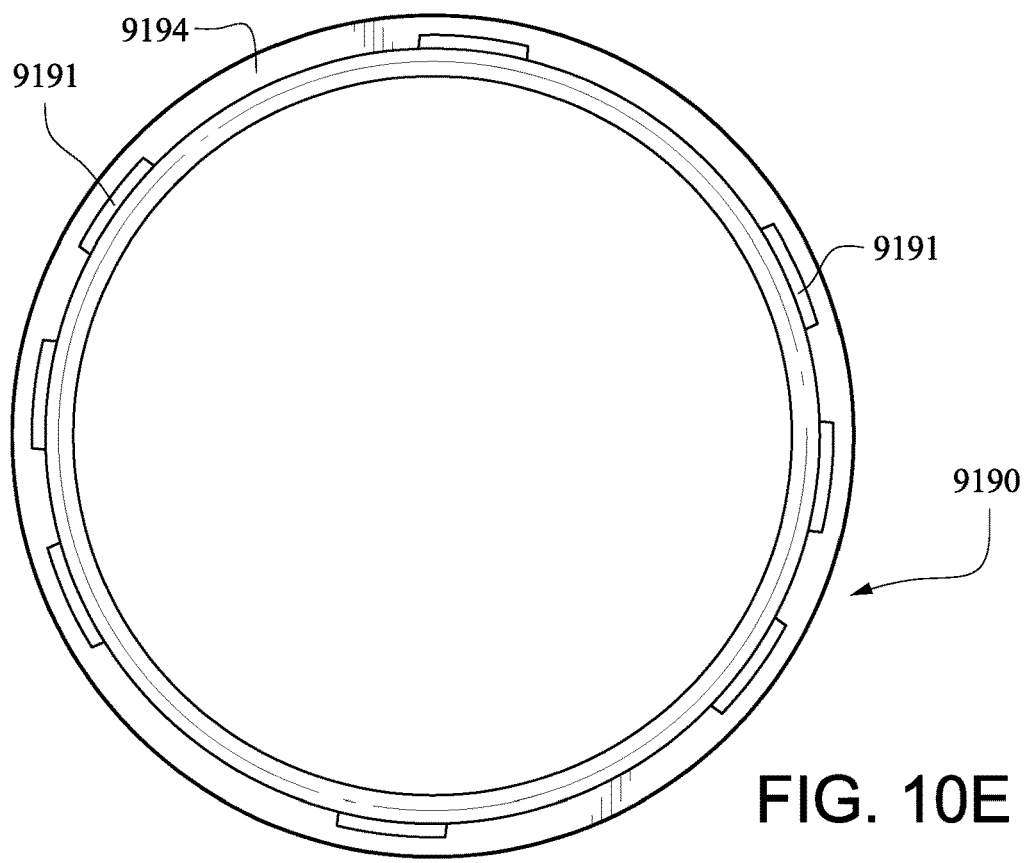

FIG. 10E shows a bottom view of a bellows seal according to an example of the present technology.

Figure 11A:
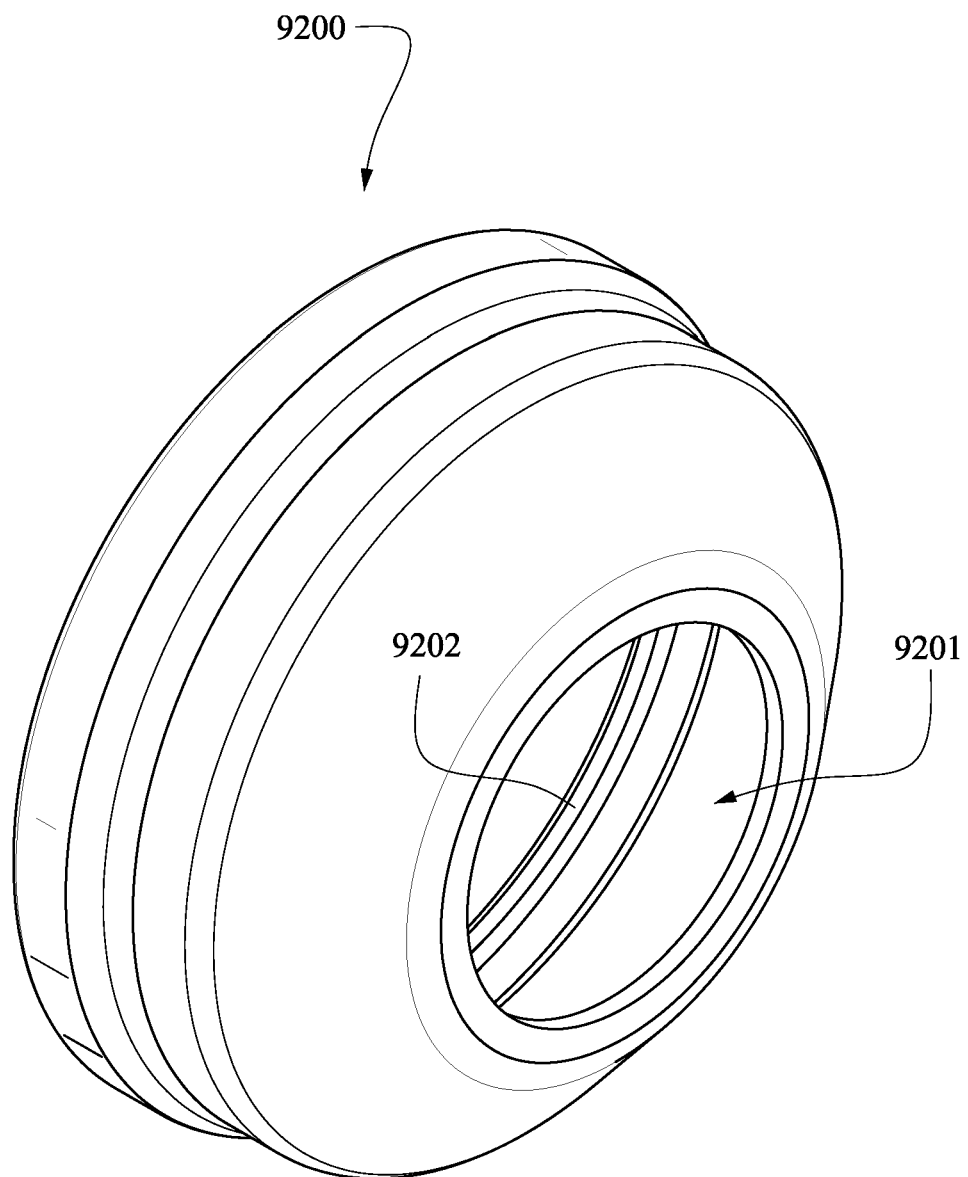

FIG. 11A shows a perspective view of a vent adaptor connector according to an example of the present technology.

Figure 11B:
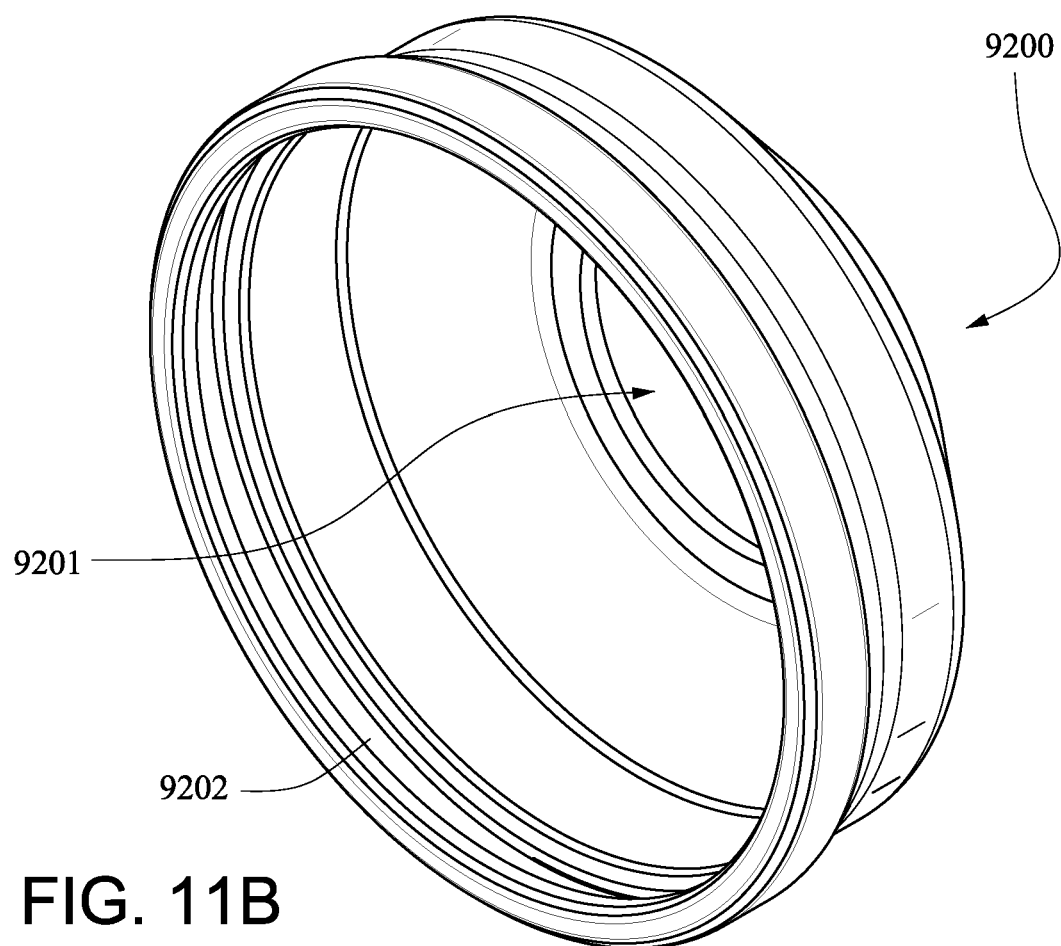

FIG. 11B shows another perspective view of a vent adaptor connector according to an example of the present technology.

Figure 11C:
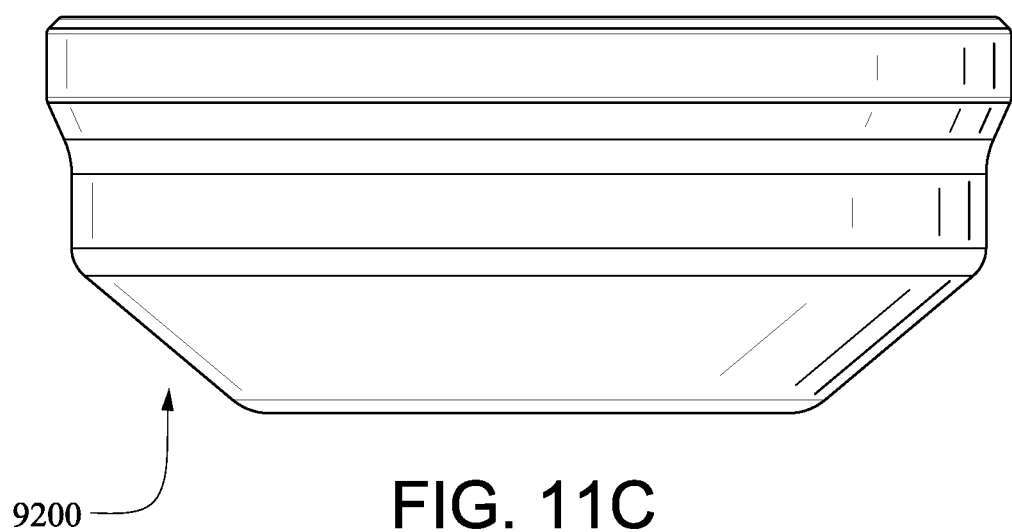

FIG. 11C shows a side view of a vent adaptor connector according to an example of the present technology.

Figure 11D:
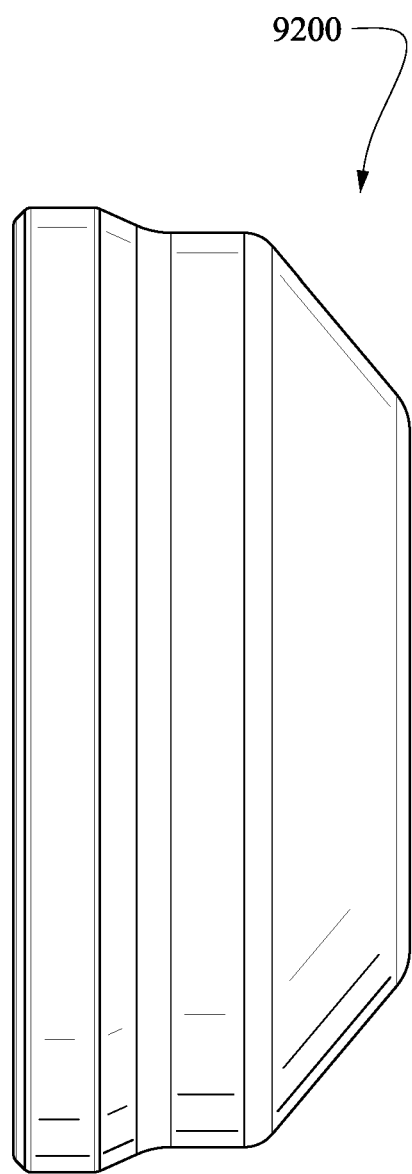

FIG. 11D shows another side view of a vent adaptor connector according to an example of the present technology.

Figure 11E:
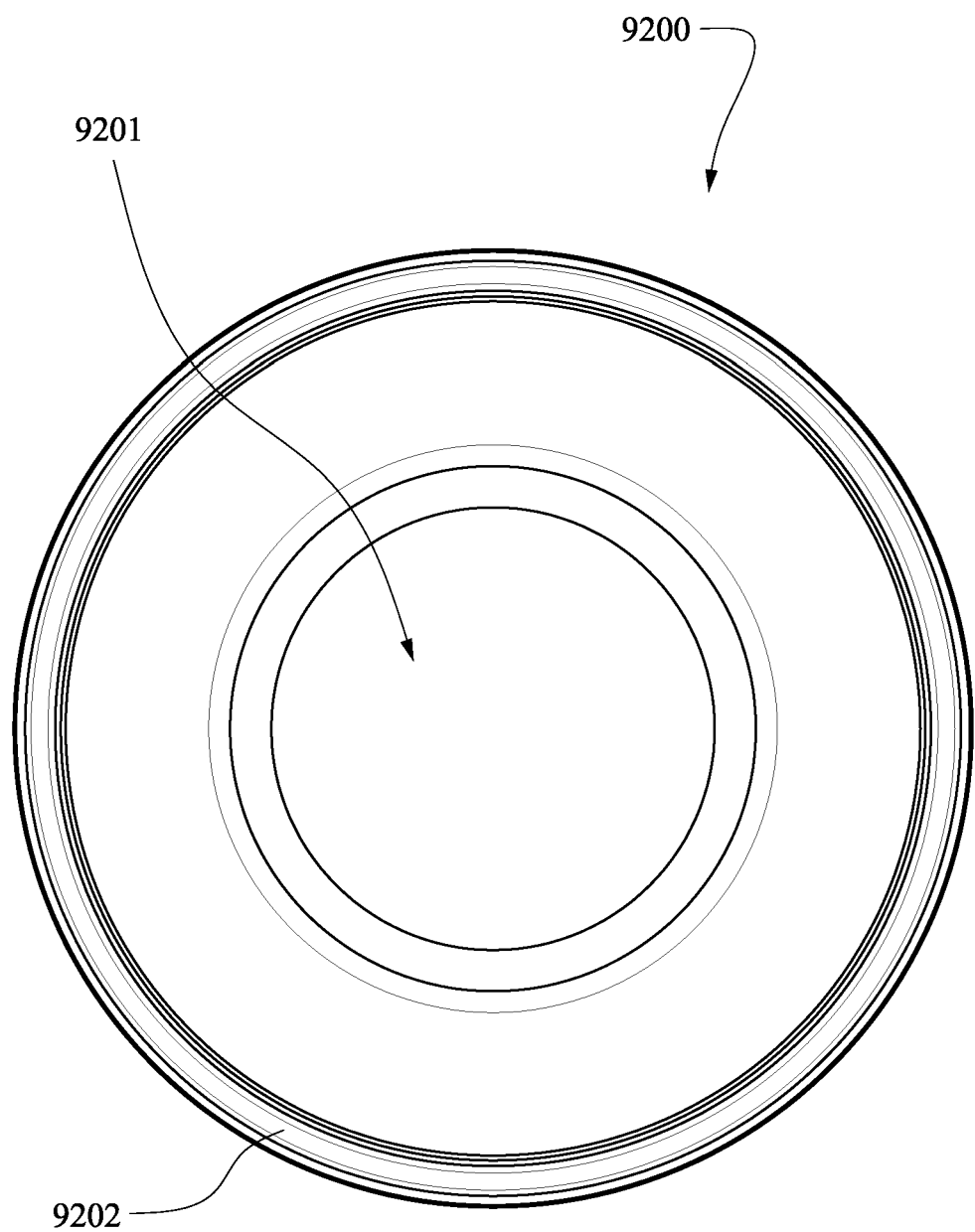

FIG. 11E shows a bottom view of a vent adaptor connector according to an example of the present technology.

Figure 12A:
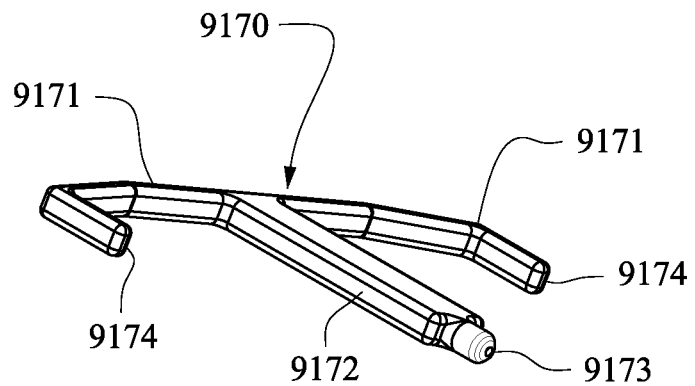

FIG. 12A shows a perspective view of a heat and moisture exchanger (HME) clip according to an example of the present technology.

Figure 12B:
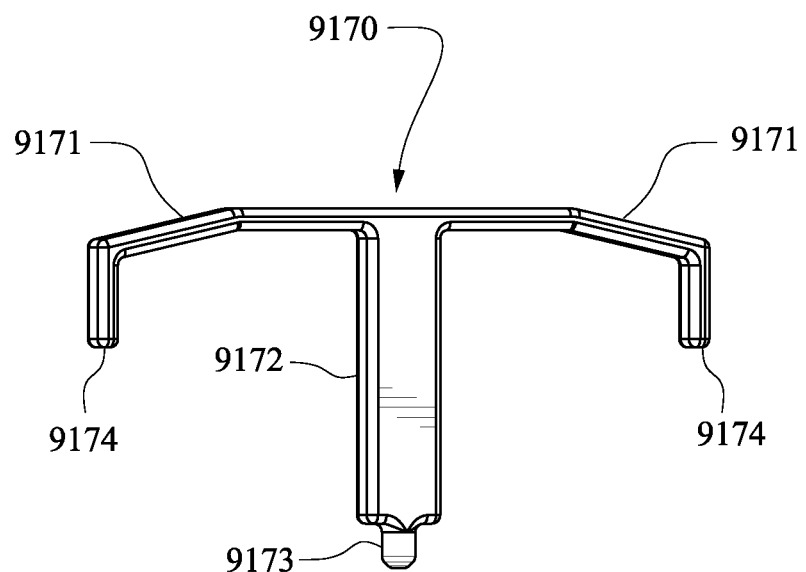

FIG. 12B shows a side view of a heat and moisture exchanger (HME) clip according to an example of the present technology.

Figure 12C:
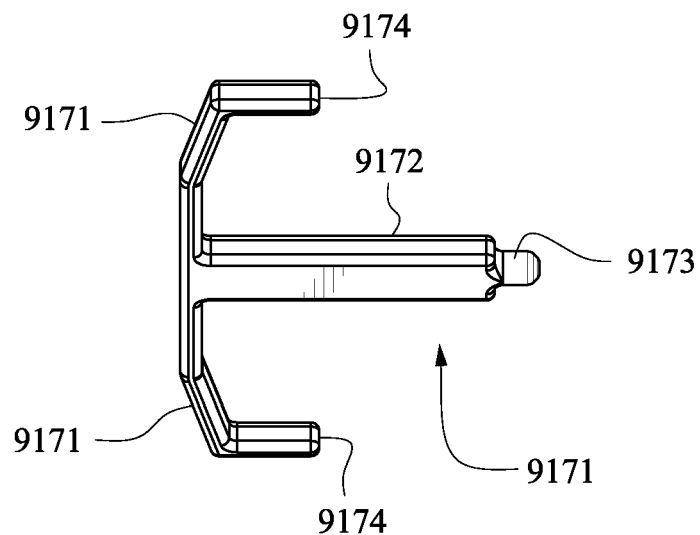

FIG. 12C shows another side view of a heat and moisture exchanger (HME) clip according to an example of the present technology.

Figure 12D:
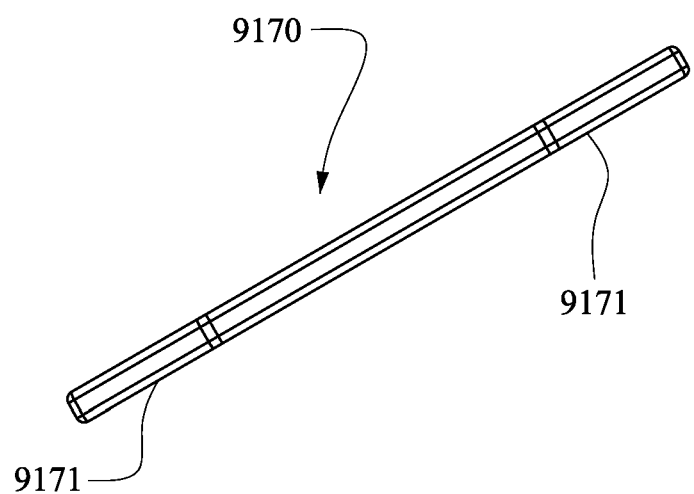

FIG. 12D shows another side view of a heat and moisture exchanger (HME) clip according to an example of the present technology.

Figure 13A:
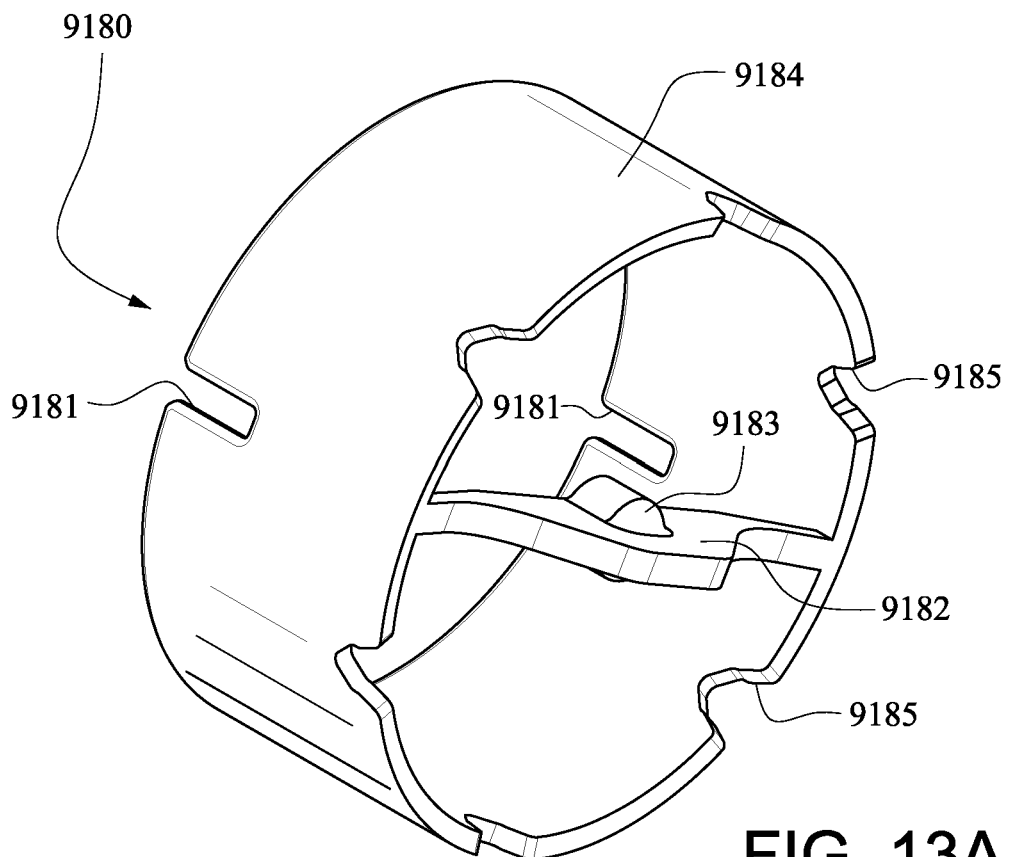

FIG. 13A shows a perspective view of a heat and moisture exchanger (HME) housing according to an example of the present technology.

Figure 13B:
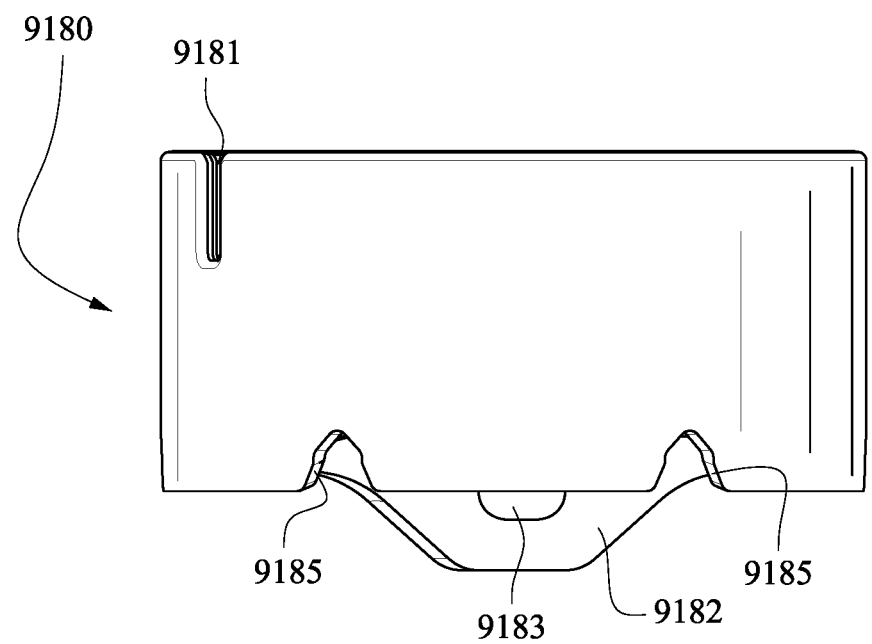

FIG. 13B shows a side view of a heat and moisture exchanger (HME) housing according to an example of the present technology.

Figure 13C:
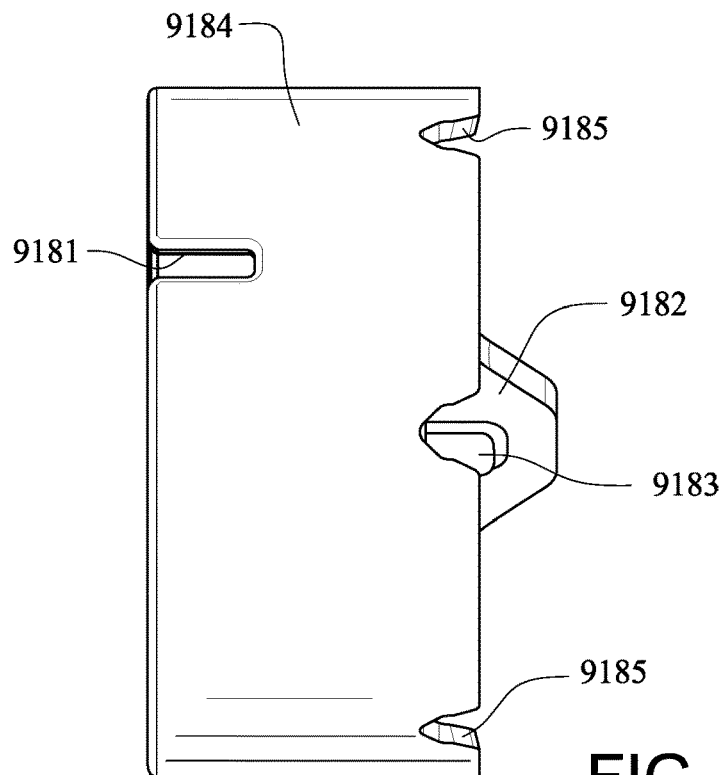

FIG. 13C shows another side view of a heat and moisture exchanger (HME) housing according to an example of the present technology.

Figure 13D:
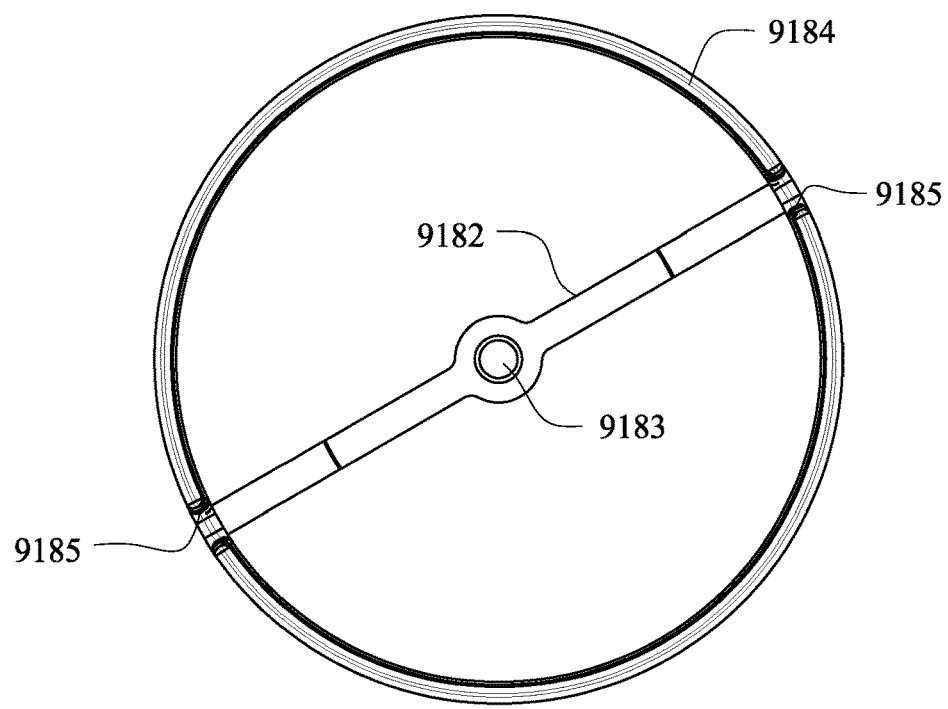

FIG. 13D shows a top view of a heat and moisture exchanger (HME) housing according to an example of the present technology.

Figure 14A:
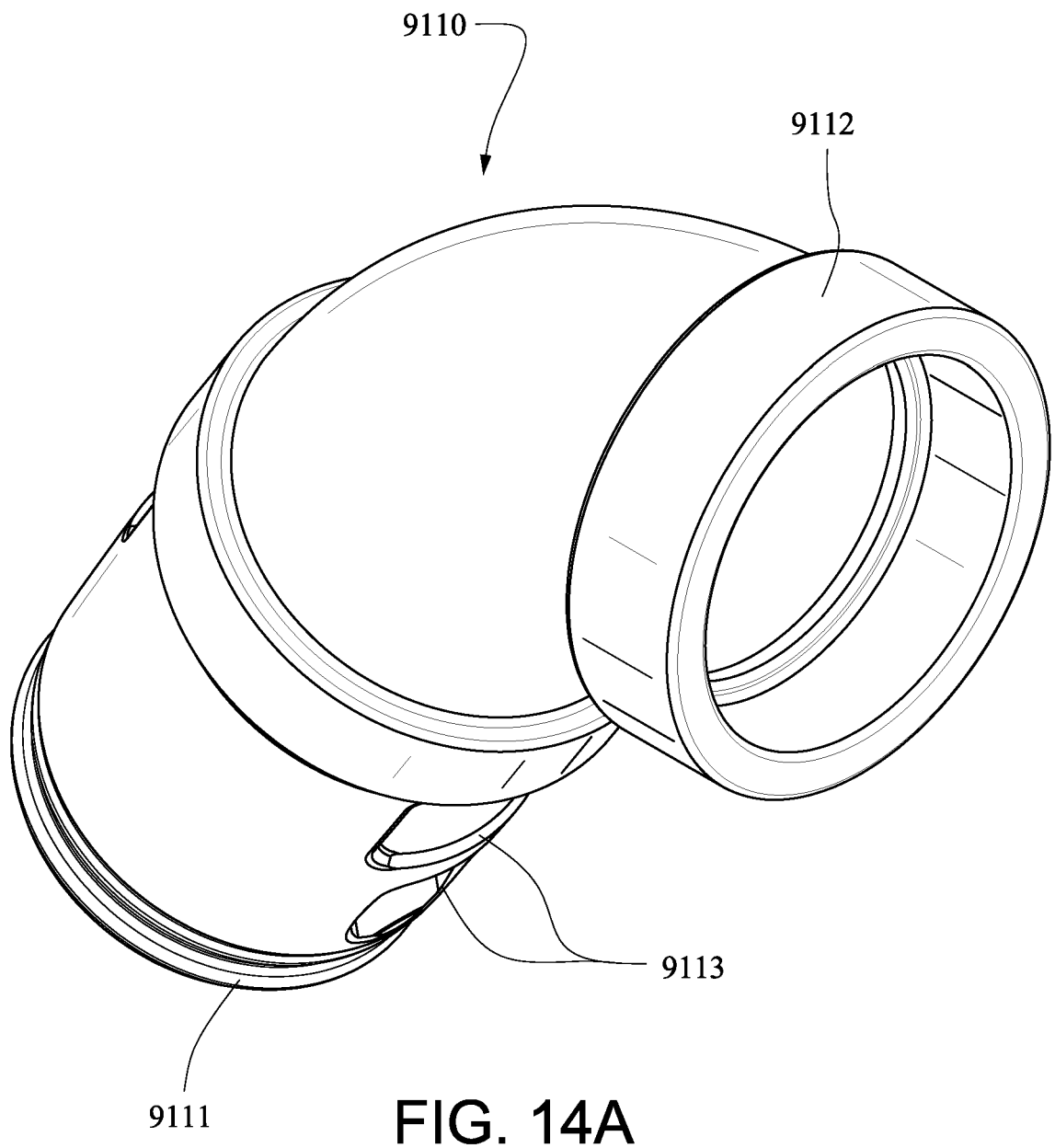

FIG. 14A shows a perspective view of a conduit connector according to an example of the present technology.

Figure 14B:
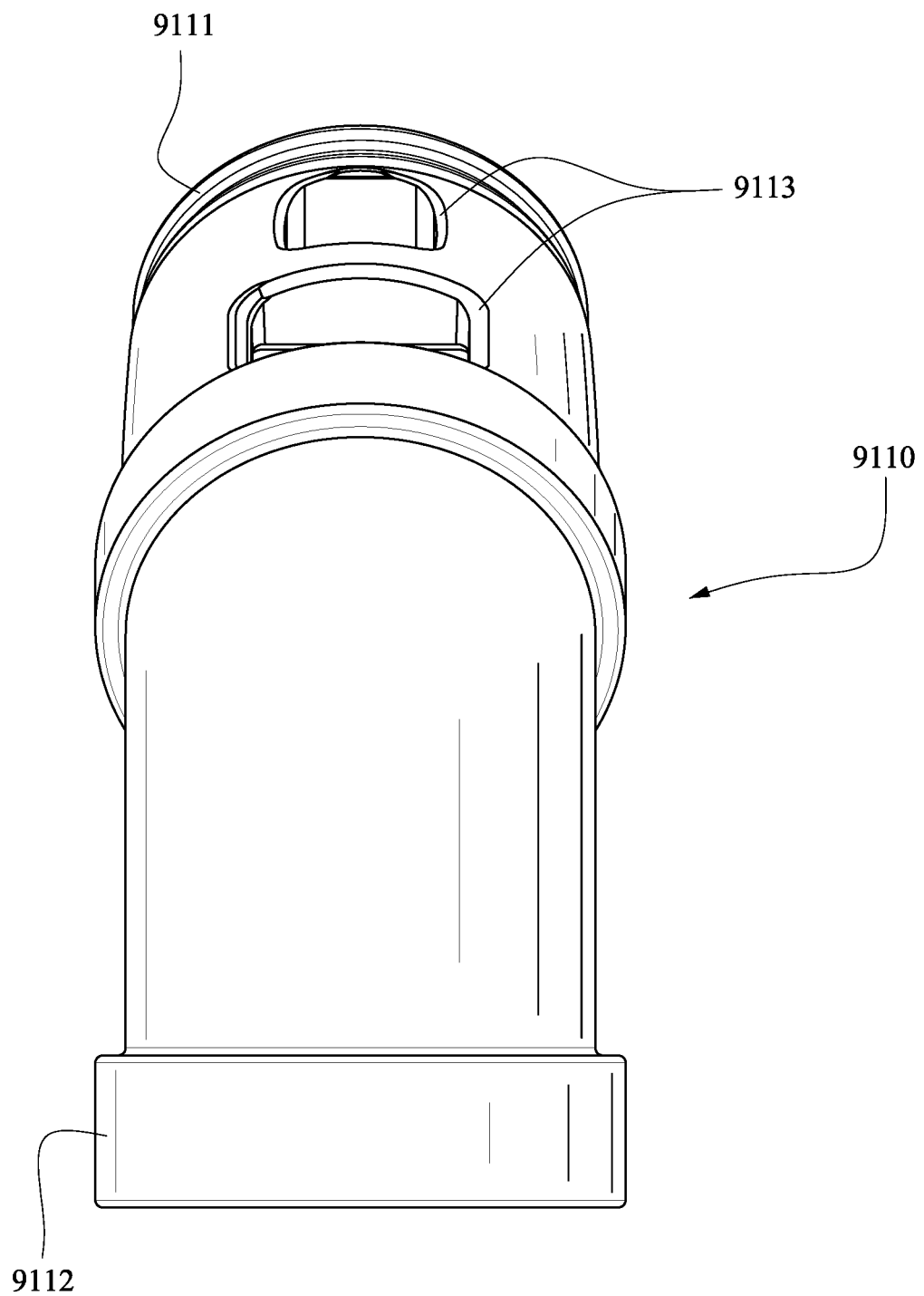

FIG. 14B shows a top view of a conduit connector according to an example of the present technology.

Figure 14C:
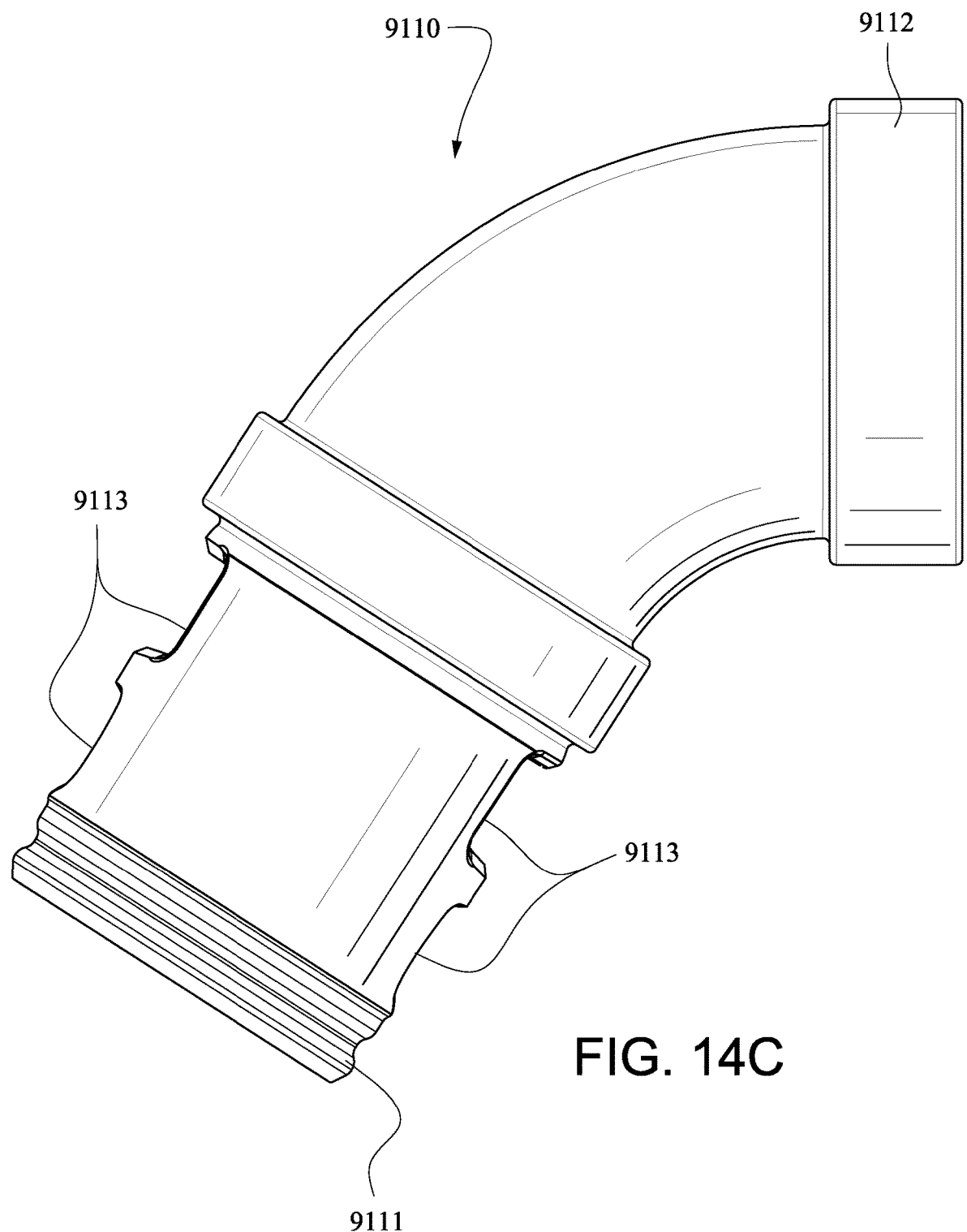

FIG. 14C shows a side view of a conduit connector according to an example of the present technology.

Figure 14D:
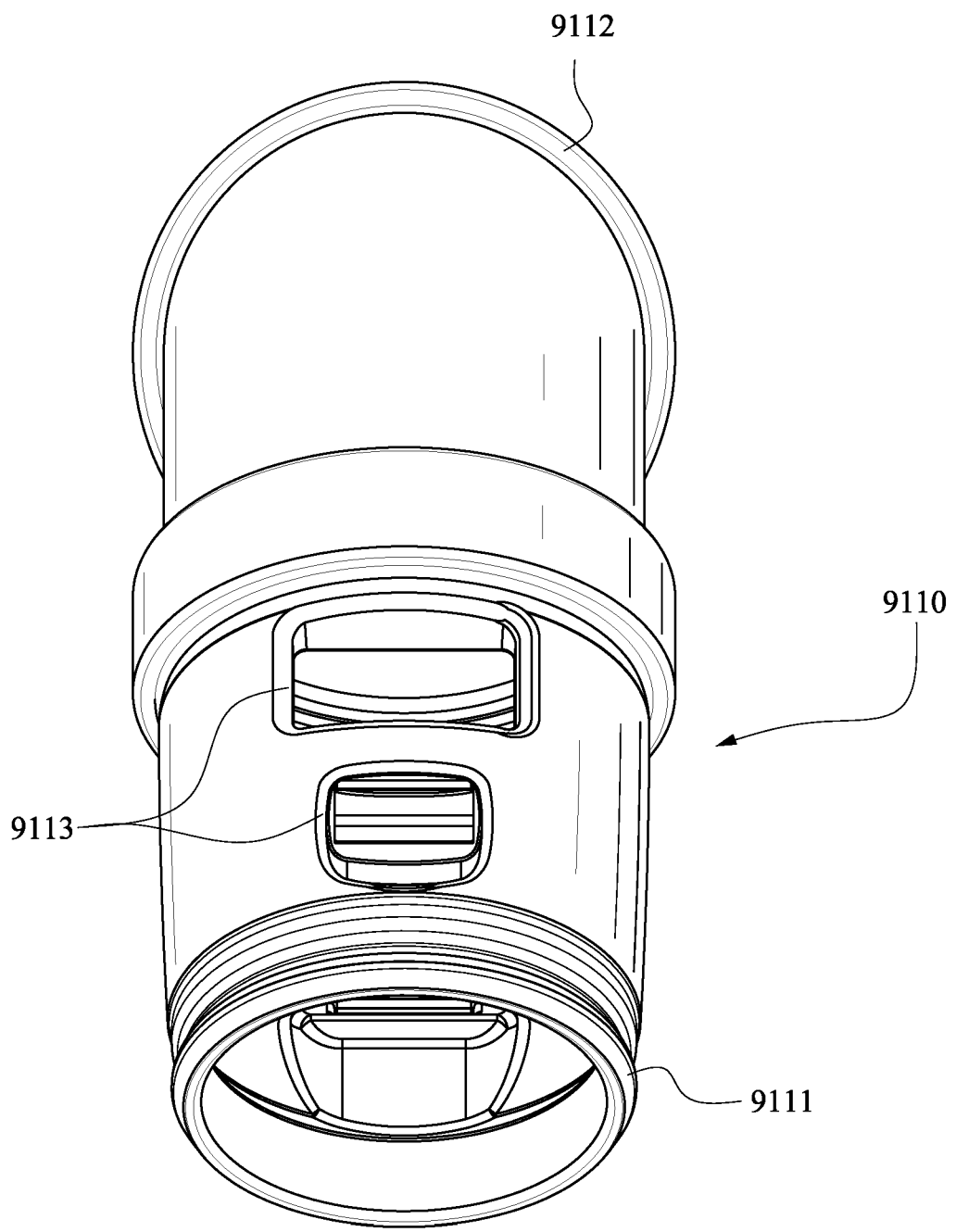

FIG. 14D shows a front view of a conduit connector according to an example of the present technology.

Figure 15A:
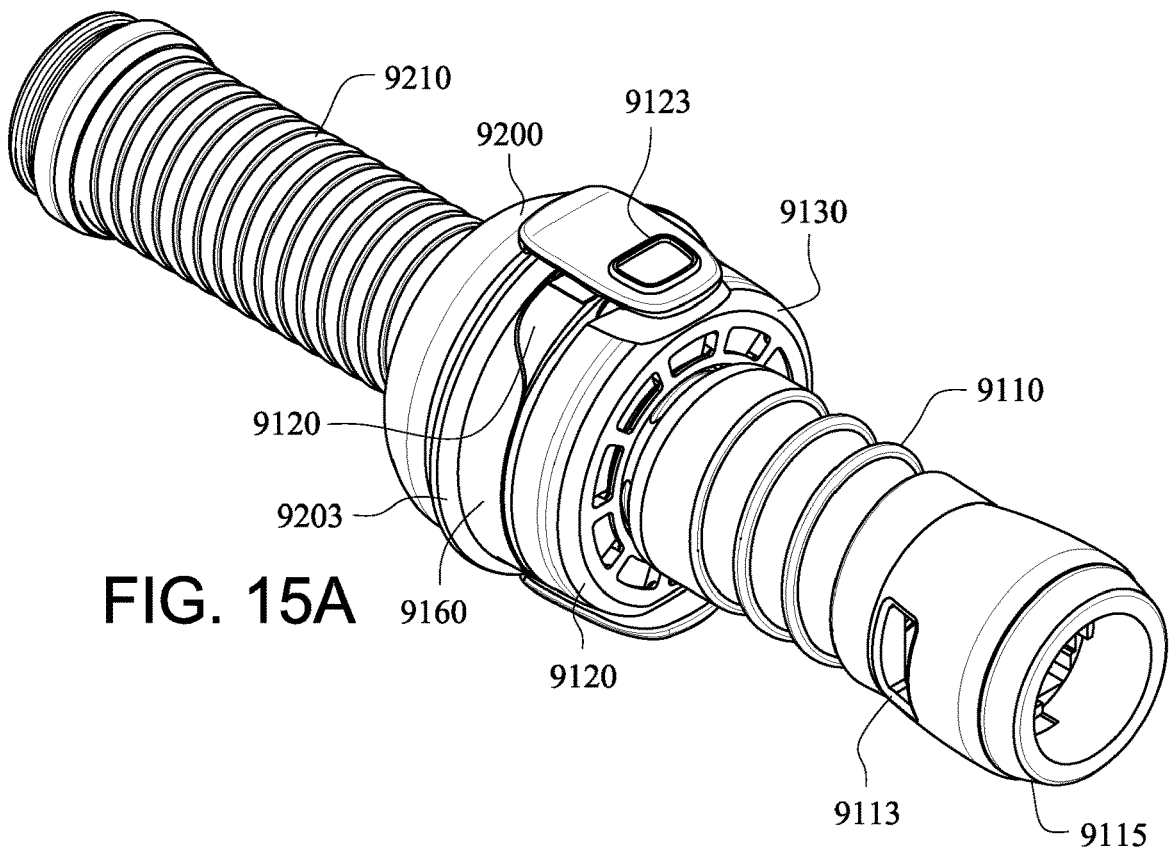

FIG. 15A shows a perspective view of a vent adaptor according to an example of the present technology.

Figure 15B:
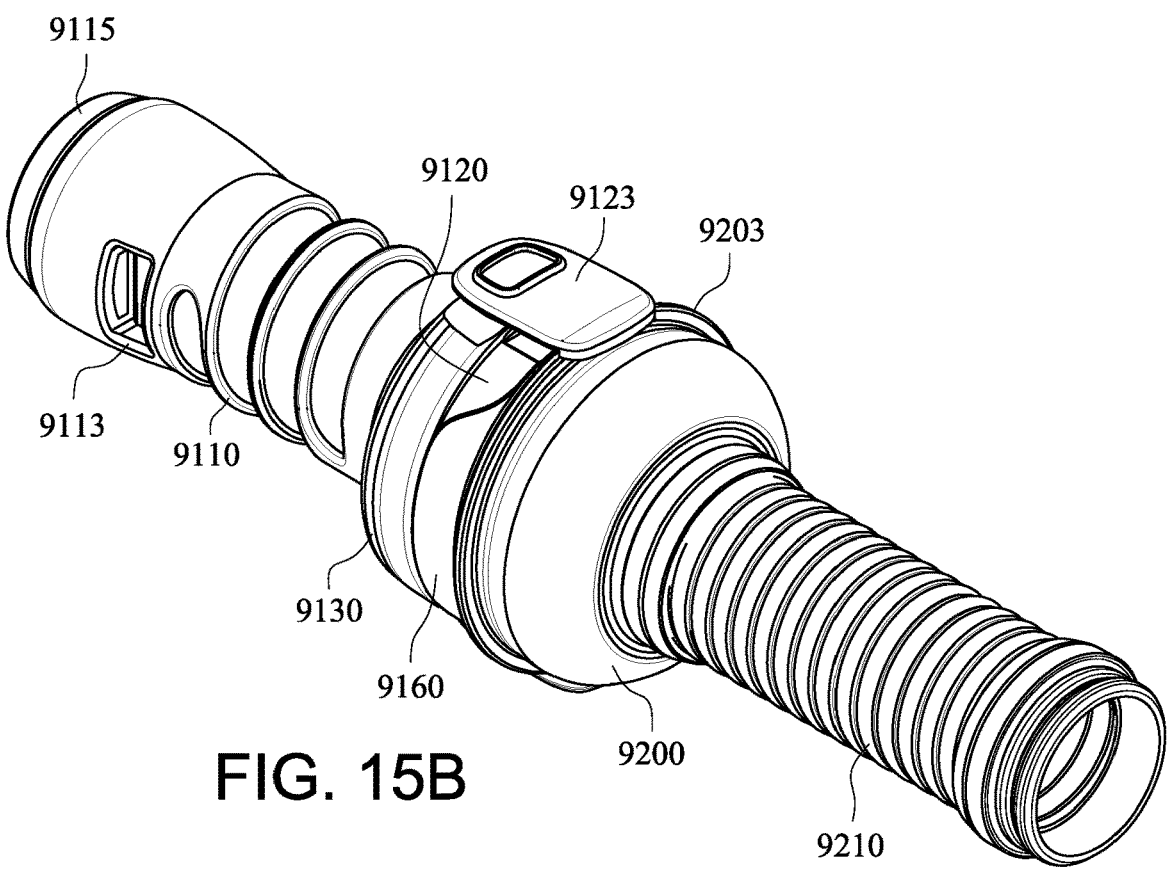

FIG. 15B shows another perspective view of a vent adaptor according to an example of the present technology.

FIG. 15C shows an exploded view of a vent adaptor according to an example of the present technology.

Figure 15D:
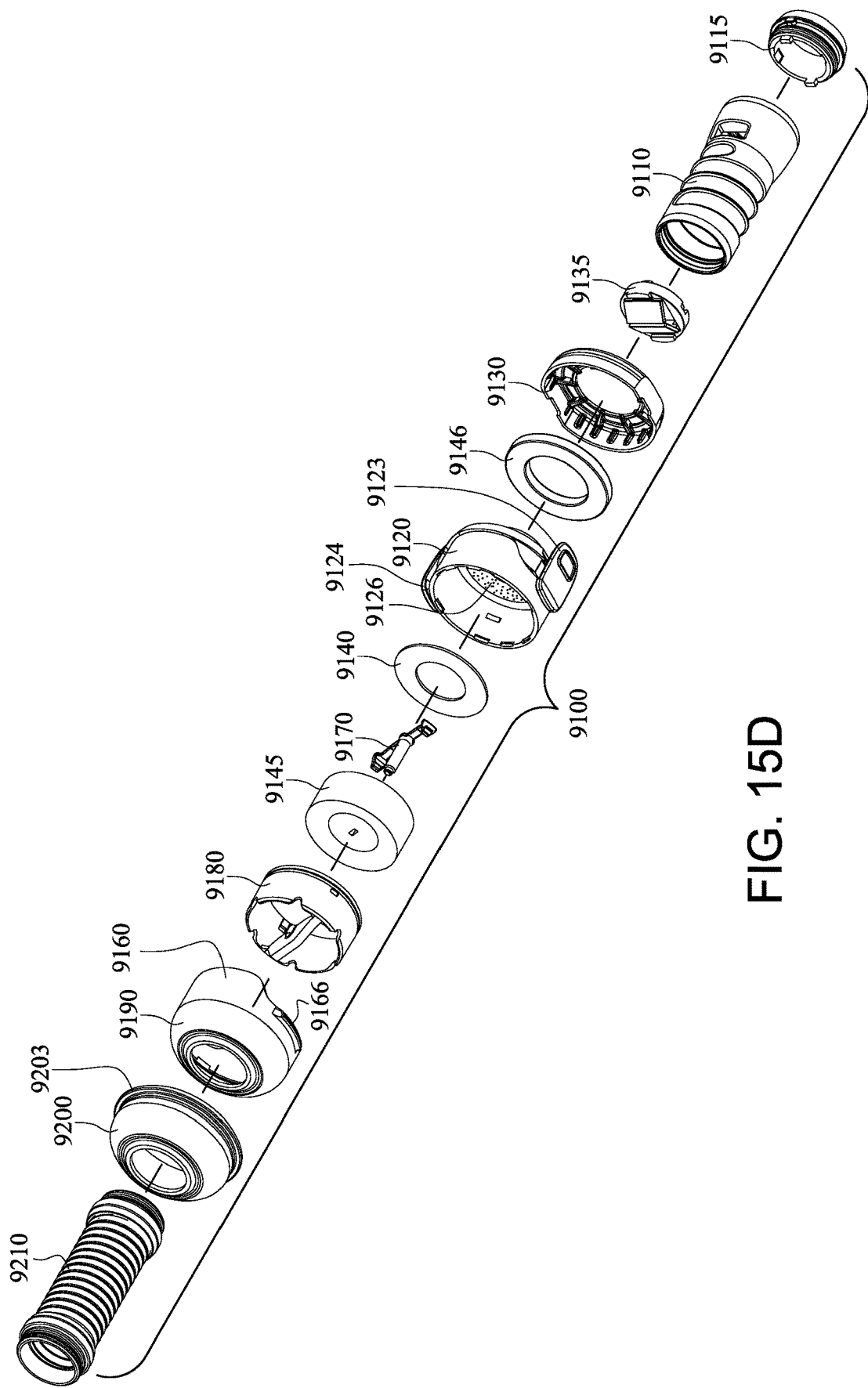

FIG. 15D shows an exploded view of a vent adaptor according to an example of the present technology.

Figure 15E:
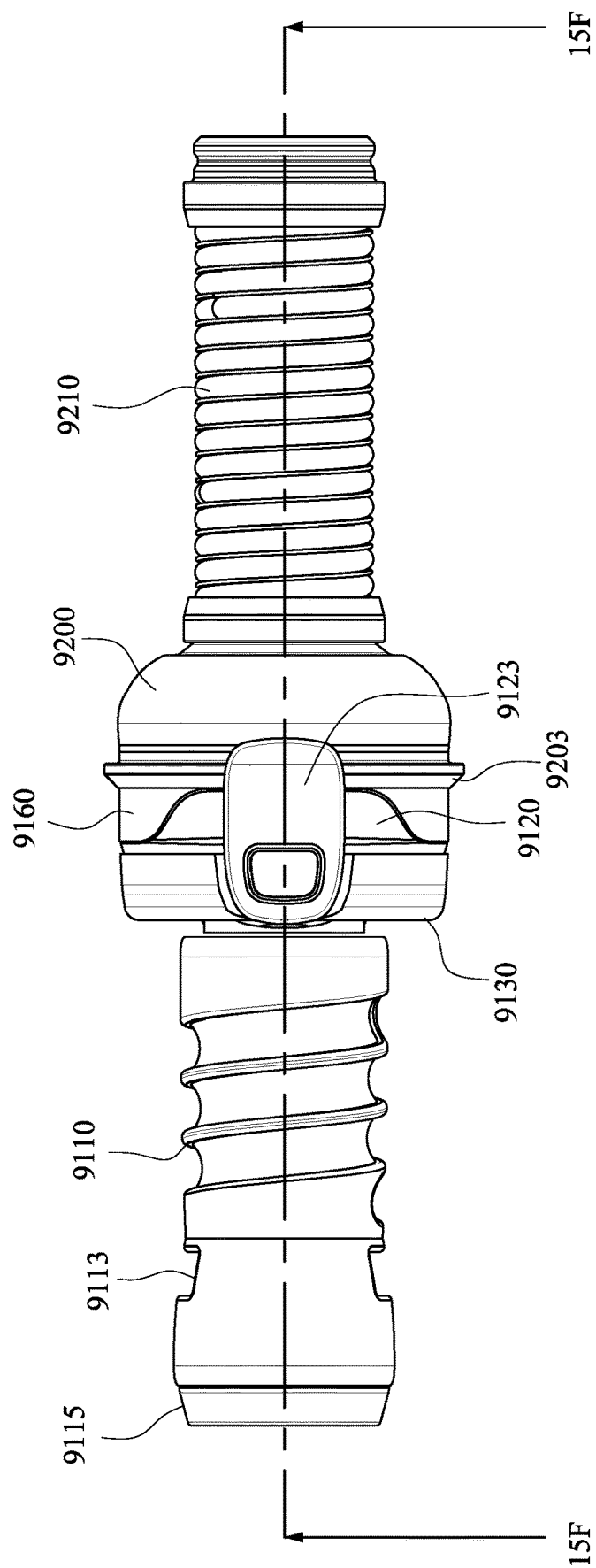

FIG. 15E shows a side view of a vent adaptor according to an example of the present technology.

Figure 15F:
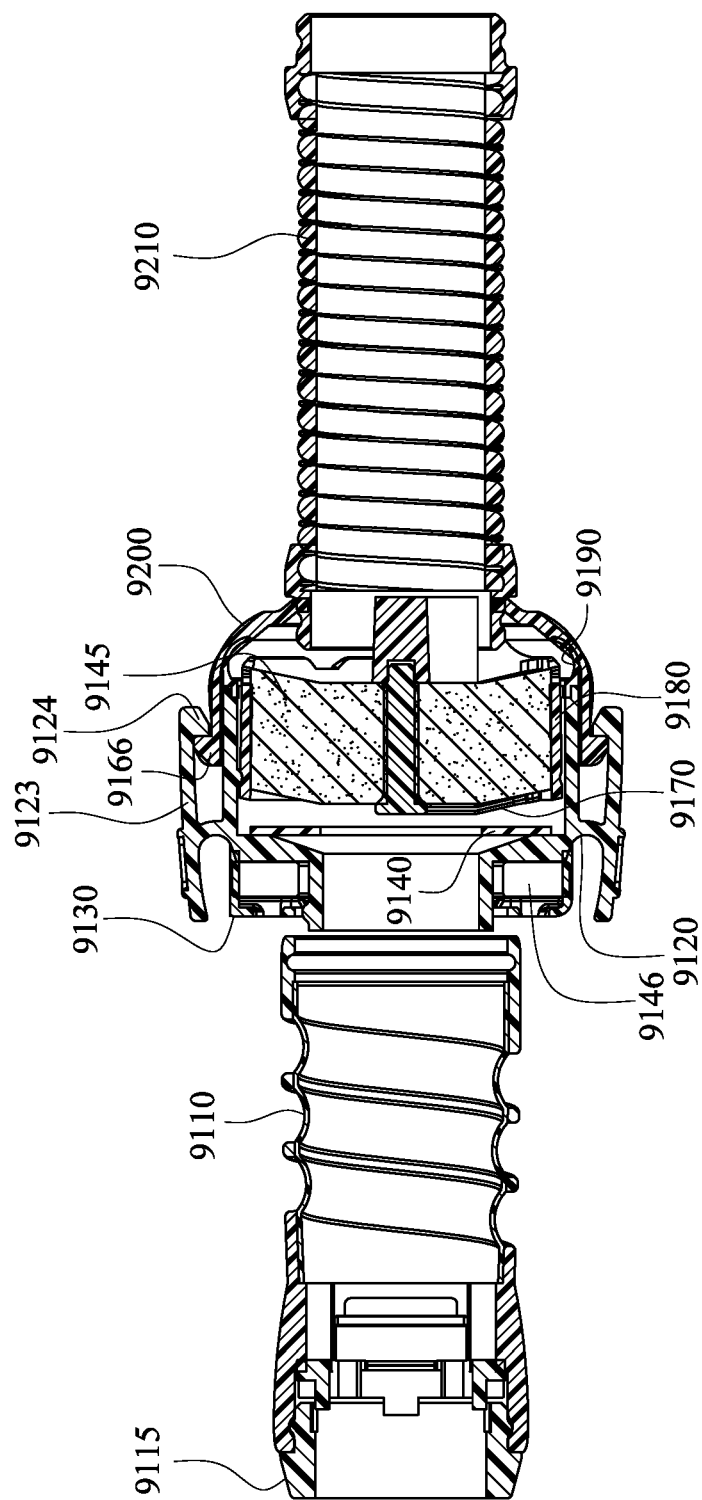

FIG. 15F shows a cross-section view of a vent adaptor according to an example of the present technology taken through line 15F-15F of FIG. 15B.

Figure 16:
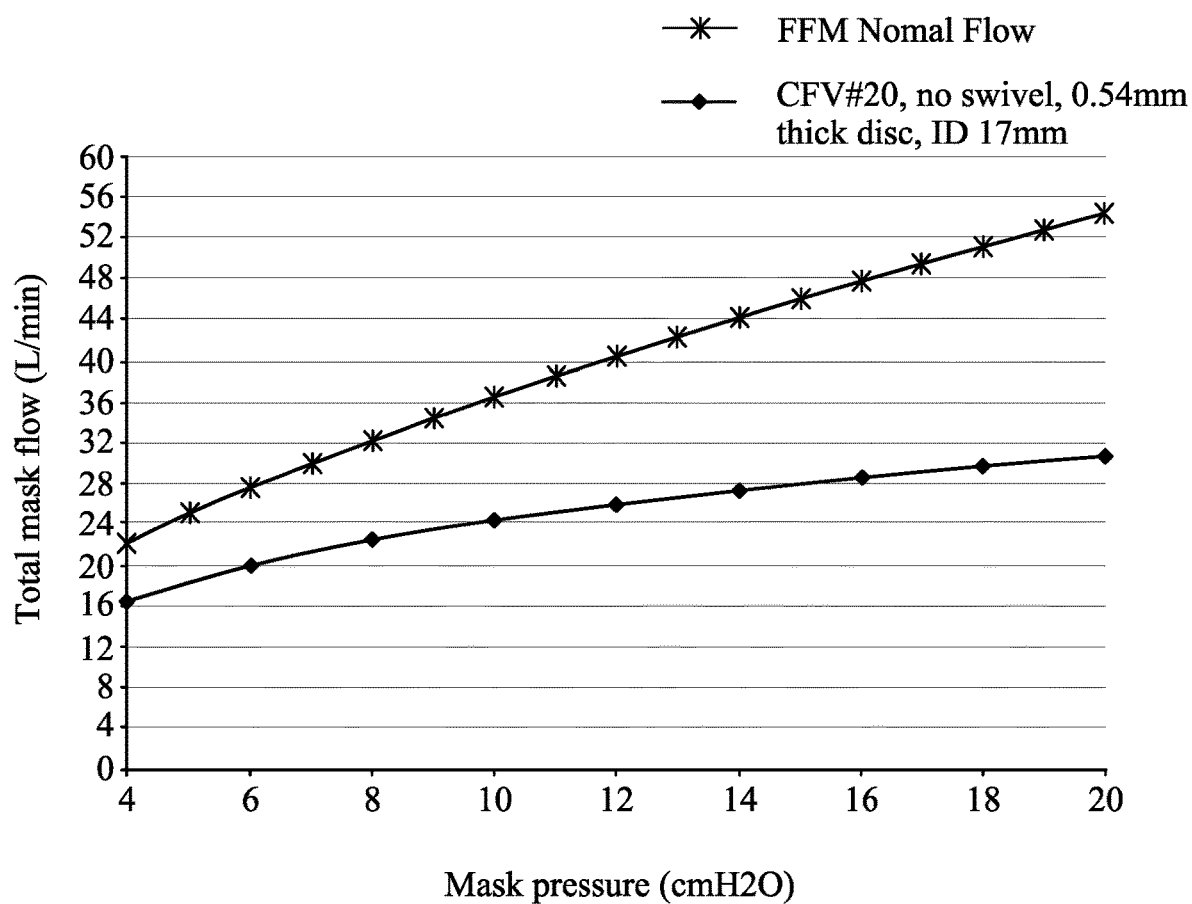

FIG. 16 shows a graph of vent flow from a full face mask compared to vent flow from a constant flow vent (CFV) according to the present technology over a range of therapeutic pressures.

Figure 17:
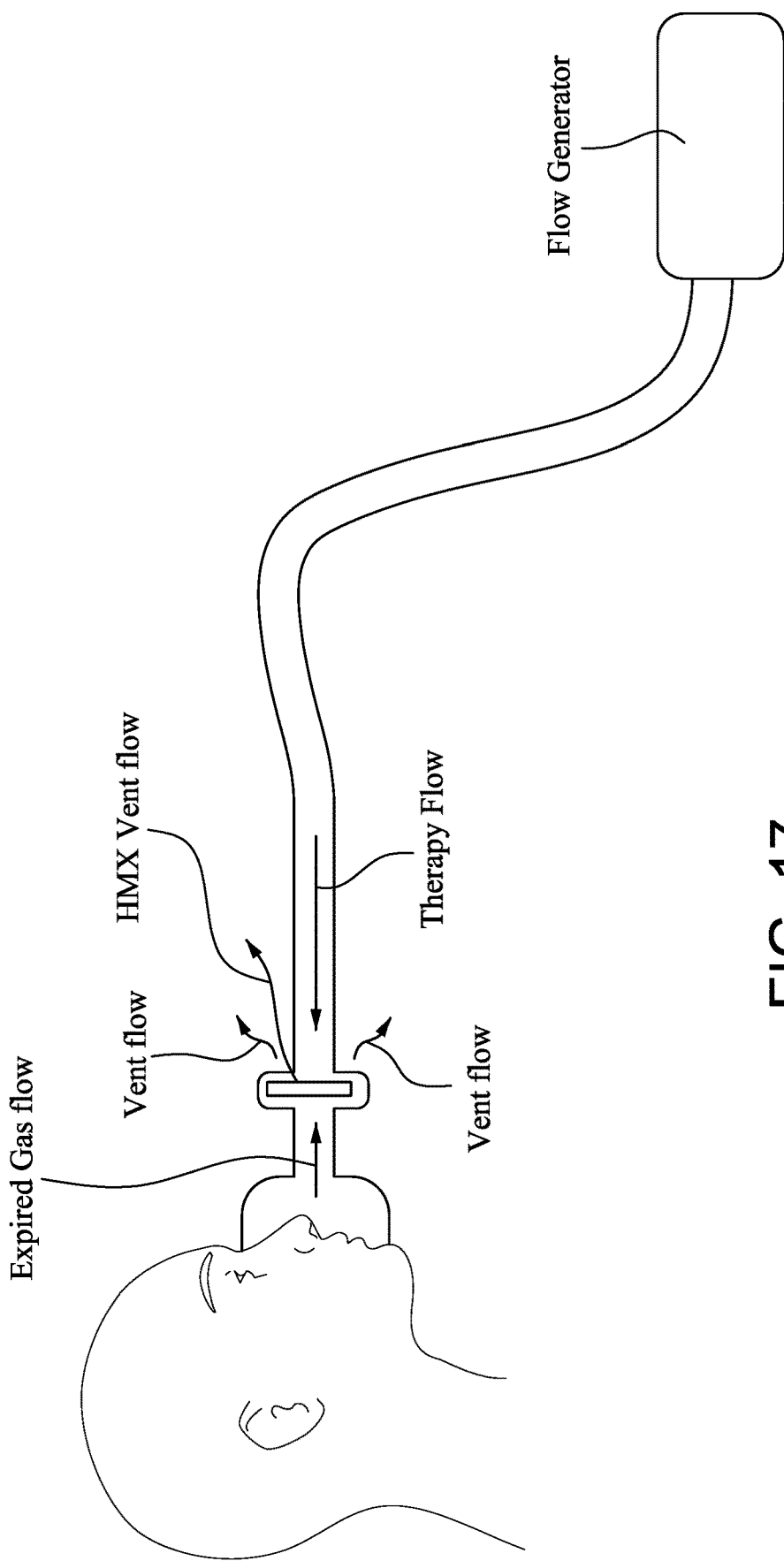

FIG. 17 shows a diagram of a patient receiving therapy according to an example of the present technology.

Figure 18:
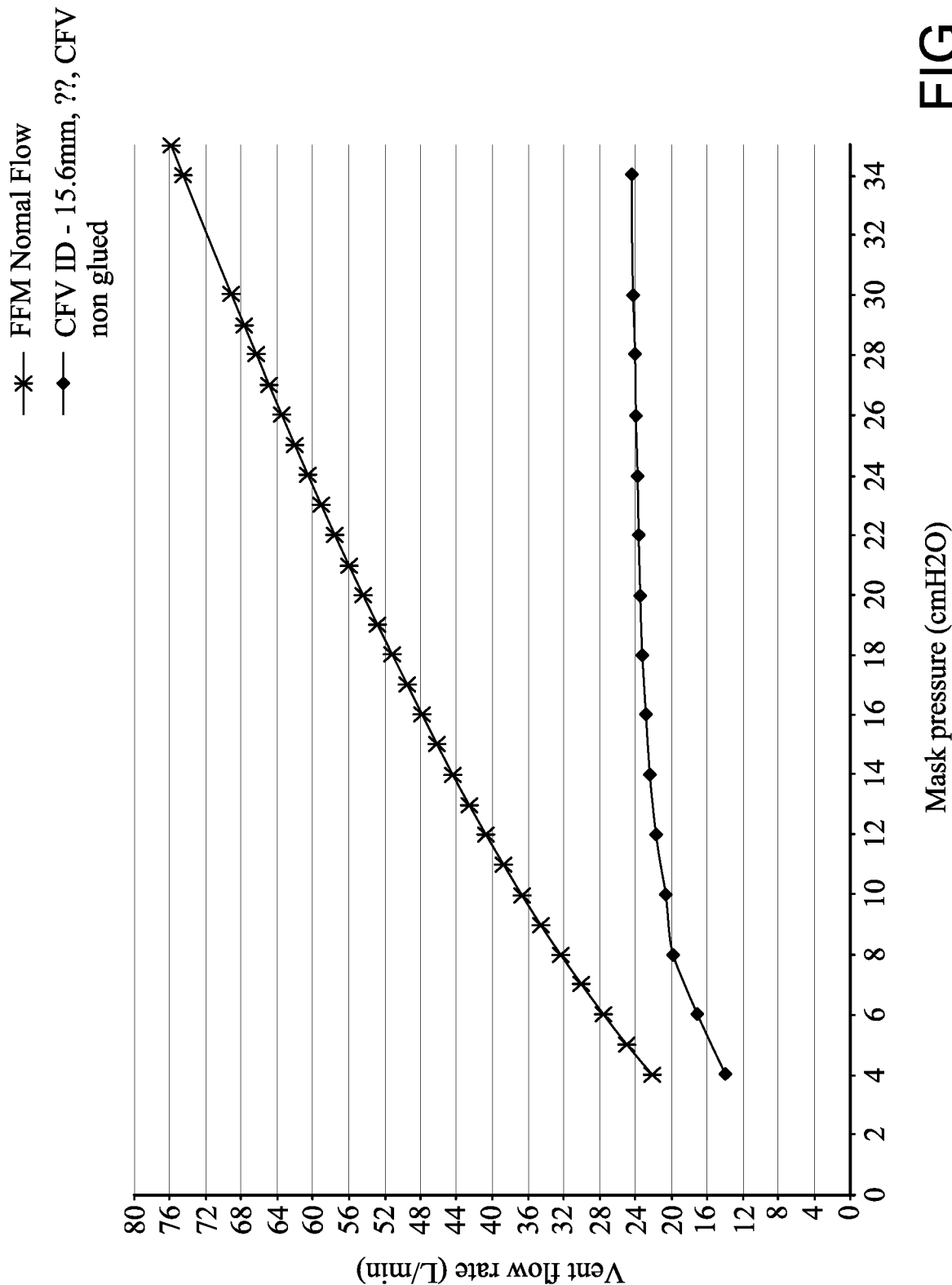

FIG. 18 shows a graph of vent flow from a full face mask compared to vent flow from a constant flow vent (CFV) according to the present technology over a range of therapeutic pressures.

Figure 19:
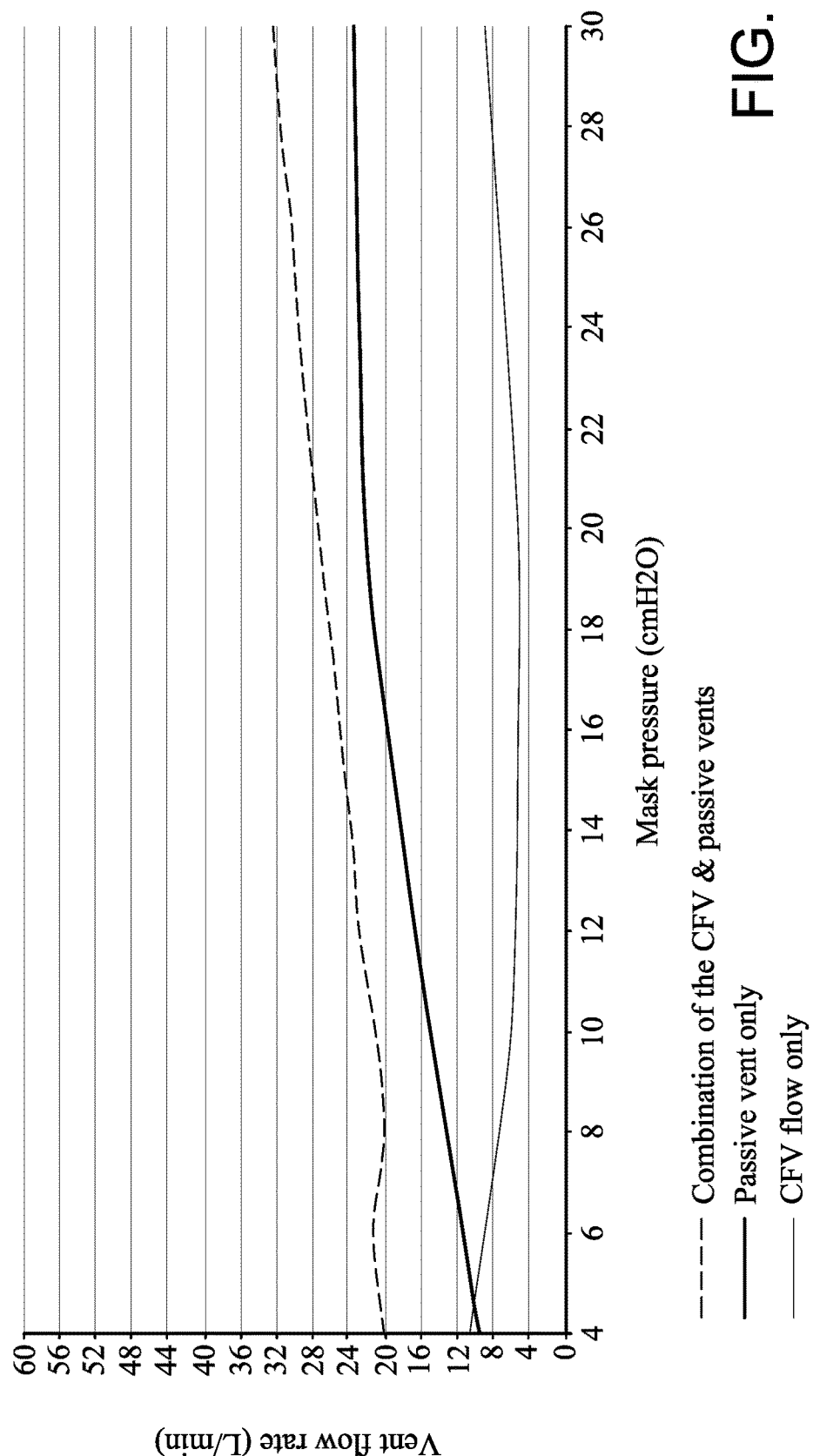

FIG. 19 shows a graph of vent flow from a constant flow vent (CFV) only, from a passive vent only, and a combination of both according to the present technology over a range of therapeutic pressures.

Figure 20:
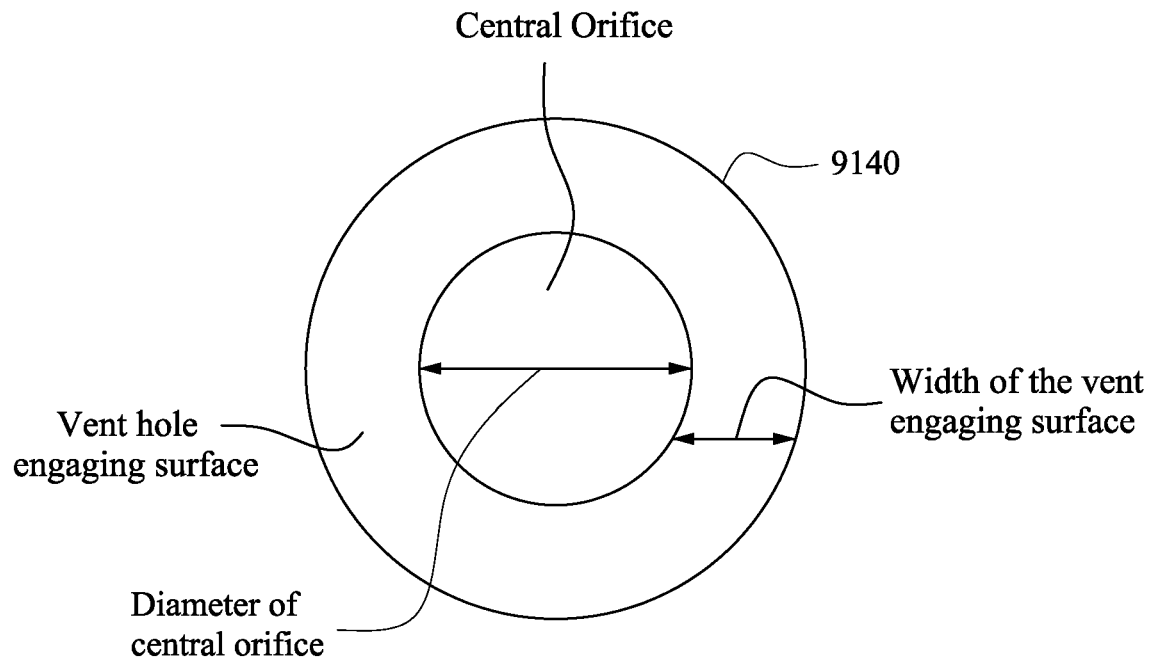

FIG. 20 shows an example of a constant flow vent (CFV) membrane according to an example of the present technology.

Figure 21A:
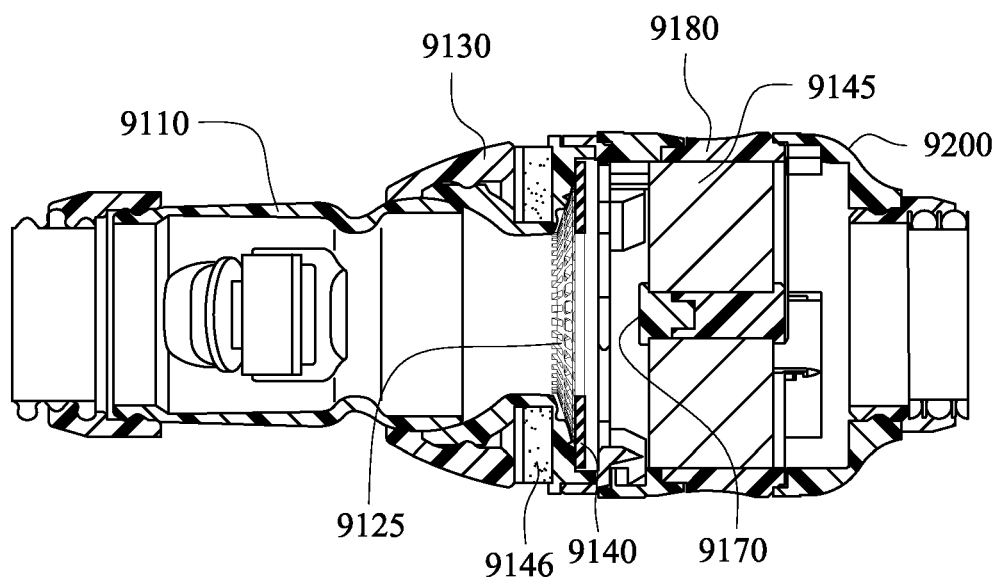

FIG. 21A shows a cross-section view of a vent adaptor according to an example of the present technology.

Figure 21B:
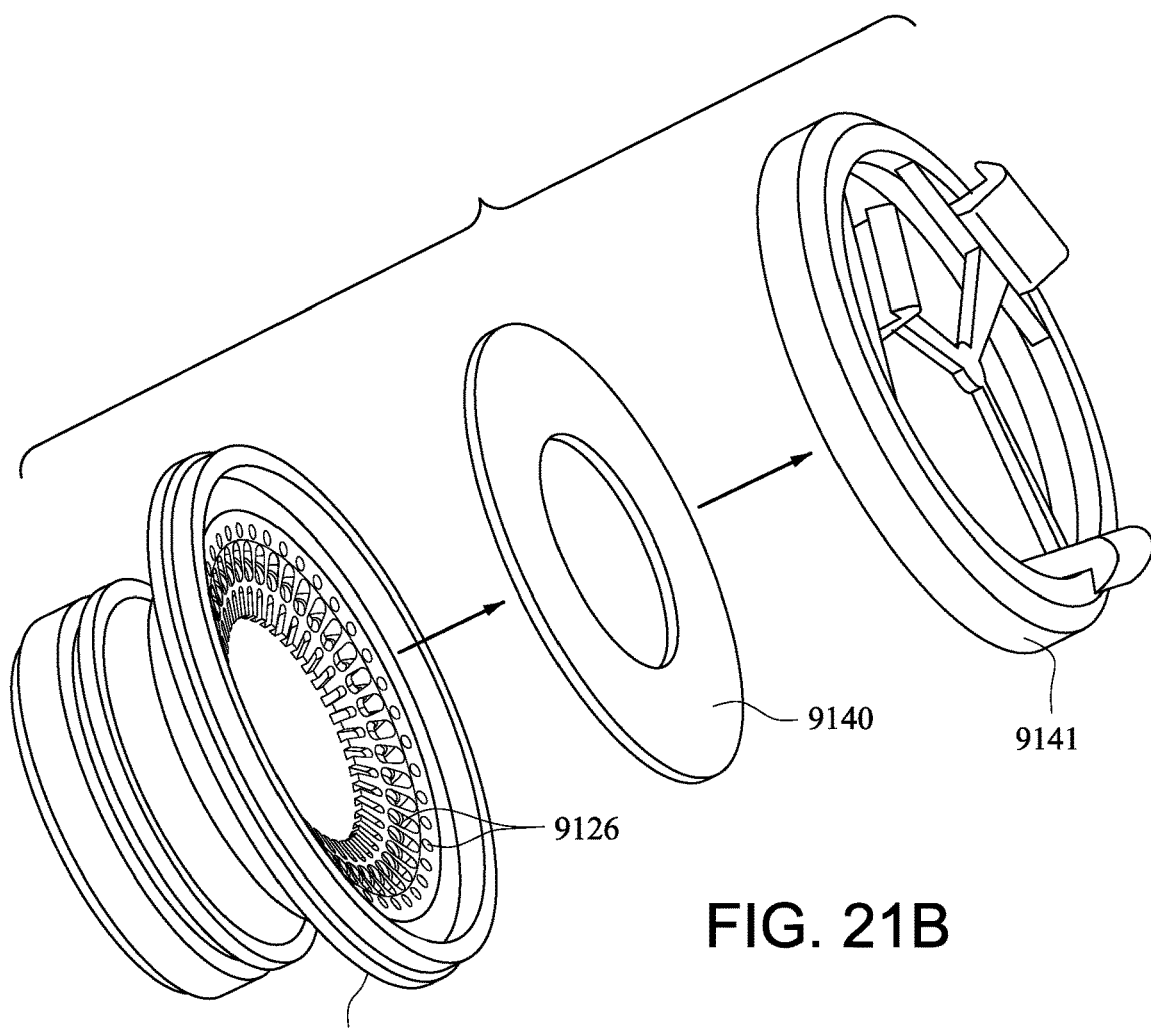

FIG. 21B shows an exploded view of a constant flow vent (CFV) of a vent adaptor according to an example of the present technology.

Figure 21C:
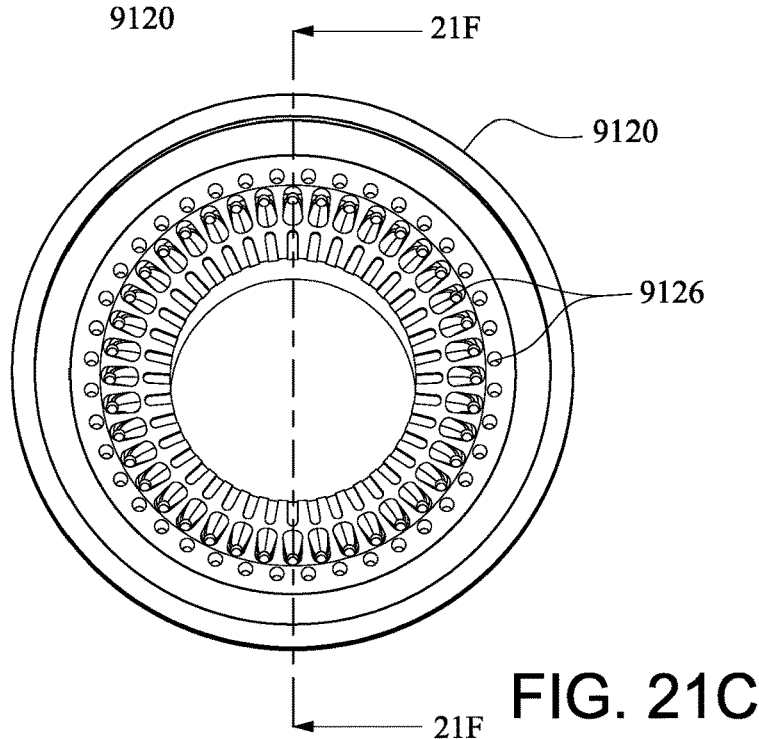

FIG. 21C shows a rear view of a constant flow vent (CFV) of a vent adaptor according to an example of the present technology.

Figures 21D, 21E:
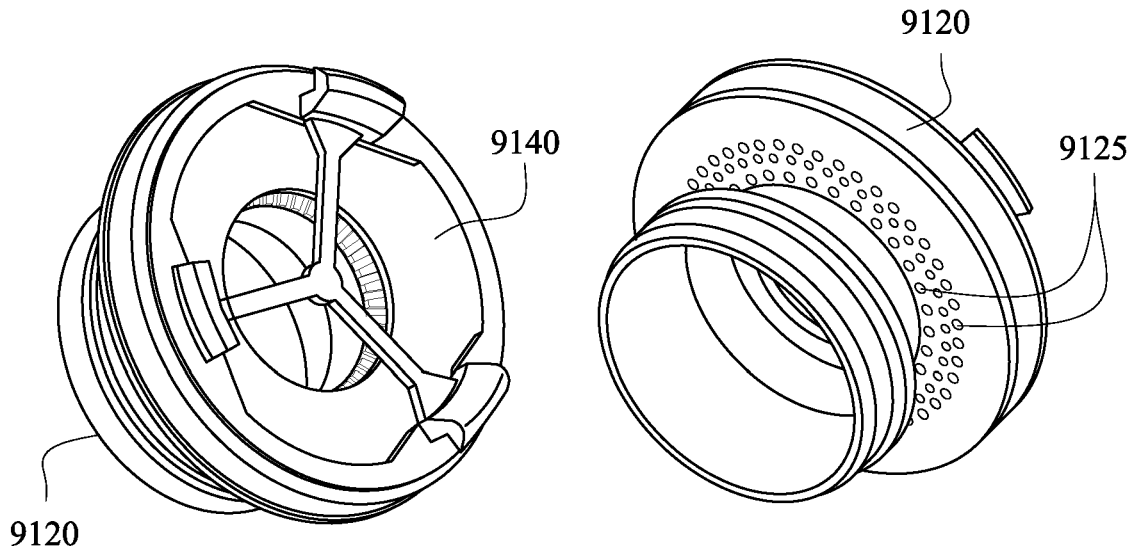

FIG. 21D shows a perspective view of a constant flow vent (CFV) of a vent adaptor according to an example of the present technology.

FIG. 21E shows another perspective view of a constant flow vent (CFV) of a vent adaptor according to an example of the present technology.

Figure 21F:
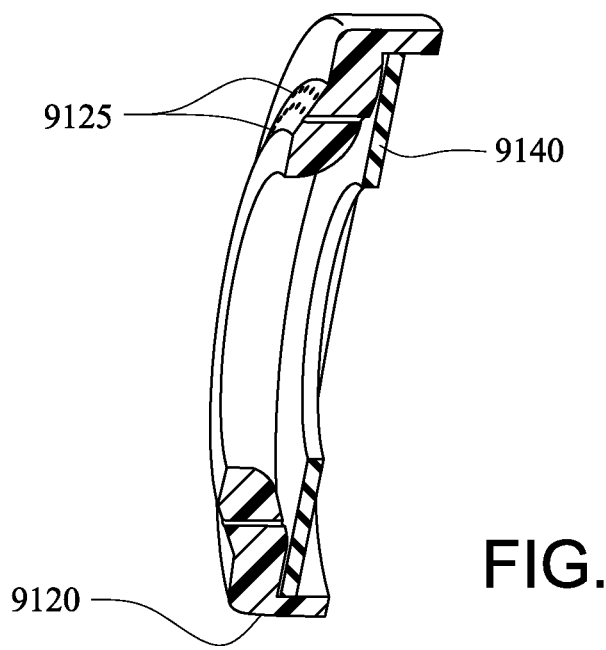

FIG. 21F shows a cross-section view of a constant flow vent (CFV) of a vent adaptor according to an example of the present technology.

FIG. 22 shows an exploded view of a vent adaptor according to an example of the present technology.

Figure 23:
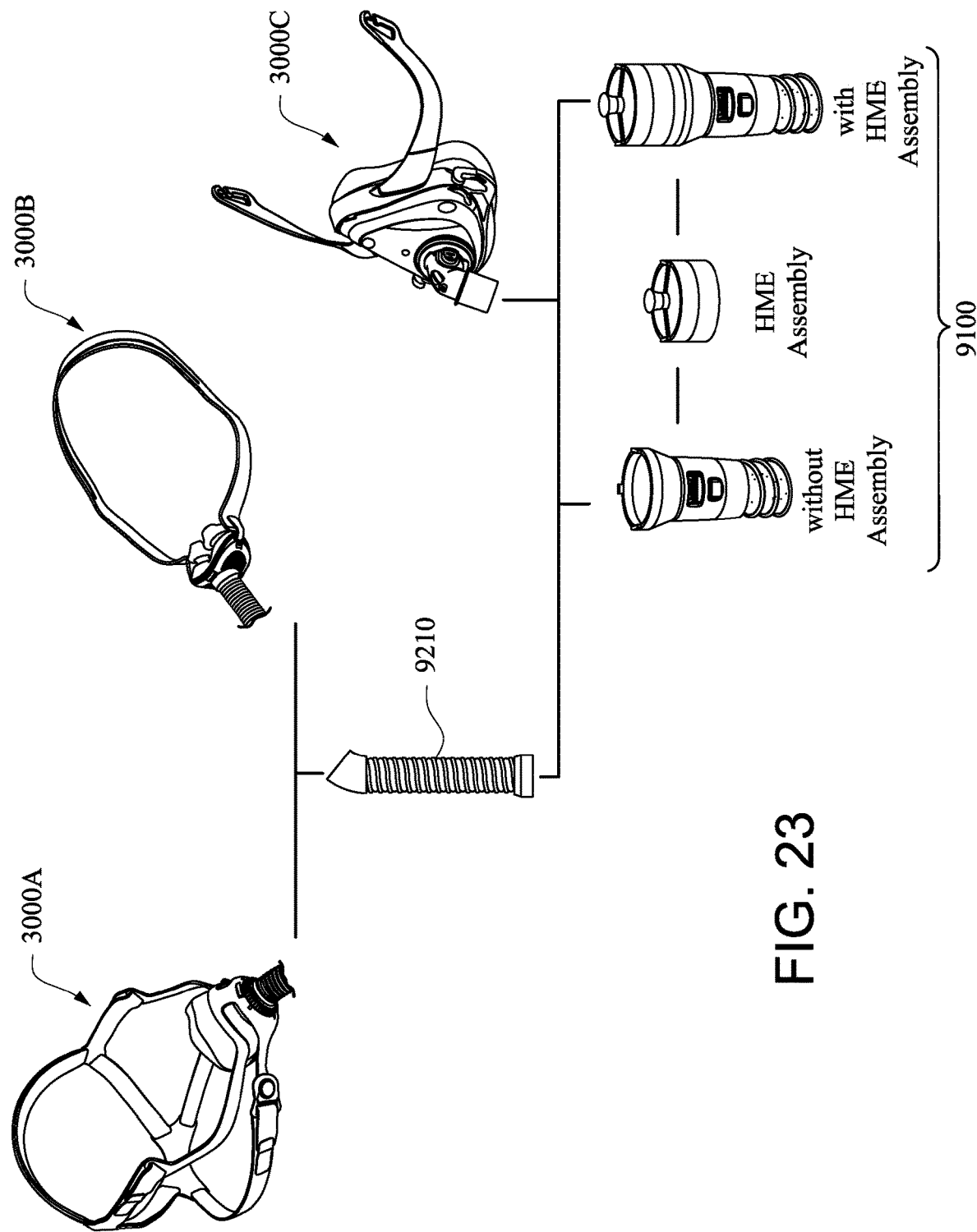

FIG. 23 shows a chart of exemplary patient interfaces according to the present technology.

Figure 24A:
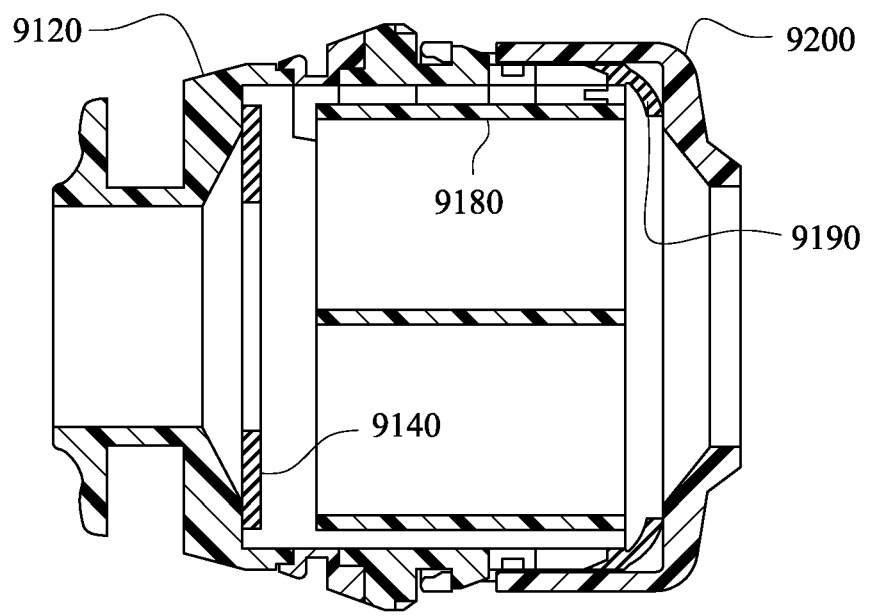

FIG. 24A shows a cross-section view of a vent adaptor according to an example of the present technology.

Figure 24B:
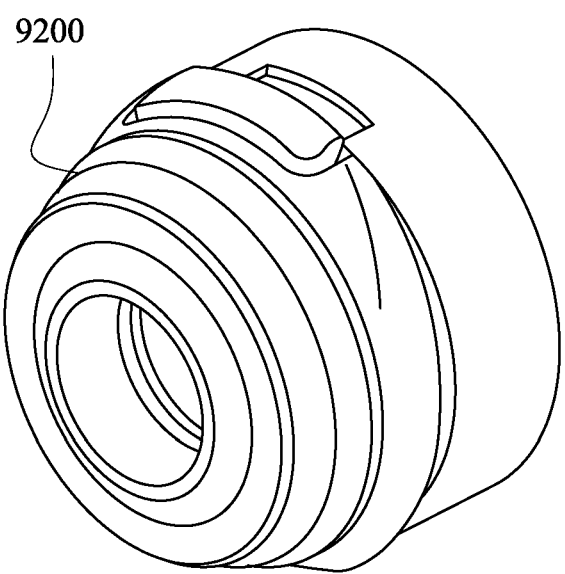

FIG. 24B shows a perspective view of a vent adaptor according to an example of the present technology.

Figure 25A:
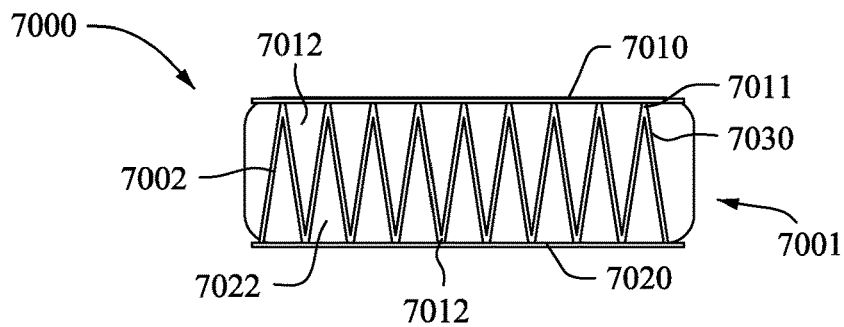

FIG. 25A shows a cross sectional view of a HME 7000 comprising a single layer 7001 in accordance with one aspect of the present technology.

Figure 25B:
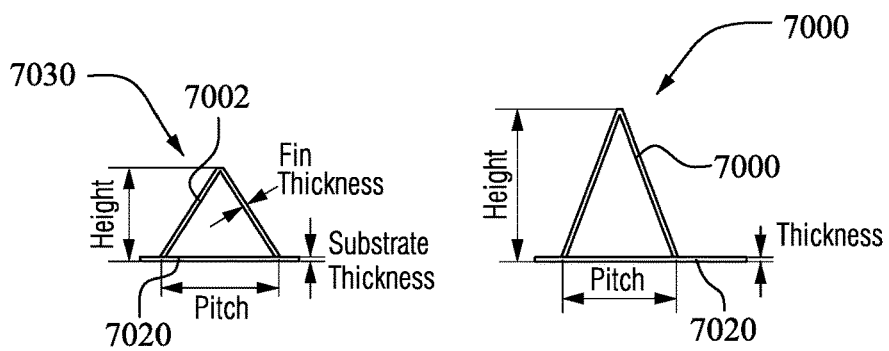

FIG. 25B shows examples of a single corrugation 7030 of a HME 7000 in accordance with one aspect of the present technology.

Figure 25C:
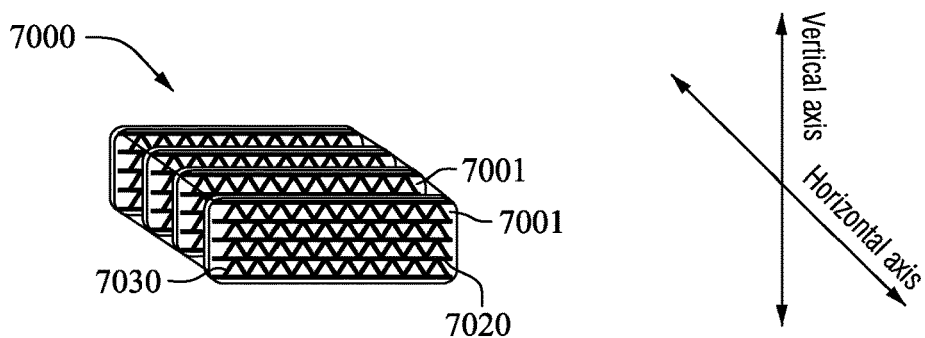

FIG. 25C is a schematic diagram showing a HME 7000 comprising a plurality of layers 7001 stacked along both a vertical and horizontal axis.

Figure 25D:
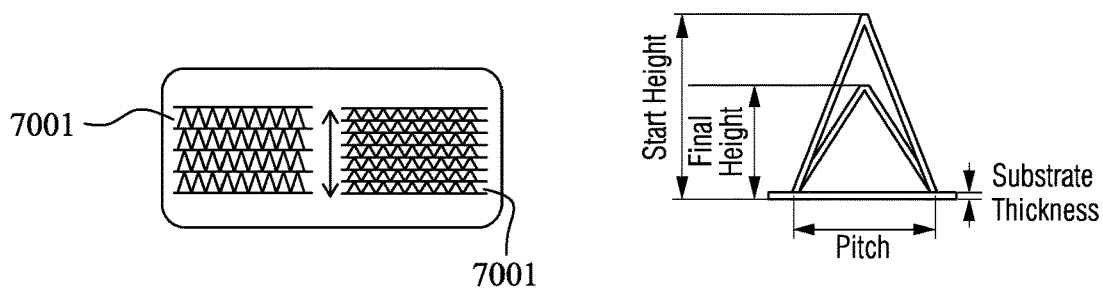

FIG. 25D is a diagram that illustrates a HME under preload to compress the corrugations in a fixed volume such that the number of layers 7001 is increased within the fixed volume.

Figure 25E:
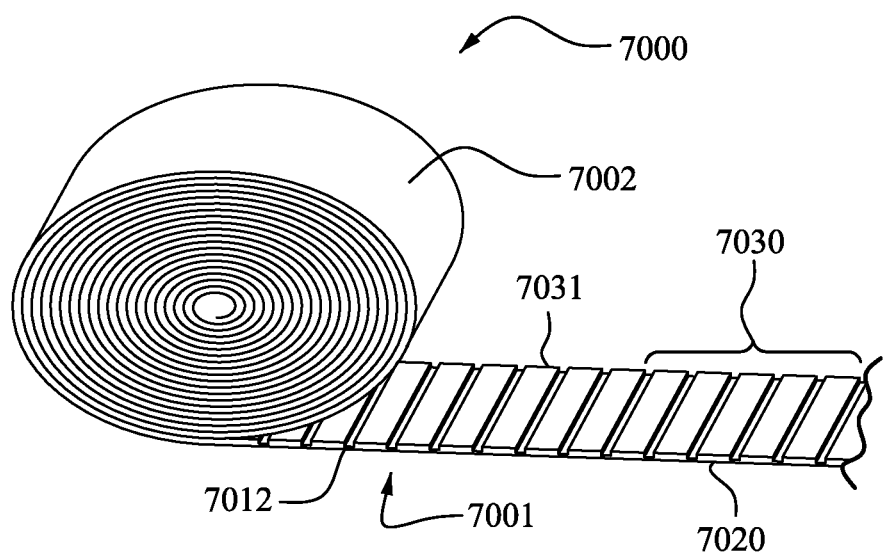

FIG. 25E displays a corrugated structure 7002 comprising a plurality of corrugations 7030, wherein the corrugated structure is rolled to form a HME 7000.

Figure 26:
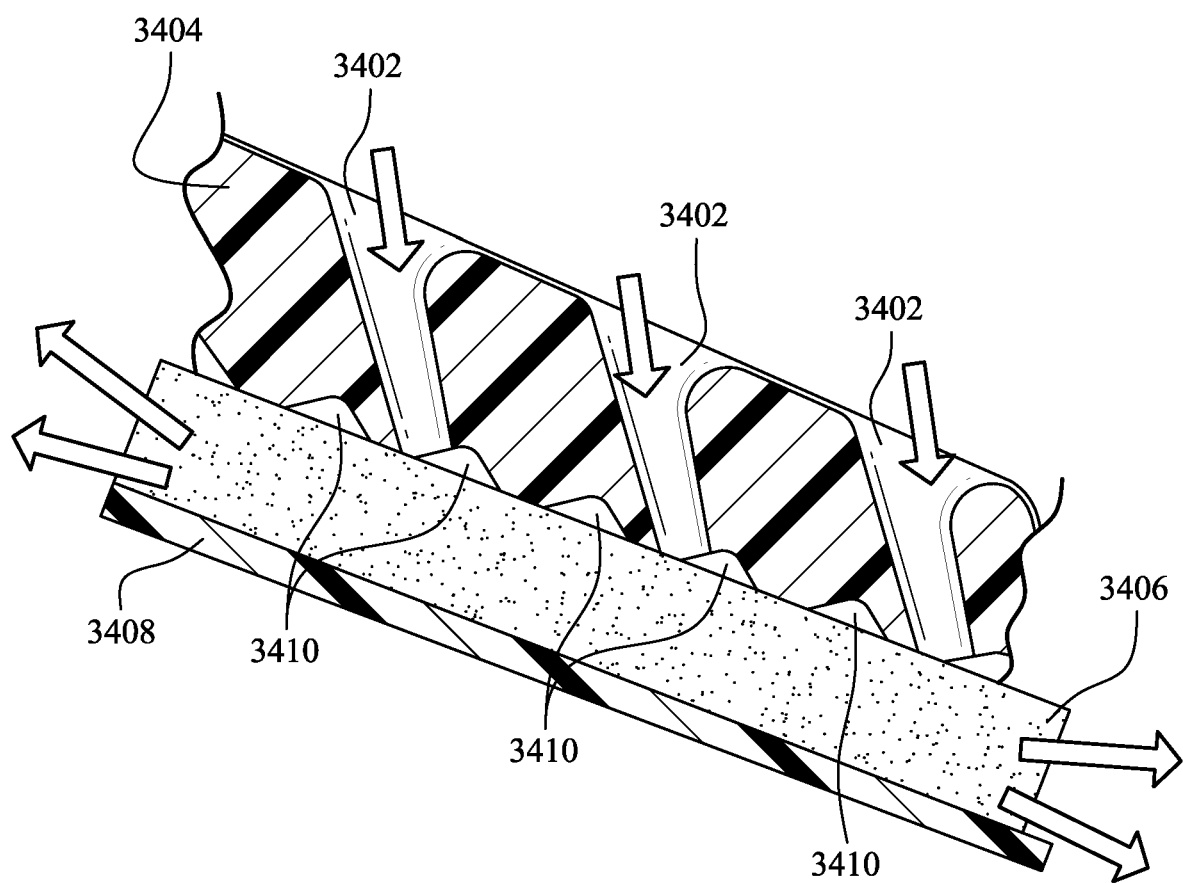

FIG. 26 depicts orifices, a diffusing member and a blocking member that form part of a gas washout vent.

Figure 27:
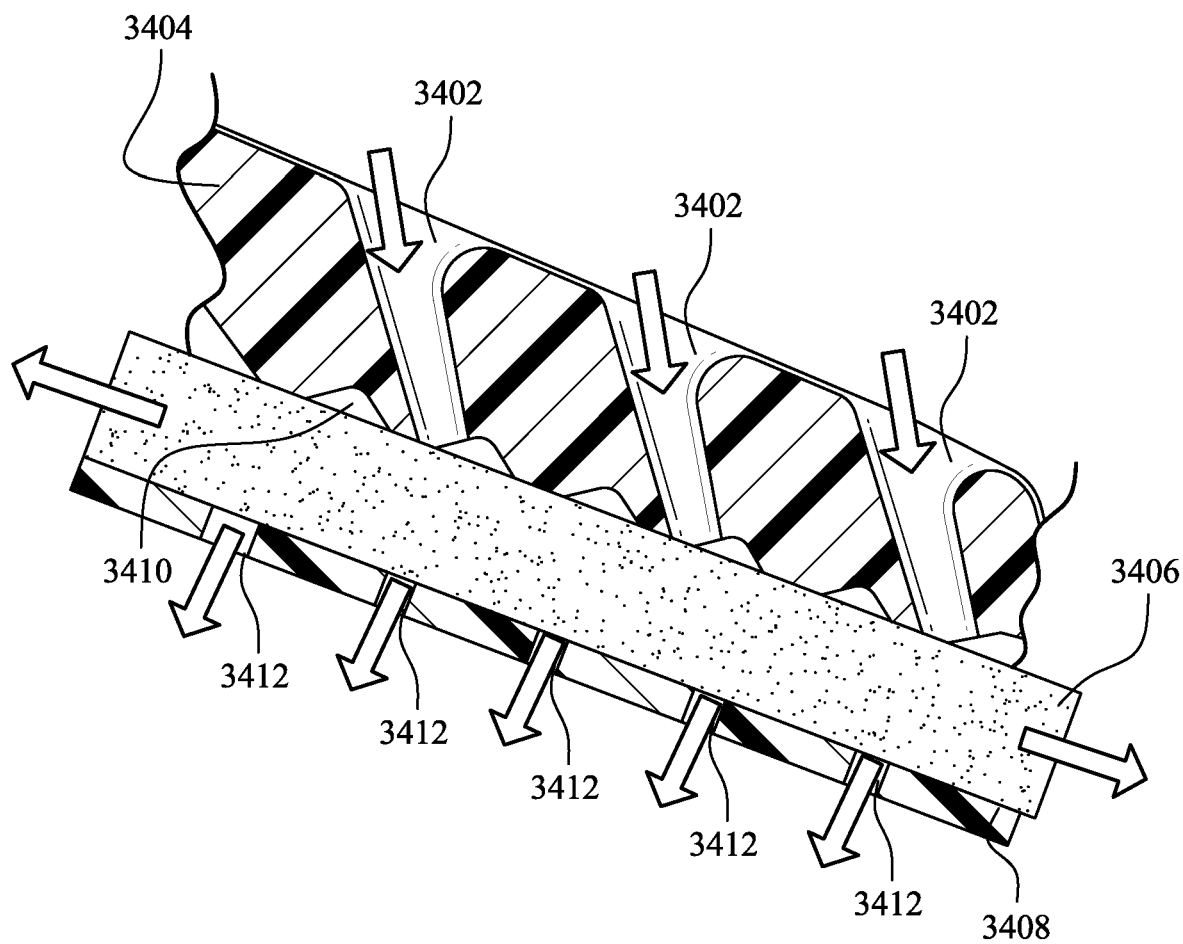

FIG. 27 depicts orifices, a diffusing member and a blocking member that form part of a gas washout vent where holes are provided in the blocking member.

Figure 28:
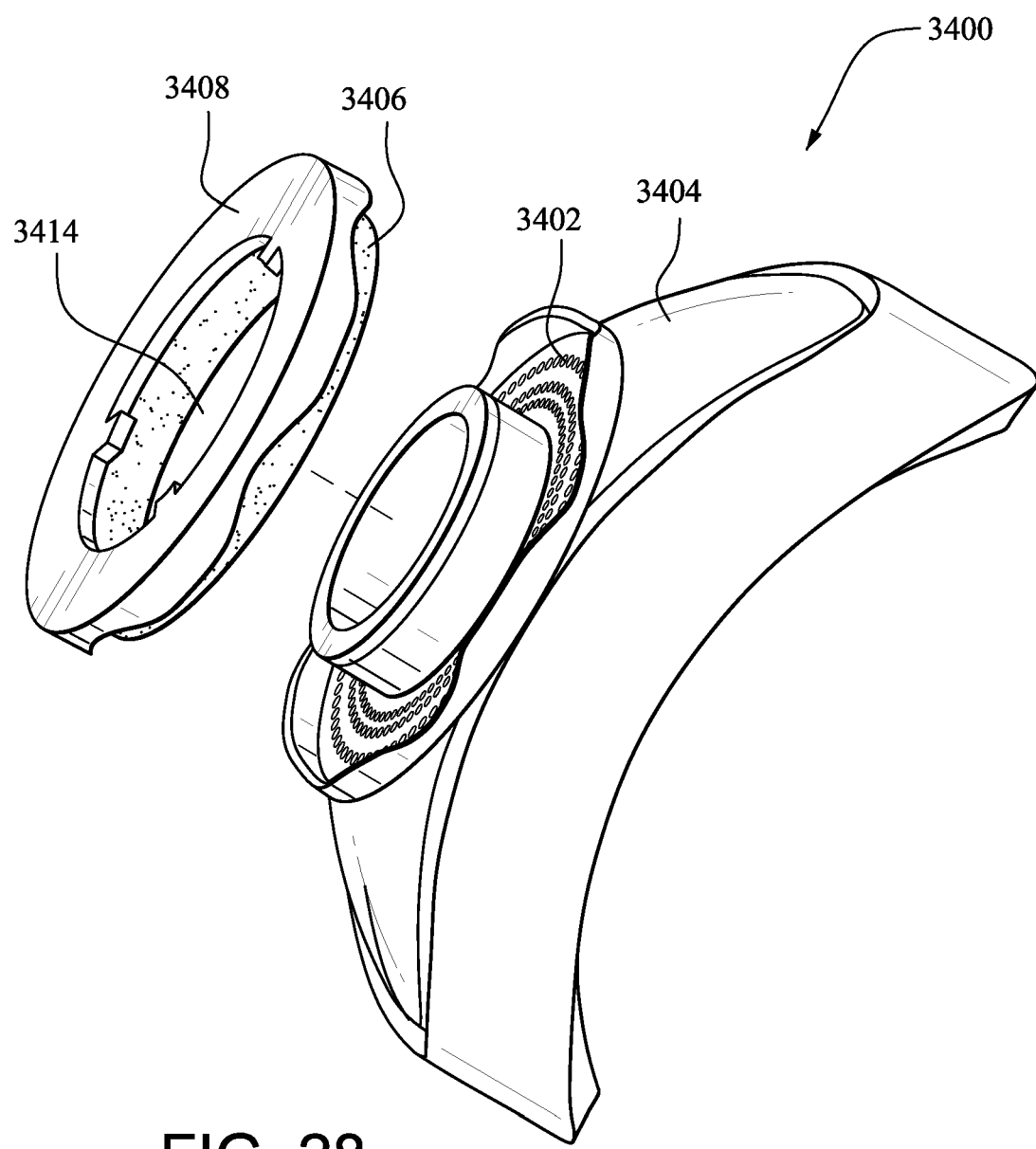

FIG. 28 depicts an exploded view of orifices, a diffusing member and a blocking member that form part of a gas washout vent formed circularly about a central hole.

Figure 29:
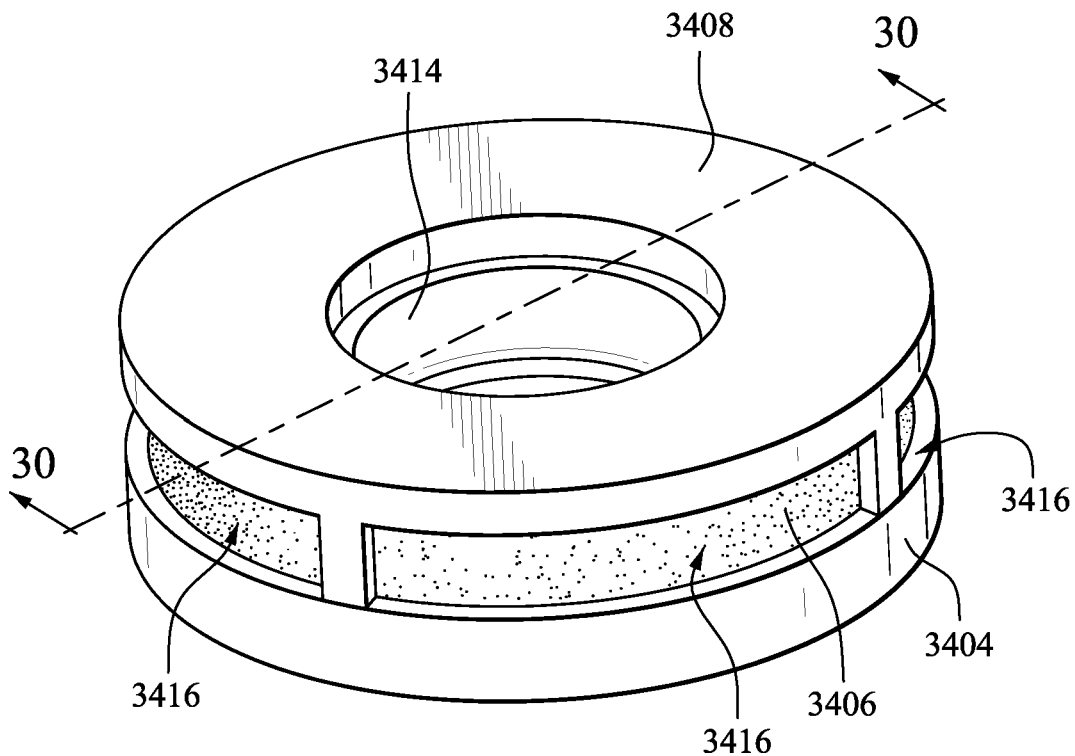

FIG. 29 depicts a simplified view of orifices, a diffusing member and a blocking member that form part of a gas washout vent formed circularly about a central hole.

Figure 30:
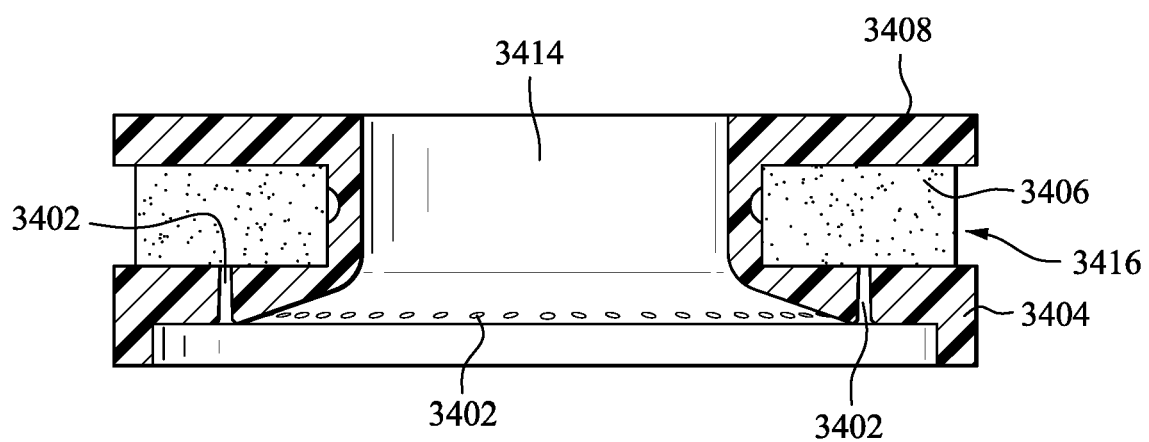

FIG. 30 depicts a cross-sectional view taken through line 30-30 of FIG. 29.

Figure 31A:
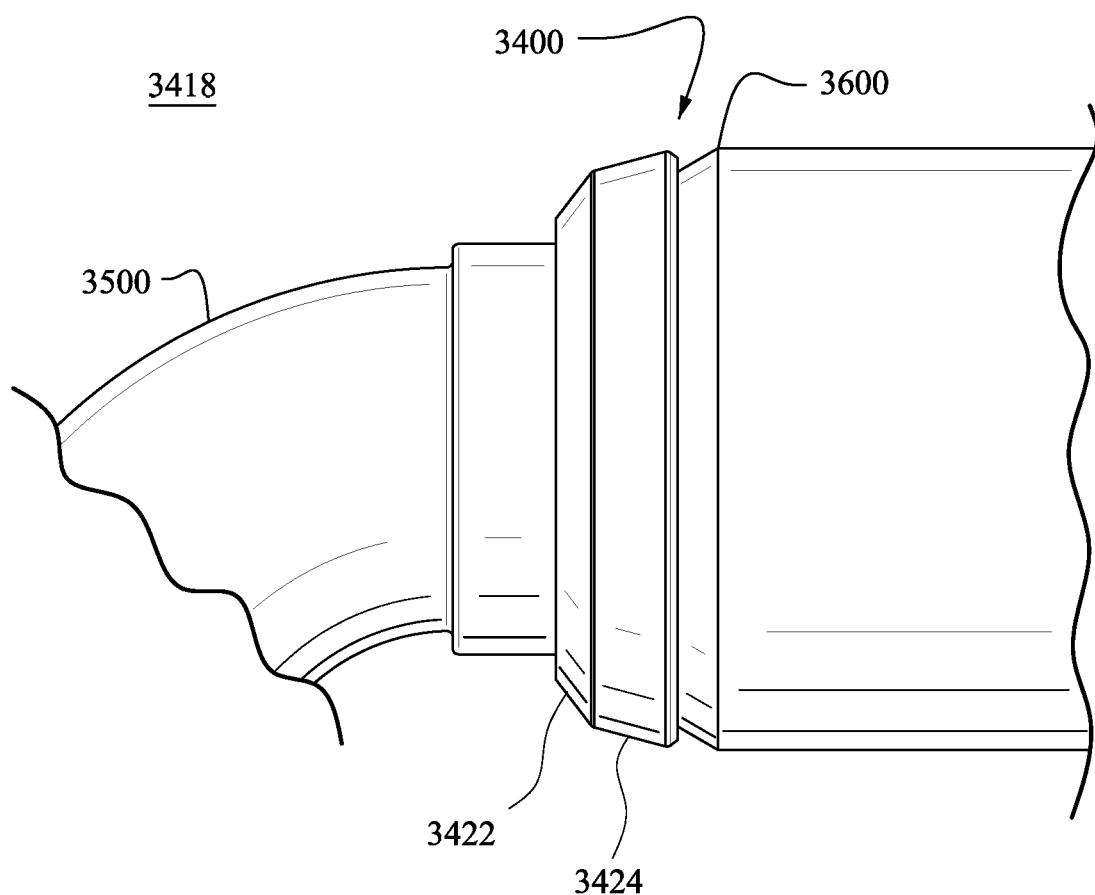

FIG. 31A depicts a partial view of an elbow with a gas washout vent with one annular outlet.

Figure 31B:
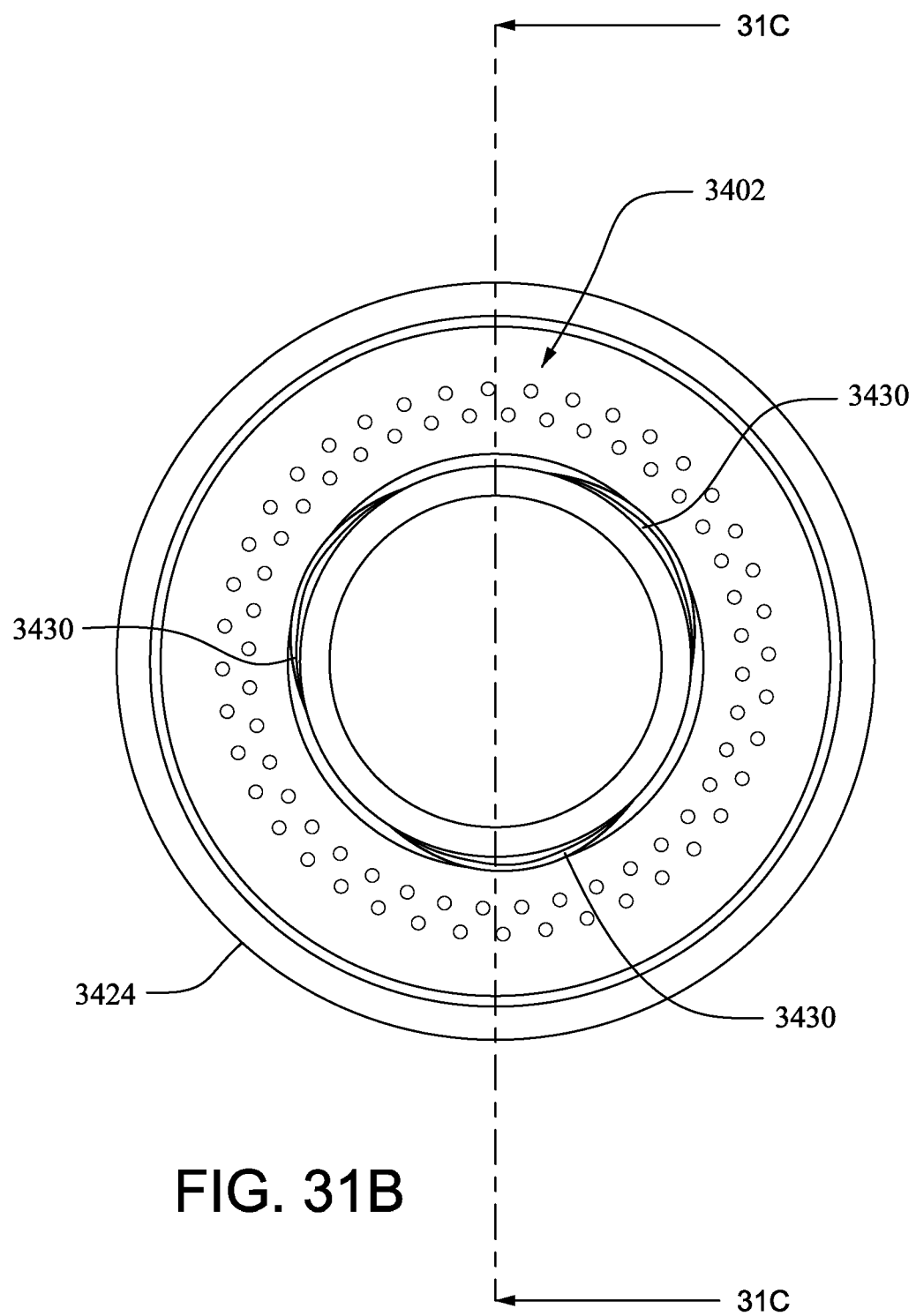

FIG. 31B depicts an axial view of orifices in the gas washout vent of FIG. 31B.

Figure 31C:
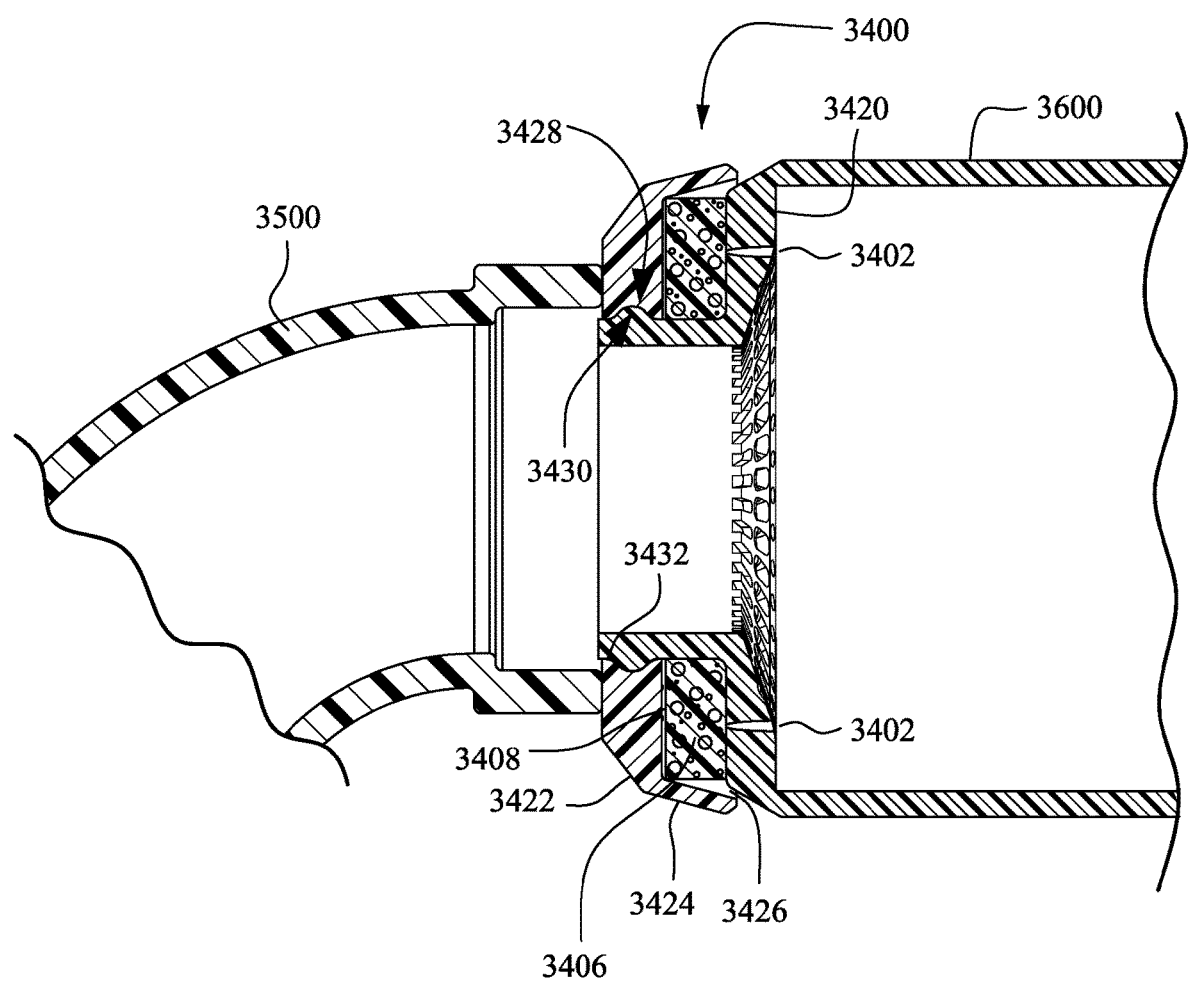

FIG. 31C depicts a cross-sectional view taken through the plane of the drawing of FIG. 31, which is equivalent to the plane labelled 31C-31C in FIG. 31B.

Figure 32A:
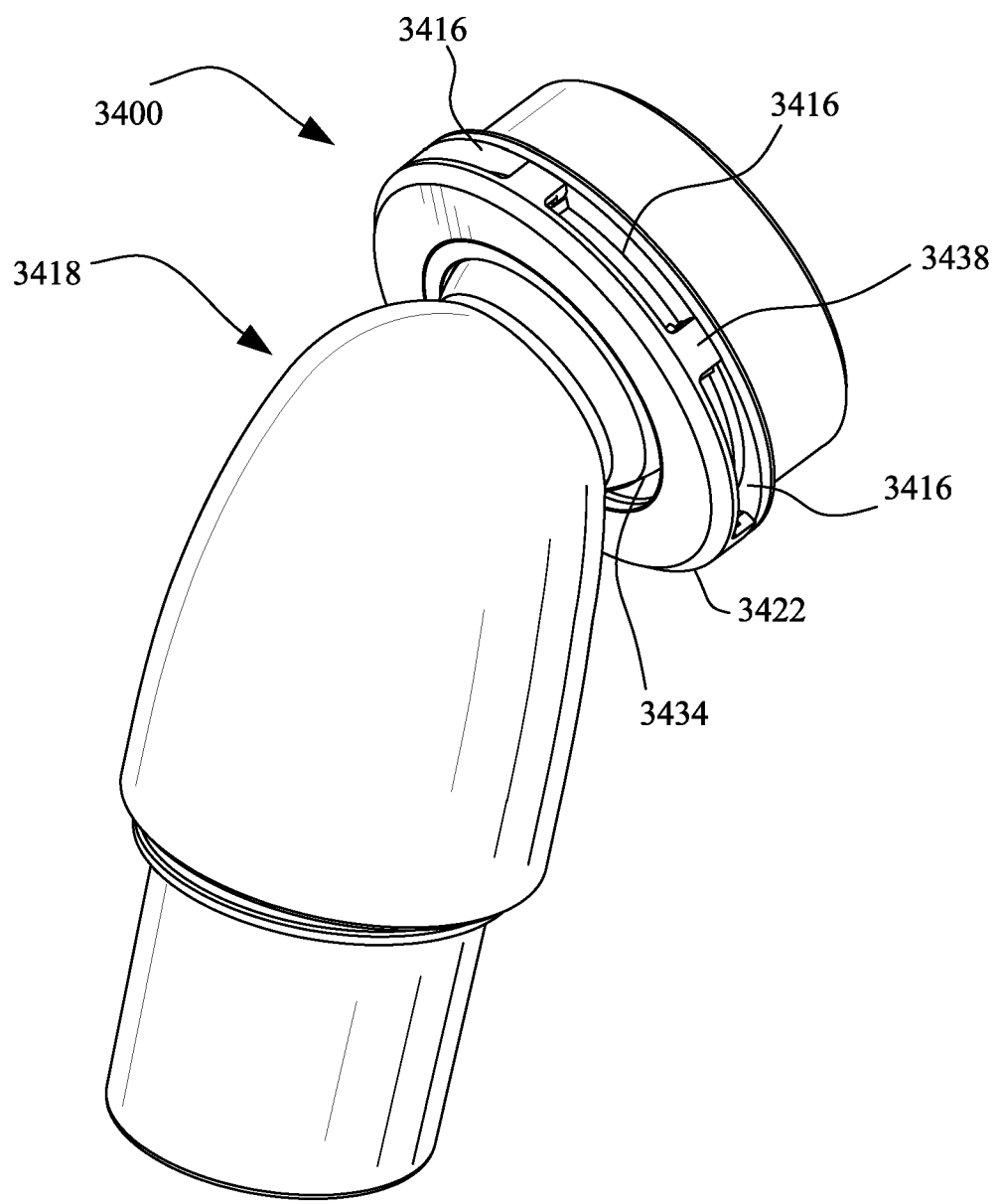

FIG. 32A depicts an elbow with a ball and socket joint and gas washout vent.

Figure 32B:
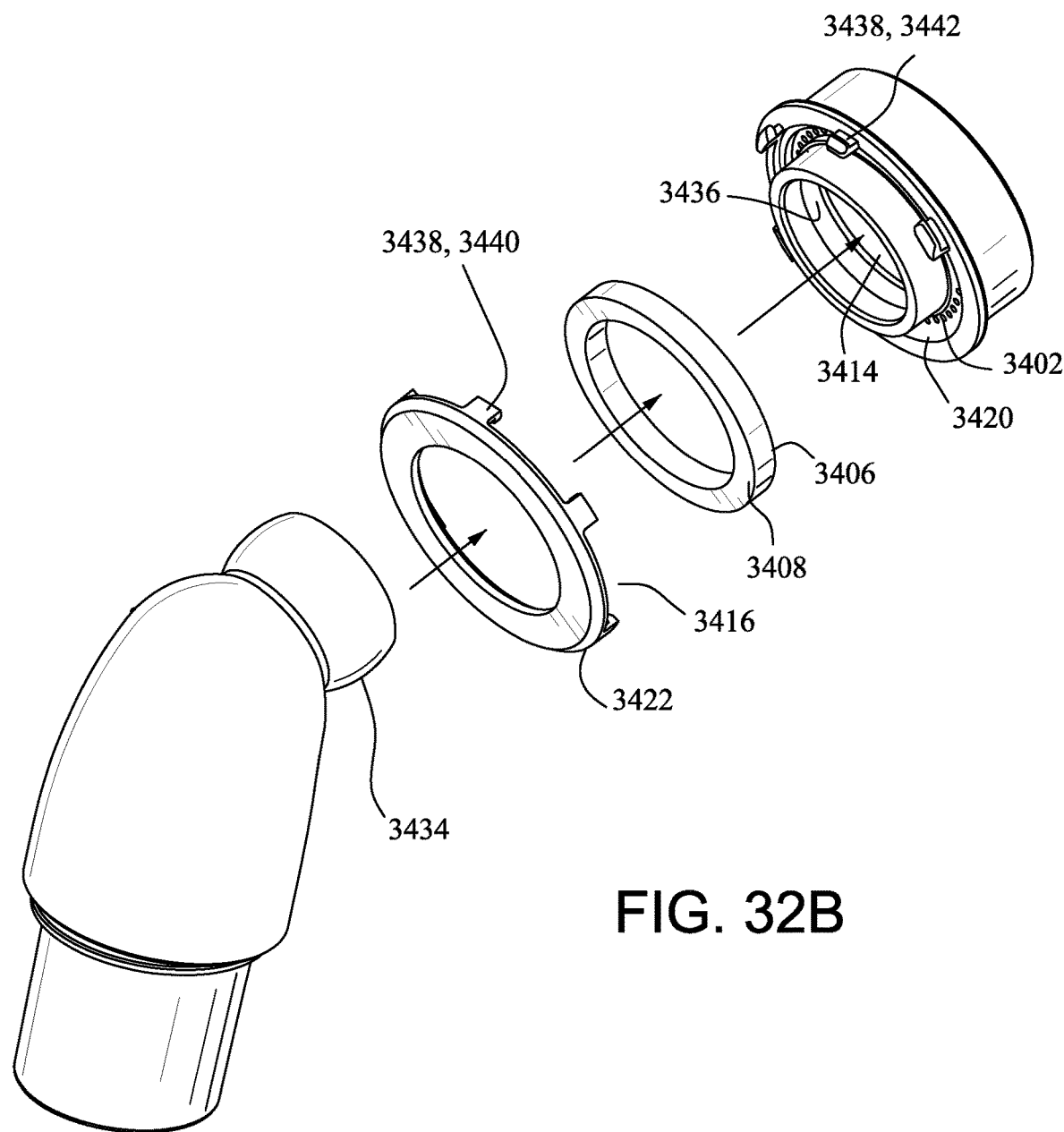

FIG. 32B depicts an exploded view of the elbow of FIG. 32A.

Figure 32C:
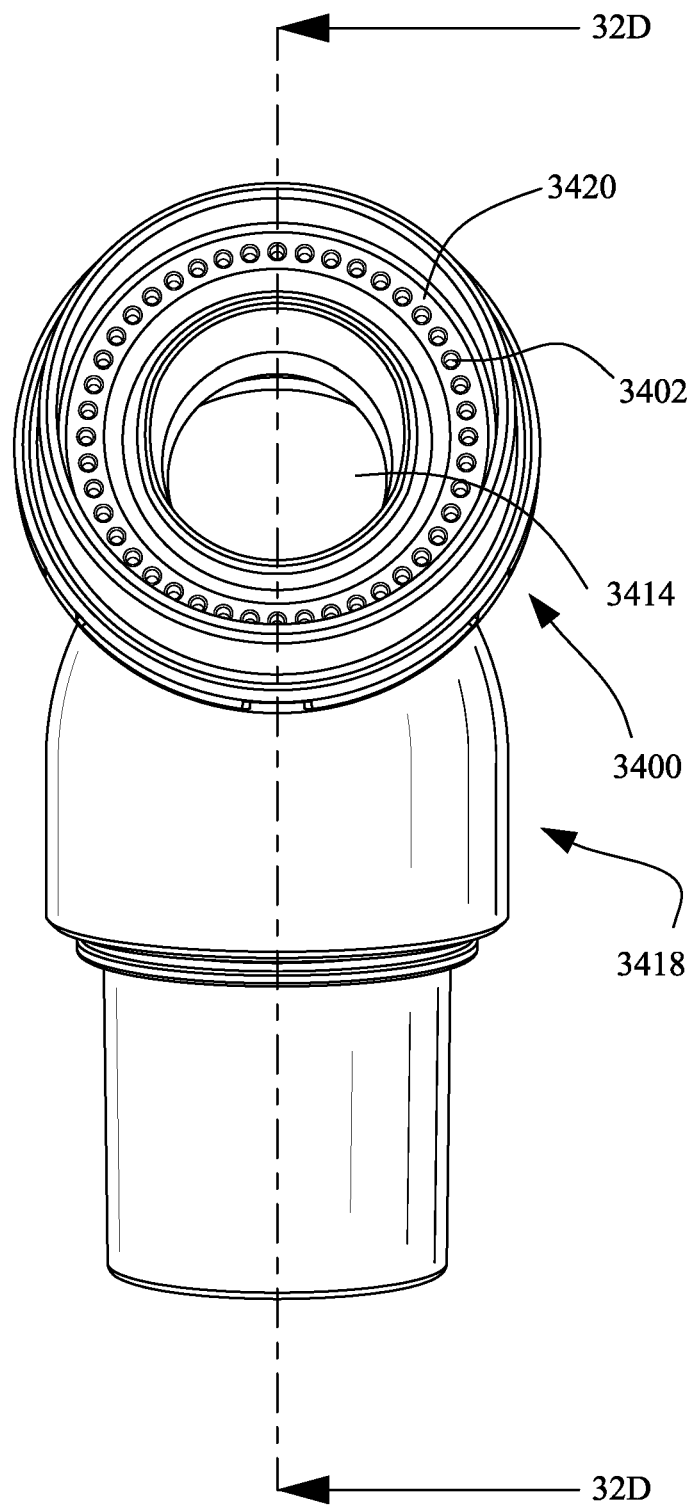

FIG. 32C depicts a side view of the elbow.

Figure 32D:
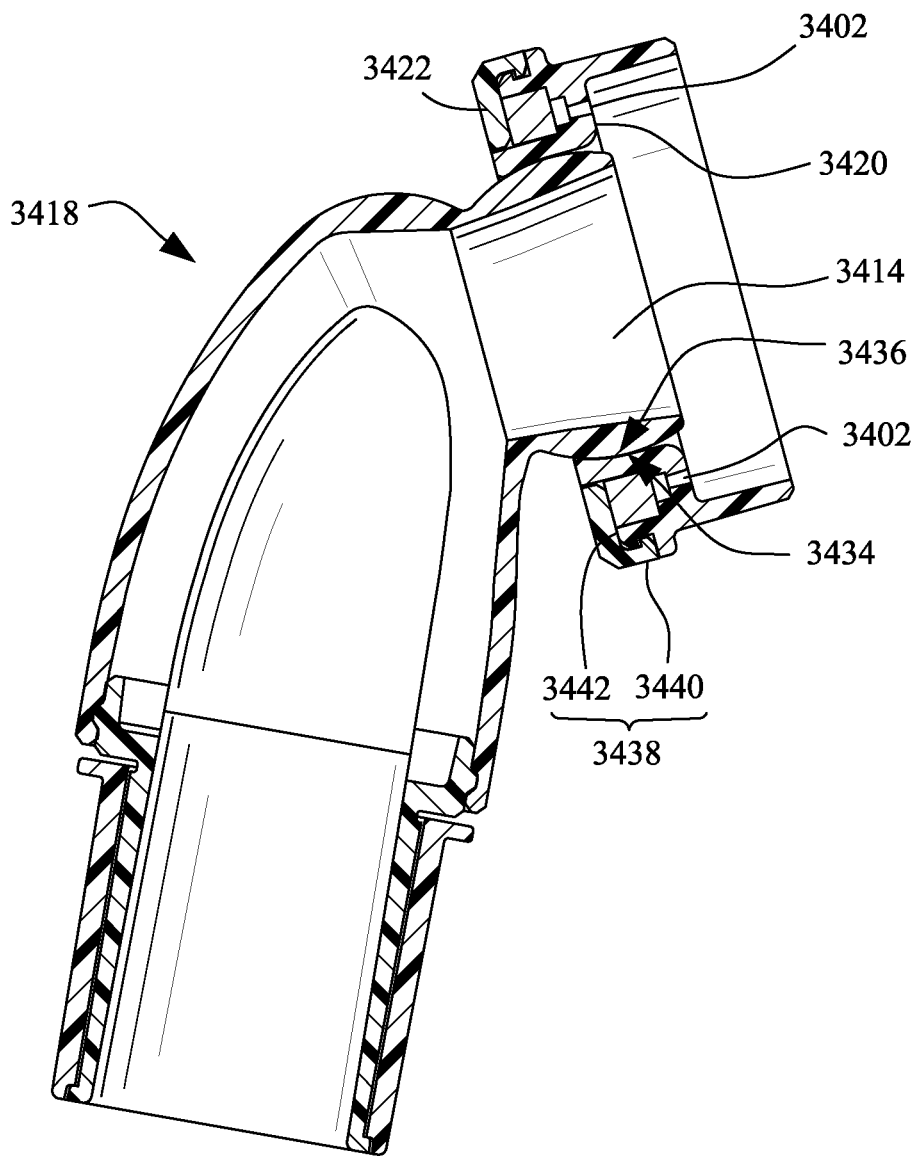

FIG. 32D depicts a cross-sectional view taking through line 32D-32D of FIG. 32C.

Figure 33A:
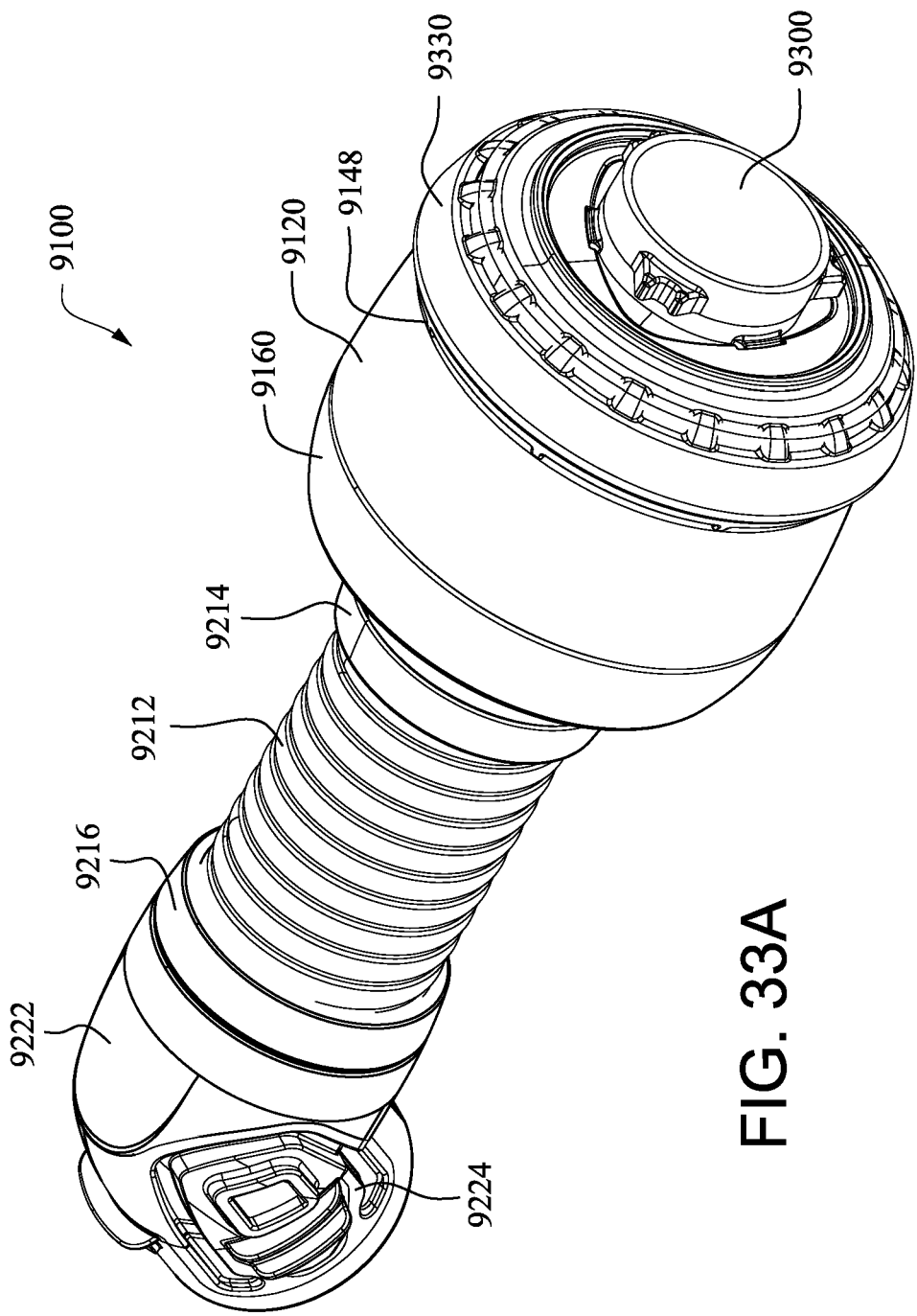

FIG. 33A depicts a perspective view of a vent adaptor according to an example of the present technology.

Figure 33B:
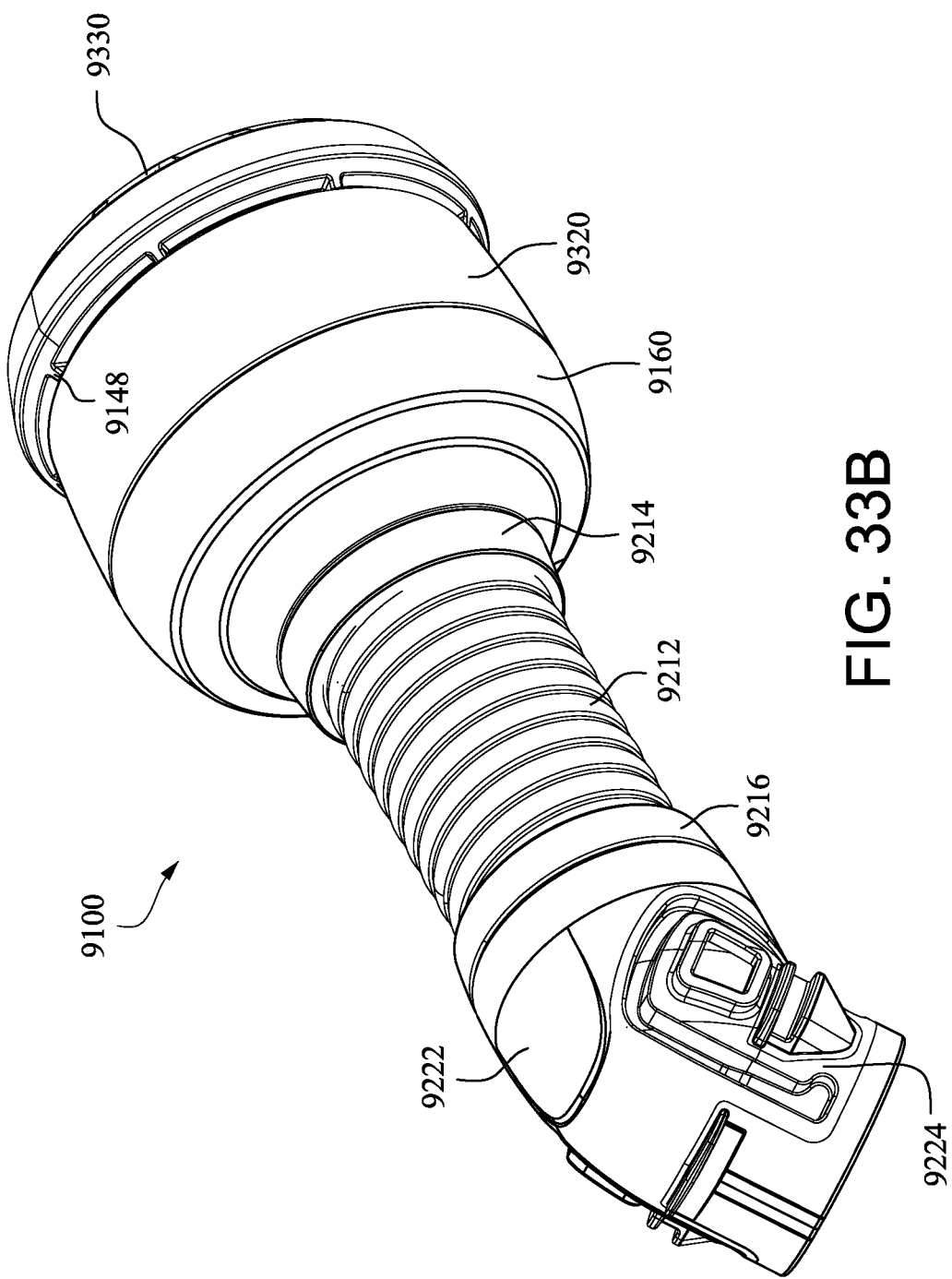

FIG. 33B depicts another perspective view of a vent adaptor according to an example of the present technology.

Figure 33C:
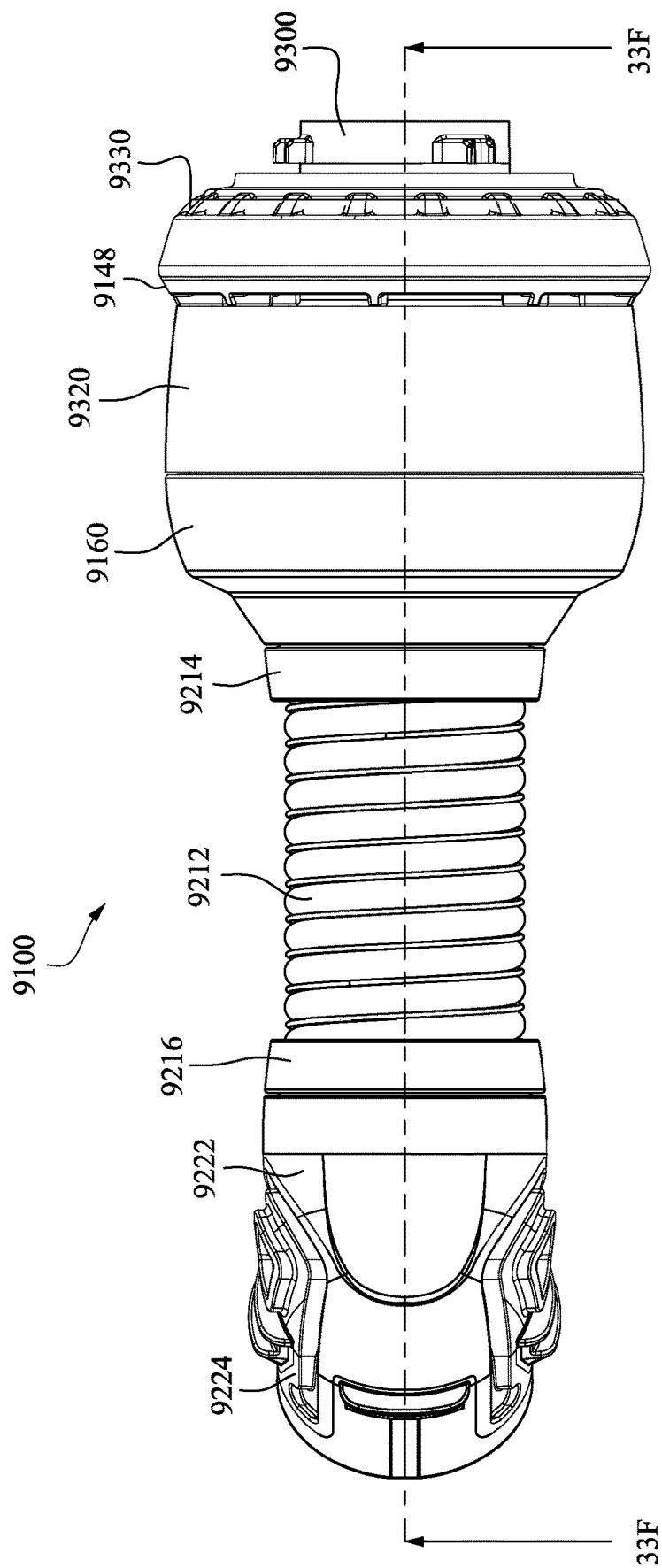

FIG. 33C depicts a superior view of a vent adaptor according to an example of the present technology.

Figure 33D:
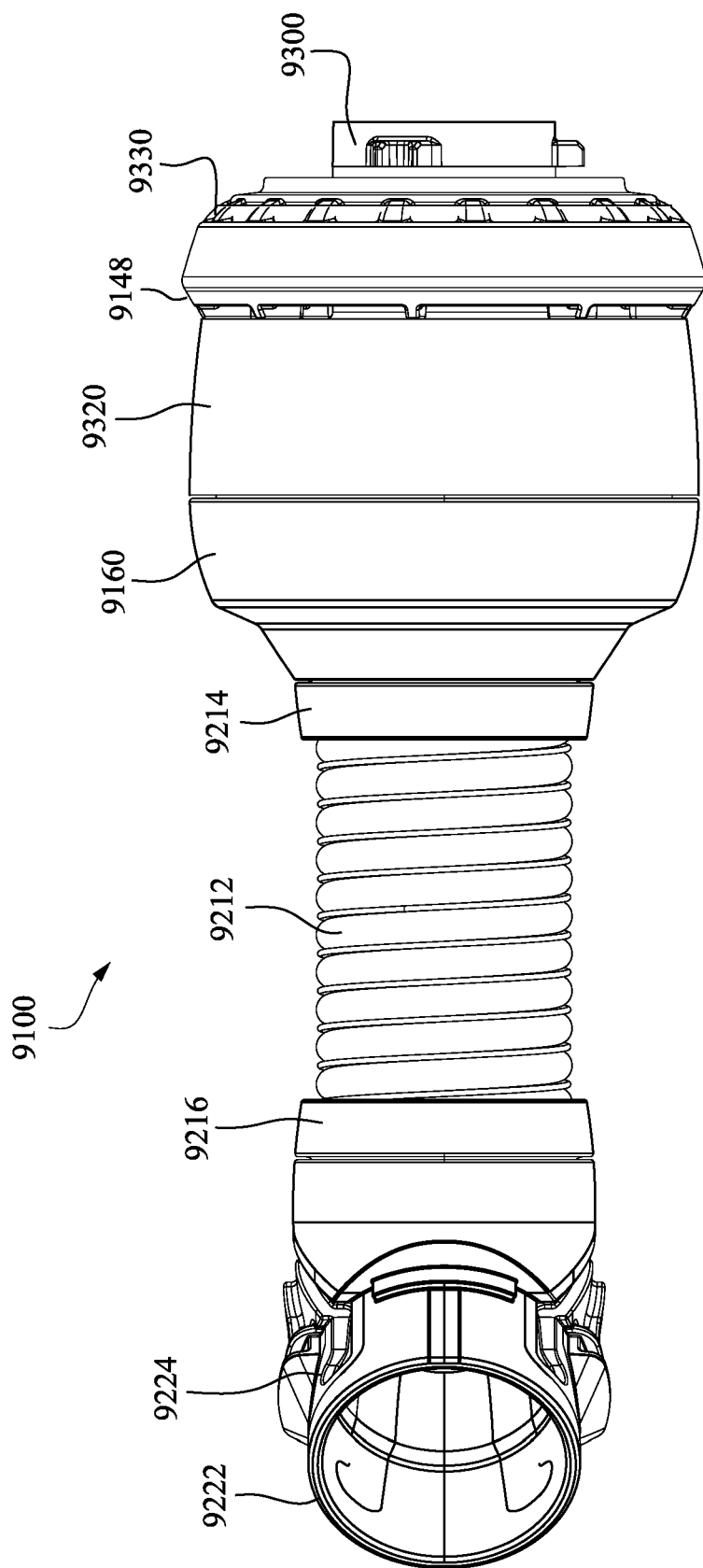

FIG. 33D depicts an inferior view of a vent adaptor according to an example of the present technology.

Figure 33E:
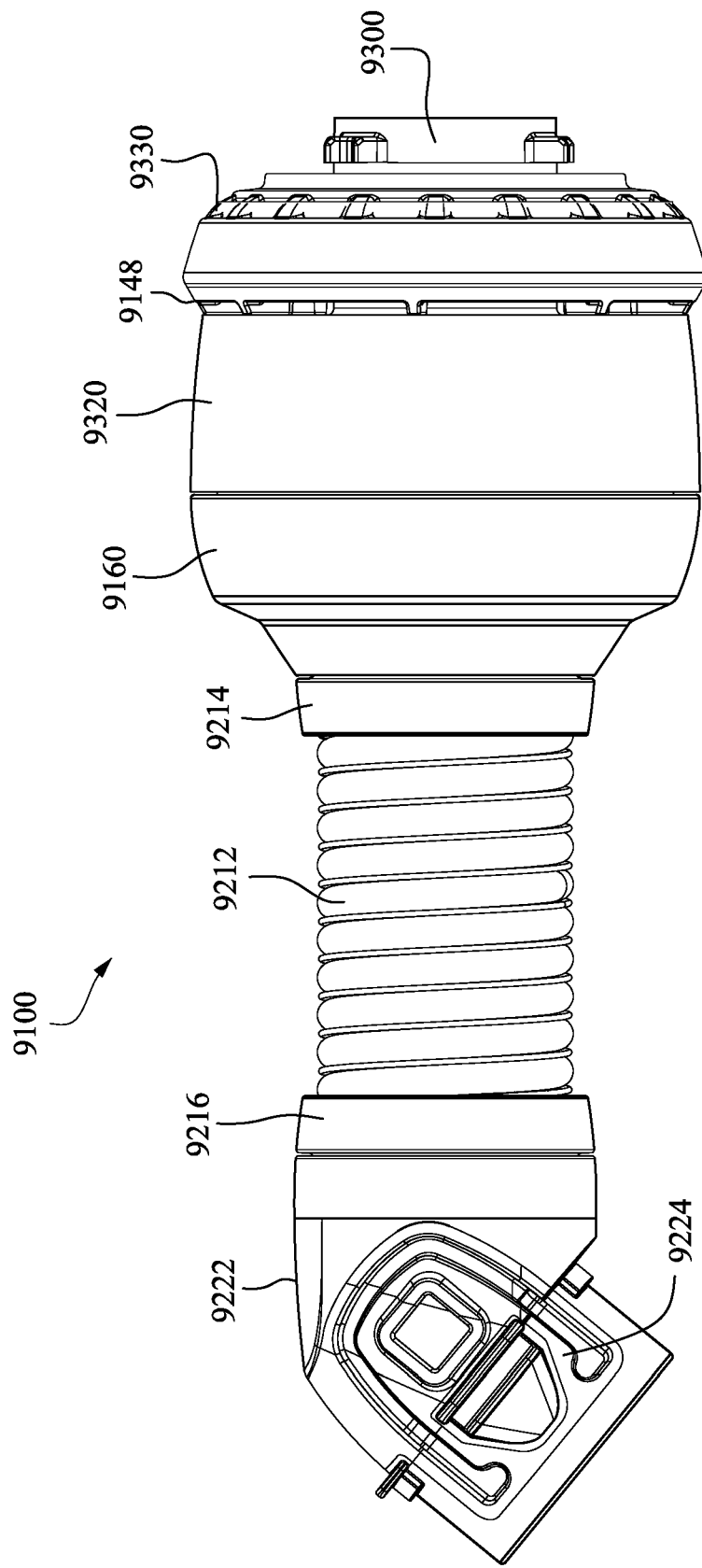

FIG. 33E depicts a lateral view of a vent adaptor according to an example of the present technology.

Figure 33F:
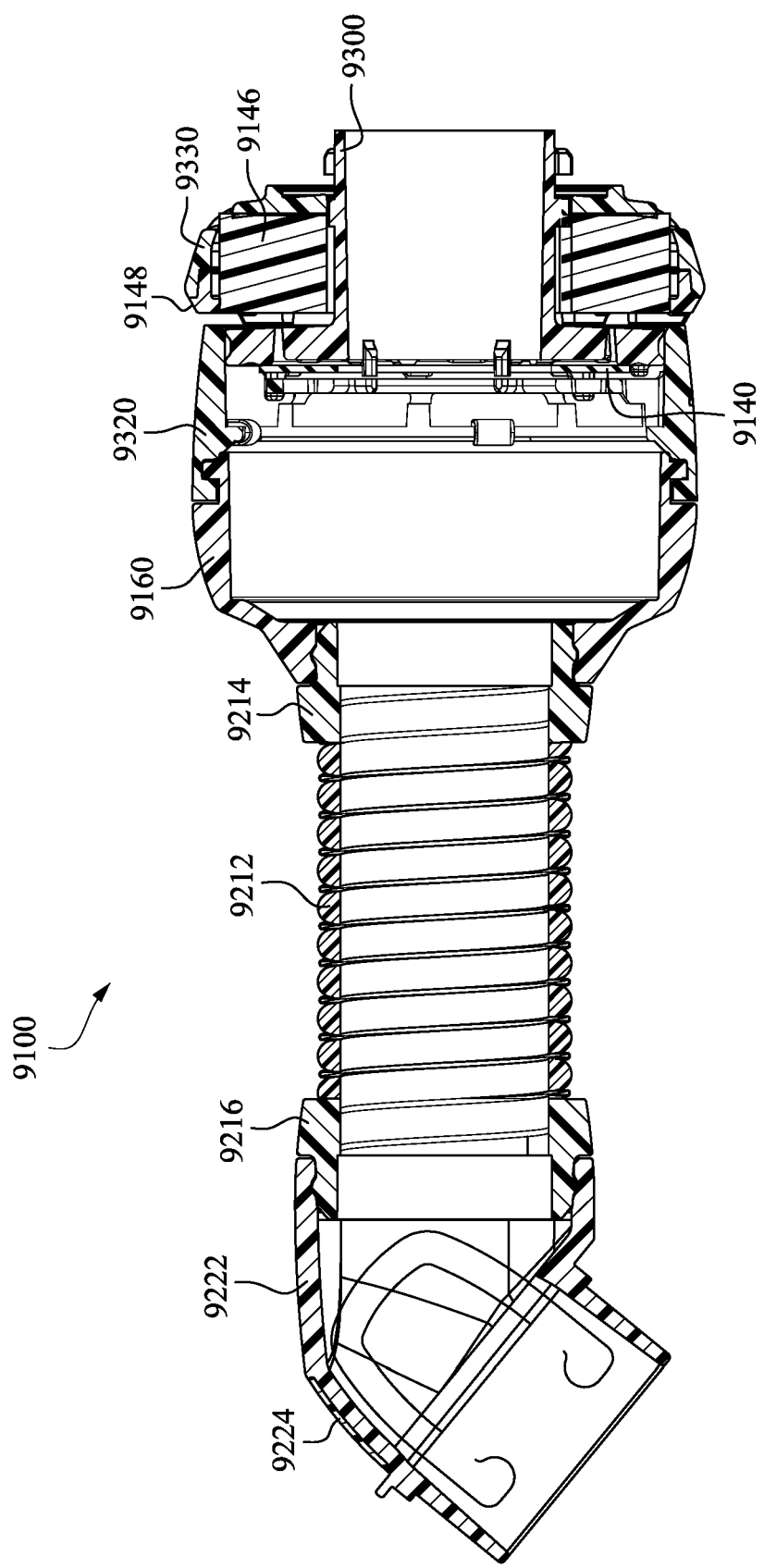

FIG. 33F depicts a cross-sectional view of a vent adaptor taken through line 33F-33F of FIG. 33C according to an example of the present technology.

Figure 33G:
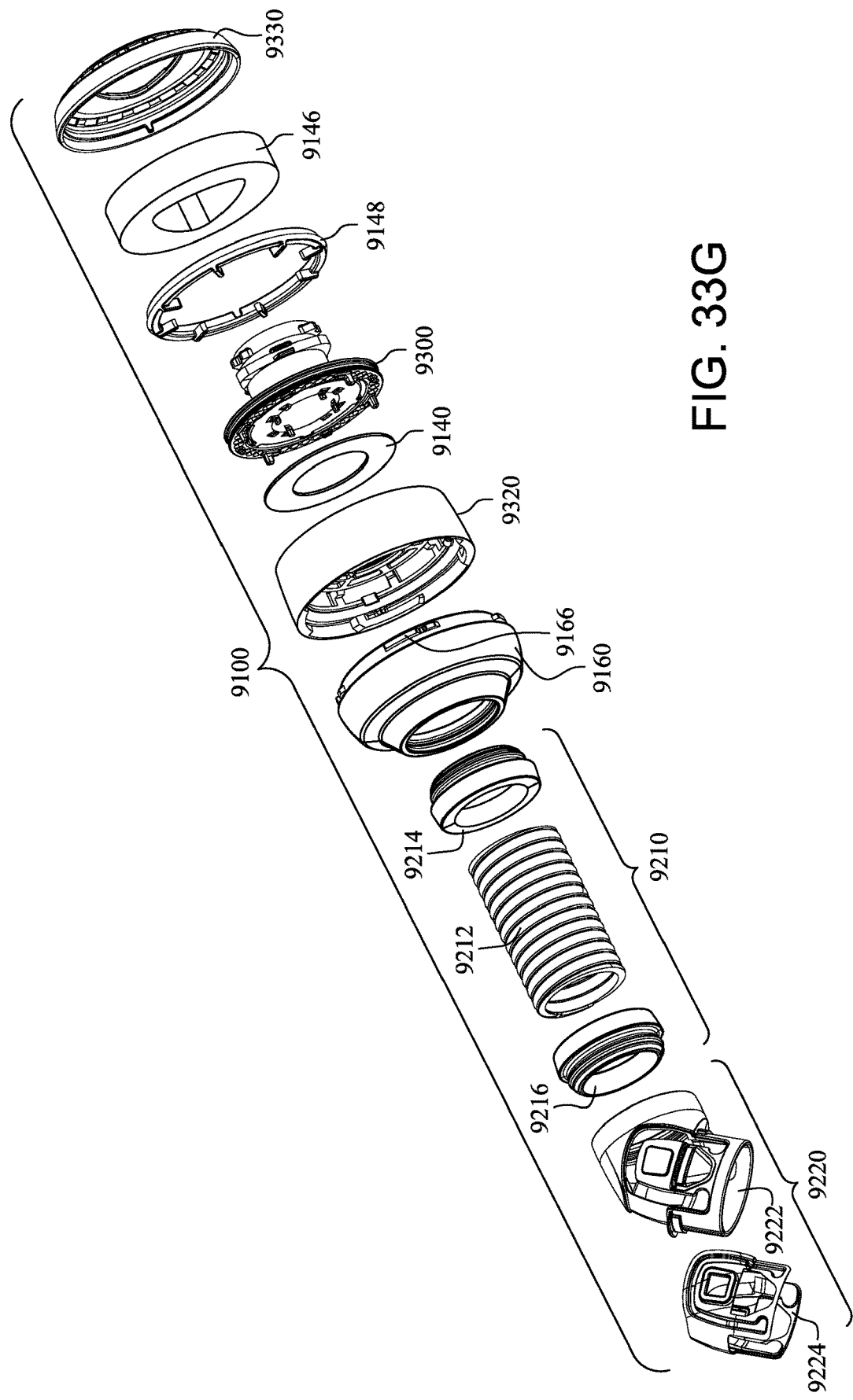

FIG. 33G depicts an exploded view of a vent adaptor according to an example of the present technology.

Figure 34A:
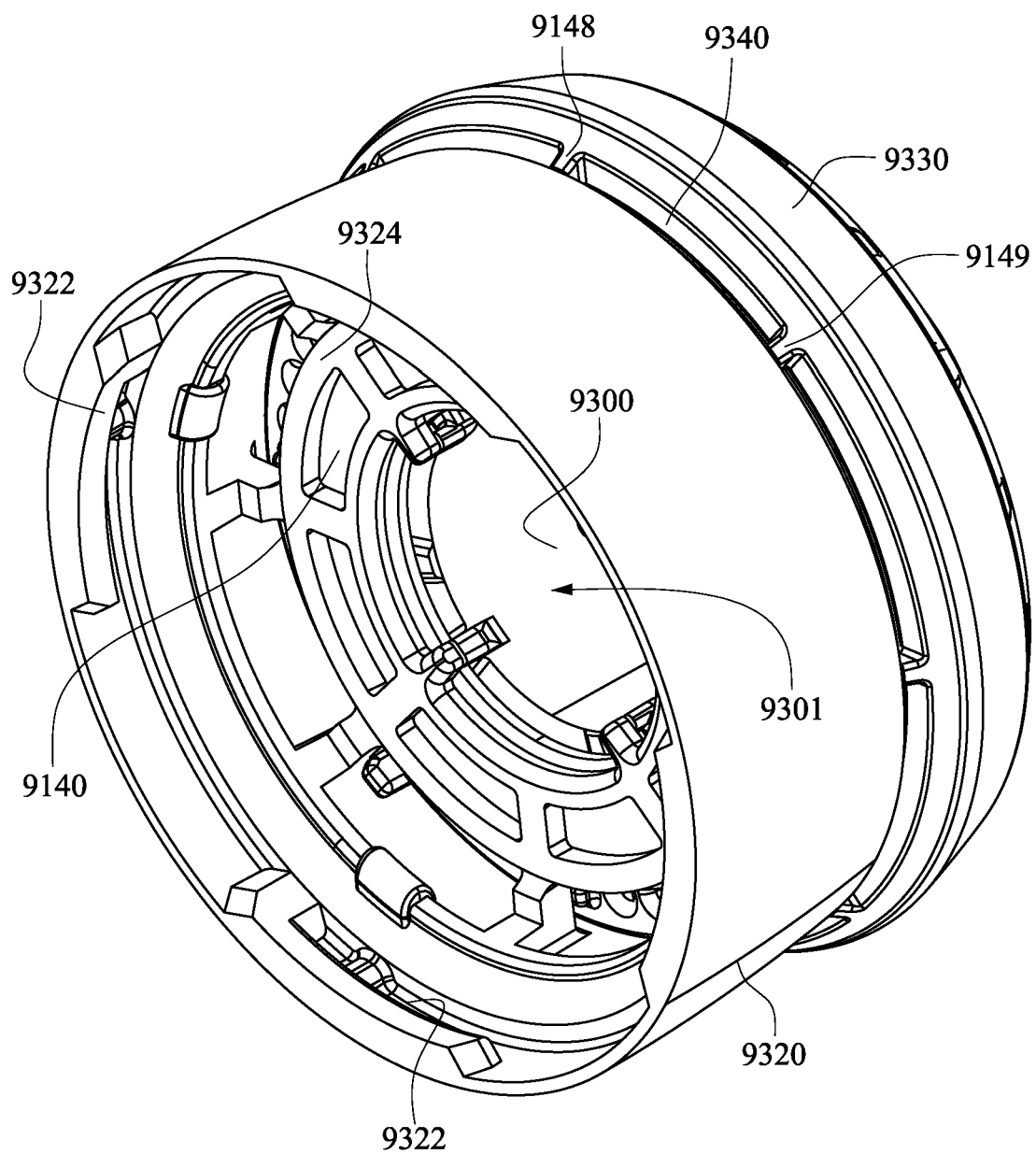

FIG. 34A depicts a perspective view of a vent assembly for a vent adaptor according to an example of the present technology.

Figure 34B:
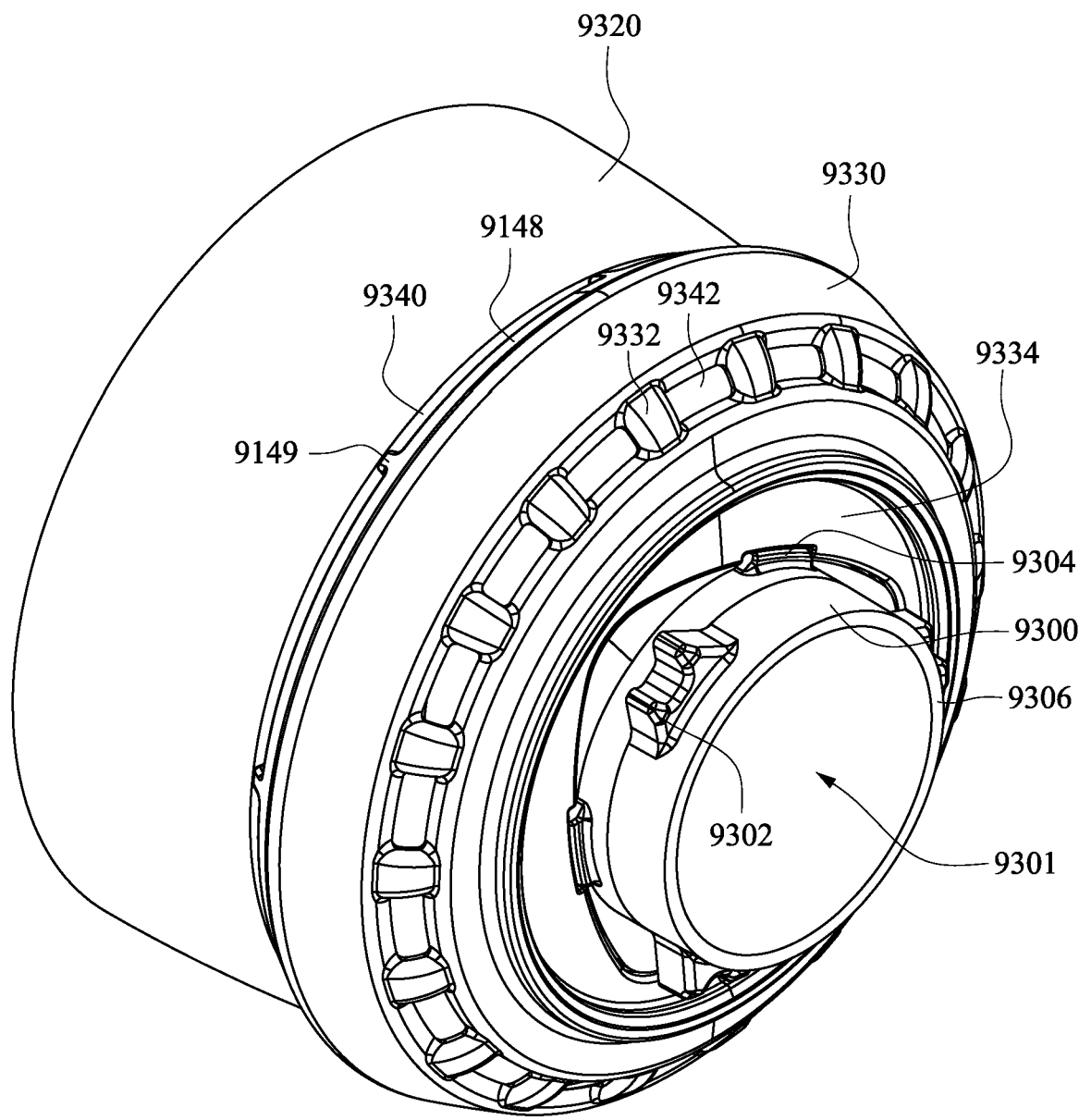

FIG. 34B depicts another perspective view of a vent assembly for a vent adaptor according to an example of the present technology.

Figure 34C:
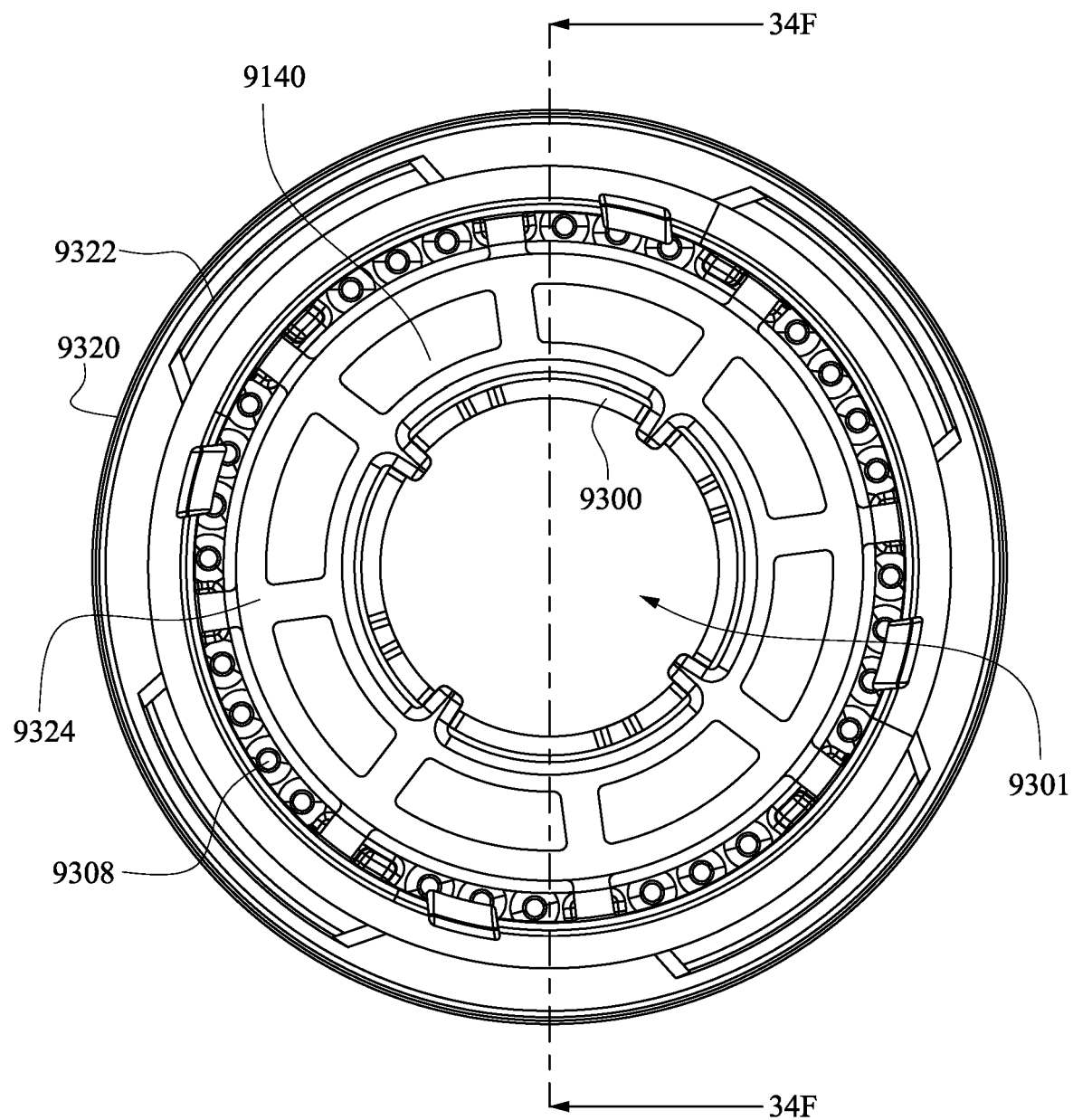

FIG. 34C depicts a posterior view of a vent assembly for a vent adaptor according to an example of the present technology.

Figure 34D:
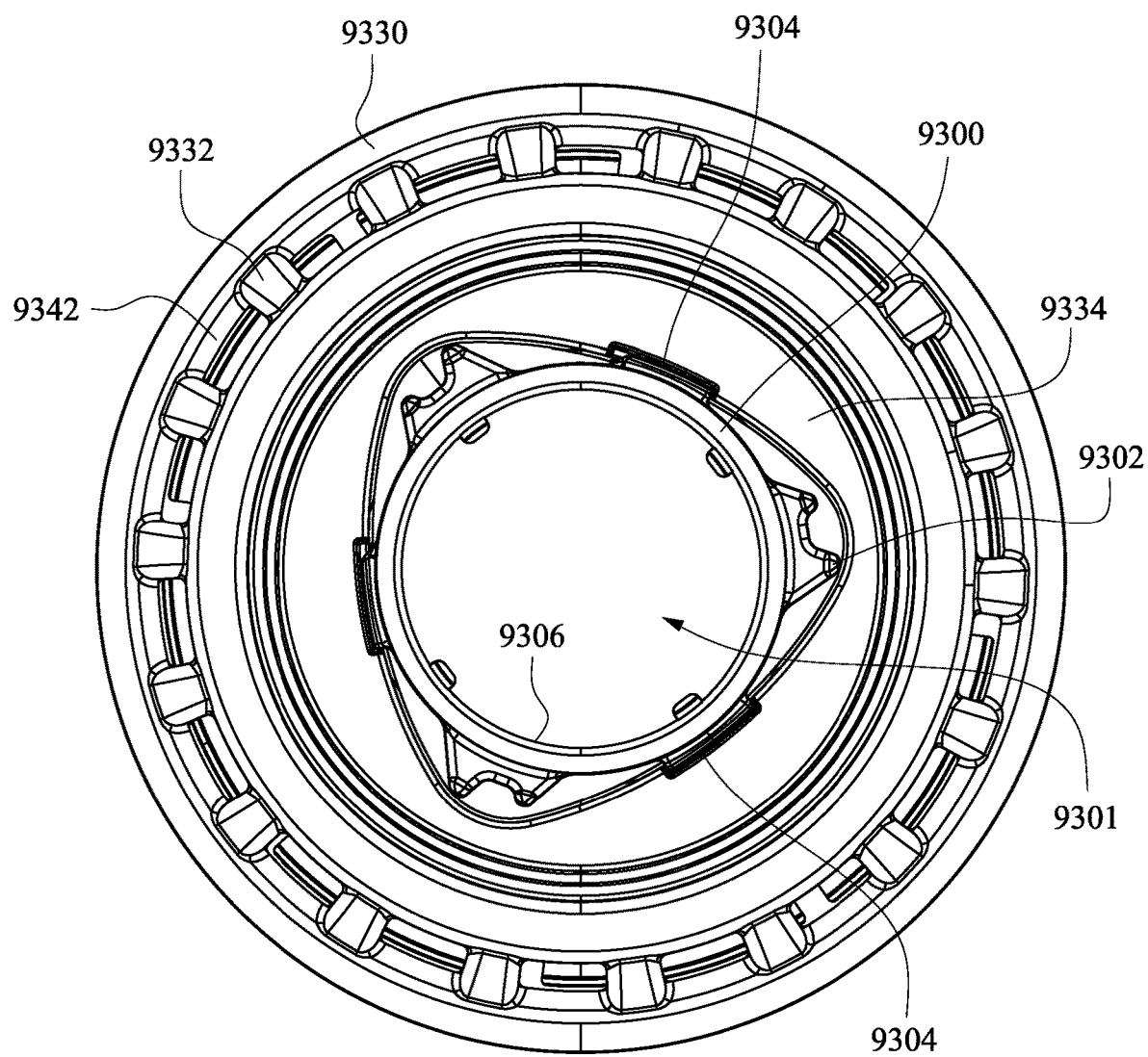

FIG. 34D depicts an anterior view of a vent assembly for a vent adaptor according to an example of the present technology.

Figure 34E:
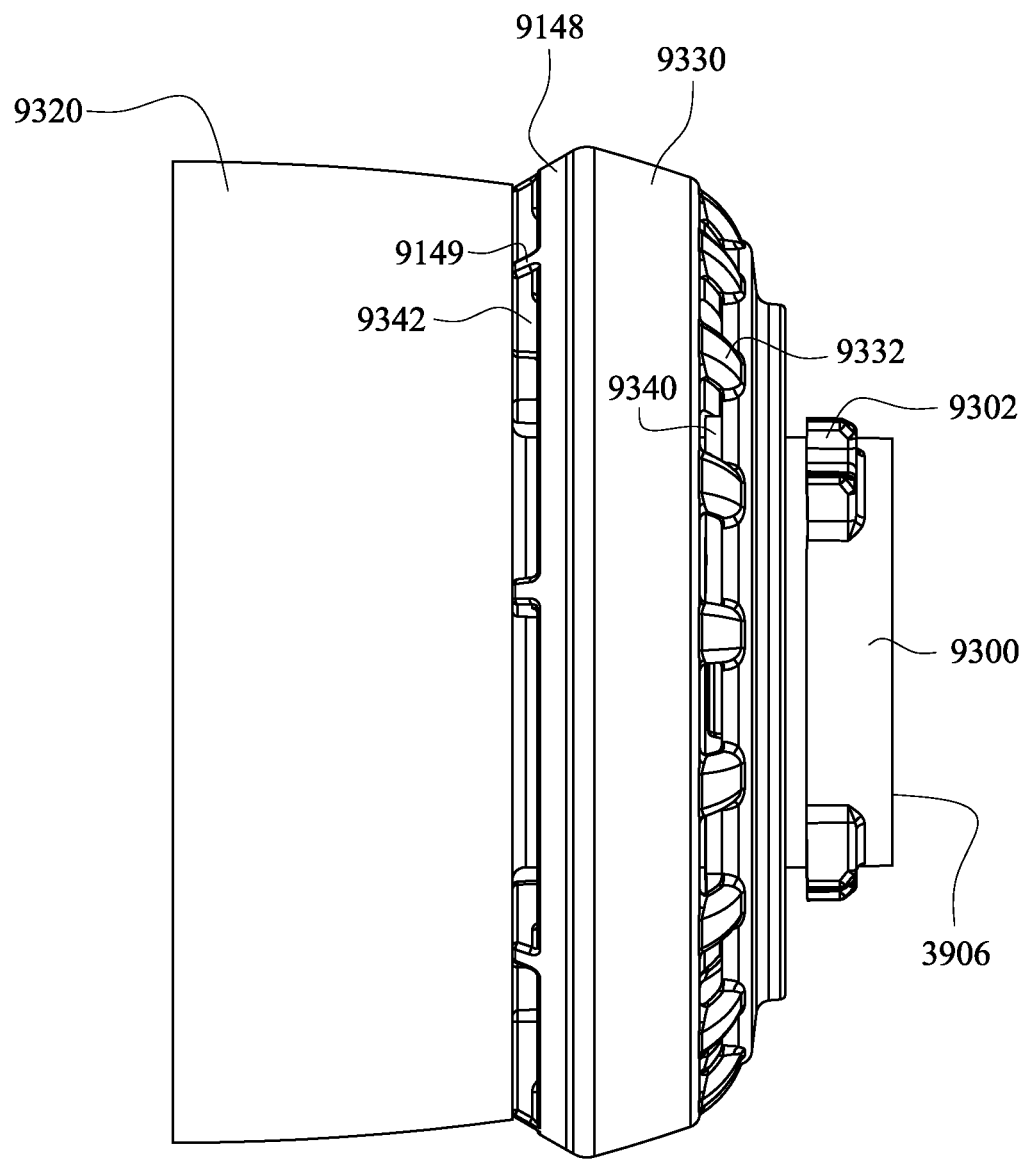

FIG. 34E depicts a lateral view of a vent assembly for a vent adaptor according to an example of the present technology.

Figure 34F:
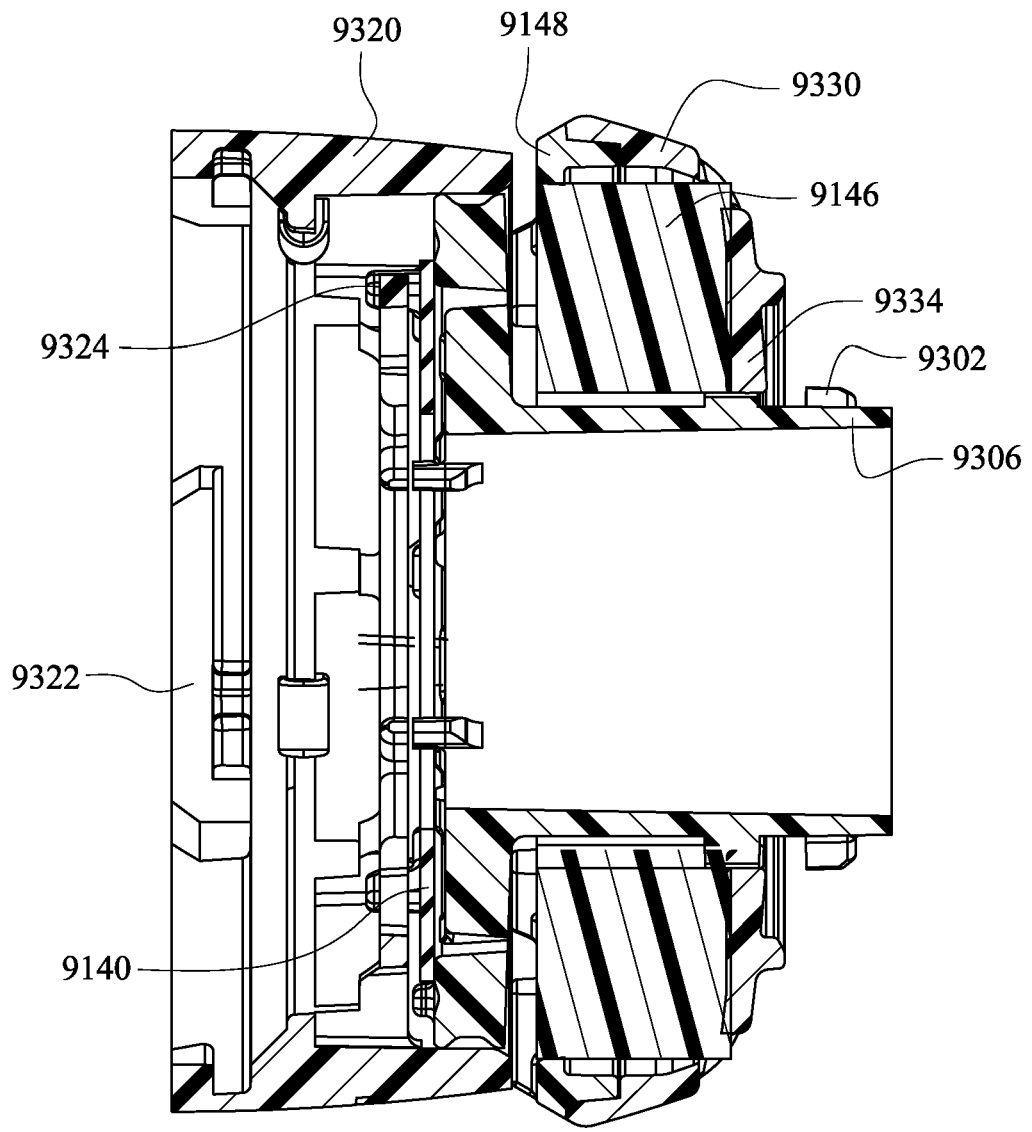

FIG. 34F depicts a cross-sectional view of a vent assembly for a vent adaptor taken through line 34F-34F of FIG. 34C according to an example of the present technology.

Figure 34G:
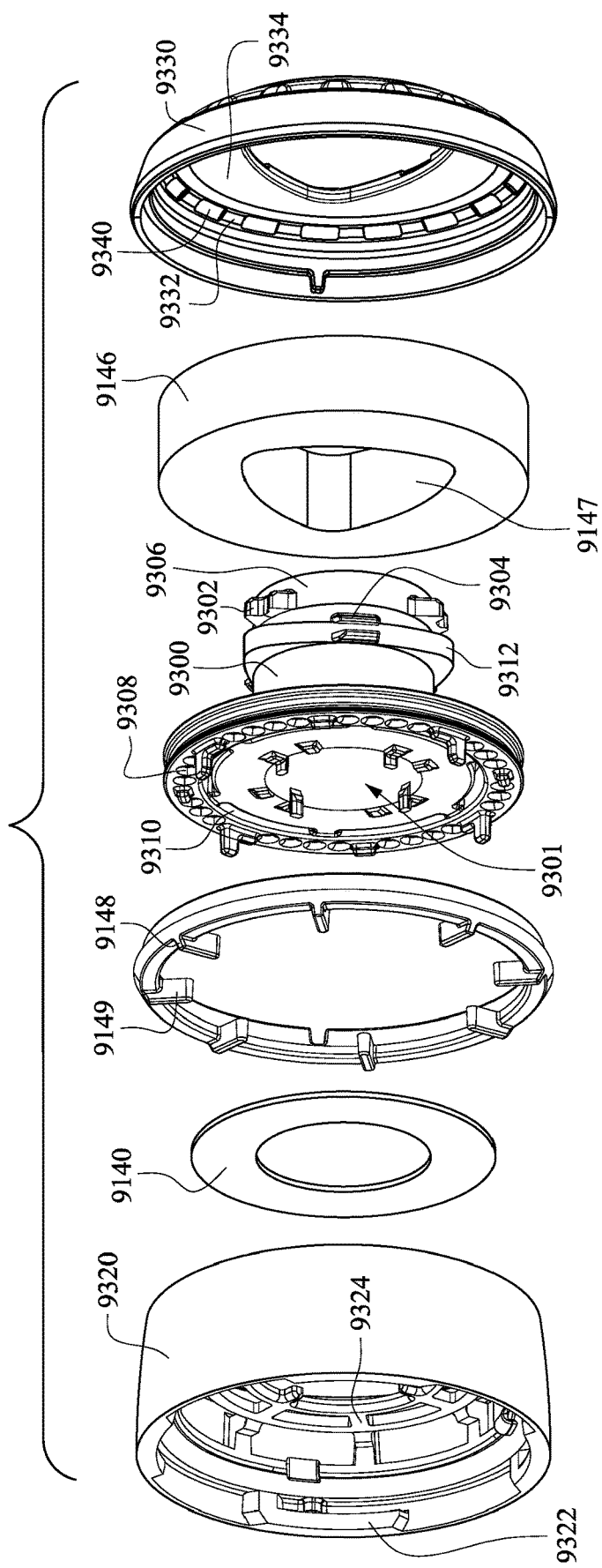

FIG. 34G depicts an exploded view of a vent assembly for a vent adaptor according to an example of the present technology.

Figure 35:
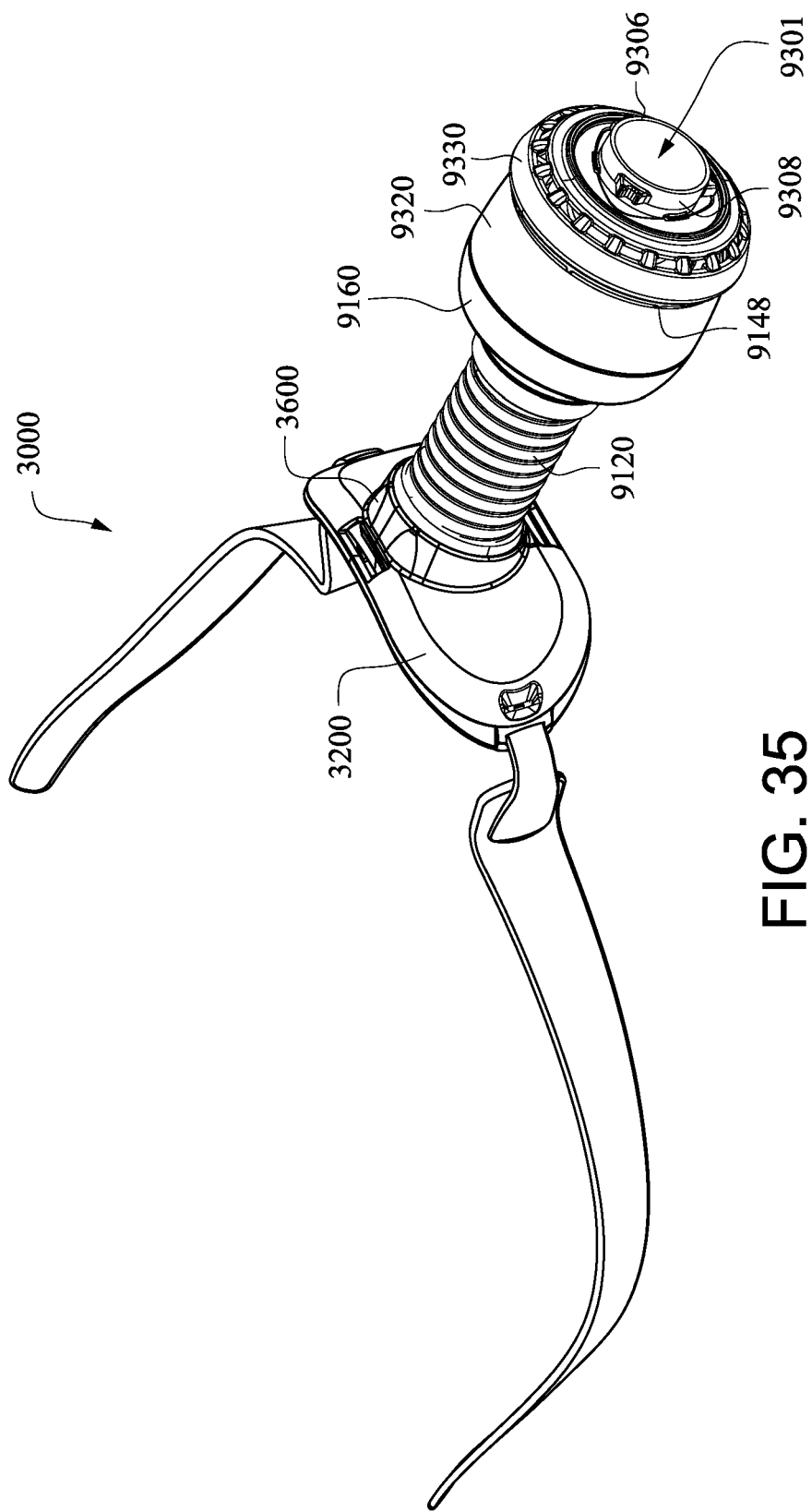

FIG. 35 depicts a perspective view of a vent adaptor with a patient interface according to an example of the present technology.

Figure 36A:
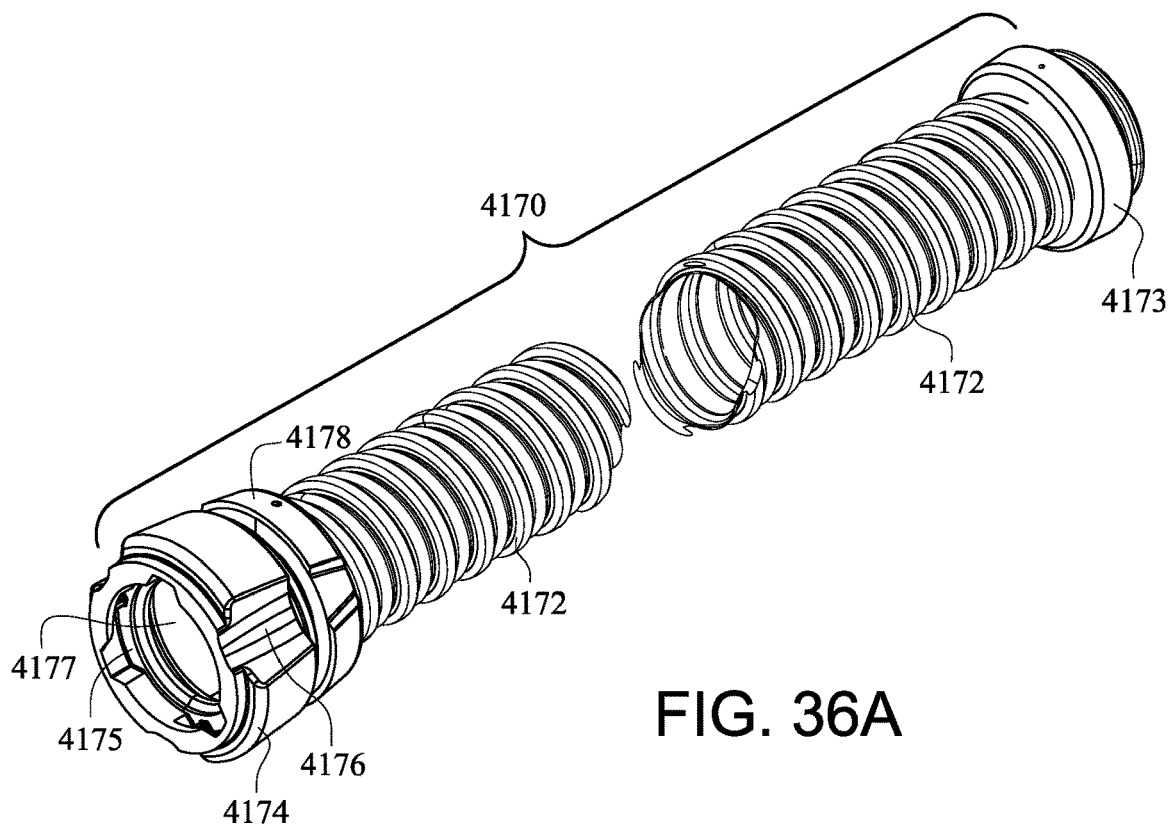

FIG. 36A depicts a perspective view of an air circuit according to an example of the present technology.

Figure 36B:
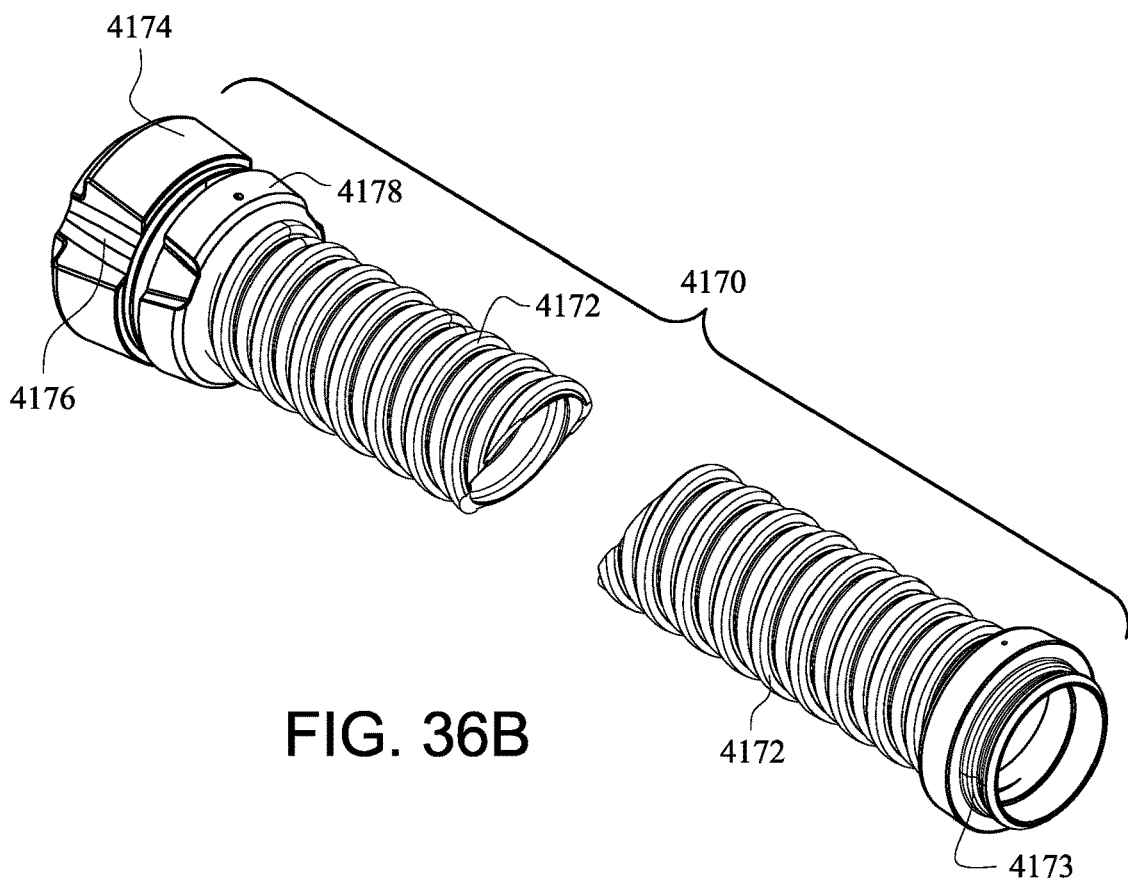

FIG. 36B depicts another perspective view of an air circuit according to an example of the present technology.

Figure 36C:
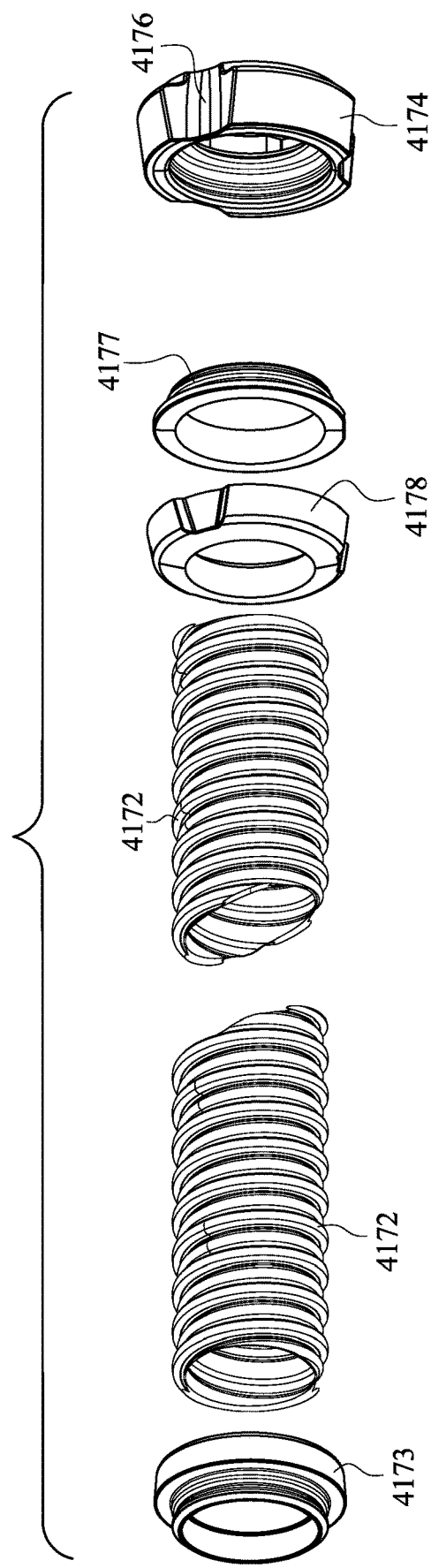

FIG. 36C depicts an exploded view of an air circuit according to an example of the present technology.

Figure 37A:
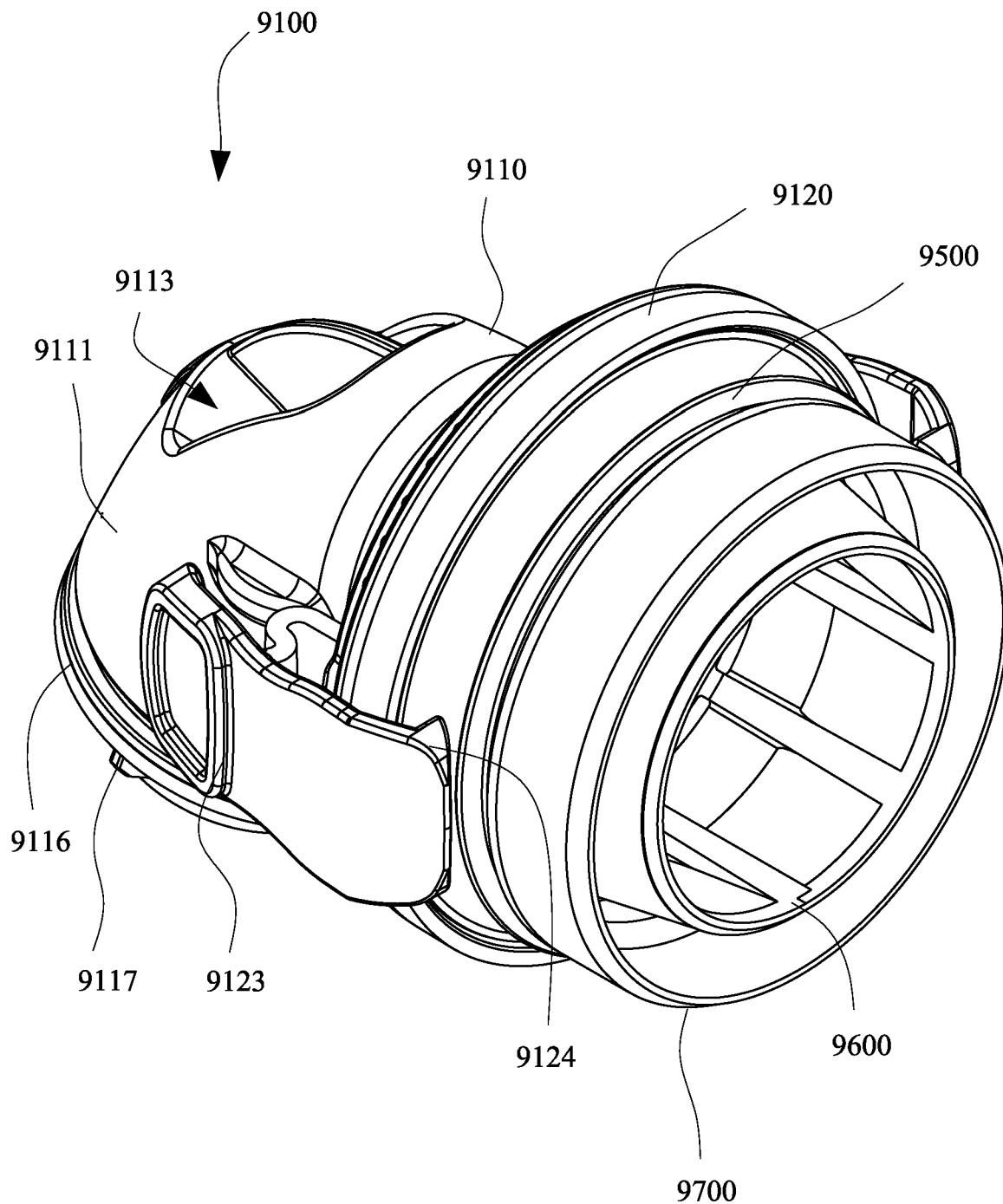

FIG. 37A depicts a perspective view of a vent adaptor according to an example of the present technology.

Figure 37B:
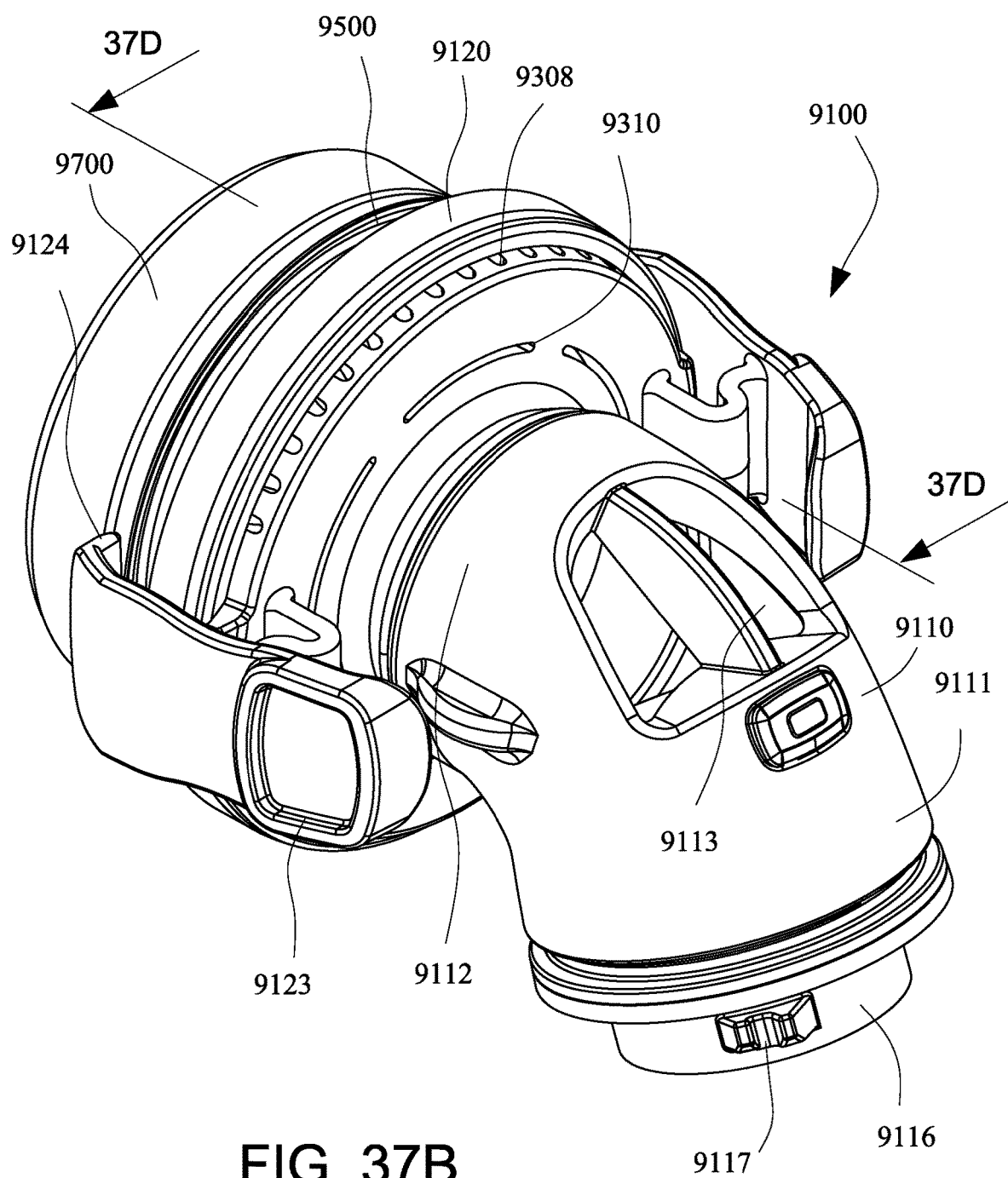

FIG. 37B depicts another perspective view of a vent adaptor according to an example of the present technology.

Figure 37C:
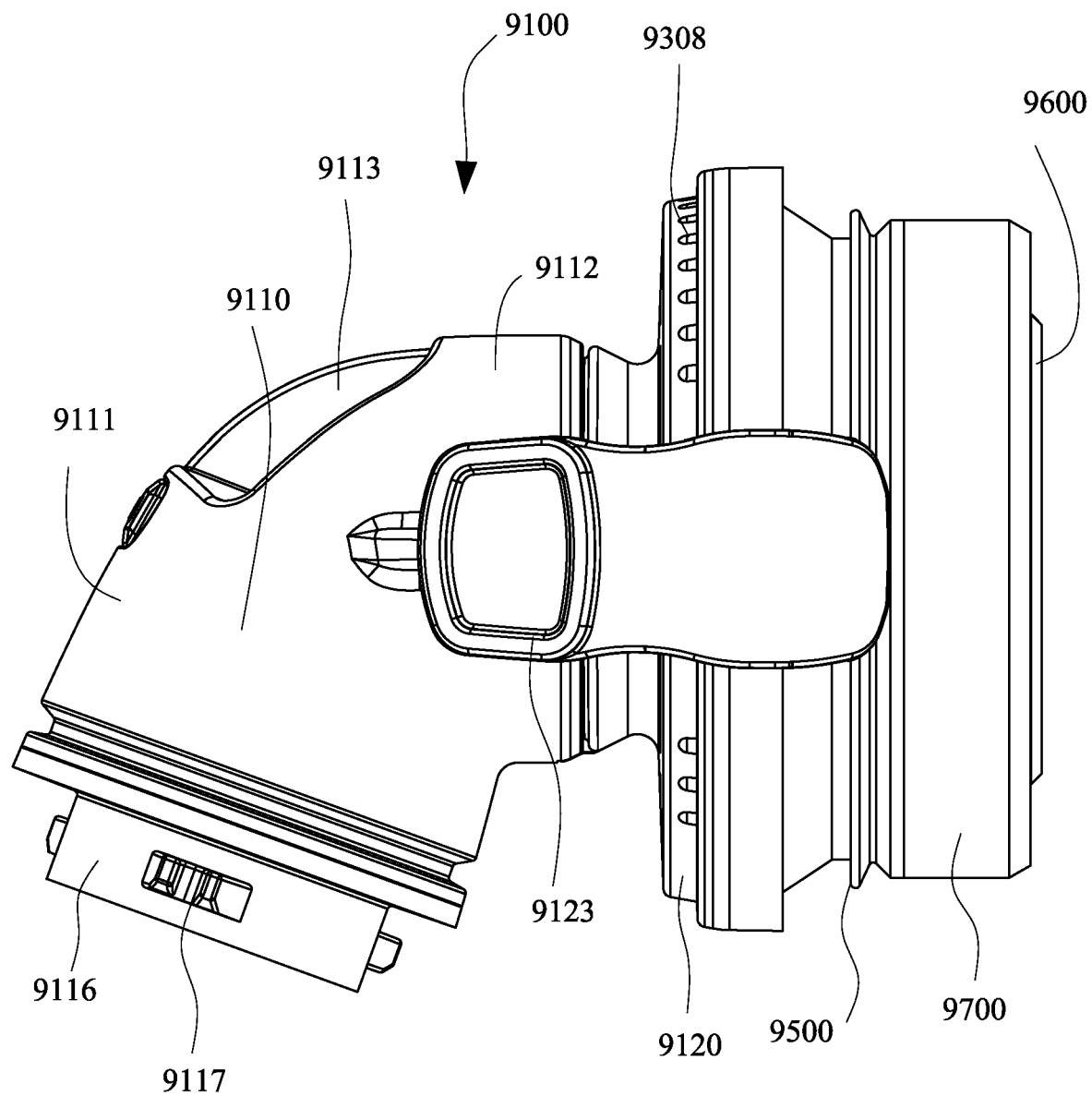

FIG. 37C depicts a lateral view of a vent adaptor according to an example of the present technology.

Figure 37D:
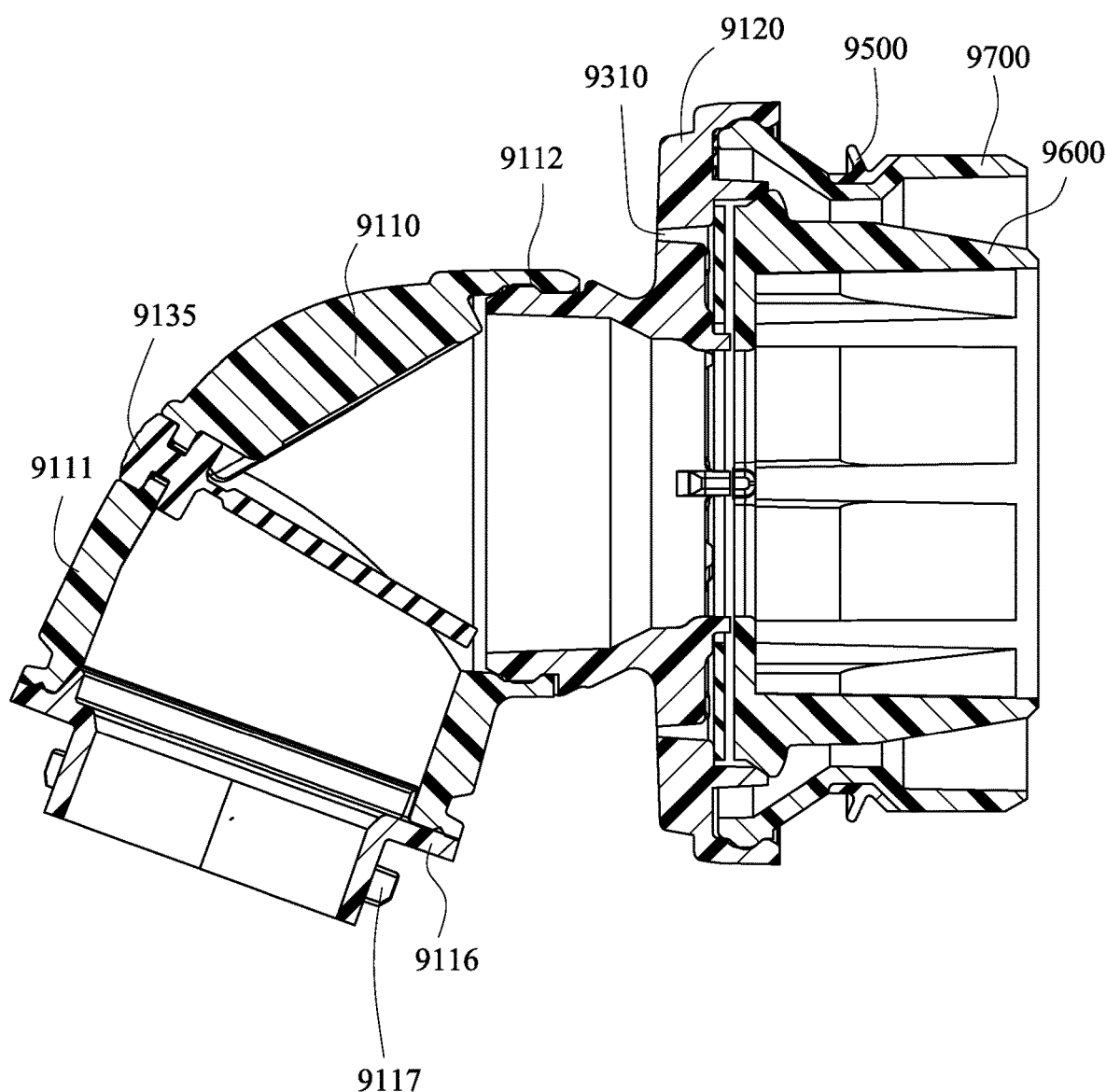

FIG. 37D depicts a cross-sectional view of a vent adaptor taken through line 37D-37D of FIG. 37B according to an example of the present technology.

Figure 37E:
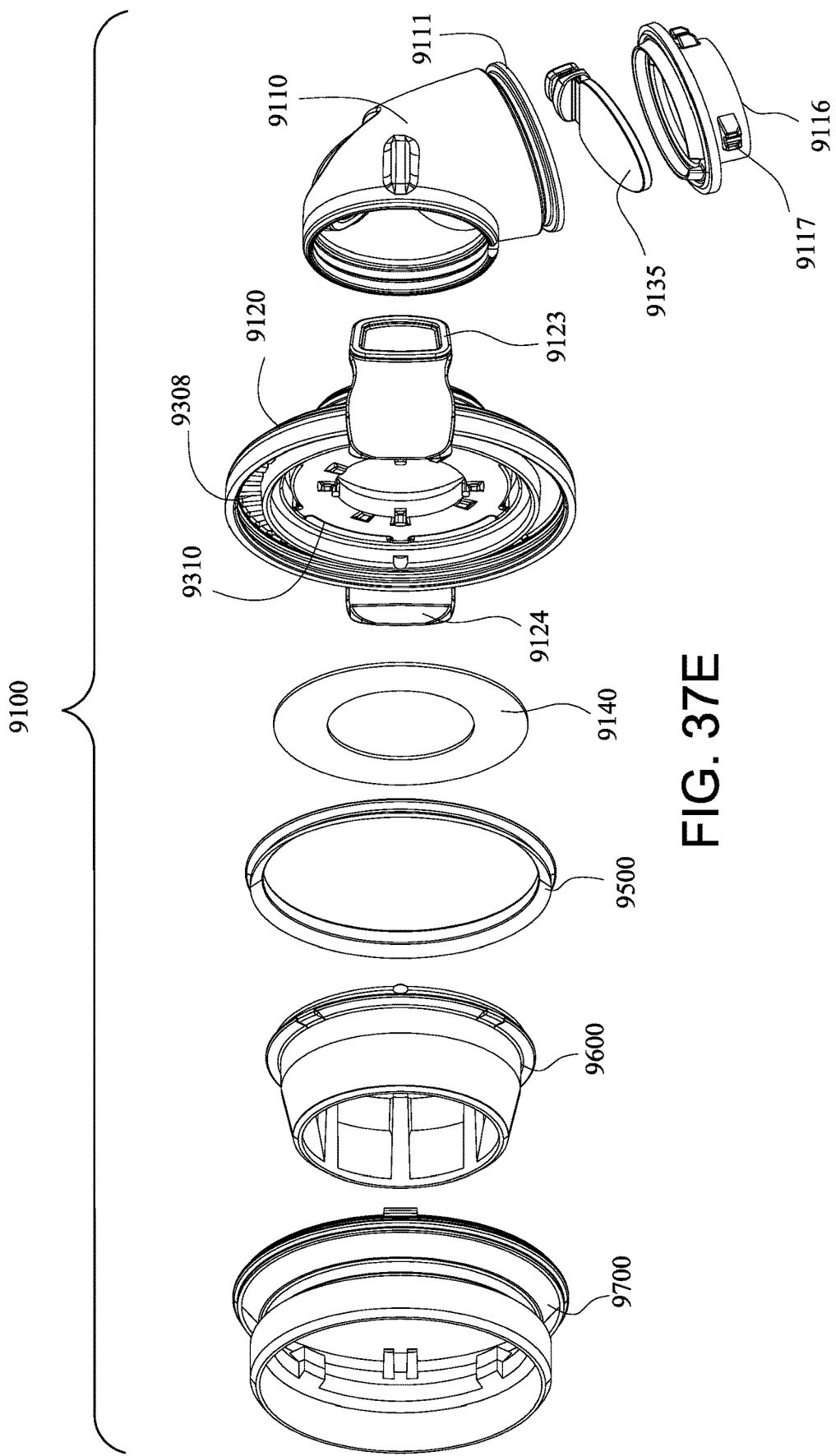

FIG. 37E depicts an exploded view of a vent adaptor according to an example of the present technology.

Figure 38A:
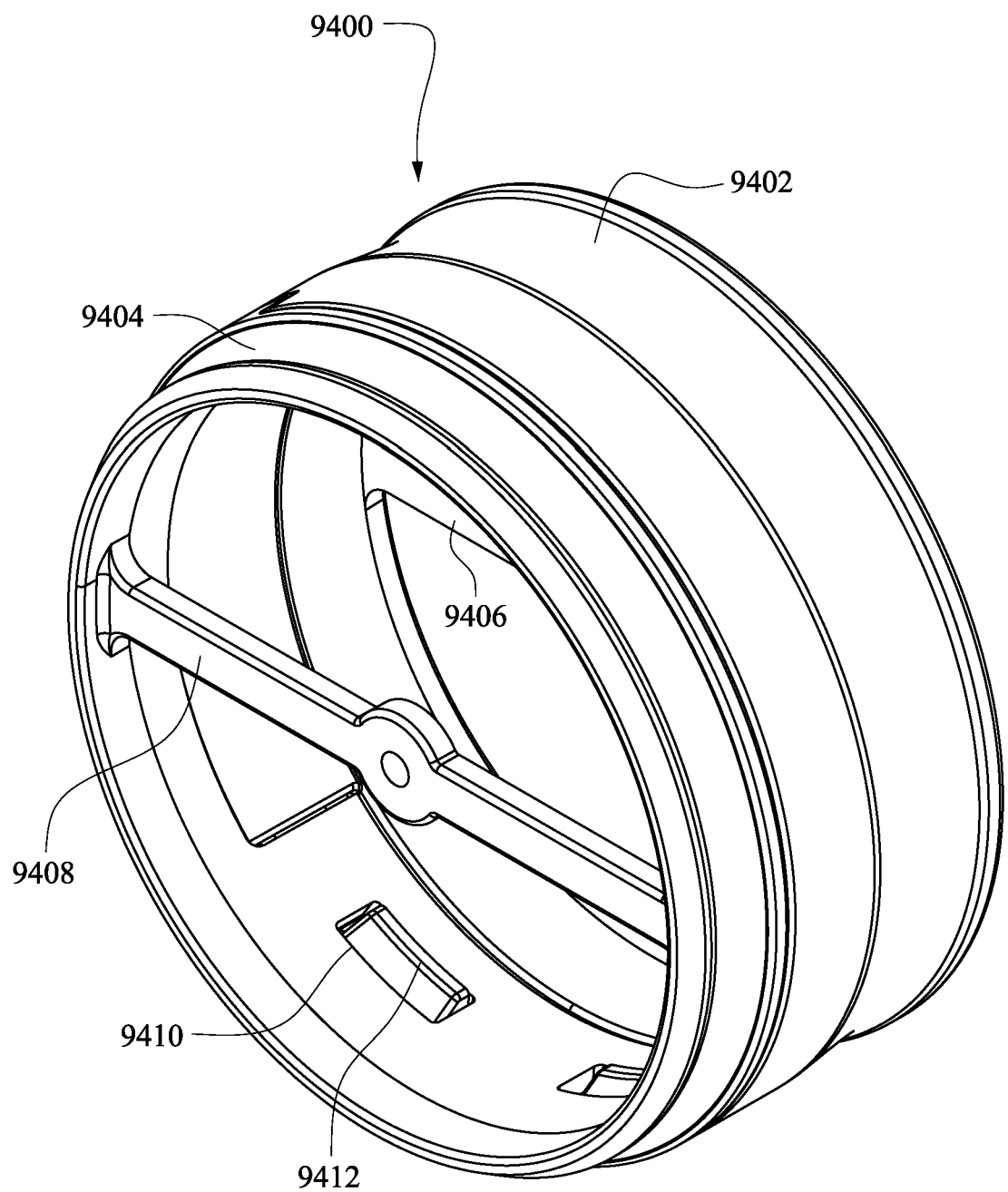

FIG. 38A depicts a perspective view of a heat and moisture exchanger (HME) housing according to an example of the present technology.

Figure 38B:
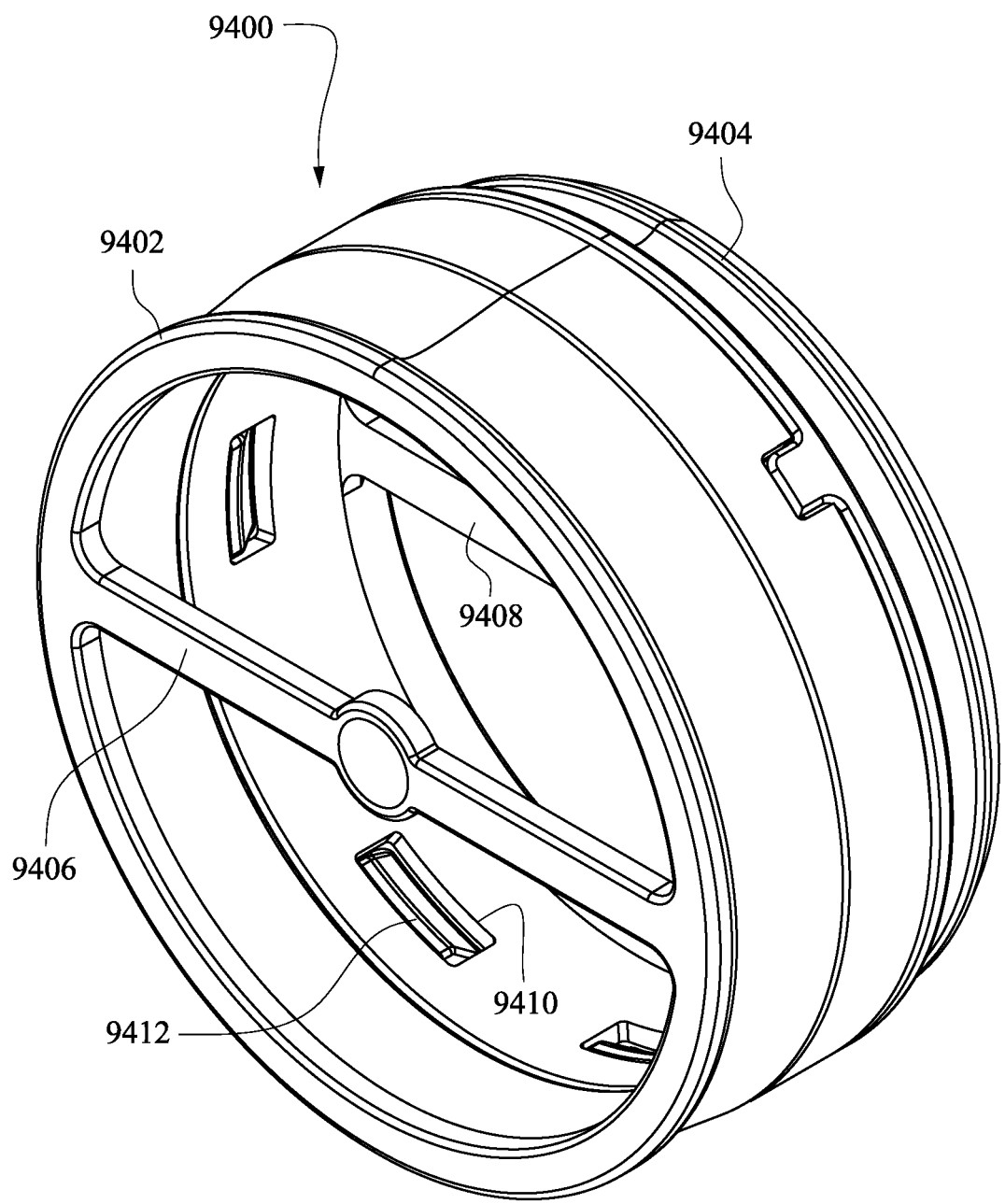

FIG. 38B depicts another perspective view of a HME housing according to an example of the present technology.

Figure 38C:
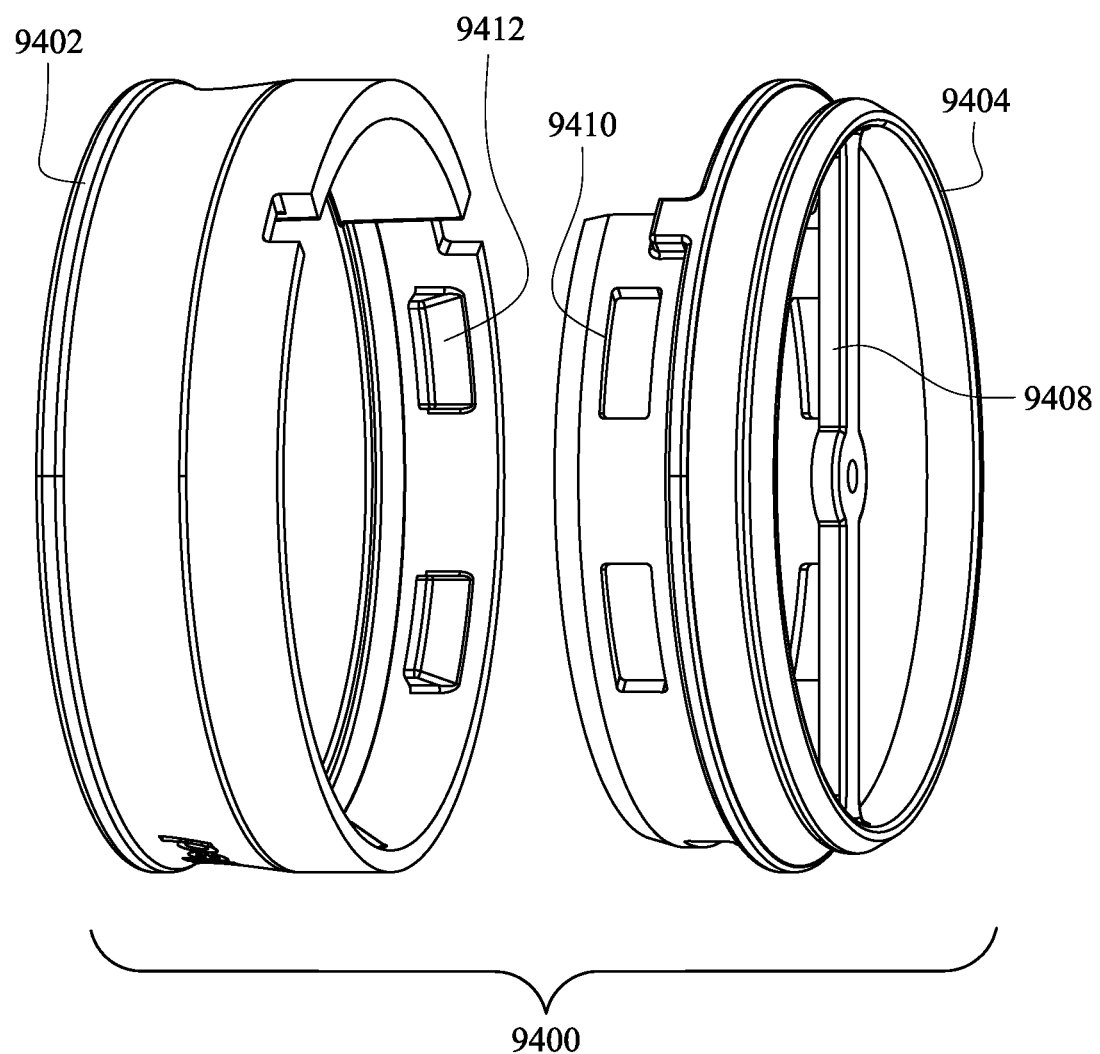

FIG. 38C depicts an exploded view of a HME housing according to an example of the present technology.

Figure 39A:
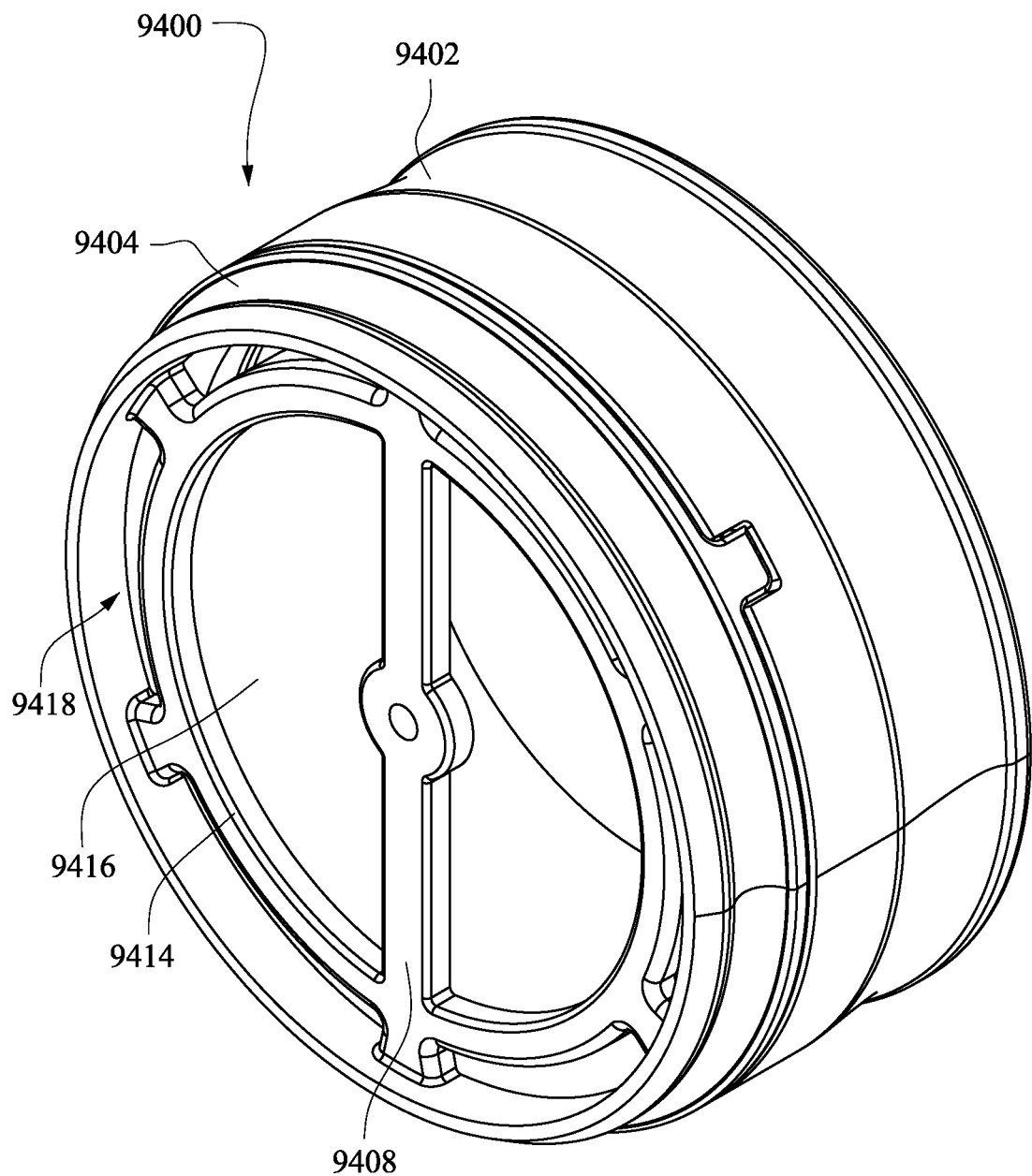

FIG. 39A depicts a perspective view of a heat and moisture exchanger (HME) housing according to an example of the present technology.

Figure 39B:
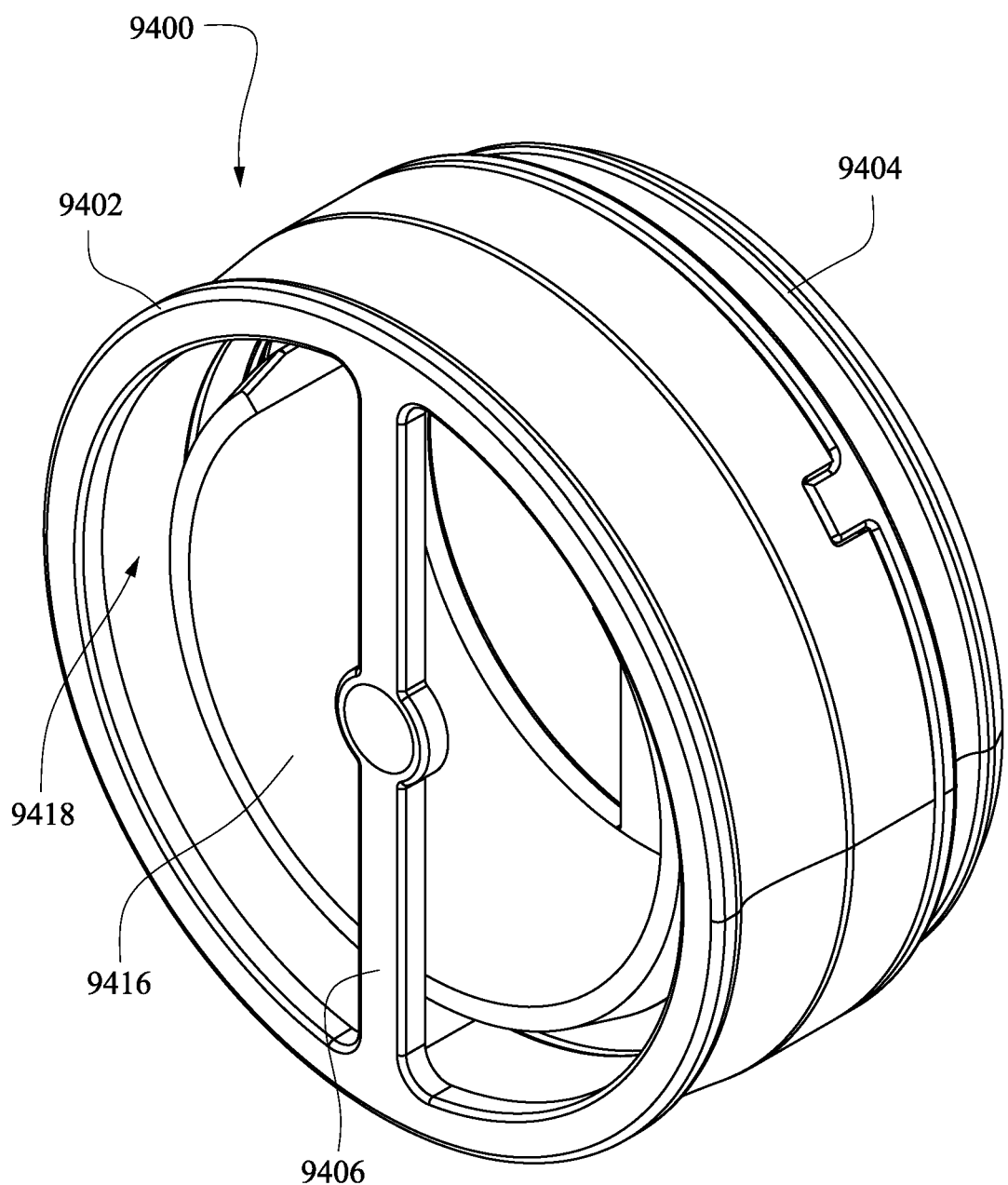

FIG. 39B depicts another perspective view of a HME housing according to an example of the present technology.

Figure 39C:
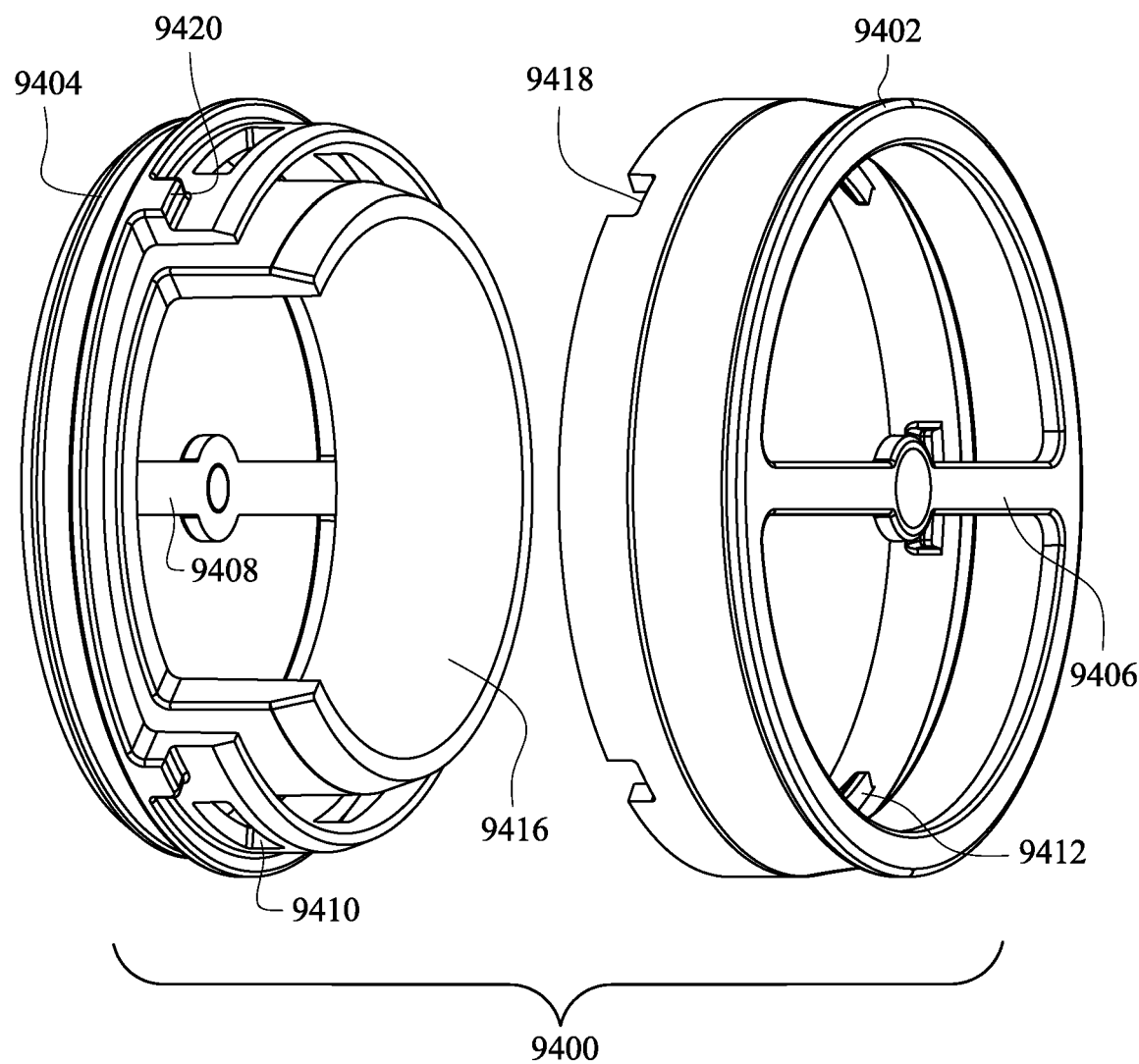

FIG. 39C depicts an exploded view of a HME housing according to an example of the present technology.

Figure 40:
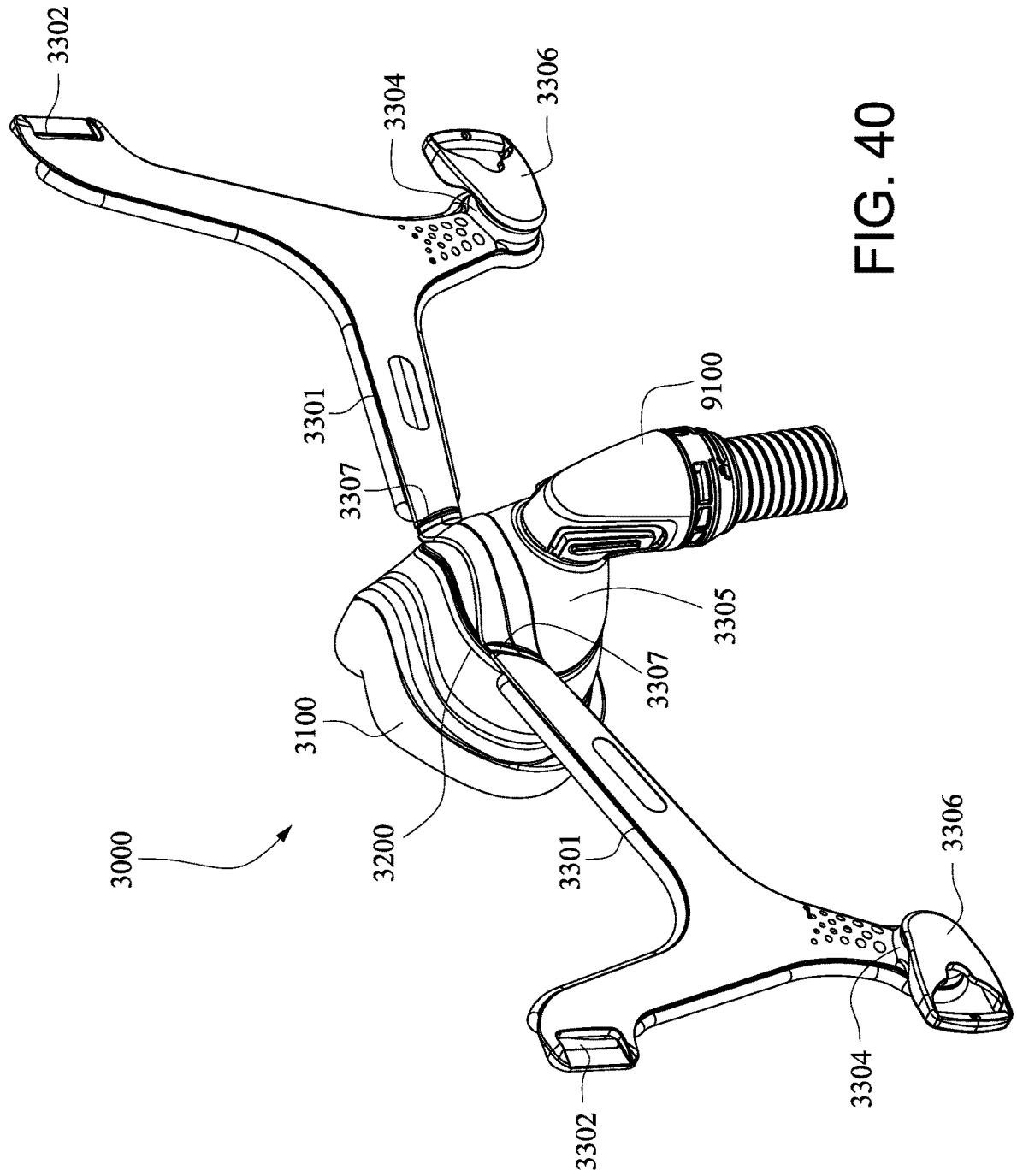

FIG. 40 depicts a perspective view of a vent adaptor with a patient interface according to an example of the present technology.

Figure 41:
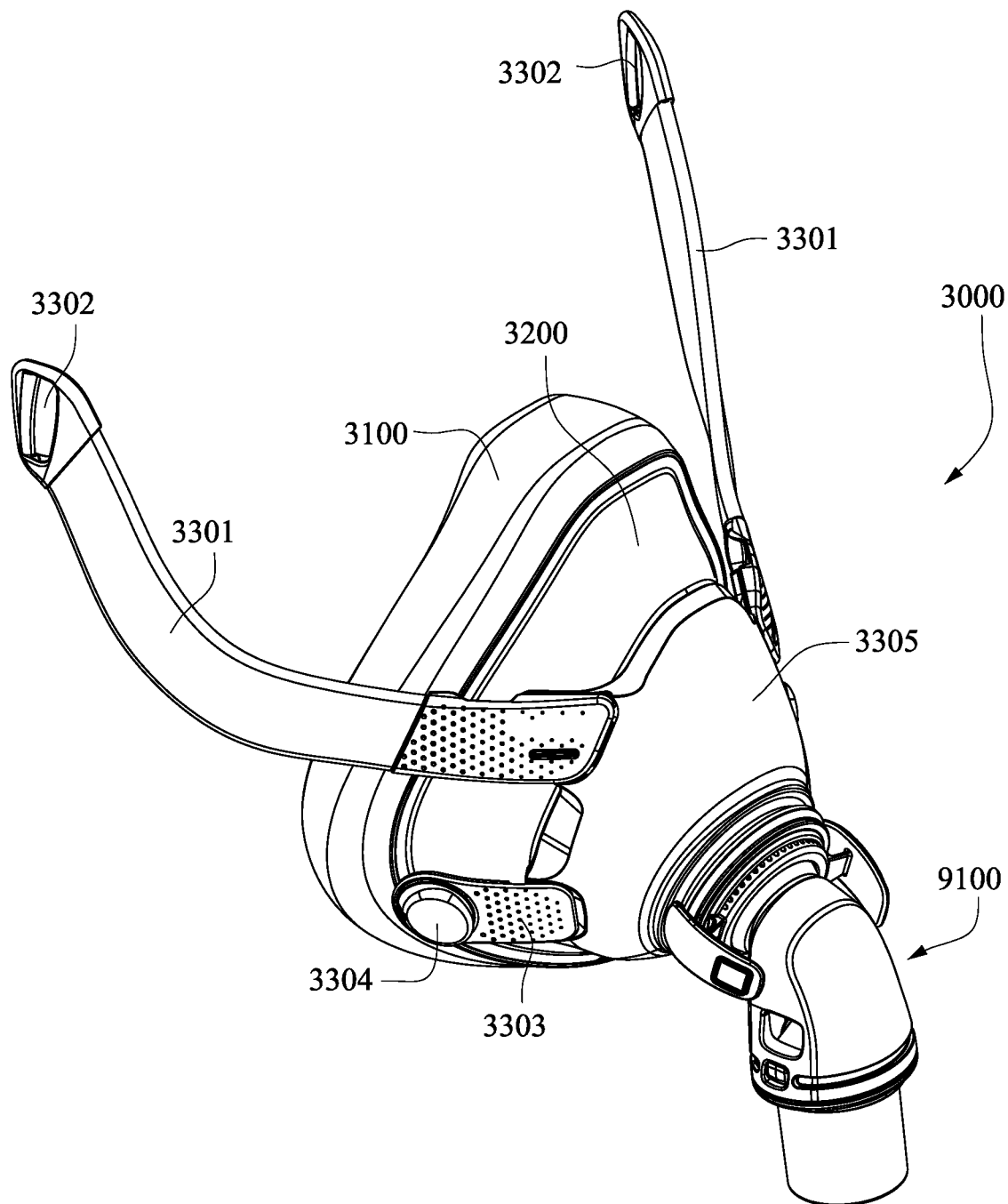

FIG. 41 depicts a perspective view of a vent adaptor with a patient interface according to an example of the present technology.

Figure 42A:
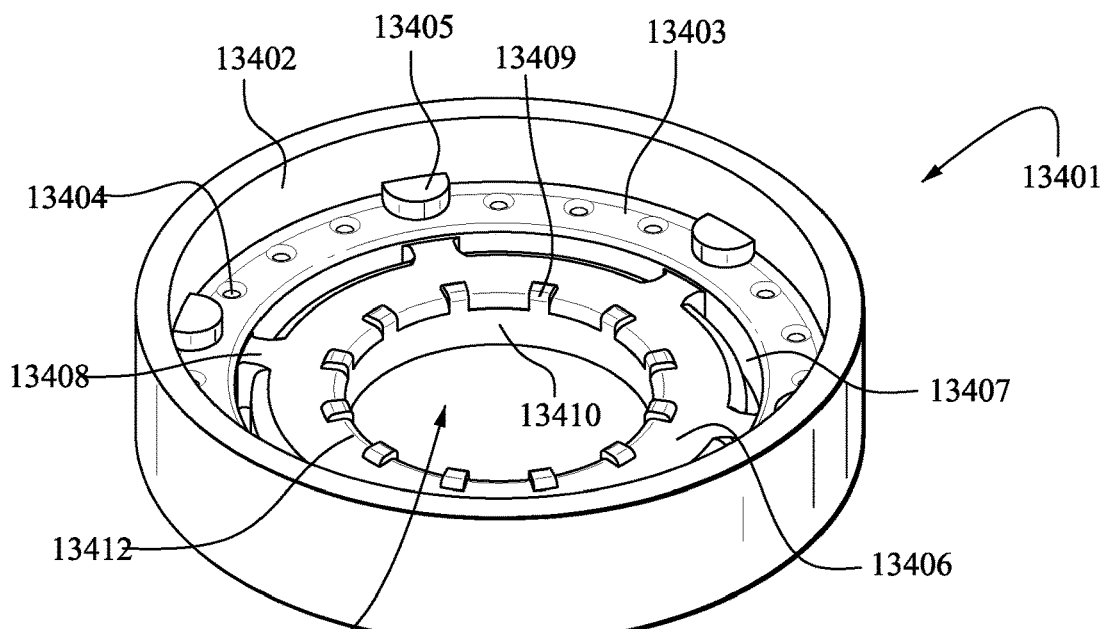

FIG. 42A shows a top perspective view of a vent housing according to another example of the present technology.

Figure 42B:
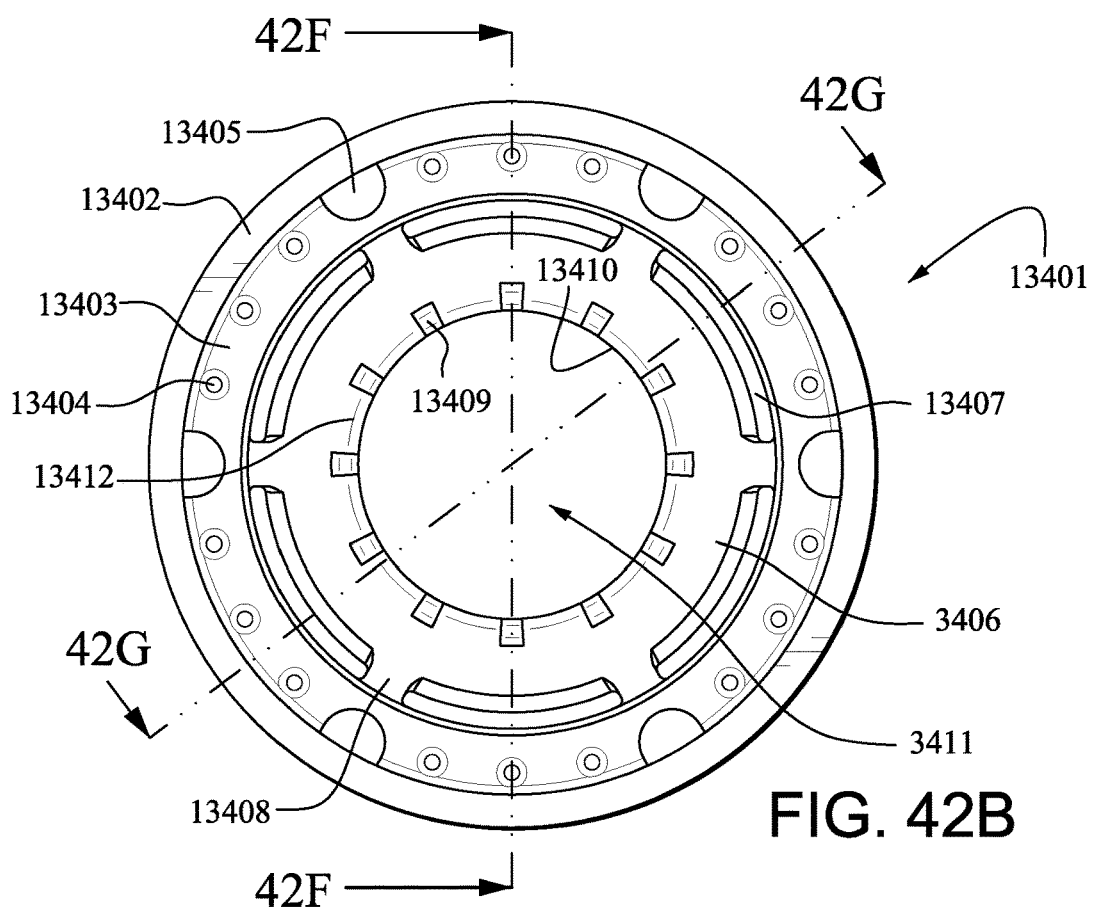

FIG. 42B shows a top view of a vent housing according to another example of the present technology.

Figure 42C:
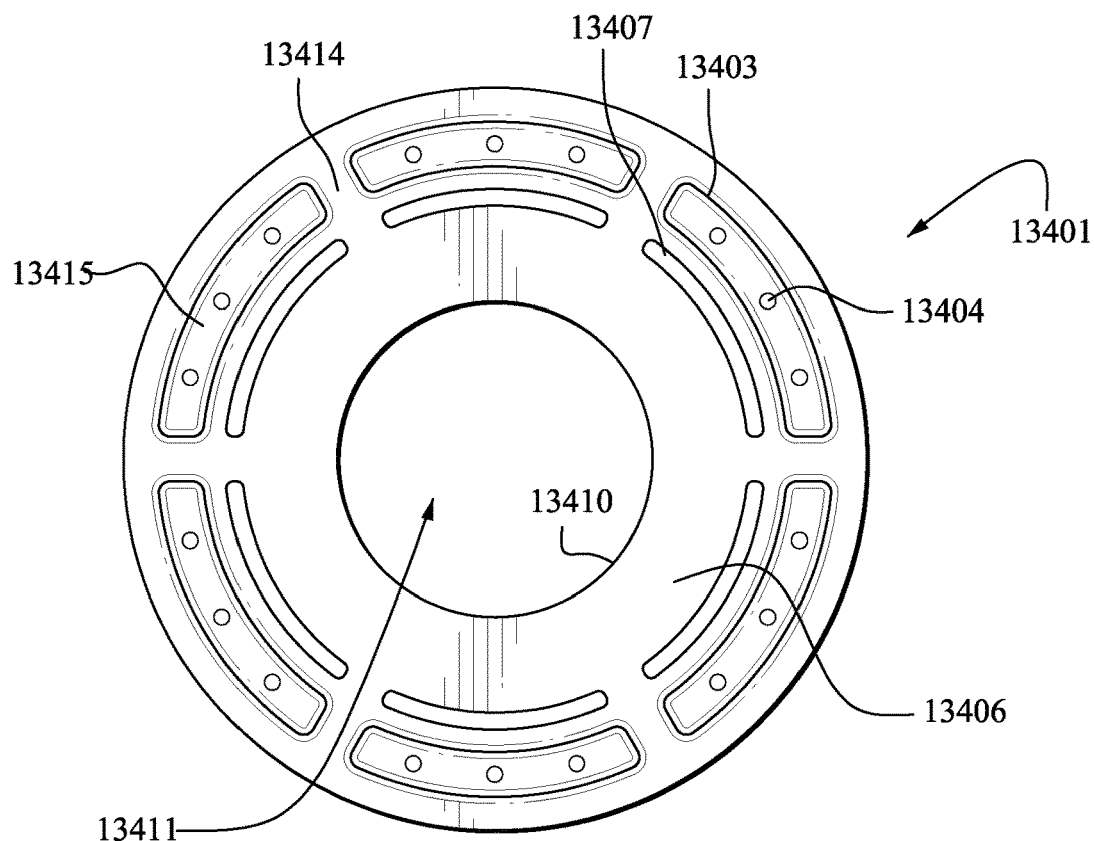

FIG. 42C shows a bottom view of a vent housing according to another example of the present technology.

Figure 42D:
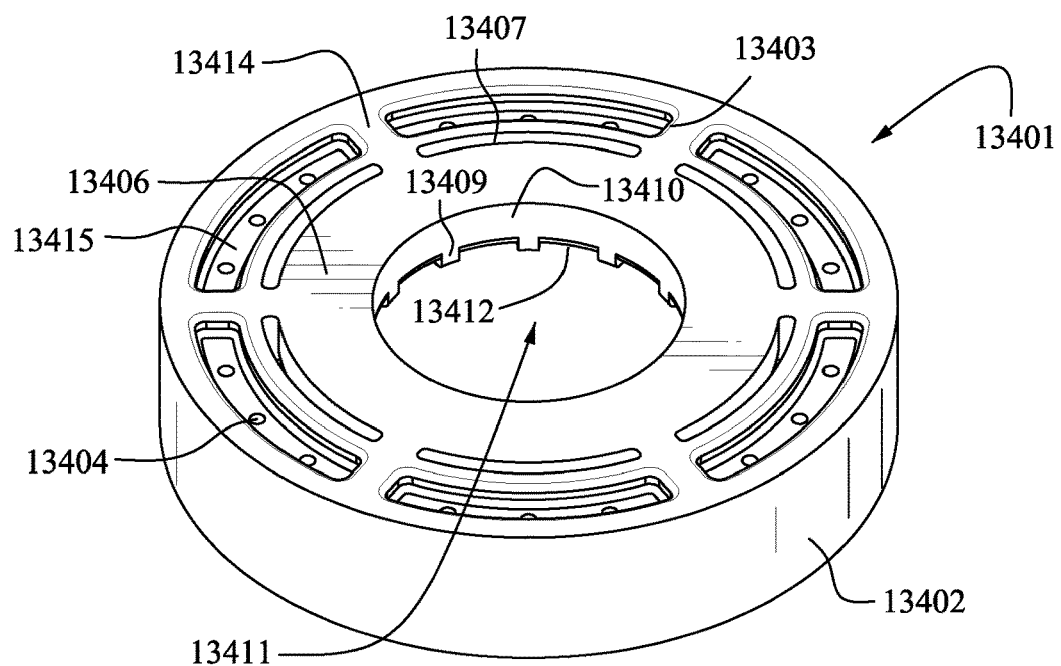

FIG. 42D shows a bottom perspective view of a vent housing according to another example of the present technology.

Figure 42E:
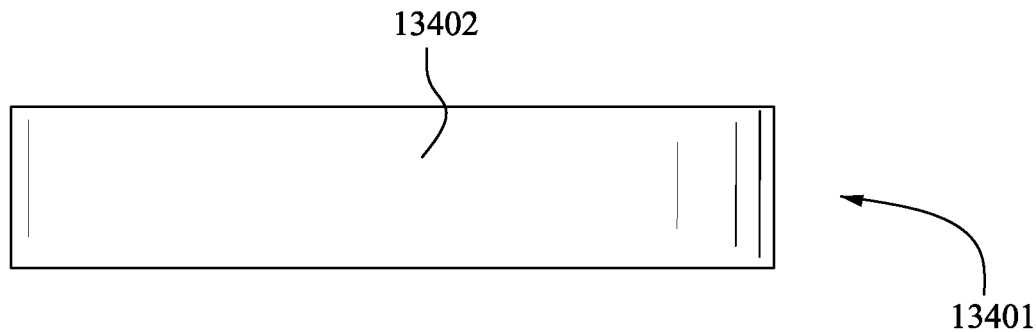

FIG. 42E shows a side view of a vent housing according to another example of the present technology.

Figure 42F:
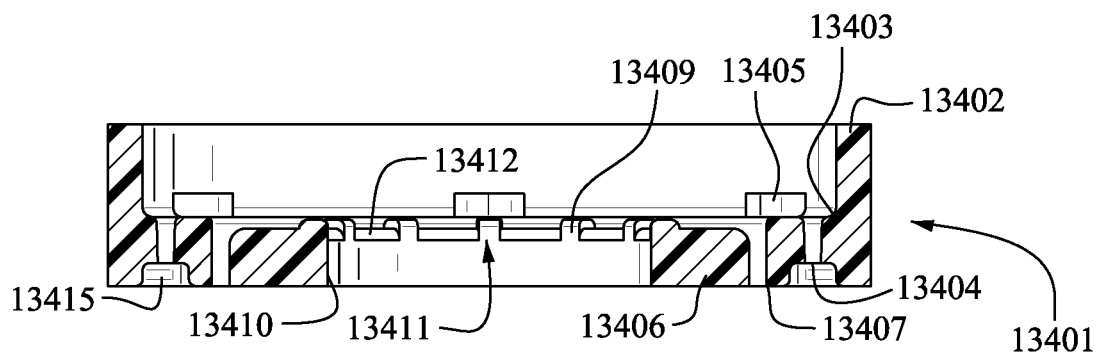

FIG. 42F shows a cross-sectional view of a vent housing according to another example of the present technology taken through line 42F-42F of FIG. 42B.

Figure 42G:
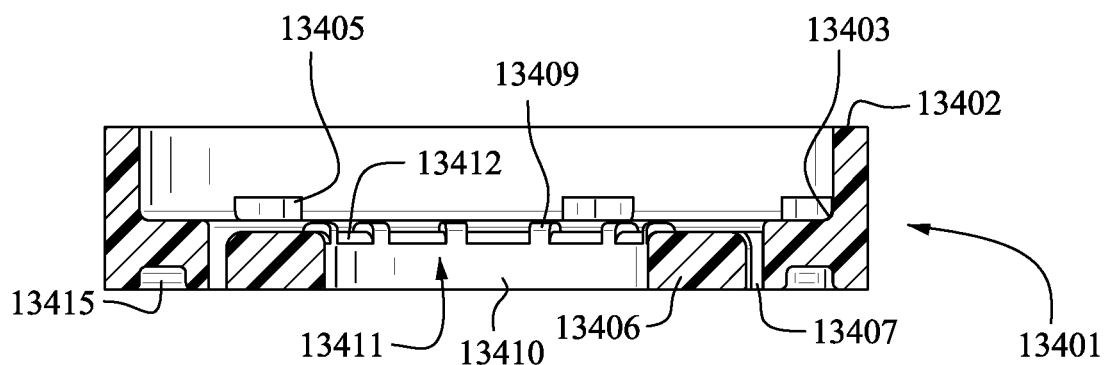

FIG. 42G shows a cross-sectional view of a vent housing according to another example of the present technology taken through line 42G-42G of FIG. 42B.

Figure 43A:
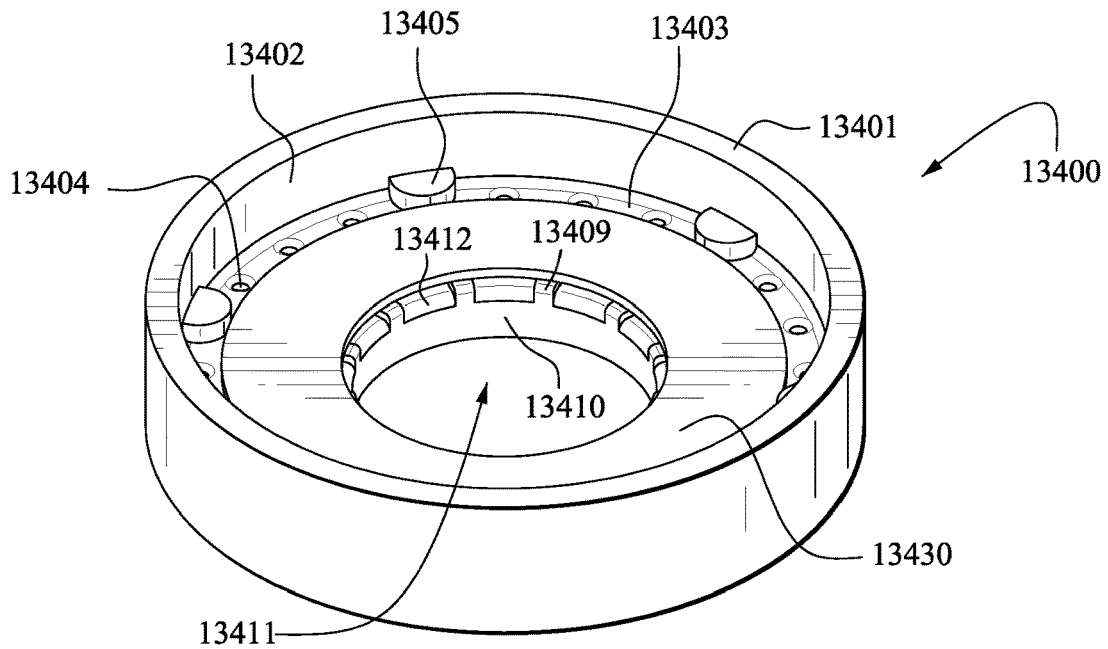

FIG. 43A shows a top perspective view of a vent system according to another example of the present technology.

Figure 43B:
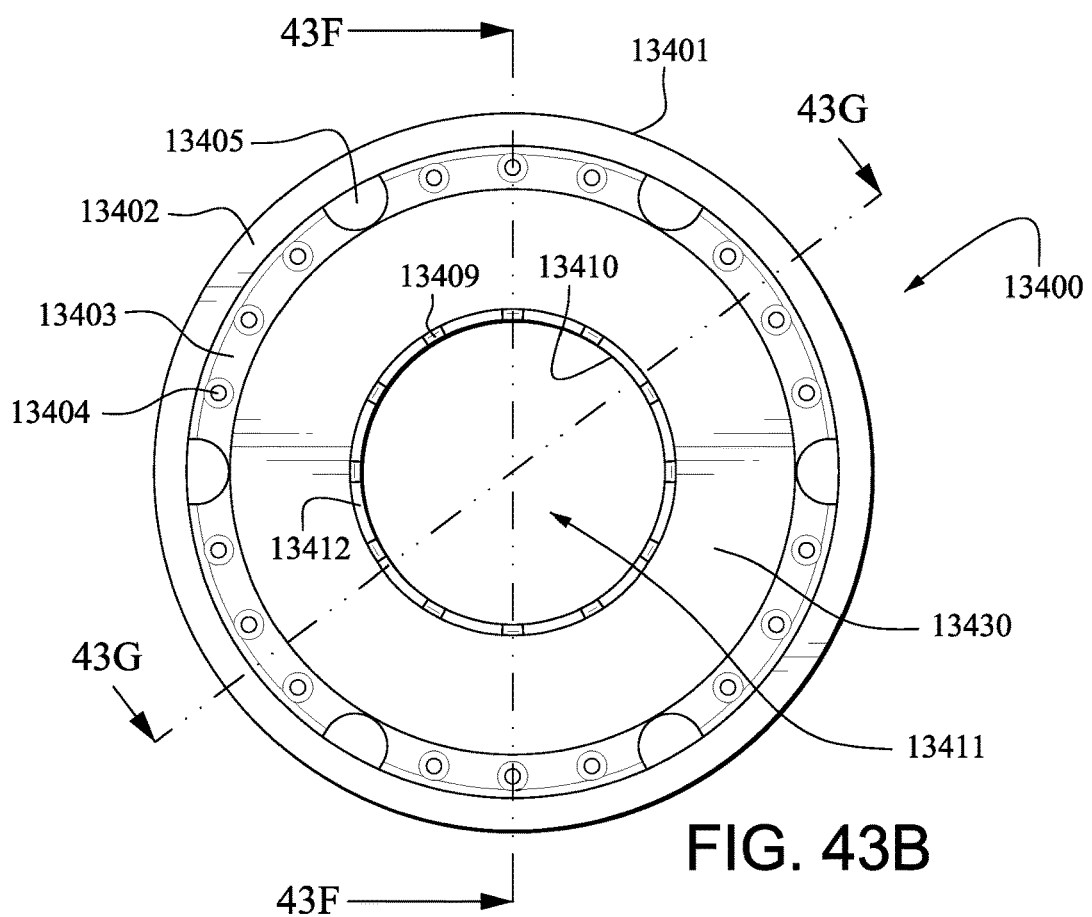

FIG. 43B shows a top view of a vent system according to another example of the present technology.

Figure 43C:
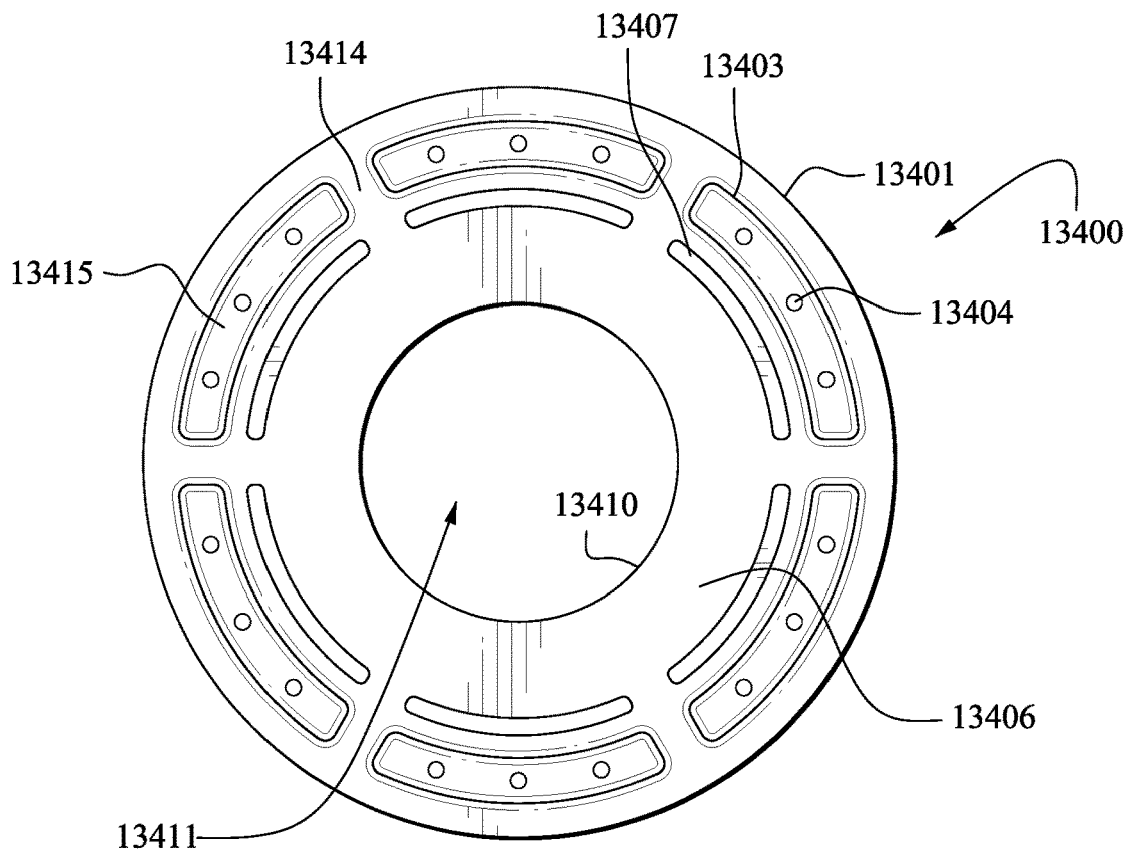

FIG. 43C shows a bottom view of a vent system according to another example of the present technology.

Figure 43D:
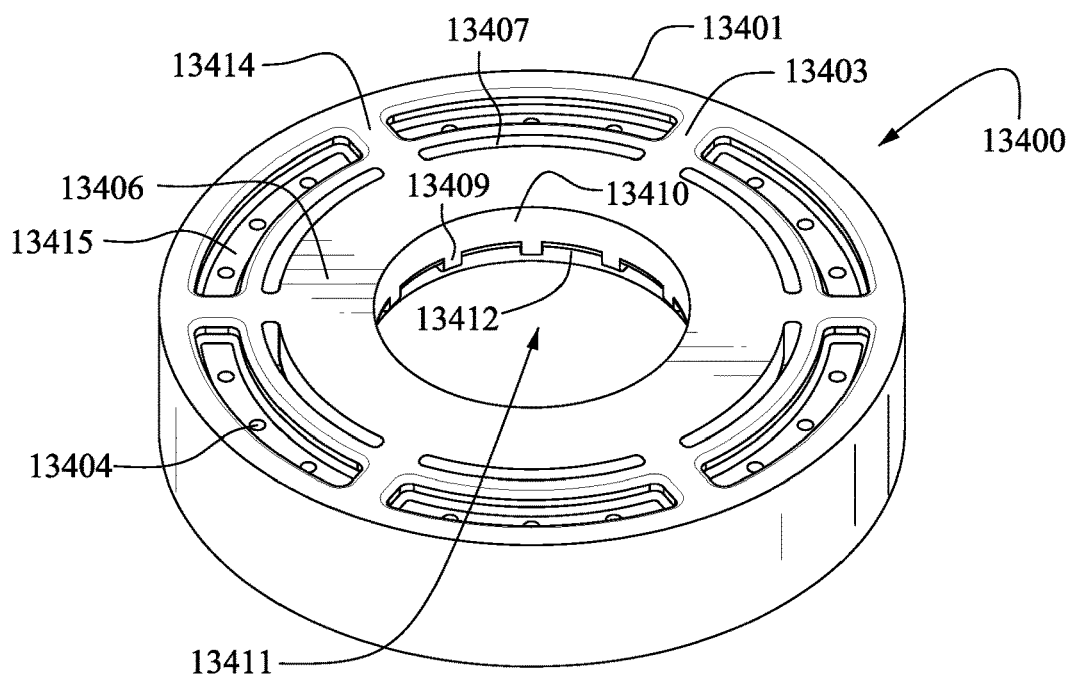

FIG. 43D shows a bottom perspective view of a vent system according to another example of the present technology.

Figure 43E:
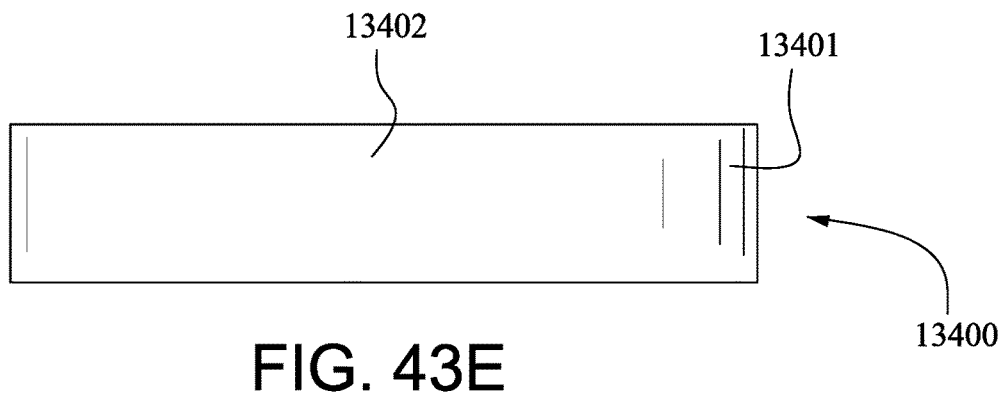

FIG. 43E shows a side view of a vent system according to another example of the present technology.

Figure 43F:
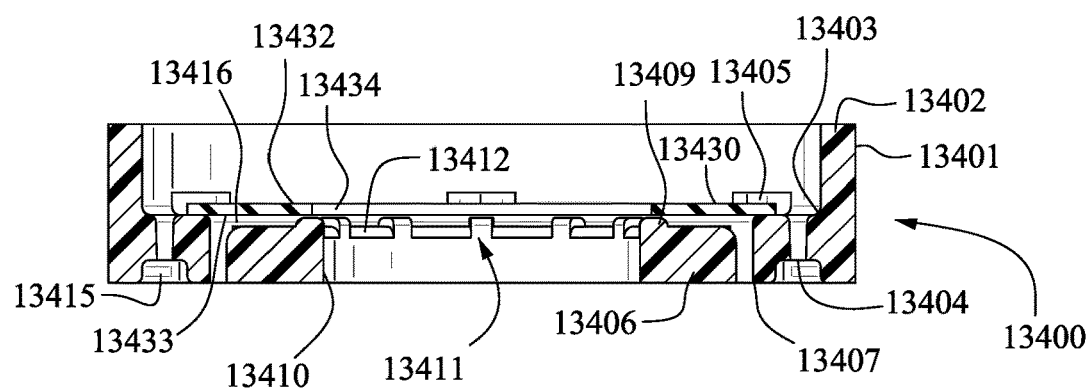

FIG. 43F shows a cross-sectional view of a vent system according to another example of the present technology taken through line 43F-43F of FIG. 43B.

Figure 43G:
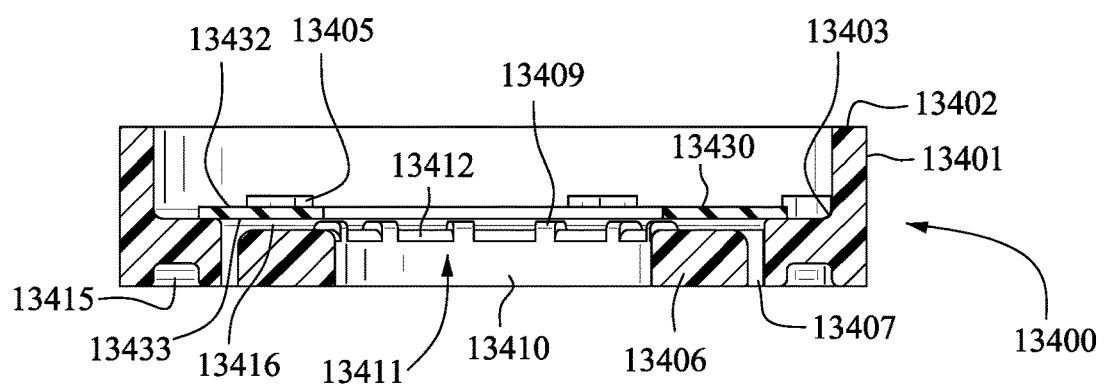

FIG. 43G shows a cross-sectional view of a vent system according to an example of the present technology taken through line 43G-43G of FIG. 43B.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. The sealing flange comprises a relatively thin member with a thickness of less than about 1 mm, for example about 0.25 mm to about 0.45 mm, that extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

5.3.3 Positioning and Stabilising Structure

The seal-forming structure 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

5.3.4 Vent

In one form, the patient interface 3000 includes a vent 3400 constructed and arranged to allow for the washout of exhaled gases, e.g. carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 Vent Adaptor 5.4.1 Constant Flow Vent

FIG. 16 shows a comparison of vent flow rate between a regular vent (FFM Nom Flow) versus the constant flow vent (CFV). The regular vent is a standard moulded vent, e.g., a vent 3400 formed on the patient interface 3000 in FIG. 3A. As can be seen in the graph, the vent flow rate is compared in a range of mask pressures between 4-20 cm of H2O, which is a standard pressure range for Respiratory Pressure Therapy for SDB and OSA. As can be seen, the vent flow rate increases logarithmically as the pressure increases. In comparison, the CFV shows a flatter curve, where the vent flow rate appears more constant and lower over the same pressure range.

Vent flow should be at least 16 L/min to washout enough CO2 within the system such that CO2 rebreathing is minimized by the patient. It has been shown that a vent flow rate of between 20-27 L/min is provides breathing comfort (patient not awakened due to increased CO2 rebreathing) and safety (avoid suffocation due to too much CO2 rebreathing). One aspect of the present technology includes providing a minimum (or minimum range) vent flow to ensure that sufficient CO2 is washed out. Any vent flow above that minimum may be considered wastage. For example, when viewing the graph shown in FIG. 16, the area between the CFV vent flow and FFM Nom flow may be considered wasted flow. The CFV achieves the minimum vent flow rate of 16 L/min required within therapeutic pressure range and keeps this vent flow rate between 16-27 L/min within the pressure range of 4-20 cm of H2O. In comparison, the FFM Nom flow ranges from 22-55 L/min. Thus, there may be greater unnecessary flow loss using the FFM nom flow vent.

To compensate for unnecessary flow loss, the flow generator or RPT device may be required to increase its flow to achieve the same pressure as compared to the CFV. Thus, more power is required and a more complex flow generator is required to allow for greater flow swings (e.g. between 16-55 L/min of vent flow) to compensate for this vent. The CFV, however, may regulate the vent flow under pressure changes to reduce the vent flow rate as pressure increases. Thus, the CFV may allow for greater power savings by the flow generator and added simplicity due to avoiding the need for complex pressure/flow control.

A constant flow vent (CFV), according to the present technology, may be a vent flow regulating valve (moveable membrane) 9140 that reacts to mask pressure to regulate vent flow. An exemplary CFV is depicted in FIGS. 21A-21F. The valve 9140 may be tuned such that the flow remains relatively constant within a predetermined range of pressure. That is, when pressure increases in the mask/system, the flap 9140 covers more internal vent holes 9126 to reduce the vent flow rate (vent flow rate increases at higher pressures); when the pressure is low in the mask/system, the flap 9140 covers fewer of the vent holes and allows more vent flow (compensates for low vent flow rates at lower pressures). This tuning may allow for a substantially constant vent flow within a range of pressures. The graph in FIG. 18 illustrates changes in flow under changes in pressure with and without the CFV. The performance of the exemplary CFV graphed in FIG. 18 has a flow rate of up to 24 L/min as pressure increases from 0-40 cm H2O.

According to an example of the present technology, the CFV may comprise a moveable flap or a CFV membrane 9140 and may be made of elastic material such as silicone or other TPE (thermoplastic elastomers). The flap 9140 may be configured such that an increase in pressure in the mask urges the flap to cover more of the internal vent holes 9126 and reduces the flow rate progressively. The flap 9140 may be positioned perpendicular to the flow of pressurized gas flowing to the patient. The vent passage of the internal vent holes 9126 may also run perpendicularly to the flow and away from the patient to exit to the atmosphere. The flap 9140 is positioned such that pressure build up in the mask may urge the flap towards the internal vent holes 9126.

FIG. 21F shows the configuration of an exemplary CFV in cross section. The CFV unit may be placed in line (that is within the air delivery conduit circuit). As shown in FIG. 21F, if pressure builds up in the mask then the position of the flap 9140 is such that the flap 9140 may move towards the internal vent holes 9126. The pressurized gas that reaches the internal vent holes 9126 that are not blocked by the flap 9140 can then be vented to atmosphere via the external vent holes 9125.

The CFV is a feature that may allow for simplification of the RPT system. Having a substantially constant vent flow rate within a range of pressures means that the complexity of the flow generator or RPT device may be reduced as substantial pressure control is no longer required to compensate for changing pressure loss due to venting. Moreover, the CFV may allow for reduced power consumption as power is no longer required to compensate for flow variations at different pressures. That is, the CFV is passively (pressure driven) and is capable of regulating pressure due to vent flow changes that would otherwise be actively compensated by changes in pressure/flow delivery from the RPT device. This simplification allows for a simpler RPT device to deliver therapy, e.g., the device may have fewer parts, it may be smaller, it may not require powered humidification, and/or it may require less power overall to deliver therapy (due to the fact that it does not need to compensate for vent flow changes). The CFV may also allow for passive humidification via a heat and moisture exchanger (HME), as described below.

A problem with known CFV concepts is that there may be vent noise associated when regulating the vent flow. It is possible that there is some interaction with the flap 9140 and the internal vent holes 9126 that disturbs vent flow and causes noise. For example, it is hypothesized that the moveable flap 9140 does not fully cover some of the internal vent holes 9126 when moving under pressure. This interaction may cause turbulence and associated noise as gas flows between the flap 9140 and the internal vent hole 9126.

One way to reduce turbulence and, therefore, noise may be to reduce the number of holes 9126 that interact with the flap 9140. However, a minimum vent flow is required to prevent CO2 rebreathing in the mask and reducing the number of vent holes 9126 that interact with the flap 9140 may not allow sufficient venting. Thus, a solution according to the present technology may involve having some of the vent holes 9126 being regulated by radial disc flap 9140 and other vent holes 9126 not engaging with the flap 9140 and remaining open at all times. Having some vent holes 9126 open, i.e., the static vents, at all times means that the vent flow rate will increase as pressure increases in the system, according to Bernoulli's principle.

To compensate for this increase in vent flow rate such that the overall vent flow is substantially constant over the therapeutic range of pressures, the vent flow of the remaining vent holes, i.e., the regulated vents, may be reduced as pressure increases. These vent holes 9126 may be regulated by the moveable flap 9140, wherein the vent holes 9126 are covered progressively as the pressure increases, thereby reducing the vent flow rate. The overall flow rate of the static vents can then be averaged with the flow rate of the regulated vents to achieve an overall substantially constant flow rate over a range of therapeutic pressures. The lower noise levels of the vents can also be attributed to moulded vent technology that produces low levels of noise as pressure and vent flow increases (e.g., by moulding small vent holes with a converging profile). This technology in combination with the regulated vent flow may allow for a low overall noise alternative for a constant flow vent.

A vent adaptor 9100 or fluid connector may comprise a constant flow vent (CFV) unit. The CFV unit may comprise: a CFV ring 9150; a flat, annular valve 9140; and a vent housing 9120. The CFV ring 9150 may hold the valve 9140 in place against the vent holes 9126. The vent housing 9120 may comprise an annular surface comprising a plurality of vent holes 9126. The annular surface may comprise a central orifice for allowing the flow of pressurised gas into the mask chamber (inlet flow). The annular surface may comprise the plurality of vent holes 9126 to allow vent flow. The valve 9140 may be adjacent to the vent holes 9126 and may be held freely between i.e., sandwiched between, the CFV ring 9150 and the annular surface of the vent housing 9120, i.e., the flap 9140 is not fixed to CFV ring 9150 or the vent housing 9120. As mask pressure increases, this increases pressure towards the vent, wherein the valve 9140 is pushed towards and covers more of the vent holes 9126. In contrast, as mask pressure decreases, less pressure is applied to the valve 9140, thus the valve 9140 moves away from and covers less of the vent holes 9126.

Reducing the vent noise for the constant flow vent design may be accomplished by altering the vent flow characteristics by the use of a flow regulating valve or membrane 9140. However, the membrane 9140 may increase vent noise over traditional moulded or static vents, i.e., the vent holes do not change form or shape during changes in pressure. This noise may be attributed to a number of factors, including: 1) the change of the velocity of flow through the regulated vents as the vent holes 9126 are opened or closed by the membrane 9140 and/or 2) flow disturbances caused by the membrane 9140 that generate noise, i.e., turbulence. For example, changing the direction of vent flow can cause turbulence, which may then result in noise from a number of factors. This can be caused by gases colliding into the surfaces of the vent (vent walls or CFV membrane) 9140, or air passing over the surface of the vent (vent walls and/or membrane) 9140. Thus, partially closing vent holes 9126 can generate more noise due to factors 1) and/or 2) above.

As mentioned above, an aspect of the present technology includes a vent with a substantially constant flow within a therapeutic pressure range (i.e., 4-20 cm H2O, or 2-40 cm H2O). To meet the desired vent flow curve under pressure changes, the vent holes' 9126 flow curve may be varied dynamically over the therapeutic pressure range. This may be accomplished by changing the size, number, and/or shape of the vent holes. Varying such characteristics may lead to changes in flow characteristics of gases passing through the vent holes, which can lead to an increase in vent noise. Using moulded vent technology that includes a converging vent hole shape as gases exit the vent into the atmosphere, i.e., converging from the internal vent holes 9126 to the external vent holes 9125, noise of the vent flow may be tuned to a minimum. However, it should be understood that moulded vent holes do not change size, shape, or number under pressure changes. Accordingly, deformable membranes or flaps 9140 that move under pressure to close off or open vents may be used to vary the flow through the vent holes 9126. Deformable membranes or flaps 9140, however, may generate undesirable noise levels due to the change of the velocity of flow through the regulated vents as the vent holes 9126 are opened or closed by the membrane 9140 and/or by having partially closed vent holes 9126.

It may be possible to reduce such noise by including membrane flaps 9140 that progressively close off vent holes 9126 as pressure increases, wherein the flap(s) 9140 is fixed on one end such that the flap 9140 deflects under pressure changes. A problem with this technology is that the membrane 9140 may only partially close off a given vent hole 9126, which can lead to flow passing between the vent hole 9126 and membrane 9140 at high velocities. This, in turn, generates noise as air passes along the surface of the vent holes 9126 and membrane 9140 or collides into these surfaces.

It is possible to overcome this issue by reducing the number of regulated vent holes, while maintaining an overall substantially constant vent flow within the therapeutic pressure range to reduce vent noise. A desired noise levels can be maintained using moulded vent holes (i.e., static vents). These vent holes, however, may not be able achieve the desired flow curve (i.e., a substantially constant flow rate over a therapeutic pressure range between 4-20 cm H2O). This may be achieved by combining some regulated vent holes with static vent holes, such that the overall vent flow is substantially constant over a therapeutic pressure range. Increasing the number of static vents, which are not regulated by a membrane, may result in a reduction in overall vent noise.

This introduction of moulded vent holes, however, may introduce a new problem, whereby it may be difficult to ensure a substantially constant vent flow within the therapeutic pressure range using a combination of static vents and regulated vents. It is known, as shown in FIG. 16, that the vent flow characteristics of moulded static vent holes is a logarithmic curve where vent flow increases as pressure increases. To compensate for the flow of the static vents, the regulated vents should provide an inverse flow curve where vent flow decreases as pressure increases. Thus, the membrane 9140 regulating the vent holes 9126 may be tuned to provide such a vent flow.

There are a number of ways to tune the membrane 9140 to provide a vent flow that is inverse to the logarithmic flow curve of the static, moulded vents. For example, the shape/structure of the membrane 9140 may be changed to tune the flow curve of the regulated vents and the material of the membrane 9140 may be changed to tune the flow curve of the regulated vents.

An annular disc membrane 9140 structure of the CFV membrane, as shown in FIG. 20, may allow the membrane 9140 to be tuned in a number of ways such that it changes the regulated vent flow. The regulated vent flow may be altered by how much of the vent holes 9126 are covered/opened under a fixed pressure. A membrane 9140 that covers more of the vents under a fixed pressure would have a lower vent flow than one that covers less. The annular disc structure 9140 may allow for the membrane 9140 to be readily tuned to cover varying amounts of the vents under a fixed pressure. One way this may be done is by changing the diameter of the central orifice or by changing the width of the vent engaging surface.

The overall size of the membrane 9140 is restricted by the size of the CFV unit housing 9120, however, it is desirable to reduce the size of the CFV as much as possible. Thus, the width of the vent hole engaging surface may be adjusted by adjusting the size of the central orifice. An increase in the size of the central orifice results in the width of the vent hole engaging surface to also be reduced. This reduction in width, in turn, results in a reduction in surface area of the membrane 9140. The reduction in surface area means there is less resistance to deformation under a fixed pressure, whereby more of the vent holes are covered at the fixed pressure compared to a wider membrane 9140 (i.e., more surface area). This principle holds true within a predetermined range of surface area. That is, if the surface area is too low such that there is not enough surface (i.e., width of the vent hole engaging surface is too low), then more force is required to deform the membrane 9140 (i.e., it bottoms out).

The membrane 9140 thickness may also be varied such that it deforms more readily under a fixed pressure. For example, a thinner membrane 9140 would more readily deform under a mask pressure of 15 cm $H_2O$ when compared to a thicker membrane 9140 of the same shape at the same pressure.

The membrane 9140 may also be structured such that it freely moves to cover the vent holes 9126 under a fixed pressure. For example, in related technologies, the membrane 9140 may be fixed at a point, e.g., on the vent housing 9120 such that it is hinged relative to the fixed point and the membrane 9140 would be deflected about the fixed point due to pressure changes.

The design of the CFV membrane 9140 according to an example of the present technology allows it to freely move between a retaining structure and a vent hole surface. This configuration may allow the membrane 9140 to be more easily tuned to adjust the vent flow when compared to a flap design, i.e., where the membrane is fixed on one end and moves relative to the fixed end.

A membrane 9140 that is more flexible/compliant may deform more readily under a fixed pressure/load, thereby covering more of the vent holes 9126 in comparison to a stiffer membrane. Thus, changing the material of a membrane 9140, while otherwise having the same size and structure, to a more flexible material will allow the membrane 9140 to deform more readily under the same pressure to cover more of the vent holes 9126 and reduce vent flow. Thus, this may allow tuning the membrane 9140 to provide the desired vent flow curve within the therapeutic pressure range.

A number of ways, as mentioned above, can be used to provide a membrane 9140 that responds to pressure within the targeted therapeutic range to provide a predetermined vent flow curve, i.e., an overall substantially constant vent flow rate between the pressures of 4-30 cm of $H_2O$. It also may be desired to provide such a constant vent flow while minimizing vent noise, one solution may be to maximize the number of static non-membrane regulated vents and have the minimum number of membrane regulated vents that provide an average total vent flow that is substantially constant. This flow curve is shown by the thicker, solid line entitled "Passive vent only" in FIG. 19. In this example, the dashed line represents the static, non-membrane regulated vents, while the thinner, solid line entitled "Combination of the CFV & passive vents" represents the combined vent flow. It is notable that the vent flow of the static vents progressively increases as pressure increases, while the CFV membrane regulated vents progressively decreases to a threshold.

Another cause of noise may be attributed to vent flow disturbances caused by the CFV membrane 9140 that may also impact the flow of air flowing through the static vents. In a related technology, the static vents were positioned proximal to the CFV membrane regulated vents, i.e., the vent holes were positioned on the same surface of the CFV housing 9120. This led to noise being generated even for the non-regulated static vents as the membrane had impact on the flow characteristics of the static vent flow. Thus, it may be desirable to position the static vents away from the CFV membrane regulated vents such that the membrane 9140 does not impact the static vent flow therethrough. In an example of the present technology, the static vent holes are positioned on a distal surface from the CFV regulated vent holes. For example, the static vent holes may be positioned on a different component than the CFV housing 9120. The positioning of the static vents may be restricted in that they may not be able to wash out $CO_2$ as well. The ability to washout $CO_2$ increases as the static vent holes are positioned closer to the patient. However, the static vent holes may also be positioned on an opposing side of the HMX relative to the patient to prevent loss of moisture during exhalation, as explained below.

5.4.1.1 Vent Housing

FIGS. 42A to 42G depict examples of a vent system 13400 according to an example of the present technology. The vent system 13400 includes a vent housing 13401 that may include an outer wall 13402 and the outer wall 13402 may define the outer periphery of the vent housing 13401. The vent housing 13401 may also include an inner wall 13410 that may define an inlet for the flow of gas generated by the RPT device 4000 and directed into the plenum chamber 3200 and toward the patient for therapy. As can be seen, the outer wall 13402 and the inner wall 13410 are formed as concentric circles in this example.

Positioned between the outer wall 13402 and the inner wall 13410 is a base. The base may further comprise an outer base 13403 and an inner base 13406. The outer base 13403 may extend from the inner periphery of the outer wall 13402 and the inner base 13406 may extend from the outer periphery of the inner wall 13410. As can be seen, the outer base 13403 and the inner base 13406 are also formed as concentric circles in this example.

The outer base 13403 may include one or more outer orifices 13404 distributed radially around the outer base 13403. These outer orifices 13404 may extend entirely through the outer base 13403 to provide a flow path from the interior of the vent system 13400 to atmosphere. The outer orifices 13404 may be straight, i.e., perpendicular to the outer base 13403, or the outer orifices 13404 may pass through the outer base 13403 with a curved path or a slanted path. The diameter of the outer orifices 13404 may be constant along their length or the diameter may be varied. The outer orifices 13404 may all be identical or some may be different from others. The edges of the outer orifices 13404 may have a chamfer or a fillet. The outer base 13403 may at least partially support the membrane 13430 to prevent the membrane 13430 from completely occluding the inner orifices 13407. Accordingly, the outer base 13403 may extend higher up than the inner base 13406, as can be seen in FIGS. 42A to 42G.

The vent housing 13401 may also include lateral membrane supports 13405 distributed about the outer base 13403 and the inner periphery of the outer wall 13402. The lateral membrane supports 13405 may abut and prevent the membrane 13430 from moving laterally during use, thereby covering the outer orifices 13404. As will be explained below, it may be desirable not to obstruct the outer orifices 13404 so that the vent system 13400 will be able to maintain a substantially constant vent flow rate over a large proportion of the range of typical therapeutic pressures. Therefore, the lateral membrane support 13405 may protrude radially inward beyond the edges of the outer orifices 13404. The lateral membrane supports 13405 may be semi-circular, as in FIGS. 42A to 42G. In the examples depicted in FIGS. 42A to 42G, the outer orifices 13404 are distributed evenly in groups of three between adjacent lateral membrane supports 13405 about the circumference of the outer base 13403.

The vent housing 13401 may also have a circular shape. However, the vent housing 13401 may also be shaped elliptically or the vent housing 13401 may have a polygonal shape, such as a triangle, a square, a rectangle, a pentagon, a hexagon, etc. In any of these configurations, the membrane 13430 may be shaped to correspond with the shape of the vent housing 13401.

The inner base 13406 may be positioned radially inward of the outer base 13403 and the inner base 13406 and the outer base 13403 may be joined by base connectors 13408 distributed radially therebetween. Between adjacent base connectors 13408 and between the inner base 13406 and the outer base 13403 there are one or more inner orifices 13407. The inner orifices 13407 in these examples are shaped as slots with an arc-shaped cross-section. However, it is envisioned that the inner orifices 13407 may be circular holes, similar to the outer orifices 13404. The inner orifices 13407 extend completely through the vent housing 13401 between the inner base 13406 and the outer base 13403. As will be explained below, it may be desirable to allow the inner orifices 3407 to be at least partially obstructed by the membrane 13430 to allow the vent system 13400 to maintain a substantially constant vent flow rate over a large proportion of the range of typical therapeutic pressures. The edges of the inner orifices 13407 may have a chamfer or a fillet.

The inner base 13406 of the vent housing 13401 may also include several membrane spacers 13409. The membrane spacers 13409 may be evenly distributed radially about the inner base 13406. As shown in FIGS. 42A to 42G, the membrane spacers 13409 may be located on the edge of the inner base 13406 so as to fade into the inner wall 13410. The membrane spacers 13409 are provided to at least partially support the membrane 13430, as will be described in greater detail below. The membrane spacers 13409 may extend from the inner base 13406 in a semi-cylindrical shape or in a rectangular shape, as in FIGS. 42A to 42G. The edges of the membrane spacers 13409 may have a chamfer or a fillet.

The vent housing 13401 may also include one or more recesses 13415 spaced around the opposite side of the outer base, as can be seen in FIGS. 42A to 42G. The recesses 13415 may be separated by recess dividers 13414. The outer orifices 13404 may extend through the outer base 13403 and open into the corresponding recesses 13415 and multiple outer orifices 13404 may open into a single recess 13415.

In an alternative example, the vent housing 13401 may only include one group of orifices that are analogous to the inner orifices 13407 described above in that the vent flow passing therethrough can be restricted by the membrane's 13430 position. Accordingly, there may also be another group of orifices provided elsewhere on the patient interface 3000 that are analogous to the outer orifices 13404 described above in that the vent flow passing therethrough is not restricted by the membrane 13430, regardless of the membrane's 13430 position. The latter group of orifices that are not restricted by the membrane 13430 may be placed on any of the plenum chamber 3200, the seal-forming structure 3100, the decoupling structure 3500, the vent connector tube 4180, or other component that is closer to the patient than the vent housing 13401. It is envisioned that the principles of operation of the vent systems 13400 described above will apply to such an alternative arrangement, but the ability to locate the orifices that are not restricted by the membrane 13430 closer to the patient may improve the discharge of exhaled $CO_2$.

The vent housing 13401 may be made from a single, homogeneous piece of material. The material of the vent housing 13401 may be relatively rigid. The material of the vent housing 13401 may be polycarbonate.

5.4.1.2 Membrane

FIGS. 43A to 43G also depict views of an exemplary membrane 13430 with the vent system 13400 and positioned adjacent to the vent housing 13401. The exemplary membrane 13430 may be used with any of the various vent housing 13401 configurations disclosed above. The membrane 13430 may be in the shape of a flat, circular disk. In other words, the thickness of the membrane 13430 (see FIGS. 43F and 43G) may be small relative to its outer diameter. The thickness of the membrane 13430 may be uniform throughout, as shown in FIGS. 43F and 43G. Alternatively, the thickness of the membrane 13430 may be variable in a radial direction.

The membrane 13430 includes a membrane opening 13431 such that when assembled onto the vent housing 13401, the flow of air through the inlet 13411 also passes through the membrane opening 13431 and along to the patient. The membrane 13430 also includes a patient-side surface 13432 that faces towards the patient in use and an atmosphere-side surface 13433 opposite the patient-side surface 13432 that faces towards the atmosphere in use.

Additionally, the atmosphere-side surface 13433 faces towards the vent housing 13401 when assembled. The membrane 13430 also includes an inner surface 13434 that defines the membrane opening 13431 and an outer surface 13435 that is opposite the inner surface 13434.

The inner radius, i.e., the radius of the inner surface 13434, and the outer radius, i.e., the radius of the outer surface 13435, may be selected such that the membrane 13430 can be located over the inner orifices 13407 in use without covering the outer orifices 13404. Also, the inner radius and the outer radius may be selected such that the membrane 13430 covers a substantial portion of the inner base 13406 while being supported on the membrane spacers 13409 proximal to the inner surface 13434 and on the outer base 13403.

The membrane 13430 may be made from a single piece of homogeneous material. The material maybe elastically deformable such that the membrane 13430 can be deflected in use by the pressure from the flow of air. The material may be silicone. The membrane 13430 may be "tuned" to deform in a desired manner by altering one or more of its thickness, length, material, shape, inner radius, and/or outer radius.

5.4.1.3 Constant Flow Rate Vent System

FIGS. 43A to 43G depict several views of exemplary vent systems 13400 with the membrane 13430 assembled with the vent housing 13401. In FIGS. 43A to 43G, the inner wall 13410 does not extend above the inner base 13406. In the examples where the inner wall 13410 extends upward from the inner base 13406, the inner wall 13410 may provide a baffle function that separates the flow of gas traveling into the vent system 13400 via the inlet 13411 from the vent flow exiting the vent system 13400, which in turn may reduce the amount of flow traveling in from the inlet 13411 and then directly out of the vent system 13400.

In the examples of FIGS. 43A to 43G, a portion of the membrane 13430 proximal to the outer surface 13435 can be seen supported on an inner portion of the outer base 13403. Also, a portion of the membrane 13430 proximal to the inner surface 3434 can be seen supported just above the membrane spacers 13409. However, the membrane 13430 may deform towards the membrane spacers 13409 by virtue of its own weight such that the membrane 13430 is also supported on the membrane spacers 13409 even though there may not be any air pressure causing the deformation.

FIGS. 43A to 43G also show the membrane's 13430 location constrained by the lateral membrane supports 13405. As explained above, the membrane 13430 may be shaped and dimensioned to cover only the inner orifices 13407 and not the outer orifices 13404. However, the membrane 13430 may not be directly attached to the vent housing 13401 and, as such, may be free to move. Therefore, a sufficient number of lateral membrane supports 13405 can prevent lateral movement of the membrane 13430 so that the membrane 13430 cannot cover one or more of outer orifices 13404 in use.

The inverse of these examples is also envisioned in which the outer orifices 13404 may be covered by the membrane 13430 and the inner orifices 13407 are not blocked by the membrane 13430. Accordingly, lateral membrane supports 13405 may be provided to prevent the membrane 13430 from covering the inner orifices 13407.

As explained above, the exemplary vent systems 13400 may include a membrane 13430 positioned over the inner orifices 13407 to at least partially restrict the flow of gas through the inner orifices 13407, while the vent flow through the outer orifices 13404 is not restricted by the membrane 13430.

It should also be understood that the features of the vent system 13400 described in sections 5.4.1.1 to 5.4.1.3 may be incorporated into any of the vent adaptors 9100 disclosed in section 5.4.5.

5.4.2 Vent Diffuser

The vent adaptor 9100 may also comprise a portion for housing a diffuser 9146. The diffuser 9146 may be removable for replacement. The diffuser 9146 may have an annular disc shape that complements the shape of the annular surface of the vent housing 9120 on the side facing the atmosphere, i.e., external to the inlet flow. The diffuser 9146 may cover the vent holes 9125 and may diffuse the vent flow after it exits the plurality of vent holes 9125. That is, the vent flow flowing through moulded vent holes 9125 may flow through the diffuser 9146 prior to reaching the atmosphere.

The diffuser 9146 may also act as a sound absorbent material to reduce some of the noise generated by the CFV membrane 9140 regulated and static vents.

FIG. 26 illustrates a cross-section through some of the orifices 3402. The orifices 3402 are illustrated as holes through a wall 3404 of the plenum chamber 3200. However, the orifices 3402 may be located in locations other than the wall 3404. For example, the orifices 3402 may be located between the decoupling structure 3500 and the connection port 3600 or in a portion of the air circuit 4170, preferably near the connection port 3600 or in the vent adaptor 9100. The holes are illustrated with a diameter that is smaller than an axial length of the hole. The length and/or diameter may be chosen so that an appropriate flow rate is generated when the plenum chamber 3200 is pressurized to the therapy pressure. The flow through the orifices 3402 may be choked (e.g. a Mach number of 1) at the therapy pressure (e.g. at 4 cmH$_2$O or greater pressure) or the flow may generate less than sufficient pressure drop to be choked. A choked flow may result in substantially all of the pressure drop in the vent 3400 being caused by the orifices 3402. The arrows conceptually illustrate direction of flow when the plenum chamber 3200 is pressurized above ambient pressure.

The orifices 3402 are formed through a thickness of material of the wall 3404. Each of the orifices 3402 defines an axis, e.g., along a center of the orifice. The axis forms an acute angle with a normal to a surface of the wall 3404. The angle may be between 15 and 75 degrees or between 30 and 60 degrees, including any integer within the stated ranges. For example, the angle may be about 45 degrees.

The orifices 3402 are covered by a diffusing member 3406 so that flow exiting the orifices 3402 impinges on and flows at least partially into the diffusing member 3406. The diffusing member 3406 may be formed from a material, such as a porous material, that allows gas to flow through the material but diffuses any jet or other flow formation exiting the orifices 3402. Some suitable examples of diffusing material include a non-woven fibrous material; a woven fibrous material; or an open cell foam material. The diffusing material may be similar to or the same as a filter media. The diffusing member 3406 may reduce perceptible noise generated by the vent 3400 in use (e.g., when therapy pressure is applied).

The diffusing member 3406 is illustrated as covered by a blocking member 3408 that prevents gas from flowing out of the orifices 3402 and directly through the diffusing member 3406. The blocking member 3408 may be constructed, at least in part, from an air-impermeable material. The air-impermeable material may be any suitable flexible or rigid material. For example, the air-impermeable material may be a rigid plastic (e.g., molded polycarbonate) or a flexible plastic (e.g., a plastic commercially available in sheet form).

The blocking member 3408 may be formed integrally with the diffusing member 3406, formed separately but permanently affixed to the diffusing member 3406, formed separately and in removable contact with the diffusing member 3406, or combinations thereof. The blocking member 3408 is illustrated as opposite the outlet orifices 3402 with respect to a thickness of the diffusing member 3406.

The blocking member may cause the flow to change direction (with respect to the direction through the orifices 3402) before exiting the diffusing member 3406. The blocking member 3408 and/or diffusing member 3406 may be configured so that flow out of the orifices 3402 must flow at least a predetermined distance through the diffusing member 3406 prior to exiting to ambient atmosphere. The blocking member 3408 may also be configured to provide a particular direction and/or orientation for flow exiting the vent 3400 to minimize any disturbance to the wearer and/or bed partner caused by the flow. For example, the blocking member 3408 may cause gas to flow through the diffusing member 3406 and generally parallel to a surface of blocking member 3408 nearest to the diffusing member 3406.

In FIG. 26, the orifices 3402 and the diffusing member 3406 are oriented relative to one another such that a central axis of each of the orifices is not perpendicular to a nearest surface of the diffusing member 3406, although a perpendicular arrangement could also be provided as illustrated in FIG. 8.

Channels 3410 may also be provided on an outer surface of the wall 3404. The channels 3410 are illustrated with a V-shaped cross-section but could be formed with any suitable cross-section such as a U-shape. The channels 3410 may be configured to allow liquid to drain away from one or more outlets of the orifices 3402. The orifices 3402 may be formed in a leg of the V-shape or U-shape.

FIG. 27 illustrates an alternate configuration of the blocking member 3408. In FIG. 27, the blocking member 3408 includes holes 3412. The holes 3412 may direct the flow out of the diffusing member 3406 on the opposite side from the orifices 3402 but in a different direction. Thus the flow path is not straight through the orifices 3402 and the diffusing member 3406. Although the arrows associated with the holes 3412 are illustrated parallel, this is for ease of illustration only. The holes 3412 may be configured to redirect the flow in multiple directions.

The holes 3412 each define an axis that is neither aligned with nor parallel to an axis defined by each of the orifices 3402. When viewed in the cross-section of FIG. 27, any one axis defined by a hole 3412 and any one axis defined by an orifice 3402 forms an angle. The angle may be between 15 and 75 degrees or between 30 and 60 degrees, including any integer within the stated ranges. For example, the angle may be about 45 degrees.

FIGS. 28-30 illustrates an alternate configuration of the vent 3400. FIG. 28 illustrates a partially exploded view, FIG. 29 illustrates a simplified assembled view and FIG. 30 illustrates a cross-sectional view taken along line 30-30 of FIG. 29. In these figures, the orifices 3402 are illustrated in a circular array around a central hole 3414. The circular array is illustrated to include three circular rows of holes where the two inner-most circular rows are closer together than the outer-most circular row, but any number of circular rows may be provided an spacing between the rows may be equal. The central hole 3414 allows for fluid communication between the plenum chamber 3200 and the connection port 3600 and thus the air circuit 4170. The diffusing member 3406 and the blocking member 3408 are also illustrated as being disposed around the central hole 3414. With this configuration, the blocking member 3408 may be removably attached (e.g., a removable snap fit or threaded engagement) or fixedly attached (e.g., permanent adhesive or a snap fit that must be broken to disassemble) and the diffusing member 3406 may be fixed to the blocking member 3408 or not fixed to but retained by the blocking member 3408. As best viewed in FIG. 29, radial openings 3416 are provided for gas to escape the diffusing member 3406 radially outward from the central hole 3414.

FIGS. 31A to 31C illustrate another alternate configuration of the vent 3400. FIG. 31A illustrates a partial view of a flow passage in the form of an elbow 3418, which may be disposed between a decoupling structure 3500 and connection port 3600, and includes a vent 3400. This configuration largely conceals the features of the vent 3400 and thus the remaining description is with respect to FIGS. 31B and 9C.

FIG. 31B illustrates an axial view with the cap 3422 and diffusing member 3406 omitted. This provides a clear view of the outlet orifices 3402. Two annular rows, each including forty of the outlet orifices 3402 are illustrated. The orifices are offset so that the outlet orifices 3402 in the inner row and the outer row are not radially aligned. This configuration may allow for annular rows to have closer radial spacing. Although two rows are illustrated, any number of rows may be provided, for example one row or three or more rows. Although forty outlet orifices 3402 are illustrated in each annular row, more or less may be provided as required to maintain appropriate levels of gas washout. For example, one, five, ten, fifteen, twenty, twenty five, thirty, thirty five, forty, forty five, fifty or more outlet orifices 3402, or any number in between, may be provided per annular row.

In FIG. 31C, the annular array of orifices 3402 are visible in the cross-section through a wall 3420. The wall 3420 is similar to wall 3404 except that the wall 3420 is illustrated remote from the plenum chamber 3200; however, the wall 3420 may be part of the plenum chamber 3200.

The diffusing member 3406 is illustrated as a ring-shape with a rectangular cross-section. The blocking member 3408 is illustrated as a relatively thin, sheet-like ring on a side of the diffusing member 3406 opposite the orifices 3402. The blocking member 3408 may be affixed to the diffusing member 3406 by any suitable means, for example by adhesive.

A cap 3422 is illustrated covering the diffusing member 3406 and the blocking member 3408. The cap 3422 may be in contact with the blocking member 3408 such that the diffusing member 3406 is compressed against the wall 3420. Alternatively, the diffusing member 3406 may not be compressed against the wall 3420. The cap 3422 may serve as the blocking member 3408, in which case the ring-shaped blocking member 3408 illustrated in FIG. 31C may be omitted.

The cap 3422 may include an angled, annular flange 3424 that may be spaced away from the wall 3420 to form an annular gap 3426. The annular flange 3424 may also be considered skirt-like or frusto-conical. The annular gap 3426 may provide a flow path to ambient atmosphere such that the flow of gas washout is not overly restricted. Alternatively, one or more openings (such as radial opening 3416) may be provided in the annular flange 3424 to provide a flow path to ambient atmosphere, which may also allow for elimination, in whole or in part, of the annular gap 3426.

The cap 3422 is illustrated with an annular groove 3428 mated with an annular protrusion 3430 to hold the cap 3422 in place. The annular protrusion may be continuous to form a snap fit or may be multiple, annularly spaced annular protrusions to provide a configuration that allows for minimal or no interference upon axial insertion followed by a twist to provide axial interference and hold the cap 3422 in place. In FIG. 31C, the annular protrusion 3430 is illustrated as three annularly spaced annular protrusions. A lip 3432 of the annular groove 3428 may be omitted in three corresponding locations and sizes to provide for reduced or no interference of the cap 3422 during the axial insertion. Other forms of attachment are possible. For example, a threaded fastening arrangement may be provided, the cap 3422 may be held in place with adhesive or welding. Releasable fastening such as the illustrated configuration or a threaded connection may allow for the diffusing member 3406 to be replaced if, for example, the diffusing member becomes damaged, clogged or dirty.

Although the vent 3400 is illustrated on one side of the bend (e.g., upstream with respect to an exhalation direction) in the elbow 3418, the vent 3400 may be upstream or downstream of the bend.

FIGS. 32A to 32C illustrate another alternate configuration of the vent 3400. Like reference numbers are similar to those described above and thus further description is omitted except as noted below. The vent 3400 in these figures is formed around an example of the decoupling structure 3500 that includes a ball 3434 and socket 3436 that are part of an elbow 3418. In the form illustrated here, the ball 3434 and socket 3436 allow three degrees of rotational freedom. However, fewer degrees of rotational freedom are possible, e.g., one or two degrees of rotational freedom.

As best viewed in FIG. 32D, the cap 3422 is connected by way of a snap fit connection 3438 with a first half 3440 located on the cap 3422 and a second half 3442 on the mating component. Six each of the first half 3440 and second half 3442 are provided between six of the radial openings 3416, three of which are visible in FIG. 32A. However, more or less may be provided as necessary to provide adequate retention and/or flow rate.

As best seen in FIG. 32C, forty-four orifices 3402 are illustrated equally spaced in a single annular row. However, the number and spacing of the orifices 3402 may take other configurations. For example, fewer orifices 3402 may be provided if, for example, lower flow rate is required or more orifices 3402 may be provided if, for example, greater flow rate is required. And as explained above, more rows may be provided. Also, the orifices need not be in an annular array. If, for example, the orifices are located other than in the illustrated location, the orifices may be arranged in a grid based on Cartesian coordinates. Alternatively, the orifices 3402 need not be in any type of row and may be located in random or pseudo random locations.

5.4.3 Heat and Moisture Exchanger (HME)

Heat and moisture exchangers (HMEs) may comprise materials that have water retaining properties. Respiratory pressure therapy (RPT) can result in drying of the airways causing breathing discomfort in patients. To prevent this, a humidifier may be used in conjunction with a respiratory pressure device to deliver humidified air to the patient. This added humidifier may increases the size and power requirements of RPT devices.

It is known that patient's generate a level of humidified air upon exhalation, which comes from the mucosa of the airways. HMEs can be used to recycle this exhaled moisture by capturing humidity from humidified air upon exhalation then redelivering this to the patient. One challenge in the use of HMEs is their efficacy (i.e., being able to capture enough heat and moisture) and their impact on therapy (i.e., the HME may be placed in the flow circuit and therefore cause flow impedance).

To improve efficacy, an aspect is to reduce any losses of heat and moisture that is captured by the HME. A problem with the use of HMEs in RPT may be that heat and moisture expired by the patient is lost through venting prior to reaching the HME. In order to minimize such losses, the HME may be placed proximal to the patient's airways (i.e., the source of humidity) and place the vent on an opposing side of the HME, i.e., away from the patient. This configuration may ensure that expired humidified gases flow through the HME such that moisture is captured by the HME prior to exiting through the vent. The vent adaptor may be configured such that the HME is positioned between the patient's airways and the constant flow vent.

The vent adaptor may also comprises an HME unit that is removable. That is, the vent adaptor can be used with or without the HME. The HME unit may comprises a housing that holds the HME is place. The housing can be opened (the housing may comprises a front and rear component) to remove the HME.

The HME may be designed to maximize surface area per unit volume for heat and moisture exchange. In addition, the HME may also be designed to decrease its impact on flow impedance. The design may comprises a plurality of corrugations to allow flow to pass through said corrugations. The HME may be formed as a coiled layer of HME material comprising the corrugations.

As described above, the CFV may reduce flow wastage by regulating vent flow to a level that is above but close to the minimum required vent flow rate. As flow wastage is reduced, the level of humidity loss in the therapy system may also be reduced. It is known in the art that patients expire humidified air, which may in turn cause drying of the mucosa. Applying RPT treatment for SDB may exacerbate this drying. Thus, reducing the amount of flow required to achieve therapeutic pressure and concurrently reducing the level of humidified air loss from the system may result in a reduction of mucosal drying.

One way to increase the level of humidified air delivered to the patient is by the use of a powered humidification. Another way to humidify the air delivered to the patient is by the use of heat and moisture exchangers (HME), which capture the water vapours in air such that they may be delivered back to the patient. An HME can be utilized to capture the humidity from patient expiration, which in turn can redeliver this humidity back to the patient. The HME should be positioned that it captures enough humidity from expired gas flow, as shown in FIG. 17, but allows this humidity to be redelivered through therapy flow. To ensure that captured humidity from expired gas flow is maximized, the HME should be placed between the patient and the vent. If the vent were to be placed between the patient and the HME, it would lead to the humidity in the expired gas flow being vented prior to reaching the HME for capture and redelivery. However, the configuration shown in FIG. 17 can also result in humidity being lost through venting via therapy flow going through the HME then directly out the vent (prior to patient delivery). This flow has been labelled "HME vent flow" in FIG. 17. The HME vent flow becomes more of an issue when the flow rate of the therapy increases. As shown in the graph in FIG. 18, the flow rate may increase as mask pressure increases. This flow may be increased to compensate for vent flow losses. When the flow rate increases, the velocity of the therapy flow increases, which may cause the therapy flow to penetrate the HME deeper. Some of this penetrating flow is delivered to the patient, however, a portion of this flow may also be directed to the vent prior to patient delivery (as shown by the HME vent flow). Therefore, the HME vent flow may also result in humidity losses by drying the HME.

As shown in the graph in FIG. 18, the CFV may reduce the vent flow rate over the same pressure range as compared to the standard FFM nom flow vent. This reduction in flow may reduce the HME vent flow, thereby reducing humidity losses. In other words, less flow occurs at the same pressures in the CFV system when compared to the standard vent system, consequently reducing the HME vent flow. This reduction in HME vent flow enhances the capability of the HME to capture and redeliver humidity from the expired gas flow thereby synergistically enhancing the HME effect to reduce mucosal drying.

Another way of reducing the HME vent flow may be to redirect the flow direction such that less flow passes through the vent and is redirected back into the system. The redirection can be achieved by structures, e.g., baffles, positioned in the flow path between the HME and the vent such that less flow is directed out the vent into the atmosphere.

The present technology is capable of achieving near powered humidification levels without the use of powered humidification. Since powered humidification is no longer required, the flow generator may be simplified further, because it no longer requires a water reservoir and heating mechanism to deliver powered humidification to therapy flow. Therefore, both the CFV and the HME may allow a flow generator associated with the present technology to be effective in providing RPT treatment for OSA and other SDB, without the need to complex pressure/flow control and powered humidification, which may ultimately benefit the patient by providing a substantially smaller flow generator with less controls.

FIGS. 25A to 25D show examples of a HME according to the present technology. FIG. 25A shows a cross section of a HME 7000 comprising a corrugated structure 7002 comprising a plurality of corrugations 7030 between a substantially planar substrate top structure 7010 and a substantially planar substrate base structure 7020 to form a concertina layer 7001. The layer 7001 comprises a plurality of superior channels 7012 formed between a superior surface of the corrugated structure 7002 and the top structure 7010. In addition, the layer 7001 comprises a plurality of inferior channels 7022 between an inferior surface of the corrugated structure 7002 and the base structure 7020. The HME 7000 allows for a flow of breathable gas and expiratory gas to flow through the plurality of superior 7012 and inferior 7022 channels along a surface of the corrugated structure to exchange heat and moisture. Moisture is absorbed from the expiratory gas exhaled from a patient and retained in the material of the corrugated structure 7002. The material of the corrugations 7030, the top structure 7010, and/or the base structure 7020 may comprise paper or a paper based material that is able to absorb water and/or heat. The material of the corrugations 7030, the top structure 7010, and/or the base structure 7020 may be porous, water-permeable, and/or air-permeable. The retained moisture may subsequently be redelivered to the patient by humidifying a flow of breathable gas delivered to the patient's airways. In other words, the flow of breathable gas delivered to the patient's airways may absorb moisture from the HME 7000. FIG. 25B depicts the various dimensions of a HME according to these examples.

The plurality of corrugations 7030 increase the surface area of the corrugated structure 7002 that allows for an increase in active surface area for the exchange of heat and moisture occurring between the corrugated structure 7002 and the surrounding volume provided by the plurality of superior 7012 and inferior 7022 channels. The top structure 7010 and the base structure 7020 may also be formed from the same heat and moisture exchanging material as the corrugated structure 7022. Alternatively, the top structure 7010 and/or the base structure 7020 may be formed of a rigid or semi-rigid material that does not absorb moisture to support the corrugated structure 7002.

The humidification performance of the HME 7000 is dependent on the effective surface area of the HME 7000 provided in a fixed volume of space. The effective surface area is the surface area of the HME 7000 that is exposed to the flow of breathable gas flowing along the surface of the HME where heat and moisture exchange occurs. The surface area per unit volume of the HME 7000 can be adjusted by providing corrugations 7030 within the heat and moisture exchange portion of the HME 7000. Furthermore, the surface area per unit volume may also be adjusted by modifying at least one of the fin thickness, pitch or height of the corrugations or flutes, which have an impact on the surface area per unit volume of the HME 7000.

The HME 7000 may comprise a plurality of layers 7001 stacked along a vertical axis of the HME 7000, as shown in FIG. 25C. The layers 7001 may be vertically stacked such that the base structure 7020 is stacked on top of the corrugated structure 7002 of an underlying adjacent layer 7001. There may be also several layers 7001 of HME stacked in the horizontal direction. Having a number of layers 7001 comprising corrugated structures 7002 that are stacked along a vertical axis of the HME 7000 further increases the surface area per unit volume of the HME. This increased surface area within a predefined volume allows for increased efficiency in heat and moisture exchange of the HME 7000. Furthermore, the layers 7001 may be compressed under a preload, as depicted in FIG. 25D, to increase the number of layers within a fixed volume to increase the surface area per unit volume. The preload is calculated by the formula:

$$P = 1 - \left(\frac{h_{final}}{h_{start}}\right)$$

where P is the Preload and $h_{start}$ is the corrugation or flute height prior to compression and wherein $h_{final}$ is the height of the corrugation post-compression.

Alternatively, the final three-dimensional shape of the HME 7000 may be formed by combining layers 7001 of different sizes and shapes to produce a HME 7000 of irregular shape adapted to fit within a plenum chamber 3200 of the patient interface 3000. The layers 7001 may be laser cut to form the desired shape and size.

As shown in FIG. 25E, displaying an alternative example, the HME 7000 may be rolled from a single strip layer 7001 comprising a corrugated structure 7002 extending from the surface of the base structure 7020 to form a plurality of corrugations 7030. The single strip layer 7001 may be rolled such that the upper folded portion 7031 of the corrugations 7030 engages the inferior surface of the base structure 7020. This configuration ensures that the plurality of channels 7012 is maintained between each roll of the single strip layer 7001.

As mentioned above, the CFV may reduce the vent flow rate over the same pressure range as compared to the standard FFM nom flow vent. This reduction in flow may reduce the HME vent flow, thereby reducing humidity losses. In other words, less flow occurs at the same pressures in the CFV system when compared to the standard vent system, consequently reducing the HME vent flow. This reduction in HME vent flow may enhance the capability of the HME to capture and redeliver humidity from the expired gas flow, thereby synergistically enhancing the HME effect to reduce mucosal drying.

The CFV membrane may allow the vent flow to be maintained at or above the minimum required level within the therapeutic pressure range and may also regulate the vent flow to below that which would occur with a standard static vent. Thus, CO2 washout would always remain at sufficient levels. The vent flow may be tuned such that it allows the minimum level required of CO2 washout. This would result in the vent flow being minimized, which would in turn minimize the loss of moisture from the HME.

Another way of reducing the HME vent flow is to redirect the flow direction such that less flow passes through the vent and is redirected back into the air delivery circuit. That is, the flow may be redirected such that it minimizes HME vent flow, wherein flow penetrates the HME and then flows directly out of the vent. The redirection of flow can be achieved by structures, e.g., baffles, positioned in the flow path between the HMX and the vent such that less flow is directed out the vent into the atmosphere.

FIGS. 38A to 38C depict an example of an HME housing 9400 according to an example of the present technology. The HME housing 9400 may have a two-part construction that includes a patient-side HME housing portion 9402 and an atmosphere-side HME housing portion 9404. The patient-side HME housing portion 9402 and the atmosphere-side HME housing portion 9404 may be assembled together to retain HME material therein. The patient-side HME housing portion 9402 may include a patient-side HME housing portion cross-bar 9406 to retain the HME material in an axial direction towards the patient in use and the atmosphere-side HME housing portion 9404 may include an atmosphere-side HME housing portion cross-bar 9408 to retain the HME material in an axial direction towards the atmosphere in use. The atmosphere-side HME housing portion 9404 may also include one or more openings 9410 that connect to corresponding tabs 9412 of the patient-side HME housing portion 9402 to join both portions together. The connection between the openings 9410 and the tabs 9412 may comprise a snap-fit and may be releasable to allow the HME housing 9400 to be disassembled so the HME material can be removed for cleaning or replacement.

FIGS. 39A to 39C depict another example of an HME housing 9400 according to an example of the present technology. The HME housing 9400 may have a two-part construction that includes a patient-side HME housing portion 9402 and an atmosphere-side HME housing portion 9404. The patient-side HME housing portion 9402 and the atmosphere-side HME housing portion 9404 may be assembled together to retain HME material therein. The patient-side HME housing portion 9402 may include a patient-side HME housing portion cross-bar 9406 to retain the HME material in an axial direction towards the patient in use and the atmosphere-side HME housing portion 9404 may include an atmosphere-side HME housing portion cross-bar 9408 to retain the HME material in an axial direction towards the atmosphere in use. The atmosphere-side HME housing portion 9404 may also include one or more openings 9410 that connect to corresponding tabs 9412 of the patient-side HME housing portion 9402 to join both portions together. The connection between the openings 9410 and the tabs 9412 may comprise a snap-fit and may be releasable to allow the HME housing 9400 to be disassembled so the HME material can be removed for cleaning or replacement. The atmosphere-side HME housing portion 9404 may also include an atmosphere-side HME housing portion ring 9414 and extending from the atmosphere-side HME housing portion ring 9414 is an HME inner housing 9416 which may contain the HME material. The HME inner housing 9416 along with the patient-side HME housing portion 9402 and the atmosphere-side HME housing portion 9404 may form an HME bypass passage 9418 to allow a portion of the flow traveling through the HME housing 9400 to bypass the HME material.

5.4.4 Custom Connection

FIG. 6a illustrates a side view of a fluid connector 9000 with a first end 9002 and a second end 9004 mated with one another. A portion of a fluid conduit 9006, which may be part of the air circuit 4170, is connected to the second end 9004. Instead of the fluid conduit 9006, an adaptor or connector to a fluid conduit may be provided. An outlet of an RPT device 4000 may comprise a second end 9004 in some forms of the present technology.

The fluid connector 9000 may be configured to removable form a sealed connection to allow a flow of air to travel therethrough, such as from the RPT device 4000 to the patient interface 3000. The fluid connector 9000 may comprise a plurality of components, such as a first end 9002 and a second end 9004, which may be releasably connected to each other to make and/or break the sealed connection.

The first end 9002 and the second end 9004 may form a pneumatic path therebetween via complementary sealing portions, and be retained to each other by complementary retaining portions that may be separate portions to the complementary sealing portions. Accordingly, each of the first end 9002 and the second end 9004 may comprise a separate sealing portion and a retaining portion, as is described in further detail elsewhere in the present document.

Where the sealing function and the retaining function are performed by separate complementary portions, each of the sealing and/or the retaining functions may be more readily optimised, to address one or more of competing design requirements. For example, where one pair of complementary portions function to seal and retain two components, formation of a tight seal may lead to a high frictional force, decreasing ease of connection and/or disconnection of the components.

Furthermore, where the usability of connection/disconnection is improved, the seal may not be as robust, such as in cases where the two components may be subject to forces and/or torques in varying directions and magnitudes. In the cases of a fluid connector such as those described in the present document, a patient wearing a patient interface 3000 may move about while asleep, or preparing to go to sleep, causing the fluid connector to be pulled and/or twisted in various directions.

Thus, one aspect of the present technology relates to a fluid connector 9000, wherein the first end 9002 and the second end 9004 are connected to each other by complementary sealing portions and complementary retaining portions.

In one form, the first end 9002 and the second end 9004 may comprise complementary sealing portions to form an air seal when connected. The air seal may be configured to form and maintain a sealing engagement to allow a flow of air to travel therethrough. The sealing engagement may be sufficient to allow a pressurised flow of air to travel therethrough, such as at pressures between 4 cm $H_2O$ to 40 cm $H_2O$ to provide respiratory therapies.

In some forms, the first end 9002 and the second end 9004 may comprise complementary portions to retain the first end 9002 and the second end 9004. The retaining portions may maintain the first end 9002 and the second end 9004 in sealing engagement with each other, such as by preventing accidental disengagement. The retaining portions may comprise latching mechanisms as will be detailed further in the present document.

FIG. 6b illustrates a sectional view of the fluid connector 9000 where the first end 9002 and the second end 9004 are not connected to one another. In this view, a seal portion 9008 is visible. The seal portion 9008 may be formed from any material that is suitable for forming a seal in an air path of a device that provides breathing gas to a patient, for example, silicone. The seal portion 9008 extends around a first opening 9010, which is illustrated as the interior of a first tube 9022. A latching portion 9012, which may be in the form of a recess, is provided in the first end 9002. The latching portion 9012 may be provided on opposed sides as illustrated in FIG. 6b, on a single side or all around a periphery of the first end 9002. As illustrated, the latching portion 9012 is an undercut that is substantially perpendicular to a central axis of the first end 9002. Other angles are possible depending on the retention force desired.

The second end 9004 includes a sealing surface 9016. The sealing surface 9016 may be formed circumferentially around a second opening 9018 that is illustrated as the interior of a second tube 9020. The sealing surface 9016 is illustrated as a substantially annular surface that extends radially and perpendicularly (i.e., at 90°) away from the second tube 9020. This may result in the sealing surface 9016 being substantially perpendicular to a direction of the fluid flow from the first end 9002 to the second end 9004. However, the sealing surface 9016 could also extend outward at an angle such that the sealing surface 9016 is beveled. For example, the sealing surface could be at 85°, 80°, 75°, 70°, 65°, 60°, 55°, 50° or 45° angle, positive or negative, or any value in between. As can be seen in FIG. 6b, the second tube 9020 may comprise an overhang portion 9034 that extends beyond the sealing surface 9016 towards the seal portion 9008. This may result in the overhang portion 9034 of the second tube 9020 extending through the seal portion 9008 as illustrated in FIG. 6c. It will be understood that the second tube 9020 need not comprise an overhang portion in some examples of the present technology.

The overhang portion may be configured to align the first end 9002 with the second end 9004 in one or more directions. The overhang portion 9034 may be configured to be inserted into a guide portion 9038 on the first end 9002 to act as a lead-in and align the second end 9004 with the first end 9002 in a radial (or transverse) direction. Thus the first end 9002 and second end 9004 may have a male/female relationship. Additionally, a stop 9030 may be provided to limit travel of the second tube 9020, for example by abutting the overhang portion 9034 at the limit of travel. Although the overhang portion 9034 is shown as a tube, the overhang portion may not extend continuously around a circumference of the second end 9004, as it would be internal to the seal created by the complementary sealing portions (seal portion 9008 and sealing surface 9016). The overhang portion may extend only partially through the seal portion 9008, such as in castellated extensions, tabs, ribs and the like.

With the configuration illustrated in FIG. 6c, the interior flow path of the fluid connector 9000 defined by the first tube 9022, second tube 9020 and stop 9030 may have very little flow restriction because the interior flow path is substantially the same as the interior of the fluid conduit 9006, for example as evaluated in cross section shape and size. Thus the fluid connector 9000 may have negligible pressure drop when air is flowing through the fluid connector 9000 throughout a patient's breathing cycle and therapy pressure (e.g., at pressures between 4 cm $H_2O$ to 40 cm $H_2O$).

The seal portion 9008 may include a portion that contacts the sealing surface 9016 in any form that is suitable for forming a face seal, such as by tangential contact therebetween. As illustrated, the seal portion 9008 contacts the sealing surface 9016 with a substantially frustoconical shape, which is similar to a bellows-shape or partial bellows-shape. Alternatively, a partial spherical, or partial toroidal surface may be provided on the seal portion 9008. With any of these shapes, the seal portion 9008 may contact the sealing surface 9016 before the latching portion 9012 and complementary latching portion 9014 are fully or even partially engaged. Alternatively, the seal portion 9008 and sealing surface 9016 may be separated by a gap even after the latching portion 9012 and complementary latching portion 9014 are fully engaged. In this scenario, internal pressurization may cause the seal portion 9008 to move into contact with the sealing surface 9016 and form a seal.

The seal portion 9008 may comprise a resilient and compliant material such that it may deform under load, while maintaining its original configuration when the load is removed therefrom. The seal portion 9008 may be configured to be readily deformed under load to form and/or maintain a seal with the sealing surface 9016. In some forms, the seal portion 9008 may comprise a membrane composed of silicone. The silicone membrane seal portion 9008 may be sufficiently compliant that it would deform to move into contact with the sealing surface 9016 due to the pressure caused by the air flow. The silicone membrane seal portion 9008 may additionally or alternatively be sufficiently compliant such that it would maintain a sealing engagement with the sealing surface 9016 even when compressed from its undeformed configuration.

The proposed configurations of the seal portion 9008 may provide a seal that is compliant with respect to a mating direction between the first end 9002 and the second end 9004 (e.g., leftwards in FIG. 6b) and/or compliant in a direction radial to an axis defined by a direction of engagement between the first end 9002 and the second end 9004 (e.g., up and down in FIG. 6b).

The force necessary to compress the seal portion 9008 (e.g. when compression is required to form and/or maintain a seal) may be sufficiently low so as to not be a significant compressive force. For example, the force required to compress the seal portion 9008 may be less than a force required to engage the latching portion 9012 with the complementary latching portion 9014, such as to overcome any friction in connecting the second end 9004 and the first end 9002. Alternatively, the force required to compress the seal portion 9008 may be less than half of the force required to engage the latching portion 9012 with the complementary latching portion 9014. Alternatively, the force required to compress the seal portion 9008 may be less than one tenth of the force required to engage the latching portion 9012 with the complementary latching portion 9014. Thus in a configuration where the seal portion 9008 contacts the sealing surface 9016 before the latching portion 9012 and complementary latching portion 9014 are fully engaged, a user may not encounter significant force that would be mistaken for full engagement. In some forms, any force caused by a compression of the seal portion 9008 for connection of the second end 9004 and the first end 9002 may be sufficiently small that it is substantially imperceptible to a user. That is, the force perceived by a user in a configuration wherein the seal portion 9008 is removed from the first end 9002 may be substantially identical to a configuration where the seal portion 9008 must be compressed for connection.

The shapes of the seal portion 9008 according to the present technology may provide a seal that is compliant opposite to a mating direction between the first end 9002 and the second end 9004 (e.g., rightwards in FIG. 6*b*). This may allow for a seal portion 9008 that can seal with the sealing surface 9016 even if a gap exists between seal portion 9008 and sealing surface 9016 when the fluid connector 9000 is unpressurized. When pressure is provided to an interior of the fluid connector 9000 (e.g., to the first tube 9022), the seal portion 9008 may expand towards and contact the sealing surface 9016 to form a seal. With this configuration, a user should not encounter any additional force when connecting the first end 9002 to the second end 9004 beyond the force necessary to engage the latching portion 9012 and complementary latching portion 9014.

Although specific configurations of the seal portion 9008 are discussed above, other configurations are possible. For example, some forms of the seal portion 9008 may include an o-ring or a gasket material.

Either the seal portion 9008 or the sealing surface 9016 or both may be configured such that misalignment between the seal portion 9008 and sealing surface 9016 still results in a seal between the seal portion 9008 and the sealing surface 9016. For example, the seal portion 9008 and/or the sealing surface 9016 may be configured to form a seal therebetween while allowing for a range of misalignments in radial (or transverse) and/or axial directions.

For example, the sealing surface 9016 may comprise an annular shape (as shown in FIG. 6H) configured to form a face seal with a surface of the seal portion 9008 in a plurality of radial positions. That is, the seal portion 9008 and the sealing surface 9016 may form a seal therebetween although an axis of the first tube 9022 and an axis of the second tube 9020 may be misaligned, for example by 0.5 mm, 1 mm, 1.5 mm, 2 mm, 3 mm or 4 mm. In one form, the sealing surface 9016 may comprise a sufficiently wide annular portion such that the seal portion 9008 may be able to form a seal thereto.

The second end 9004 also includes a complementary latching portion 9014. The complementary latching portion 9014 is illustrated as a cantilevered hook including a protrusion that mates or engages with the latching portion 9012. As with the latching portion 9012, the complementary latching portion 9014 may be provided on a plurality of (e.g. opposed) sides as illustrated in FIG. 6*b* or on a single side. The complementary latching portion 9014 may be in the form of U-shaped or C-shaped cut-through as illustrated in FIG. 6*d*. The complementary latching portion 9014 may be depressed to engage or disengage the complementary latching portion 9014 from the latching portion 9012 and allow engagement or disengagement between the first end 9002 and the second end 9004. Although providing more than two of the complementary latching portion 9014 is possible, doing so may make it unnecessarily difficult to disengage the second end 9004 from the first end 9002.

In combination, the stop 9030 and latching portion 9012 may define a predetermined distance (travel) that the second end 9004 can move with respect to the first end 9002 while the two ends are connected. For example, if a first axial distance between the stop 9030 and latching portion 9012 is greater than a second axial distance between an end of the second tube 9020 and the protrusion on the complementary latching portion 9014, then the difference between the first axial distance and the second axial distance will define a predetermined amount of travel that is non-zero. If the first axial distance and the second axial distance are equal, then no travel will be possible. However, there may be benefits associated with a non-zero travel at least with respect to ease of manufacture because a non-zero travel will allow for manufacturing tolerance that may reduce cost. Thus it may also be beneficial for the seal portion 9008 to be configured to form a seal with the sealing surface 9016 with a worst case manufacturing tolerance and after a predetermined amount of wear and/or creep in the fluid connector 9000. The shapes for the seal portion 9008 discussed above may allow for the seal portion 9008 to account for such a worst case scenario.

As best seen in FIG. 6*b*, the second end 9004 may include an inner portion 9024 and an outer portion 9026 that are rotatably coupled to one another at an interface 9028. The inner portion 9024 may include the seal portion 9008 and the outer portion 9026 may include the complementary latching portion 9014. As illustrated, the inner portion 9024 is rigidly or fixedly connected to the fluid conduit 9006 such that the inner portion 9024 and the fluid conduit 9006 may rotate together with respect to the outer portion 9026. At least a part of the fluid conduit 9006 may be overmolded onto the inner portion 9024 to form the rigid connection therebetween. In other forms, the fluid conduit 9006 may be friction fit, or interference fit into the inner portion 9024 so as to form a rigid connection.

As best viewed in FIG. 6*d*, the outer portion 9026 may have an outer profile that has four sides but also have some features of a circle, which may be uniquely identifiable in comparison to a typical circular profile. The first end 9002 may include a complementarily shaped recess. Thus the first end 9002 includes a female portion and the second end 9004 includes a male portion. Including male and female portions in the above form, or any other non-standard shape or configuration, may provide benefits. First, the fluid connector 9000 comprising non-standard shapes and/or configurations may not conform to industry standards (e.g., ISO 5356-1), which include use of a circular spigot including a lead-in taper, onto which a cuff (e.g. rubber) is inserted over. Although not confirming to an industry standard may seem counter intuitive, there may be benefits. For example, the fluid connector 9000 may be used to connect an RPT device and patient interface that are designed to operate optimally together. For example, if the RPT device provides a lower flow rate that can only be taken advantage of by a patient interface that is designed to operate with that lower flow rate, having a fluid connector 9000 that does not mate with an industry standard will ensure that only the correct RPT device and patient interface are used together. Second, particularly with the illustrated profile, the first end and the second end 9004 may be mated with one another only in a predetermined number of relative orientations (e.g., four). The present four-sided shape also may provide well-defined sides that are easy to identify and grip for actuation of the complementary latching portion 9014. Thirdly, a non-standard shape such as that described herein, or others, may allow a user to readily identify which end of a patient conduit 4170 may be a complementary connector to another connector, such as an outlet of the RPT device.

FIG. 6*e* illustrates another example of a present technology, wherein a port 9032 is included in the first end 9002. The port 9032 may be used to sense pressure downstream of a blower and outside of a housing of the blower, such as by sensing a pressure downstream of the RPT device. The port

9032 may be in fluid connection to the second end 9004 to determine a pressure of the air in the second opening 9018.

In one form, the port 9032 may be in fluid communication with an interior of the second opening 9018, such as by forming a fluid connection to an opening in the interior of the seal portion 9008. The opening in the interior of the seal portion 9008 may be in turn in fluid communication with a pressure tap 9036 to the second opening 9018. Thus the first end 9002 and the second end 9004 may form two fluid connections therebetween when connected to each other. The port 9032 may provide an advantage of being able to measure pressure closer to a patient than if pressure is measured in the RPT device. Due to pressure losses inherent in internal fluid flow as well as possible leaks throughout the air path from the blower to the patient, measuring the pressure closer to the patient may provide a more accurate measurement than a pressure measure carried out further from the patient.

Also, the present arrangement allows for the second end 9004 to be rotated with respect to the first end 9002 while still maintaining two fluid connections (i.e. one to deliver the flow of air, another to measure pressure). This may be advantageous for allowing the fluid conduit 9006 to rotate with respect to the outer portion 9026, thus reducing torque imposed on the fluid conduit and/or the outer portion 9026. Furthermore, such a configuration may also allow a user to connect the first end 9002 and the second end 9004 in one of a plurality of rotational orientations to each other while maintaining the two fluid connections.

FIG. 6f illustrates the first end 9002 integrated into an RPT device with the second end 9004 disconnected. FIG. 6g illustrates the first end 9002 integrated into the RPT device with the second end 9004 connected.

Although the preceding description generally describes both halves of a connector system together, e.g., a first end 9002 and a second end 9004, it is to be understood that the description of either half may be considered in isolation.

It may also be advantageous to ensure that the appropriate masks are used with the CFV membrane regulated vents. Masks according to examples of the present technology may be non-vented masks designed specifically to be compatible with the CFV membrane regulated venting described above. The system may be designed such that the flow generator is also compatible with the vent adaptor, meaning that the flow generator will be programmed to work with a mask system having a constant vent flow. That is, each mask type (nasal, pillows and full face), may connect to the same vent adaptor and, therefore, the vent adaptor should allow for enough CO2 washout for each of the mask types. The lowest CO2 washout is generally seen in the full face mask as there is an increase in the volume of mask dead space. Hence, the vent adaptor must allow for sufficient CO2 washout for the full face mask (i.e., the worst case scenario). Since the system of the present technology, including the flow generator, vent adaptor, and each mask type, may be designed specifically to work together, it may be advantageous to prevent non-compatible masks from connecting to the CFV connector.

As such, a connection mechanism may be provided such that the seal formed between two detachably connecting components is achieved by the connection mechanism. As previously described, the nasal and pillows mask may connect to a short tube connector, which will then connect to the vent adaptor. In contrast, the full face mask may connect directly to the vent adaptor 9100. In another example, the HME may comprise a separate detachable housing, which could be detached from the vent adaptor. However, to reduce overall size, the HME may be incorporated into the vent adaptor with the CFV unit, wherein the HME slides into the same housing as the CFV. Such a design means that when the HME is removed there may be an unused, empty space in the CFV housing of the vent adaptor 9100.

In the full face version of a mask according to the present technology the short tube connector end may be formed as the inlet of the full face mask. That is, the same bellows engaging surface is designed as part of the mask shell, which may form part of the mask plenum chamber.

The bellows sealing membrane may be structured to move under pressure such that the membrane moves towards the sealing surface on the opposing connector. The pressure supported seal may mean that the seal between the CFV unit and the connector remains robust under high pressures.

The bellows seal may allow for a seal to be formed between the CFV unit and the connector with minimal friction between the two components, which allows a swivel connection. For example, sealing using interference fit, a lip seal, a gasket configuration, or other forms of compression seals between the components may not allow for easy enough movement between the components such that the components can swivel, while maintaining a robust seal.

5.4.5 Exemplary Vent Adaptors

An example of a vent adaptor 9100 and its components are shown in FIGS. 7A-14D. The vent adaptor 9100 according to this example of the present technology may include a conduit connector 9110, a vent housing 9120, a vent diffuser cover 9130, a membrane 9140, a CFV ring 9150, a vent housing connector 9160, a heat and moisture exchanger (HME) clip 9170, a HME housing 9180, a bellows seal 9190, and a vent adaptor connector 9200.

The vent housing 9120 may include an end 9121 with protrusions 9122 to connect the vent housing 9120 to the conduit connector 9110 at a vent adaptor end 9112. The end 9121 may define the central orifice of the vent housing 9120 through which the flow of pressurized gas is provided to the patient. The vent housing 9120 may include external vent holes 9125 and internal vent holes 9126 that define passageways for venting pressurized gas from the RPT system, i.e., gas may be discharged from the internal vent holes 9126, through said passageways, to the external vent holes 9125, and out to atmosphere. The vent housing 9120 may also include a tab 9123 joined to a lip 9124 via a support 9128 to releasably attach the vent housing 9120 to the vent housing connector 9160 and the vent adaptor connector 9200. The patient may actuate the tab 9123 to depress the support 9128 such that the lip 9124 is disengaged from the vent housing connector 9160 and the vent adaptor connector 9200. When attached, the lip 9124 allows the vent housing 9120 to rotate relative to the vent adaptor connector 9200 while remaining connected. The vent housing 9120 may also a shoulder 9127 to fit into a corresponding notch 9164 of the vent housing connector 9160. The vent housing 9120 may also include notches 9129 to receive corresponding bellows seal connectors 9191 that attach the bellows seal 9190 to the vent housing 9120 to seal the interior of the vent adaptor 9100 against the vent adaptor connector 9200 when assembled.

The vent housing connector 9160 may include a first bar 9161 and a second bar 9162 that form a receptacle 9163 that receives a corresponding lip 9124 of the vent housing 9120 to attach the vent housing connector 9160 to the vent housing 9120. The notch 9164 also receives the shoulder 9127 of the vent housing 9120, as described above. The vent housing connector 9160 may also include a curved outer surface 9165.

The bellows seal 9190 may be a bellows seal similar to the features described above in relation to FIGS. 6A-6H. The bellows seal 9190 may have a shoulder surface 9194 with bellows seal connectors 9191 to attach the bellows seal 9190 to the notches 9129 of the vent housing 9120. The bellows seal 9190 may also have an inner surface 9193 that is contacted by the pressurized gas and urged outward such that an outer surface 9192 forms a seal against the vent adaptor connector 9200 when assembled.

The vent adaptor connector 9200 may have an orifice 9201 through which pressurized gas passes from the vent adaptor 9100 and on to the patient during therapy. Also, the exhaled gas may be discharged into the vent adaptor 9100 via the orifice 9201. The vent adaptor connector 9200 may be connected at the orifice 9201 to the patient interface via another tube (not shown). The vent adaptor connector 9200 may also have a rim 9202 to connect to the lip(s) 9124 of the vent housing 9120 to allow the vent housing 9120 to connect to and rotate relative to the vent adaptor connector 9200. It should be understood that in another form of the present technology, the vent adaptor connector 9200 may be connected directly to the patient interface or it may be formed integrally with the patient interface, e.g., the mask shell.

The vent adaptor 9100 may also include an HME clip 9170 and an HME housing 9180 to retain HME material within the vent adaptor 9100 in a position that is between the internal vent holes 9126 and the patient, as described above. The HME material (not shown) may be a coiled or cylindrical structure that is inserted into the HME housing 9180 and retained therein by the HME clip 9170. The HME clip 9170 may have a pair of arms 9171 extending from a central shaft 9172. The central shaft 9172 may extend through the center of the HME material to secure a shaft end 9173 into a receiver 9183 suspended on a cross-member 9182 of the HME housing 9180 to secure the HME material inside of the HME housing 9180. The HME housing 9180 may also include a pair of slots 9181 in an outer wall 9184 that correspond to the arms 9171 and receive arm ends 9174 such that when assembled the HME clip 9170 does not rotate relative to the HME housing 9180. Thus, the HME material would be secured between the arms 9171 and the cross-member 9182. The outer wall 9184 may include a plurality of cut-outs 9185.

The conduit connector 9110 may include the vent adaptor end 9112 and a conduit end 9111. As explained above, the vent adaptor end 9112 may connect to the vent housing 9120 and the conduit end may be connected to a conduit (not shown) that is connected at the other end to an RPT device to receive a flow of pressurized gas. The conduit connector 9110 may also include anti-asphyxia valve (AAV) openings 9113.

Another example of a vent adaptor 9100 and its components are shown in FIGS. 15A-15F. This example includes may features similar to the examples shown in FIGS. 7A-14D above. In this example, the vent adaptor connector 9200 includes a rim 9203 that connects to the tab 9123 of the vent housing 9120 to connect the vent adaptor connector 9200 to the vent housing 9120. Also, this example shows an anti-asphyxia valve (AAV) 9135 that may installed in the conduit connector 9110. The conduit connector 9110 may also have a ring 9115 to connect to a conduit (not shown). Also, in this example the bellows seal 9190 can be seen attached to the vent housing connector 9160. The vent housing connector 9160 also has a ridge to allow for attachment to the vent housing 9120 by the tab 9123. Furthermore, examples of HME material 9145 and the diffuser 9146 are shown.

Another example of a vent adaptor 9100 and its components are shown in FIGS. 21A-21F. This example includes may features similar to the examples shown in FIGS. 7A-14D and FIGS. 15A-15F above. In this example, the HME housing 9180 is not completely contained inside of the vent adaptor 9100. Rather, it is exposed partially such that it forms part of the structure that connects the vent housing 9120 to the vent adaptor connector 9200.

Another example of a vent adaptor 9100 and its components are shown in FIG. 22. This example includes may features similar to the examples shown in FIGS. 7A-14D and FIGS. 15A-15F above. FIG. 22 also includes a flap retaining structure 9141 that may be attached to the HME clip 9170 on one side and abut the flap 9140 on the other side to hold the flap 9140 in an operational position relative to the vent housing 9120.

Another example of a vent adaptor 9100 and its components are shown in FIGS. 24A-24B. This example includes may features similar to the examples shown in FIGS. 7A-14D and FIGS. 15A-15F above.

FIG. 23 depicts a diagram of the ways the vent adaptor 9100 may be attached to different patient interfaces. In the case of the nasal cushion patient interface 3000A or the nasal pillows patient interface 3000B, the vent adaptor 9100 may be joined to either patient interface via a short tube 9210. One end of the short tube 9210 may be joined to the patient interface 3000A, 3000B and the other end may be joined to the vent adaptor connector 9200 described above. Alternatively, in the case of the full face patient interface 3000C, the vent adaptor 9100 does not include the vent adaptor connector 9200 and the vent adaptor 9100 is connected directly to the full face patient interface 3000C such that no short tube 9210 is provided.

FIGS. 33A to 33G depict another example of a vent adaptor 9100 according to an example of the present technology. This vent adaptor 9100 may be connected to a patient interface 3000, as shown in FIG. 35 for example, to provide the functions of its components.

The vent adaptor includes an elbow assembly 9220 to provide a fluid connection with the patient interface 3000, e.g., via a connection port 3600 on the plenum chamber 3200. This example of the elbow assembly 9220 includes an elbow frame 9222 and an elbow overmould 9224. The elbow assembly 9220 may provide a releasable connection with the plenum chamber 3200 at the connection port. The elbow frame 9222 may include tabs that are elastically deformable for the releasable connection and the elbow overmould 9224 may provide a fluid-tight seal around openings in the elbow frame 9222, as well as added resiliency for the elbow frame 9222. The elbow assembly 9220 may also be rotatable relative to the plenum chamber 3200 to reduce the effects of tube drag from the other components of the vent adaptor 9100 and the air circuit 4170. The elbow assembly 9220 may also be removably connected to a patient interface 3000 and may be able to swivel relative to the patient interface 3000.

The vent adaptor 9100 may also include a short tube assembly 9210. The short tube assembly 9210 may decouple the other components of the vent adaptor 9110, e.g., the vent housing 9320 and the vent core structure 9300, from the elbow assembly's 9220 connection with the plenum chamber 3200. By decoupling the other components of the vent adaptor 9110 in this manner, the mass that must be carried directly on the patient's head via the patient interface 3000 can be reduced, which in turn provides a lighter and more comfortable experience for the patient. The short tube assembly 9210 may include a tube 9212, which may be comprised of one or more helical coils. The short tube assembly 9210 may include a tube-elbow connector 9216 to provide a connection with the elbow assembly 9220. The connection between the tube-elbow connector 9216 and the elbow assembly 9220 may comprise a snap-fit. The connection between the tube-elbow connector 9216 and the elbow assembly 9220 may be permanent—in other words, the connection may not be separated without damaging the components. The short tube assembly 9210 may include a tube-housing connector 9214 to provide a connection with the vent housing connector 9160. The connection between the tube-housing connector 9214 and the vent housing connector 9160 may comprise a snap-fit. The connection between the tube-housing connector 9214 and the vent housing connector 9160 may be permanent—in other words, the connection may not be separated without damaging the components.

The vent adaptor 9100 may include a vent housing connector 9160 to join the short tube assembly 9210 with the vent housing 9320. As described above, the vent housing connector 9160 may be joined to the short tube assembly 9210 with the tube-housing connector 9214 that may be a snap-fit and that may be permanent. The vent housing connector 9160 may also include a bayonet connector 9166 to facilitate a releasable bayonet-style connection with the vent housing 9320 or a heat and moisture exchanger (HME) housing 9400 such as those shown in FIGS. 38A to 39C. Thus the HME associated with the HME housing 9400 may be optional and, as such, is not shown in FIGS. 33A to 33G. The bayonet connectors 9166 may be male or female. Also, making the vent housing 9320 removably connectable to the vent housing connector 9160 allows the vent components to be removed and disassembled for cleaning.

FIGS. 34A to 34G show examples of the vent housing 9320, the flap or membrane 9140, the vent core structure 9300, the diffusing member 9146, the diffuser retaining ring 9148, and the vent diffuser cover 9330. These components may be assembled into a sub-assembly, as shown in FIGS. 34A to 34G, and joined to the vent housing connector 9160 for use. The components of the sub-assembly depicted in FIGS. 34A to 34G may be inseparable via a permanent snap-fit or the components may be separable by the user. In the case of inseparability, the snap-fit may be permanent such that the components cannot be separated without damaging them.

The vent housing 9320 may also include bayonet connectors 9322 to correspondingly connect with the bayonet connectors 9166 of the vent housing connector 9160 to removably connect the vent housing 9320 to the vent housing connector 9160. The vent housing 9320 may also include a membrane retainer 9324 to hold the membrane 9140 against the vent core structure 9300 when assembled. The membrane retainer 9324 may comprise an open, radial, and cage-like structure to allow the vent flow to travel through the membrane retainer 9324 for discharge by the vent core structure 9300. The membrane retainer 9324 may also be open in its center to allow the therapy flow to pass along to the patient from the RPT device 4000.

The flap or membrane 9140 may be positioned between the membrane retainer 9324 and the vent core structure 9300. The membrane 9140 may be held in position between these two structures, but may be otherwise be free to be deformed by pressure within the vent adaptor 9100. The membrane 9140 may function similarly to other examples of the membrane 9140 disclosed above.

The vent core structure 9300 may include an inlet 9301 to allow the flow of gas generated by the RPT device 4000 to pass through the vent adaptor 9100 and along to the patient for therapy. The vent core structure 9306 may include a vent core extension 9306 through which the inlet 9301 may be defined. The vent core extension 9306 may extend axially and may include air circuit connectors 9302 to connect the vent core 9300 to the air circuit 4170. As can be seen, the vent core extension 9306 is shaped and dimensioned to extend through the diffuser retaining ring 9148, the diffuser 9146, and the vent diffuser cover 9330 to align these components when the vent adaptor 9100 is assembled. The vent core structure 9300 may also include clips 9304 on an alignment structure 9312 that connect to the connection surface 9334 of the vent diffuser cover 9330. The clips 9304 may be connected to the connection surface 9334 with a snap-fit to allow the vent diffuser cover 9330 to be removed for disassembly to allow cleaning and/or replacement of vent adaptor components 9100 such as the diffuser 9146. The alignment structure 9312 may also facilitate axial alignment of the vent core structure 9300 with the diffuser 9146 and the vent diffuser cover 9330 by virtue of corresponding shapes.

The vent core structure 9300 may also include a plurality of outer orifices 9308 and a plurality of inner orifices 9310. The plurality of inner orifices 9310 may be configured such that vent flow to atmosphere through the inner orifices 9310 may be obstructed or restricted by the membrane 9140 in use. The plurality of outer orifices 9308 may be configured such that vent flow to atmosphere through the outer orifices 9308 may not be obstructed or restricted at any point by the membrane 9140 in use. However, the membrane 9140 may also be configured such that it does not completely occlude the inner orifices 9310 at any pressure at least within a typical range of therapeutic pressure (e.g., between about 6 cmH2O and about 20 cmH2O). In other words, vent flow may be discharged through both the inner orifices 9310 and the outer orifices 9308 at any pressure within a typical range of therapeutic pressure, while the pressure within the vent adaptor 9110 deforms the membrane 9140 to vary the proportion of vent flow traveling through the outer orifices 9308 and the inner orifices 9310 so as to maintain a constant vent flow rate, as described above.

The diffuser 9146 may include a diffuser opening 9147 through which the vent core extension 9306 may pass. The diffuser 9146 may include similar features to the diffusers described above.

The diffuser 9146 may be held in position downstream of the inner orifices 9310 and the outer orifices 9308 relative to the vent flow by the diffuser retaining ring 9148 and the vent diffuser cover 9330. The diffuser retaining ring 9148 may be secured to the vent diffuser cover 9330, e.g., with a snap-fit, to retain the diffuser 9146. The diffuser retaining ring 9148 may include radial diffuser retainers 9149 to hold the diffuser 9146 against the vent diffuser cover 9330. The diffuser retaining ring 9148 and the radial diffuser retainers 9149 may define posterior vent outlets 9342 around the vent housing 9320. Vent flow exiting the vent core structure 9300 may pass through the diffuser 9148 and out through the posterior vent outlets 9340. The vent diffuser cover 9332 may include a series of cover spacers 9332 spaced radially about the vent diffuser cover 9330 to define the anterior vent outlets 9342. Vent flow exiting the vent core structure 9300 may pass through the diffuser 9148 and out through the anterior vent outlets 9342.

The exemplary vent adaptor 9100 disclosed above and in FIGS. 33A to 34G is shown connected to a patient interface 3000 in FIG. 35. The elbow assembly 9220 is excluded in this example, because the plenum chamber 3200 includes a connection port 3600 that is angled so as to point in an inferior direction relative to the patient's head in use, thereby directing the vent adaptor 9100 away from the patient's head. Also, the short tube assembly 9210 may be permanently connected to the plenum chamber 3200 at the connection port 3600.

FIGS. 37A to 37E depict another example of a vent adaptor 9100 according to the present technology. The vent adaptor 9100 may include a plenum chamber connector 9700 to connect the vent adaptor 9100 directly to the connection port 3600 of the plenum chamber 3200 and/or to a shroud 3305 thereof (see FIG. 41) to provide a fluid connection for the flow of pressurized gas from the vent adaptor 9100 to the plenum chamber 3200.

The vent adaptor 9100 may also include a baffle 9600. The baffle 9600 may separate the incoming flow of pressurized gas from the RPT device 4000 from the outgoing vent flow exiting via the outer orifices 9308 and the inner orifices 9310 of the vent housing 9120. The baffle 9600 may be positioned internally of the plenum chamber connector 9700. The baffle 9600 and the plenum chamber connector 9700 may be aligned when connected to form concentric circles.

The vent adaptor 9100 may also include a lip seal 9500 that fits around the exterior periphery of the plenum chamber connector 9700. The lip seal 9500 may form a seal with the interior periphery of the connection port 3600 of the plenum chamber 3200 and/or the shroud 3305 thereof to provide a pneumatic seal while allow rotation of the vent adaptor 9100 relative to the patient interface 3000.

The vent adaptor 9140 may also include the flap or membrane 9140 to regulate the vent flow through the inner orifices 9310 and the outer orifices 9308 of the vent housing 9120 in accordance with the examples described above, e.g., the examples pictured in FIGS. 33A to 34G.

The vent housing 9120 may include inner orifices 9310 and outer orifices 9308 and these orifices may permit vent flow to exit the vent adaptor 9100 to atmosphere, as described in the examples above such as the examples of FIGS. 33A to 34G.

The vent housing 9120 may also include tabs 9123 and lips 9124 to provide a releasable and rotatable connection with the connection port 3600 of the plenum chamber 3200 and/or the shroud 3305 thereof. The tabs 9123 may be manually depressed to release the lips 9123 from a corresponding annular protrusion (not shown) of the connection port 3600 of the plenum chamber 3200 and/or the shroud 3305 thereof. When connected, the lips 9124 allow the vent adaptor 9100 to maintain a connection with the connection port 3600 of the plenum chamber 3200 and/or the shroud 3305 thereof while being rotatable to reduce the effects of tube drag.

The vent housing 9120 may be connected to a conduit connector 9110 that in turn may connect the vent adaptor 9100 to an air circuit. The conduit connector 9110 may be in the form of an elbow. The conduit connector 9110 may have a conduit end 9111 that connects to the air circuit 4170 and a vent adaptor end 9112 that connects to the vent housing 9120. The connection between the vent adaptor end 9112 of the conduit connector 9110 and the vent housing 9120 may comprise a snap-fit, may be permanent such that the connection cannot be separated without damaging at least one of the components, and/or may be non-rotatable to prevent the conduit connector 9110 from contacting the tabs 9123. The conduit connector 9110 may also include one or more anti-asphyxia valve (AAV) openings 9113 for the AAV 9135.

The vent adaptor 9100 may also include an air circuit connector 9116 that may be attached to the conduit end 9111 of the conduit connector 9110. The air circuit connector 9116 may include bayonet connectors 9117 to correspondingly connect to the connectors 4175 of the exemplary air circuit 4170 of FIGS. 36A to 36C. The connection between the air circuit connector 9116 and the air circuit 4170 may be releasable.

The vent adaptor depicted in FIGS. 37A to 37E may not include heat and moisture exchanger (HME) material 9145. The absence of a heat and moisture exchanger material 9145 positioned within the vent flow path may minimise vent flow impedance, thereby minimising $CO_2$ build up within the plenum chamber 3200. The depicted vent adaptor 9100 may be, for example, suitable for use with a full face patient interface as depicted in FIG. 41.

The vent adaptor 9100 depicted in FIGS. 37A to 37E may form an elbow assembly that may be removably connected to a patient interface 3000, e.g., as shown in FIG. 41, and may be able to swivel relative to the patient interface.

FIGS. 40 and 41 show further examples of vent adaptors 9100 joined to patient interfaces 3000.

FIG. 40 depicts a patient interface 3000 with a seal-forming structure 3100 that forms a seal around only the patient's nose in use (i.e., a nasal mask). The vent adaptor 9100 is shown joined to a shroud 3305 that covers a portion of the plenum chamber 3200. In this example, the vent adaptor 9100 features are combined in an elbow that is attached directly and rotatably to the shroud 3305 to provide a fluid connection with the plenum chamber 3200. However, it should be understood that the vent adaptor of FIGS. 33A to 33G could be attached to the shroud 3305 to form a fluid connection with the plenum chamber 3200 via the elbow assembly 9220. The shroud 3305 has rigidiser arms 3301 joined to the shroud 3305 at hinges 3307. The lateral arms 3301 may include superior attachment points 3302 and inferior attachment points 3304 to attach straps of a positioning and stabilising structure 3300. The superior attachment points 3302 may form loops through which superior straps can be passed and the inferior attachment points 3304 may receive clips 3306, which in turn receive inferior straps.

FIG. 40 depicts an exemplary patient interface 3000 that may include a seal-forming structure 3100 to form a seal over the patient's nose and mouth in use. The vent adaptor 9100, such as the example depicted in FIGS. 37A to 37E, may be connected to the shroud 3305 to provide a fluid connection with the plenum chamber 3200. The shroud 3305 may be joined to rigidiser arms 3301 that may have superior attachment points 3302 to attach straps of a positioning and stabilising structure 3300. The shroud 3305 may be connected to inferior strap connectors 3303 separate from the rigidiser arms 3301 to attach straps of a positioning and stabilising structure 3300 at inferior attachment points 3304. The superior attachment points 3302 may form loops through which superior straps can be passed and the inferior attachment points 3304 may receive clips 3306, which in turn receive inferior straps.

5.5 RPT Device

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items and mufflers 4120, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.5.1 RPT Device Mechanical & Pneumatic Components

An RPT device may comprise one or more of the following components in an integral unit. In an alternative form, one or more of the following components may be located as respective separate units.

5.5.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140. See FIG. 4B.

In one form, an outlet air filter 4114, for example an antibacterial filter, is located between an outlet of the pneumatic block 4020 and a patient interface 3000. See FIG. 4B.

5.5.1.2 Muffler(s)

In one form of the present technology, an inlet muffler 4122 is located in the pneumatic path upstream of a pressure generator 4140. See FIG. 4B.

In one form of the present technology, an outlet muffler 4124 is located in the pneumatic path between the pressure generator 4140 and a patient interface 3000. See FIG. 4B.

5.5.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.5.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.5.1.4.1 Flow Rate Sensor

A flow rate sensor in accordance with the present technology may be based on a differential pressure transducer, for example, an SDP600 Series differential pressure transducer from SENSIRION.

In one form, a signal representing a flow rate such as a total flow rate Qt from the flow rate sensor is received by the central controller 4230.

5.5.1.4.2 Pressure Sensor

A pressure sensor in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure sensor is received by the central controller 4230.

5.5.1.4.3 Motor Speed Transducer

In one form of the present technology a motor speed transducer is used to determine a rotational velocity of the motor 4144 and/or the blower 4142. A motor speed signal from the motor speed transducer may be provided to the therapy device controller 4240. The motor speed transducer may, for example, be a speed sensor, such as a Hall effect sensor.

5.5.1.5 Anti-Spill Back Valve

In one form of the present technology, an anti-spill back valve 4160 is located between the humidifier 5000 and the pneumatic block 4020. The anti-spill back valve 4160 is constructed and arranged to reduce the risk that water will flow upstream from the humidifier 5000, for example to the motor 4144.

5.5.1.6 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. In other words, the air circuit 4170 may be a heated air circuit 4171. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in United States Patent Application No. US/2011/0023874, which is incorporated herewithin in its entirety by reference.

FIGS. 36A to 36C depict examples of an air circuit 4170 according to an example of the present technology. The air circuit 4170 may include a tube 4172 that is comprised of one or more helical coils. The air circuit 4173 may include an RPT device connector 4173 at one end that is configured to connect to an RPT device 4000 to receive the flow of pressurized gas. At the other end, the air circuit 4170 may include a vent adaptor connector 4174 that may be connected to a vent adaptor 9100, such as in the examples disclosed in FIGS. 33A to 34G. The vent adaptor connector 4174 may include connectors 4175 to join with corresponding air circuit connectors 9302 of the vent adaptor 9300. The connectors 4175 may be in the form of female bayonet connectors that correspond to the air circuit connectors 9302. The vent adaptor connector 4174 may also include grip recesses 4176 to allow the patient to grip the vent adaptor connector 4174 to rotate the air circuit 4170 to connect to or disconnect from the vent adaptor 9100. The vent adaptor connector 4174 may also include a seal 4177 to form a pneumatic seal between the vent adaptor connector 4174 and a tube connector 4178 that connects the vent adaptor connector 4174 to the tube 4172.

5.5.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.5.2 RPT Device Electrical Components

5.5.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.5.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.5.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5.2.4 Clock

The RPT device 4000 may include a clock that is connected to the central controller 4230.

5.5.2.5 Therapy Device Controller

In one form of the present technology, a therapy device 4350 may include a therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.5.2.6 Protection Circuits

The one or more protection circuits 4250 in accordance with the present technology may comprise an electrical protection circuit, a temperature and/or pressure safety circuit.

5.5.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.5.2.8 Data Communication Systems

In one form of the present technology, a data communication interface 4280 is provided, and is connected to the central controller 4230. Data communication interface 4280 may be connectable to a remote external communication network and/or a local external communication network. The remote external communication network may be connectable to a remote external device. The local external communication network may be connectable to a local external device.

In one form, data communication interface 4280 is part of the central controller 4230. In another form, data communication interface 4280 is separate from the central controller 4230, and may comprise an integrated circuit or a processor.

In one form, remote external communication network is the Internet. The data communication interface 4280 may use wired communication (e.g. via Ethernet, or optical fibre) or a wireless protocol (e.g. CDMA, GSM, LTE) to connect to the Internet.

In one form, local external communication network utilises one or more communication standards, such as Bluetooth, or a consumer infrared protocol.

In one form, remote external device is one or more computers, for example a cluster of networked computers. In one form, remote external device may be virtual computers, rather than physical computers. In either case, such a remote external device may be accessible to an appropriately authorised person such as a clinician.

The local external device may be a personal computer, mobile phone, tablet or remote control.

5.5.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.5.2.9.1 Display Driver

A display driver receives as an input the characters, symbols, or images intended for display on the display, and converts them to commands that cause the display to display those characters, symbols, or images.

5.5.2.9.2 Display

A display is configured to visually display characters, symbols, or images in response to commands received from the display driver. For example, the display may be an eight-segment display, in which case the display driver converts each character or symbol, such as the figure "0", to eight logical signals indicating whether the eight respective segments are to be activated to display a particular character or symbol.

5.5.3 RPT Device Algorithms 5.5.3.1 Pre-Processing Module

A pre-processing module 4310 in accordance with one form of the present technology receives as an input a signal from a transducer 4270, for example a flow rate sensor or pressure sensor, and performs one or more process steps to calculate one or more output values that will be used as an input to another module, for example a therapy engine module 4320.

In one form of the present technology, the output values include the interface or mask pressure $Pm$, the respiratory flow rate $Qr$, and the leak flow rate $Ql$.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

5.5.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, $Pm$, in the patient interface 3000.

5.5.3.1.2 Vent Flow Rate Estimation

In one form of the present technology, a vent flow rate estimation algorithm 4314 receives as an input an estimated pressure, $Pm$, in the patient interface 3000 and estimates a vent flow rate of air, $Qv$, from a vent 3400 in a patient interface 3000.

5.5.3.1.3 Leak Flow Rate Estimation

In one form of the present technology, a leak flow rate estimation algorithm 4316 receives as an input a total flow rate, $Qt$, and a vent flow rate $Qv$, and provides as an output an estimate of the leak flow rate, $Ql$. In one form, the leak flow rate estimation algorithm estimates the leak flow rate $Ql$ by calculating an average of the difference between total flow rate $Qt$ and vent flow rate $Qv$ over a period sufficiently long to include several breathing cycles, e.g. about 10 seconds.

In one form, the leak flow rate estimation algorithm 4316 receives as an input a total flow rate $Qt$, a vent flow rate $Qv$, and an estimated pressure, $Pm$, in the patient interface 3000, and provides as an output a leak flow rate $Ql$, by calculating a leak conductance, and determining a leak flow rate $Ql$ to be a function of leak conductance and pressure, $Pm$. Leak conductance is calculated as the quotient of low pass filtered non-vent flow rate equal to the difference between total flow rate $Qt$ and vent flow rate $Qv$, and low pass filtered square root of pressure $Pm$, where the low pass filter time constant has a value sufficiently long to include several breathing cycles, e.g. about 10 seconds. The leak flow rate $Ql$ may be estimated as the product of leak conductance and a function of pressure, $Pm$.

5.5.3.1.4 Respiratory Flow Rate Estimation

In one form of the present technology, a respiratory flow rate estimation algorithm 4318 receives as an input a total flow rate, $Qt$, a vent flow rate, $Qv$, and a leak flow rate, $Ql$, and estimates a respiratory flow rate of air, $Qr$, to the patient, by subtracting the vent flow rate $Qv$ and the leak flow rate $Ql$ from the total flow rate $Qt$.

5.5.3.2 Therapy Engine Module

In one form of the present technology, a therapy engine module 4320 receives as inputs one or more of a pressure, $Pm$, in a patient interface 3000, and a respiratory flow rate of air to a patient, $Qr$, and provides as an output one or more therapy parameters.

In one form of the present technology, a therapy parameter is a treatment pressure $Pt$.

In one form of the present technology, therapy parameters are one or more of a level of pressure support, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.5.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to 2π radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the inhalation time Ti and the exhalation time Te are first estimated from the respiratory flow rate Qr. The phase Φ is then determined as the half the proportion of the inhalation time Ti that has elapsed since the previous trigger instant, or 0.5 revolutions plus half the proportion of the exhalation time Te that has elapsed since the previous cycle instant (whichever was more recent).

5.5.3.2.2 Waveform Determination

In one form of the present technology, the therapy parameter determination algorithm 4329 provides an approximately constant treatment pressure throughout a respiratory cycle of a patient.

In other forms of the present technology, the therapy parameter determination algorithm 4329 controls the pressure generator 4140 to provide a treatment pressure Pt that varies throughout a respiratory cycle of a patient according to a waveform template.

In one form of the present technology, a waveform determination algorithm 4322 provides a waveform template Π(Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is substantially less than 0.5 revolutions, and a smooth fall from 1 to 0 for values of phase within a "fall time" after 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template Π(Φ, t). In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.5.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

5.5.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scaler to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

5.5.3.2.5 Determination of Apneas and Hypopneas

In one form of the present technology, the central controller 4230 executes an apnea/hypopnea determination algorithm 4325 for the determination of the presence of apneas and/or hypopneas.

The apnea/hypopnea determination algorithm 4325 receives as an input a respiratory flow rate signal Qr and provide as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.5.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further the snore determination algorithm 4326 may comprise a step of filtering the respiratory flow rate signal Qr to reduce background noise, e.g., the sound of airflow in the system from the blower.

5.5.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.5.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.5.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \qquad (1)$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.5.3.3 Therapy Control Module

Therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

5.5.3.4 Detection of Fault Conditions

In one form of the present technology, the central controller 4230 executes one or more methods for the detection of fault conditions 4340. The fault conditions detected by the one or more methods may include at least one of the following:

Power failure (no power, or insufficient power)

Transducer fault detection

Failure to detect the presence of a component

Operating parameters outside recommended ranges (e.g. pressure, flow rate, temperature, $PaO_2$)

Failure of a test alarm to generate a detectable alarm signal.

Upon detection of the fault condition, the corresponding algorithm signals the presence of the fault by one or more of the following:

Initiation of an audible, visual &/or kinetic (e.g. vibrating) alarm

Sending a message to an external device

Logging of the incident

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Mechanical Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.3 Humidifier Electrical & Thermal Components

The humidifier 5000 may comprise a number of electrical and/or thermal components such as those listed below.

5.6.3.1 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.3.1.1 Pressure Transducer

One or more pressure transducers 5212 may be provided to the humidifier 5000 in addition to, or instead of, a pressure sensor provided in the RPT device 4000.

5.6.3.1.2 Flow Rate Transducer

One or more flow rate transducers 5214 may be provided to the humidifier 5000 in addition to, or instead of, a flow rate sensor provided in the RPT device 4000.

5.6.3.1.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.3.1.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier

5000. The humidity sensor may be an absolute humidity sensor or a relative humidity sensor.

5.6.3.2 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.6.3.3 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4170 and/or a heating element controller 5252 configured to control the temperature of a heating element 5240.

5.7 Respiratory Pressure Therapy Modes

Various respiratory pressure therapy modes may be implemented by the RPT device 4000 depending on the values of the parameters A and $P_0$ in the treatment pressure equation (1) used by the therapy parameter determination algorithm 4329 in one form of the present technology.

5.7.1 CPAP Therapy

In some implementations of this form of the present technology, the amplitude A is identically zero, so the treatment pressure Pt is identically equal to the base pressure $P_0$ throughout the respiratory cycle. Such implementations are generally grouped under the heading of CPAP therapy. In such implementations, there is no need for the therapy engine module 4320 to determine phase Φ or the waveform template Π(Φ).

In CPAP therapy modes, the base pressure $P_0$ may be a constant value that is hard-coded or manually entered to the RPT device 4000. This alternative is sometimes referred to as constant CPAP therapy. The constant value for the base pressure $P_0$ may be selected for a given patient via a process known as titration. During titration, a clinician typically adjusts the treatment pressure Pt in response to observations of flow limitation, apnea, hypopnea, patency, and snore during a titration session. The titrated base pressure $P_0$ may be then computed as a statistical summary of the treatment pressure Pt during the titration session.

Alternatively, the therapy parameter determination algorithm 4329 may continuously compute the base pressure $P_0$ during CPAP therapy. In this alternative, the therapy parameter determination algorithm 4329 continuously computes the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy. Because the continuous computation of the base pressure $P_0$ resembles the manual adjustment of the treatment pressure Pt by a clinician during titration, APAP therapy is also sometimes referred to as auto-titrating CPAP.

5.7.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates Π(Φ, t) described above, the therapy parameter determination algorithm 4329 increases the treatment pressure Pt to $P_0+A$ (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a prescribed treatment pressure that has the same purpose as the treatment pressure in CPAP therapy modes, and the EPAP is the IPAP minus the amplitude A, which has a "small" value (a few cmH$_2$O) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may continuously compute the IPAP and/or the EPAP during CPAP with EPR. In this alternative, the therapy parameter determination algorithm 4329 continuously computes the EPAP and/or the IPAP as a function of indices or measures of sleep disordered breathing returned by the respective algorithms in the therapy engine module 4320 is analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 cmH$_2$O. The predetermined pressure support value is a setting of the RPT device 4000, and may be set for example by hard-coding during configuration of the RPT device 4000 or by manual entry through the input device 4220.

In some forms of pressure support ventilation therapy, known as servo-ventilation, the therapy parameter determination algorithm 4329 takes as input the current measure Vent of ventilation and the target value Vtgt of ventilation provided by the target ventilation determination algorithm 4328 and continuously adjusts the parameters of equation (1) to bring the current measure Vent of ventilation towards the target value Vtgt of ventilation. In a form of servo-ventilation known as adaptive servo-ventilation (ASV), which has been used to treat CSR, the target ventilation Vtgt is computed by the target ventilation determination algorithm 4328 from the typical recent ventilation Vtyp, as described above.

In some forms of servo-ventilation, the therapy parameter determination algorithm 4329 applies a control methodology to continuously compute the pressure support A so as to bring the current measure Vent of ventilation towards the target ventilation Vtgt. One such control methodology is Proportional-Integral (PI) control. In one implementation of PI control, suitable for ASV modes in which a target ventilation Vtgt is set to slightly less than the typical recent ventilation Vtyp, the pressure support is computed as:

$$A = G \int (\text{Vent} - V_{tgt}) dt \quad (2)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as $-0.4$ cmH$_2$O/(L/min)/sec. Alternatively, the gain G may be varied between therapy sessions, starting small and increasing from session to session until a value that all but eliminates CSR is reached. Conventional means for retrospectively analysing the parameters of a therapy session to assess the severity of CSR during the therapy session may be employed in such implementations. In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220. A minimum pressure support Amin of 3 cmH$_2$O is of the order of 50% of the pressure support required to perform all the work of breathing of a typical patient in the steady state. A maximum pressure support Amax of 12 cmH$_2$O is approximately double the pressure support required to perform all the work of breathing of a typical patient, and therefore sufficient to support the patient's breathing if they cease making any efforts, but less than a value that would be uncomfortable or dangerous.

In pressure support ventilation therapy modes, the EPAP is the base pressure P$_0$. As with the base pressure P$_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure P$_0$ in constant CPAP therapy.

Alternatively, the therapy parameter determination algorithm 4329 may continuously compute the base pressure P$_0$ during pressure support ventilation therapy. In such implementations, the therapy parameter determination algorithm 4329 continuously computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the overall therapy is known as auto-titrating EPAP pressure support ventilation therapy, or auto-EPAP pressure support ventilation therapy.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

5.8.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Pressure: Force per unit area. Pressure may be measured in a range of units, including $cmH_2O$, $g$-$f/cm^2$, hectopascal. 1 $cmH_2O$ is equal to 1 $g$-$f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ Pascal (Pa), considered the threshold of human hearing.

5.8.4 Terms for Ventilators

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

Ventilator: A mechanical device that provides pressure support to a patient to perform some or all of the work of breathing.

5.8.5 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.8.6 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.7 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles.

The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.8 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.8.9 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie: A tie will be taken to be a structural component designed to resist tension.

Vent: (noun) the structure that allows a flow of air from an interior of the mask, or conduit, to ambient air to allow clinically effective washout of exhaled gases. For example, a clinically effective washout may involve a flow rate of about 10 litres per minute to about 100 litres per minute, depending on the mask design and treatment pressure.

5.8.10 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:

Readily conforming to finger pressure.
Unable to retain its shape when caused to support its own weight.
Not rigid.
Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during respiratory pressure therapy.

5.8.11 Curvature

Products in accordance with the present technology may comprise one or more real three-dimensional structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.11.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.11.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

Also, it should be appreciated that one or more aspects of the present technology may be combinable with one or more aspects of: PCT Application No. PCT/AU2016/050891, filed Sep. 23, 2016 and entitled "Patient Interface", which claims the benefit of U.S. Provisional Application No. 62/222,593, filed Sep. 23, 2015 and U.S. Provisional Application No. 62/376,961, filed Aug. 19, 2016; U.S. Provisional Application No. 62/377,217, filed Aug. 19, 2016 and entitled "Patient Interface with a Seal-Forming Structure having Varying Thickness"; U.S. Provisional Application No. 62/377,158, filed Aug. 19, 2016 and entitled "Patient Interface with a Seal-Forming Structure having Varying Thickness"; PCT Application No. PCT/AU2016/050892, filed Sep. 23, 2016 and entitled "Elbow Assembly", which claims the benefit of U.S. Provisional Application No. 62/222,435, filed Sep. 23, 2015 and U.S. Provisional Application No. 62/376,718, filed Aug. 18, 2016; U.S. Provisional Application No. 62/377,217, filed Aug. 19, 2016 and entitled "Patient Interface with a Seal-Forming Structure having Varying Thickness"; U.S. Provisional Application No. 62/377,158, filed Aug. 19, 2016 and entitled "Patient Interface with a Seal-Forming Structure having Varying Thickness"; and/or PCT Application No. PCT/AU2016/050228 filed Mar. 24, 2016 and entitled "Patient Interface with Blowout Prevention for Seal-Forming Portion", which claims the benefit of U.S. Provisional Application No. 62/138,009, filed Mar. 25, 2015 and U.S. Provisional Application No. 62/222,503, filed Sep. 23, 2015; each of the above-noted applications of which is incorporated herein by reference in its entirety.

5.10 Reference Characters List

| | |
|---|---|
| patient | 1000 |
| bed partner | 1100 |
| patient interface | 3000 |
| seal - forming structure | 3100 |
| plenum chamber | 3200 |
| positioning and stabilising structure | 3300 |
| rigidiser arm | 3301 |
| superior attachment point | 3302 |
| inferior strap connector | 3303 |
| inferior attachment point | 3304 |
| shroud | 3305 |
| clip | 3306 |
| hinge | 3307 |
| vent | 3400 |
| orifice | 3402 |
| wall | 3404 |
| diffusing member | 3406 |
| blocking member | 3408 |
| channels | 3410 |
| hole | 3412 |
| central hole | 3414 |
| radial opening | 3416 |
| elbow | 3418 |
| wall | 3420 |
| cap | 3422 |
| annular flange | 3424 |
| annular gap | 3426 |

-continued

| | |
|---|---|
| annular groove | 3428 |
| annular protrusion | 3430 |
| lip | 3432 |
| ball | 3434 |
| socket | 3436 |
| snap fit connection | 3438 |
| first half | 3440 |
| second half | 3442 |
| decoupling structure | 3500 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| mechanical and pneumatic components | 4100 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| heated air circuit | 4171 |
| tube | 4172 |
| RPT device connector | 4173 |
| vent adaptor connector | 4174 |
| bayonet connector | 4175 |
| grip recess | 4176 |
| seal | 4177 |
| tube connector | 4178 |
| supplemental oxygen | 4180 |
| electrical components | 4200 |
| printed circuit board assembly (PCBA) | 4202 |
| power supply | 4210 |
| input device | 4220 |
| central controller | 4230 |
| therapy device controller | 4240 |
| protection circuits | 4250 |
| memory | 4260 |
| transducer | 4270 |
| data communication interface | 4280 |
| output device | 4290 |
| algorithms | 4300 |
| pre - processing module | 4310 |
| pressure compensation algorithm | 4312 |
| vent flow rate estimation algorithm | 4314 |
| leak flow rate estimation algorithm | 4316 |
| respiratory flow rate estimation algorithm | 4318 |
| therapy engine module | 4320 |
| fuzzy phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| airway patency determination algorithm | 4327 |
| target ventilation determination algorithm | 4328 |
| therapy parameter determination algorithm | 4329 |
| therapy control module | 4330 |
| fault condition detection | 4340 |
| therapy device | 4350 |
| humidifier | 5000 |
| humidifier inlet | 5002 |
| humidifier outlet | 5004 |
| humidifier base | 5006 |
| humidifier reservoir | 5110 |
| conductive portion | 5120 |
| humidifier reservoir dock | 5130 |
| locking lever | 5135 |
| water level indicator | 5150 |

-continued

| | |
|---|---|
| humidifier transducer | 5210 |
| pressure transducer | 5212 |
| air flow rate transducer | 5214 |
| temperature transducer | 5216 |
| humidity sensor | 5218 |
| heating element | 5240 |
| humidifier controller | 5250 |
| central humidifier controller | 5251 |
| heating element controller | 5252 |
| air circuit controller | 5254 |
| HME | 7000 |
| layer | 7001 |
| corrugated structure | 7002 |
| top structure | 7010 |
| superior channel | 7012 |
| base structure | 7020 |
| inferior channel | 7022 |
| corrugation | 7030 |
| upper folded portion | 7031 |
| fluid connector | 9000 |
| first end | 9002 |
| second end | 9004 |
| fluid conduit | 9006 |
| seal portion | 9008 |
| first opening | 9010 |
| latching portion | 9012 |
| complementary latching portion | 9014 |
| sealing surface | 9016 |
| second opening | 9018 |
| second tube | 9020 |
| first tube | 9022 |
| inner portion | 9024 |
| outer portion | 9026 |
| interface | 9028 |
| stop | 9030 |
| port | 9032 |
| overhang portion | 9034 |
| pressure tap | 9036 |
| guide portion | 9038 |
| vent adaptor | 9100 |
| conduit connector | 9110 |
| conduit end | 9111 |
| vent adaptor end | 9112 |
| anti-asphyxia valve (AAV) openings | 9113 |
| ring | 9115 |
| air circuit connector | 9116 |
| bayonet connector | 9117 |
| vent housing | 9120 |
| end | 9121 |
| protrusions | 9122 |
| tab | 9123 |
| lip | 9124 |
| external vent hole | 9125 |
| internal vent hole | 9126 |
| shoulder | 9127 |
| support | 9128 |
| notches | 9129 |
| vent diffuser cover | 9130 |
| anti-asphyxia valve (AAV) | 9135 |
| flap | 9140 |
| flap retaining structure | 9141 |
| HME material | 9145 |
| diffuser | 9146 |
| diffuser opening | 9147 |
| diffuser retaining ring | 9148 |
| radial diffuser retainer | 9149 |
| CFV ring | 9150 |
| vent housing connector | 9160 |
| first bar | 9161 |
| second bar | 9162 |
| receptacle | 9163 |
| notch | 9164 |
| curved outer surface | 9165 |
| bayonet connector | 9166 |
| HME clip | 9170 |
| arm | 9171 |
| central shaft | 9172 |
| shaft end | 9173 |
| arm ends | 9174 |

-continued

| | |
|---|---|
| HME housing | 9180 |
| slots | 9181 |
| cross-member | 9182 |
| receiver | 9183 |
| outer wall | 9184 |
| cut-outs | 9185 |
| bellows seal | 9190 |
| bellows seal connector | 9191 |
| outer surface | 9192 |
| inner surface | 9193 |
| shoulder surface | 9194 |
| vent adaptor connector | 9200 |
| orifice | 9201 |
| rim | 9202 |
| rim | 9203 |
| short tube assembly | 9210 |
| tube | 9212 |
| tube-housing connector | 9214 |
| tube-elbow connector | 9216 |
| elbow assembly | 9220 |
| elbow frame | 9222 |
| elbow overmould | 9224 |
| vent core structure | 9300 |
| inlet | 9301 |
| air circuit connector | 9302 |
| clip | 9304 |
| vent core extension | 9306 |
| outer orifices | 9308 |
| inner orifices | 9310 |
| alignment structure | 9312 |
| vent housing | 9320 |
| bayonet connector | 9322 |
| membrane retainer | 9324 |
| vent diffuser cover | 9330 |
| cover spacers | 9332 |
| connection surface | 9334 |
| posterior vent outlet | 9340 |
| anterior vent outlet | 9342 |
| HME housing | 9400 |
| patient-side HME housing portion | 9402 |
| atmosphere-side HME housing portion | 9404 |
| patient-side HME housing portion cross-bar | 9406 |
| atmosphere-side HME housing portion cross-bar | 9408 |
| opening | 9410 |
| tab | 9412 |
| atmosphere-side HME housing portion ring | 9414 |
| HME inner housing | 9416 |
| HME bypass passage | 9418 |
| lip seal | 9500 |
| baffle | 9600 |
| plenum chamber connector | 9700 |
| nasal cushion patient interface | 3000A |
| nasal pillows patient interface | 3000B |
| full face patient interface | 3000C |
| vent system | 13400 |
| vent housing | 13401 |
| outer wall | 13402 |
| outer base | 13403 |
| outer orifice | 13404 |
| lateral membrane support | 13405 |
| inner base | 13406 |
| inner orifice | 13407 |
| base connector | 13408 |
| membrane spacer | 13409 |
| inner wall | 13410 |
| inlet | 13411 |
| membrane spacer gap | 13412 |
| inner base slot | 13413 |
| recess divider | 13414 |
| recess | 13415 |
| membrane | 13430 |
| membrane opening | 13431 |
| patient-side surface | 13432 |
| atmosphere-side surface | 13433 |
| inner surface | 13434 |
| outer surface | 13435 |

The invention claimed is:

1. A vent adaptor for a respiratory pressure therapy (RPT) system for providing RPT to a patient, the vent adaptor comprising:
   a vent assembly comprising:
      a vent housing defining a central orifice for a flow of pressurized gas to pass through the vent assembly from a delivery conduit to a patient interface, the vent housing having an annular surface around the central orifice, and the annular surface having a plurality of holes to discharge a vent flow of pressurized gas to atmosphere;
      a membrane positioned adjacent to the annular surface; and
      a diffusing member configured to allow the vent flow of pressurized gas to flow through the diffusing member prior to reaching atmosphere, the diffusing member having an annular disc shape that complements the shape of the annular surface of the vent housing on the side facing atmosphere, and the diffusing member having a diffusing member opening such that the diffusing member surrounds the central orifice,
   wherein the membrane is movable such that the membrane is urged against the annular surface of the vent housing as the pressure of the pressurized gas within the vent assembly increases.

2. The vent adaptor of claim 1, wherein the plurality of holes comprises a first group of holes and a second group of holes, the first group of holes being proximal to the central orifice relative to the second group of holes.

3. The vent adaptor of claim 2, wherein the membrane is shaped and dimensioned such that the membrane does not cover the first group of holes.

4. The vent adaptor of claim 2, wherein the membrane is structured to cover more of the second group of holes as the pressure of the pressurized gas within the vent assembly increases.

5. The vent adaptor of claim 2, wherein the first group of holes is positioned upstream of the second group of holes relative to the flow of pressurized gas.

6. The vent adaptor of claim 1, wherein the vent housing further comprises a membrane retainer having a cage-like structure and configured to retain the membrane in a position adjacent to the annular surface of the vent housing while allowing the vent flow to travel through the membrane retainer.

7. The vent adaptor of claim 1, wherein the membrane is constructed from an elastic material.

8. The vent adaptor of claim 1, wherein the membrane is ring-shaped.

9. The vent adaptor of claim 1, wherein the membrane is not joined to the vent housing.

10. The vent adaptor of claim 1, wherein the membrane is shaped and dimensioned such that an outer edge of the membrane is adjacent to an inner periphery of the vent housing.

11. The vent adaptor of claim 1, wherein each of the plurality of holes has a shape that converges from an internal surface of the vent housing to an external surface of the vent housing.

12. The vent adaptor of claim 1, further comprising a heat and moisture exchanger (HME) that is positioned downstream of the plurality of holes relative to the flow of pressurized gas, the HME comprising an HME material and an HME housing.

13. The vent adaptor of claim 1, wherein the diffusing member is positioned externally of the vent housing to at least partly cover the plurality of holes.

14. The vent adaptor of claim 13, further comprising a blocking member having an air-impermeable material, the blocking member being configured to prevent gas exiting from the plurality of holes from flowing through the diffusing member to atmosphere in a linear path.

15. The vent adaptor of claim 14, wherein the diffusing member and the blocking member are configured to direct the gas exiting from the plurality of holes outward from the diffusing member in an orientation different than the plurality of holes.

16. The vent adaptor of claim 14, wherein the diffusing member is configured to provide a flow path parallel to a surface of the blocking member that is in contact with the diffusing member.

17. The vent adaptor of claim 1, wherein the diffusing member is constructed from a porous material.

18. The vent adaptor of claim 1, wherein the diffusing member is constructed from an open cell foam.

19. The vent adaptor of claim 1, wherein the diffusing member is constructed from a fibrous material.

20. An RPT system, comprising:
   the vent adaptor of claim 1;
   an RPT device configured to generate a flow of pressurized gas in the range of 4-20 cm H2O;
   a patient interface configured to receive the flow of pressurized gas from the vent adaptor and deliver the flow of pressurized gas to the patient's airways; and
   a delivery conduit connected to the vent adaptor to deliver the flow of pressurized gas from the RPT device to the patient interface via the vent adaptor.

21. The RPT system of claim 20, wherein the RPT system does not include a humidifier.

22. The RPT system of claim 20, wherein the patient interface is non-vented.

23. The vent adaptor of claim 12, wherein the HME is positioned inside of the vent assembly.

* * * * *